United States Patent [19]

Liang

[11] Patent Number: 5,393,733
[45] Date of Patent: * Feb. 28, 1995

[54] HERBICIDAL PYRIDINESULFONYLUREAS

[75] Inventor: Paul H. Liang, Wilmington, Del.

[73] Assignee: E. I. Du Pont de Nemours and Company, Wilmington, Del.

[*] Notice: The portion of the term of this patent subsequent to Apr. 7, 2009 has been disclaimed.

[21] Appl. No.: 52,970

[22] Filed: Apr. 27, 1993

Related U.S. Application Data

[60] Division of Ser. No. 806,749, Dec. 13, 1991, Pat. No. 5,209,770, which is a division of Ser. No. 507,926, Apr. 12, 1990, Pat. No. 5,102,444, which is a continuation-in-part of Ser. No. 399,485, May 26, 1989, abandoned, which is a continuation-in-part of Ser. No. 39,491, Apr. 16, 1987, abandoned, which is a continuation-in-part of Ser. No. 939,428, Dec. 8, 1986, abandoned.

[51] Int. Cl.$^6$ .................. C07D 401/12; A01N 43/54
[52] U.S. Cl. ..................... 504/215; 504/197; 544/320; 544/321; 544/324; 544/331; 544/243; 544/122; 544/123
[58] Field of Search ............... 504/215, 197; 544/320, 544/321, 324, 331, 243, 122, 123

[56] References Cited

U.S. PATENT DOCUMENTS

| | | | |
|---|---|---|---|
| 4,435,206 | 3/1984 | Levitt | 71/92 |
| 4,456,469 | 6/1984 | Adams | 544/207 |
| 4,518,776 | 5/1985 | Meyer et al. | 544/206 |
| 4,521,597 | 6/1985 | Kristinsson | 544/3 |
| 4,522,645 | 6/1985 | Levitt | 71/93 |
| 4,544,401 | 10/1985 | Levitt | 71/92 |
| 4,844,727 | 7/1989 | Dean | 544/329 |
| 4,875,923 | 10/1989 | Schurter et al. | 504/215 |
| 5,084,082 | 1/1992 | Sebastian | 71/90 |
| 5,139,565 | 8/1992 | Kimura et al. | 544/320 |
| 5,221,315 | 6/1993 | Fory et al. | 544/320 |

FOREIGN PATENT DOCUMENTS

| | | |
|---|---|---|
| 084224 | 7/1983 | European Pat. Off. . |
| 101670 | 2/1984 | European Pat. Off. . |
| 155762 | 9/1985 | European Pat. Off. . |
| 164269 | 12/1985 | European Pat. Off. . |
| 184385 | 6/1986 | European Pat. Off. . |

*Primary Examiner*—John M. Ford

[57] ABSTRACT

This invention relates to herbicidal pyridinesulfonylureas which are highly active as preemergence and postemergence herbicides.

10 Claims, No Drawings

HERBICIDAL PYRIDINESULFONYLUREAS

CROSS-REFERENCE TO RELATED APPLICATION

This application is a division of prior application Ser. No. 07/806,749, filed Dec. 13, 1991, now U.S. Pat. No. 5,209,770, granted May 11, 1993, which is a division of prior application Ser. No. 07/507,926, filed Apr. 12, 1990, now granted as U.S. Pat. No. 5,102,444, granted Apr. 7, 1992; which is in turn a continuation-in-part of application Ser. No. 399,485, filed May 26, 1989, now abandoned; which in turn derives from PCT Application Ser. No. US87/03111, filed Dec. 4, 1987; which in turn was a continuation-in-part of U.S. application Ser. No. 07/039,491, filed Apr. 16, 1987, now abandoned; which in turn was a continuation-in-part of application Ser. No. 939,428, filed Dec. 8, 1986, now abandoned.

BACKGROUND OF THE INVENTION

Pyridinesulfonylureas of the instant application show high activity as preemergence and postemergence herbicides. In particular, safety to corn is demonstrated by many of the herbicides.

EP-A-13,480 discloses herbicidal sulfonamides of the formula

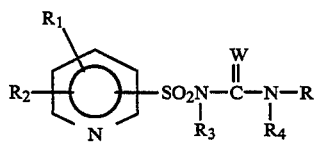

wherein $R_1$ is H, Cl, Br, F, $C_1$-$C_4$ alkyl, $C_1$-$C_4$ alkoxy, $C_1$-$C_4$ alkylthio, $NO_2$ or $CO_2R_5$.

U.S. Pat. No. 4,435,206, issued Mar. 6, 1984 and U.S. Pat. No. 4,522,645, issued Jun. 11, 1983, disclose 2-pyridinesulfonylureas substituted in the 3-position by $R_1$, wherein $R_1$ is H, Cl, Br, F, $C_1$-$C_4$ alkyl, $C_1$-$C_4$ alkoxy, $C_1$-$C_4$ alkylthio, $NO_2$, $CF_3$, $CO_2R_5$ or $SO_2NR_6R_7$.

U.S. Pat. No. 4,339,267 discloses herbicidal sulfonamides of the formula

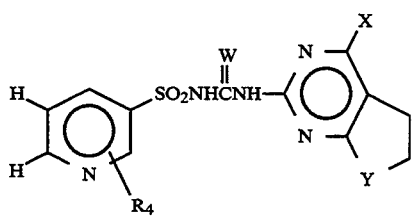

wherein $R_4$ is H, Cl, Br, F, $C_1$-$C_4$ alkyl, $C_1$-$C_4$ alkoxy, $NO_2$, $CO_2R_6$ or $SR_{13}$.

EP-A-30,433 discloses herbicidal sulfonamides of the formula

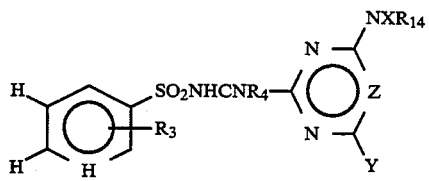

wherein

X is H;

$R_{14}$ is H or $CH_3$; and $R_3$ is H, F, Cl, Br, $CH_3$, $OCH_3$, $NO_2$, $CO_2R_{11}$ or $S(O)_nR_{12}$.

U.S. Pat. No. 4,456,469 discloses herbicidal sulfonamides of the formula

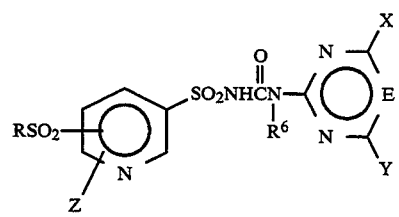

wherein

R is $C_1$-$C_6$ alkyl, $C_3$-$C_6$ alkenyl, $C_2$-$C_4$ alkoxyalkyl, $C_5$-$C_6$ cycloalkyl, $R'OCH_2CH_2OCH_2$, $R'OCH_2CH_2OCH_2CH_2$,

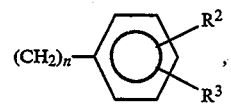

$CF_3$, $CF_3CH_2$, HGLCCF$_2$ or HCF$_2$; and

Z is H, F, Cl, Br, $CH_3$, $OCH_3$ or $SCH_3$.

U.S. Pat. No. 4,487,626 discloses herbicidal sulfonamides of the formula

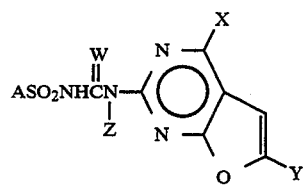

wherein

A is

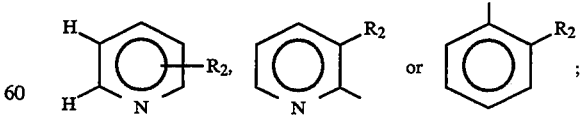

and $R_2$ is H, F, Cl, Br, $C_1$-$C_4$ alkyl, $C_1$-$C_4$ alkoxy, $NO_2$, $CO_2R_{15}$, $S(O)_mR_{16}$, $SO_2NR_{18}R_{19}$ or $SO_2N(OCH_3)CH_3$.

U.S. Pat. No. 4,421,550 discloses herbicidal sulfonamides of the formula

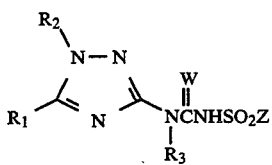

wherein
Z is

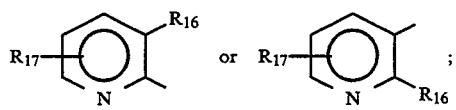

and
R16 is H, $C_1$-$C_4$ alkyl, $C_1$-$C_4$ alkoxy, F, Cl, Br, $CF_3$, $CO_2R_{20}$, $SO_2NR_{10}R_{11}$, $SO_2N(OCH_3)CH_3$ or $S(O)_nR_{13}$.

U.S. Pat. No. 4,496,392 discloses herbicidal sulfonamides of the formula

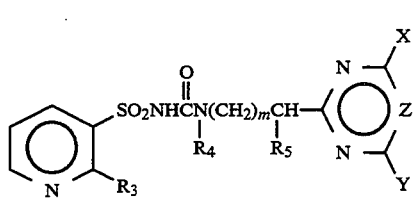

wherein
$R_3$ is Cl, $SO_2CH_3$ or $SO_2N(CH_3)_2$.

EP-A-84,224 discloses herbicidal sulfonamides of the formula

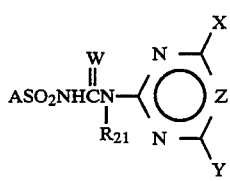

wherein
A is

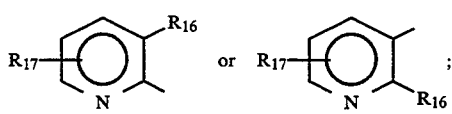

and
$R_{16}$ is H, $C_1$-$C_4$ alkyl, $C_1$-$C_4$ alkoxy, F, Cl, Br, $CF_3$, $CO_2R_9$, $SO_2NR_{10}R_{11}$, $SO_2N(OCH_3)CH_3$ or $S(O)_nR_{13}$.

EP-A-125,846 discloses herbicidal sulfonamides of the formula

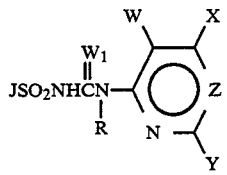

wherein
J is

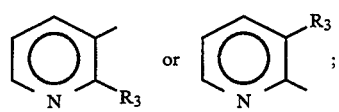

and
$R_3$ is Cl, $SO_2CH_3$, $SO_2N(CH_3)_2$, $OCH_3$, $NO_2$ or $N(CH_3)_2$.

EP-A-155,767 discloses herbicidal sulfonamides of the formula

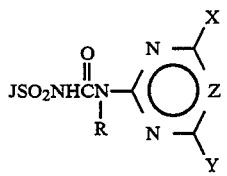

wherein
J is

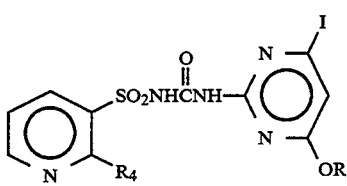

and
$R_5$ is H, $CH_3$, Cl, Br, $CO_2R_{15}$, $C(O)NR_{16}R_{17}$, $SO_2NR_{16}R_{17}$, $SO_2N(OCH_3)CH_3$, $SO_2R_{18}$ or $NO_2$.

EP-A-161,905 discloses herbicidal sulfonamides of the formula

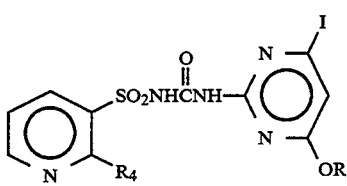

wherein
$R_4$ is $CH_3$, $CH_2CH_3$, $OCH_3$, $OCH_2CH_3$, F, Cl, Br, $SO_2NR_{16}R_{17}$, $SO_2N(OCH_3)CH_3$, $S(O)_nR_{19}$, $C_3$-$C_4$ alkenyloxy or $C_3$-$C_4$ alkynyloxy.

EP-A-164,269 discloses herbicidal sulfonamides of the formula

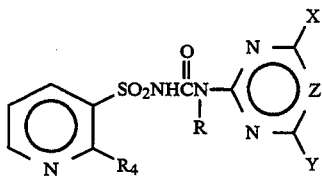

wherein
R$_4$ is CH$_3$, CH$_2$CH$_3$, OCH$_3$, OCH$_2$CH$_3$, F, Cl, Br, SO$_2$NR$_{11}$R$_{12}$, SO$_2$N(OCH$_3$)CH$_3$ or S(O)$_n$R$_{13}$.

EP-A-171,286 discloses herbicidal sulfonamides of the formula

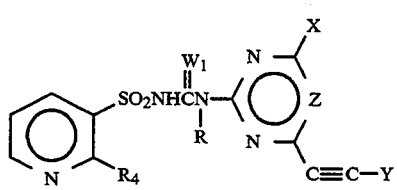

wherein
R$_4$ is CH$_3$, CH$_2$CH$_3$, OCH$_3$, OCH$_2$CH$_3$, F, Cl, Br, SO$_2$NR$_{18}$R$_{19}$, SO$_2$N(OCH$_3$)CH$_3$, S(O)$_n$R$_{21}$, C$_3$-C$_4$ alkenyloxy, CH$_2$OCH$_3$ or CH$_2$OCH$_2$CH$_3$.

South African Patent Application 83/4305, published Dec. 14, 1983, discloses herbicidal sulfonamides of the formula

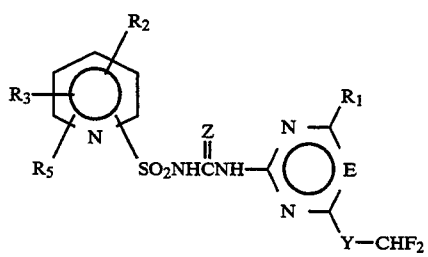

wherein
R$_2$ is H, C$_1$-C$_3$ alkyl, C$_1$-C$_3$ haloalkyl, halogen, NO$_2$, C$_1$-C$_3$ alkoxy, C(W)R$_8$, SO$_2$NR$_6$R$_7$, S(O)$_n$—C$_1$-C$_3$ alkyl or C(O)R$_9$;
R$_3$ is H, halogen, C$_1$-C$_3$ alkyl, OCH$_3$, NO$_2$ or CF$_3$;
R$_5$ is H, NO$_2$, F, Cl, Br, CH$_3$, CF$_3$, S(O)$_n$C$_1$-C$_3$ alkyl, C(O)C$_1$-C$_4$ alkoxy or C$_1$-C$_3$ alkoxy;
Y is O or S.

South African Patent Application 83/6639, published Mar. 8, 1984, discloses herbicidal sulfonamides of the formula

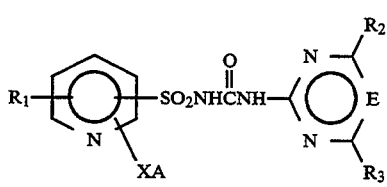

wherein
A is a C$_3$-C$_6$ alkynyl radical, a C$_1$-C$_6$ alkyl radical which is substituted by halogen, C$_1$-C$_4$ alkoxy, C$_1$-C$_4$ alkylthio, C$_1$-C$_4$ alkylsulfinyl, C$_1$-C$_4$ alkylsulfonyl, C$_1$-C$_4$ haloalkoxy, C$_1$-C$_4$ haloalkylthio, C$_1$-C$_4$ haloalkylsulfinyl or C$_1$-C$_4$ haloalkylsulfonyl, or is a C$_2$-C$_4$ alkenyl radical which is unsubstituted or substituted as for C$_1$-C$_6$ alkyl, or is a phenyl radical which is unsubstituted or substituted by halogen, cyano, nitro, C$_1$-C$_4$ alkyl, C$_1$-C$_4$ haloalkyl, an —X—C$_1$-C$_4$ alkyl, C$_1$-C$_4$ alkoxycarbonyl, amino, mono- or di(C$_1$-C$_4$ alkyl)amino, carbamoyl, mono- or di-(C$_1$-C$_4$ alkyl)carbamoyl, sulfamoyl, mono- or di-(C$_1$-C$_4$ alkyl)sulfamoyl radical;
R$_1$ is hydrogen, halogen, C$_1$-C$_4$ alkyl, C$_1$-C$_4$ alkoxy, C$_1$-C$_4$ haloalkyl, C$_1$-C$_4$ haloalkoxy, C$_2$-C$_5$ alkoxyalkoxy, C$_1$-C$_5$ alkylthio, C$_1$-C$_5$ alkylsulfinyl or C$_1$-C$_5$ alkylsulfonyl; and
X is O, S, SO or SO$_2$.

U.S. Pat. No. 4,518,776 discloses a process for the preparation of herbicidal sulfonamides of the formula

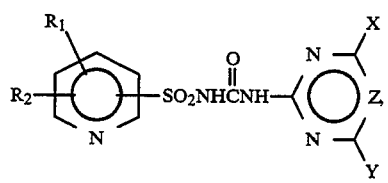

wherein
R$_1$, in part, is S(O)$_n$C$_1$-C$_4$ alkyl, SO$_2$di-C$_1$-C$_4$ alkylamino or CO$_2$-C$_1$-C$_2$ alkyl; and
R$_2$ is H, halogen, CF$_3$, NO$_2$, C$_1$-C$_4$ alkyl or C$_1$-C$_4$ alkoxy.

This patent generically discloses some, but does not claim any, compounds of the instant invention.

EP-A-101,670, published Feb. 29, 1984, discloses a process for the preparation of herbicidal sulfonamides of the formula

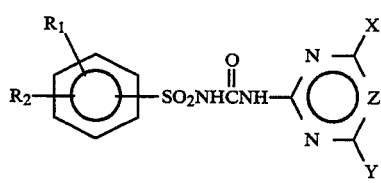

wherein
R$_1$ is Q-C$_1$-C$_4$ alkyl, SO$_2$-di-C$_1$-C$_4$ alkylamino or CO$_2$-C$_1$-C$_4$ alkyl;
Q is S or S(O)$_n$; and
R$_2$ is H, halogen, CF$_3$, NO$_2$, C$_1$-C$_4$ alkyl or C$_1$-C$_4$ alkoxy.

This application generically discloses some of the compounds of the instant invention.

U.S. Pat. No. 4,521,597 discloses a process for the preparation of herbicidal sulfonamides of the formula

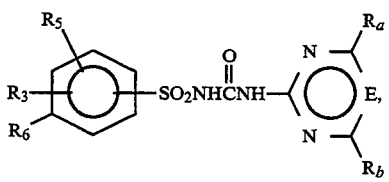

wherein
R$_3$ is H, F, Cl, Br, NO$_2$, OCH$_3$ or CF$_3$;
R$_5$ is S(O)$_m$C$_1$-C$_5$ alkyl, SO$_2$NR$_8$R$_9$ or COR$_7$; and
R$_6$ is H, F, CH$_3$ or OCH$_3$.

This patent generically discloses some, but does not claim any, compounds of the instant invention.

EP-A-184,385, published Jun. 11, 1986, discloses the following compound for selective weed control in tomatoes and turf.

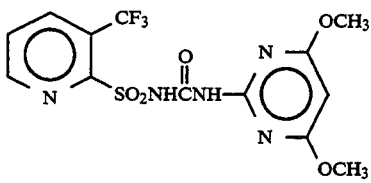

U.S. Ser. No. 874,307 discloses herbicidal o-alkylcarbonyl-pyridinesulfonylureas.

U.S. Ser. No. 943,137 discloses herbicidal o-substituted-pyridinesulfonylureas.

SUMMARY OF THE INVENTION

This application pertains to novel compounds of Formula I, agriculturally suitable compositions containing them and their method-of-use as preemergent and/or postemergent herbicides or plant growth regulants.

      I wherein
J is

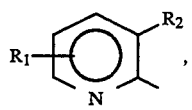      J-1

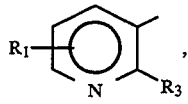      J-2

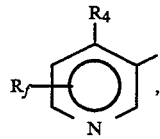      J-3

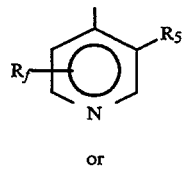      J-4 or

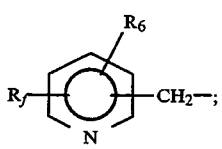      J-5

R is H or CH$_3$;
W is O or S;
R$_1$ is R$_f$ or R$_g$;

R$_f$ is H, C$_1$-C$_3$ alkyl, C$_1$-C$_3$ haloalkyl, halogen, NO$_2$, C$_1$-C$_3$ alkoxy, C$_1$-C$_3$ alkylthio or CN;

R$_g$ is C$_1$-C$_3$ haloalkyl, C$_2$-C$_3$ alkyl, cyclopropyl, C$_1$-C$_3$ alkyl substituted by C$_1$-C$_3$ alkoxy, OH, C$_1$-C$_2$ alkylthio or CN, CN, W$_2$R$_{11}$, amino, C$_1$-C$_3$ alkylamino or C$_1$-C$_3$ dialkylamino;

R$_2$ is C$_1$-C$_4$ alkylsulfinyl, C$_1$-C$_4$ alkylsulfonyl, C$_3$-C$_5$ cycloalkylthio, C$_3$-C$_5$ cycloalkylsulfinyl, C$_3$-C$_5$ cycloalkylsulfonyl, SO$_2$NH$_2$, SO$_2$NR$_d$R$_e$, SO$_2$NR'$_7$R$_8$, SO$_2$NR$_7$R$_8$, OSO$_2$R$_8$, SO$_2$OR$_8$, N$_3$, P(W$_1$)(OC$_1$-C$_2$ alkyl)$_2$, CN, CO$_2$R$_9$, CO$_2$R'$_9$, CH$_2$F, CF$_2$H, CH$_2$Cl, CCl$_2$H or C$_2$-C$_4$ haloalkyl;

R$_3$ is C$_1$-C$_4$ alkylsulfinyl, C$_3$-C$_5$ cycloalkylthio, C$_3$-C$_5$ cycloalkylsulfinyl, C$_3$-C$_4$ cycloalkylsulfonyl, SO$_2$NH$_2$, SO$_2$NR$_d$R$_e$, SO$_2$NR$_7$R$_8$, SO$_2$NR'$_7$R$_8$, OSO$_2$R$_8$, SO$_2$OR$_8$, N$_3$, P(W$_1$)(OC$_1$-C$_2$ alkyl)$_2$, CN, CO$_2$R$_9$, CO$_2$R'$_9$ or C$_1$-C$_4$ haloalkyl;

R$_4$ is C$_1$-C$_4$ alkylsulfinyl, C$_3$-C$_5$ cycloalkylthio, C$_3$-C$_5$ cycloalkylsulfinyl, C$_3$-C$_4$ cycloalkylsulfonyl, SO$_2$NH$_2$, SO$_2$NR$_d$R$_e$, SO$_2$NR$_7$R$_8$, OSO$_2$R$_8$, SO$_2$OR$_8$, N$_3$, P(W$_1$)(OC$_1$-C$_2$ alkyl)$_2$, CN, CO$_2$R$_9$ or C$_1$-C$_4$ haloalkyl;

R$_5$ is C$_1$-C$_4$ alkylsulfinyl, C$_1$-C$_4$ alkylsulfonyl, C$_3$-C$_5$ cycloalkylthio, C$_3$-C$_5$ cycloalkylsulfinyl, C$_3$-C$_5$ cycloalkylsulfonyl, SO$_2$NH$_2$, SO$_2$NR$_d$R$_e$, SO$_2$NR$_7$R$_8$, OSO$_2$R$_8$, SO$_2$OR$_8$, N$_3$, P(W$_1$)(OC$_1$-C$_2$ alkyl)$_2$, CN, CO$_2$R$_9$ or C$_1$-C$_4$ haloalkyl;

R$_6$ is C$_1$-C$_4$ alkylthio, C$_1$-C$_4$ alkylsulfinyl, C$_1$-C$_4$ haloalkylthio, C$_1$-C$_4$ haloalkylsulfinyl, C$_1$-C$_4$ haloalkylsulfonyl, C$_3$-C$_4$ alkenylthio, C$_3$-C$_4$ alkenylsulfinyl, C$_3$-C$_4$ alkenylsulfonyl, C$_3$-C$_4$ alkynylthio, C$_3$-C$_4$ alkynylsulfinyl, C$_3$-C$_4$ alkynylsulfonyl, C$_3$-C$_5$ cycloalkylthio, C$_3$-C$_5$ cycloalkylsulfinyl, C$_3$-C$_5$ cycloalkylsulfonyl, SO$_2$NR$_d$R$_e$, SO$_2$NR$_7$R$_8$, OSO$_2$R$_8$, SO$_2$OR$_8$, N$_3$, P(W$_1$)(OC$_1$-C$_2$ alkyl)$_2$, CN, CO$_2$R$_9$ or C$_1$-C$_4$ haloalkyl;

R$_7$ is H, C$_2$-C$_3$ cyanoalkyl, C$_3$-C$_4$ alkenyl or C$_3$-C$_4$ alkynyl;

R'$_7$ is C$_1$-C$_4$ alkyl;

R$_8$ is C$_1$-C$_4$ alkyl, C$_1$-C$_4$ haloalkyl, C$_3$-C$_4$ alkenyl, C$_3$-C$_4$ alkynyl, C$_2$-C$_4$ alkoxyalkyl or cyclopropyl; or R$_7$ and R$_8$ may be taken together as —(CH$_2$)$_3$—, —(CH$_2$)$_4$—, —(CH$_2$)$_5$— or —CH$_2$CH$_2$OCH$_2$CH$_2$—;

R$_9$ is CH$_2$CH$_2$R$_{10}$, CH$_2$CF$_3$, C$_3$-C$_4$ haloalkyl, C$_3$-C$_4$ alkynyl, C$_2$-C$_4$ alkylthioalkyl, C$_3$-C$_5$ cycloalkyl or C$_4$-C$_7$ cycloalkylalkyl;

R'$_9$ is C$_1$-C$_4$ alkyl, C$_3$-C$_4$ alkenyl, CH$_2$CH$_2$Cl, CH$_2$CH$_2$Br, CH$_2$CH$_2$OCH$_3$ or CH$_2$CH$_2$OC$_2$H$_5$;

R$_{10}$ is OH, F, CN, OSO$_2$(C$_1$-C$_3$ alkyl) or OSO$_2$(C$_1$-C$_3$ haloalkyl);

R$_{11}$ is C$_1$-C$_3$ alkyl, C$_1$-C$_3$ haloalkyl, C$_3$-C$_4$ alkenyl or C$_3$-C$_4$ alkynyl;

W$_1$ is O or S;
W$_2$ is O or S;
A is

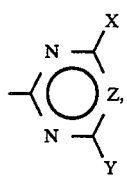      A-1

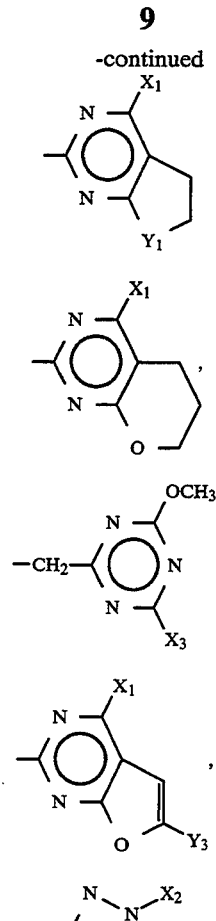

-continued

A-2

A-3

A-4

A-5

A-6

A-7

X is H, $C_1$–$C_4$ alkyl, $C_1$–$C_4$ alkoxy, $C_2$–$C_4$ haloalkoxy, $C_1$–$C_4$ haloalkyl, $C_2$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_2$–$C_4$ haloalkoxy, $C_2$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_2$–$C_4$ alkynyl, $C_3$–$C_5$ cycloalkyl, azido,

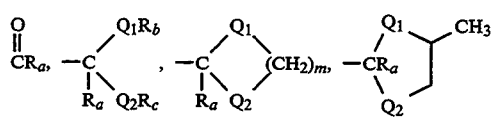

$N(OCH_3)CH_3$;
m is 2 or 3;

$Q_1$ and $Q_2$ are independently O or S;
$R_a$ is H or $C_1$–$C_3$ alkyl;
$R_b$ and $R_c$ are independently $C_1$–$C_3$ alkyl;
$R_d$ is H or $C_1$–$C_2$ alkyl;
$R_e$ is $C_1$–$C_2$ alkoxy;
Z is CH, N, $CCH_3$, $CC_2H_5$, CCl or CBr;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $CH_3$ or $CH_2CH_3$;
$X_3$ is $CH_3$ or $OCH_3$;
$Y_3$ is H or $CH_3$;
$X_4$ is $CH_3$, $OCH_3$, $OC_2H_5$, $CH_2OCH_3$ or Cl;
$Y_4$ is $CH_3$, $OCH_3$, $OC_2H_5$ or Cl;

and their agriculturally suitable salts; provided that 1) when X is halogen, then Z is CH and Y is $OCH_3$, $OC_2H_5$, $NH_2$, $NHCH_3$, $N(CH_3)_2$ or $N(OCH_3)CH_3$;
2) when W is S, then R is H, A is A-1, Z is CH or N, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or $$\begin{array}{c} O \\ / \\ CH \\ \backslash \\ O \end{array}\Big];$$

3) when the total number of carbon atoms of X and Y is greater than four, then the combined number of carbons of $R_1$, $R_2$, $R_3$, $R_4$, $R_5$ or $R_6$ is less than or equal to six;
4) when J is J-1 and $R_2$ is $C_1$–$C_4$ alkylsulfinyl, $C_1$–$C_4$ alkylsulfonyl, $SO_2NR_dR_e$, $SO_2NR'_7R_8$ or $CO_2R'_9$, or when J is J-2 and $R_3$ is $C_1$–$C_4$ alkylsulfinyl, $CF_3$, $SO_2NR_dR_e$, $SO_2NR'_7R_8$ or $CO_2R'_9$, then Y is other than $C_2$–$C_5$ alkylthioalkyl, $C_2$–$C_5$ alkylsulfinylalkyl, $C_2$–$C_5$ alkylsulfonylalkyl, $$\underset{R_a \ Q_2R_c}{\overset{Q_1R_b}{C}}, \underset{R_a \ Q_2}{\overset{Q_1}{C}}(CH_2)_m \text{ or } -CR_a\underset{Q_2}{\overset{Q_1}{\diagdown}}CH_3 \ ;$$

5) when J is J-2 or J-3 and $R_3$ or $R_4$ is $C_1$–$C_4$ alkylsulfinyl, then X and Y are other than $NH_2$ or $NHCH_3$;
6) when J is J-2 and $R_3$ is $C_1$–$C_4$ alkylsulfinyl or $SO_2NR_dR_e$, or $R_7$ is H, then X and Y are other than $C_2$–$C_4$ haloalkoxy;
7) when J is J-5, then $R_7$ is other than H and $R_6$ is other than $SO_2NR_dR_e$;
8) when J is J-2 and $R_3$ is $SO_2NH_2$ or $SO_2NR_dR_e$, or $R_7$ is H, then X is other than iodine;
9) when J is J-2 and $R_7$ is H or $R_3$ is $SO_2NR_dR_e$, then Y is other than $C_2$–$C_4$ alkynyl;
10) $X_4$ and $Y_4$ are not simultaneously Cl;
11) when J is J-1, J-2, J-3, J-4 and A is A-5, then $R_f$ is other than H;
12) when J is J-1 or J-2, then A is other than A-6;
13) when J is J-1 and A is A-7, then $R_2$ is other than $C_1$–$C_4$ alkylsulfonyl;
14) when $R_2$ or $R_3$ is $CO_2R'_9$ or $SO_2NR'_7R_8$, then $R_1$ is $R_g$ and when $R_2$ or $R_3$ is other than $CO_2R'_9$ or $SO_2NR'_7R_8$, then $R_1$ is $R_f$; and
15) when J is J-2 and $R_1$ is adjacent to the sulfonylurea bridge, then $R_g$ is $C_1$–$C_3$ haloalkyl, $C_2$–$C_3$ alkyl, cyclopropyl, CN, $W_2R_{11}$, amino, $C_1$-$C_3$ alkylamino or $C_1$-$C_3$ dialkylamino.

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propyloxy or isopropyloxy.

Alkenyl denotes straight chain or branched alkenes, e.g. 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Alkylsulfonyl denotes methylsulfonyl, ethylsulfonyl and the different propylsulfonyl and butylsulfonyl isomers.

Cycloalkyl denotes cyclopropyl, cyclobutyl and cyclopentyl.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms which may be the same or different. Examples of haloalkyl include $CH_2CH_2F$, $CF_2CF_3$ and $CH_2CHFCl$. Similarly, this definition applies to haloalkoxy and haloalkylthio.

The total number of carbon atoms in a substituent group is indicated by the $C_i$-$C_j$ prefix where i and j are numbers from 1 to 5. For example, $C_1$-$C_3$ alkylsulfonyl would designate methylsulfonyl through propylsulfonyl, $C_2$ alkoxyalkoxy would designate $OCH_2OCH_3$, $C_2$ cyanoalkyl would designate $CH_2CN$ and $C_3$ cyanoalkyl would designate $CH_2CH_2CN$ and $CH(CN)CH_3$.

PREFERRED COMPOUNDS

Preferred for reasons of increased ease of synthesis and/or greater herbicidal efficacy are:

1. Compounds of Formula I where
   X is $C_1$-$C_2$ alkyl, $C_1$-$C_2$ alkoxy, Cl, F, Br, I, $CH_2F$, $CF_3$, $OCH_2CH_2F$, $OCH_2CHF_2$, $OCH_2CF_3$, $CH_2Cl$ or $CH_2Br$; and
   Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$,

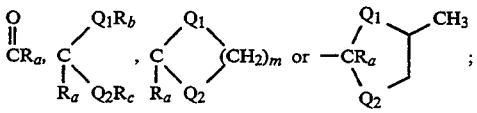

$CH_2SCH_3$, cyclopropyl, $C\equiv CH$ or $C\equiv CCH_3$;
   $R_a$ is H or $CH_3$; and
   Z is CH or N.

2. Compounds of Preferred 1 where
   W is O;
   $R_f$ is H, $CH_3$, $C_1$ haloalkyl, halogen or $OCH_3$;
   $R_g$ is $C_1$-$C_2$ haloalkyl, ethyl, $W_2R_{11}$, $CH_2OCH_3$, $CH_2SCH_3$, $CH_2CN$, $C_1$-$C_2$ alkylamino or $N(CH_3)_2$;
   $R_2$ is $C_1$-$C_4$ alkylsulfinyl, $C_1$-$C_4$ alkylsulfonyl, $SO_2NH_2$, $SO_2NR_dR_e$, $SO_2NR_7R_8$, $SO_2NR'_7R_8$, $OSO_2R_8$, $SO_2OR_8$, $N_3$, $P(W_1)(OC_1$-$C_2$ alkyl$)_2$, CN, $CO_2R_9$, $CO_2R'_9$, $CHF_2$, $CF_2H$, $CH_2Cl$, $CCl_2H$ or $C_2$-$C_4$ haloalkyl;

$R_3$ is $C_1$-$C_4$ alkylsulfinyl, $SO_2NH_2$, $SO_2NR_dR_e$, $SO_2R_7R_8$, $SO_2NR'_7R_8$, $OSO_2R_8$, $SO_2OR_8$, $N_3$, $P(W_1)(OC_1$-$C_2$ alkyl$)_2$, CN, $CO_2R_9$, $CO_2R'_9$ or $C_1$-$C_4$ haloalkyl;

$R_4$ is $C_1$-$C_4$ alkylsulfinyl, $SO_2NH_2$, $SO_2N(OCH_3)CH_3$, $SO_2NR_7R_8$, $OSO_2R_8$, $SO_2OR_8$, $N_3$, $P(W_1)(OC_1$-$C_2$ alkyl$)_2$, CN, $CO_2R_9$ or $C_1$-$C_4$ haloalkyl;

$R_5$ is $C_1$-$C_4$ alkylsulfinyl, $C_1$-$C_4$ alkylsulfonyl, $SO_2NH_2$, $SO_2N(OCH_3)CH_3$, $SO_2NR_7R_8$, $OSO_2R_8$, $SO_2OR_8$, $N_3$, $P(W_1)(OC_1$-$C_2$ alkyl$)_2$, CN, $CO_2R_9$ or $C_1$-$C_4$ haloalkyl;

$R_6$ is $C_1$-$C_4$ alkylthio, $C_1$-$C_4$ alkylsulfinyl, $C_1$-$C_4$ haloalkylthio, $C_1$-$C_4$ haloalkylsulfinyl, $C_1$-$C_4$ haloalkylsulfonyl, $C_3$-$C_4$ alkenylthio, $C_3$-$C_4$ alkenylsulfinyl, $C_3$-$C_4$ alkenylsulfonyl, $C_3$-$C_4$ alkynylthio, $C_3$-$C_4$ alkynylsulfinyl, $C_3$-$C_4$ alkynylsulfonyl, $SO_2N(OCH_3)CH_3$, $SO_2NR_7R_8$, $OSO_2R_8$, $SO_2OR_8$, $N_3$, $P(W_1)(OC_1$-$C_2$ alkyl$)_2$, CN, $CO_2R_9$ or $C_1$-$C_4$ haloalkyl;

$R_7$ is H, $C_2$-$C_3$ cyanoalkyl, $C_3$-$C_4$ alkenyl or $C_3$-$C_4$ alkynyl;

$R_8$ is $C_1$-$C_4$ alkyl, $C_1$-$C_4$ haloalkyl, $C_3$-$C_4$ alkenyl, $C_3$-$C_4$ alkynyl, $C_2$-$C_4$ alkoxyalkyl or cyclopropyl; and $R_{11}$ is $C_1$-$C_3$ alkyl, $C_1$-$C_2$ haloalkyl, allyl or propargyl.

3. Compounds of Preferred 2 where J is J-1.
4. Compounds of Preferred 2 where J is J-2.
5. Compounds of Preferred 2 where J is J-3.
6. Compounds of Preferred 2 where J is J-4.
7. Compounds of Preferred 2 where J is J-5.
8. Compounds of Preferred 3 where
   $R_7$ is H, $C_2$-$C_3$ cyanoalkyl, allyl or propargyl;
   $R'_7$ is $C_1$-$C_3$ alkyl;
   $R_8$ is $C_1$-$C_3$ alkyl, allyl, propargyl or cyclopropyl;
   $R_9$ is $CH_2CH_2R_{10}$, $CH_2CH_2SCH_3$, propargyl or cyclopropylmethyl;
   $R'_9$ is $C_1$-$C_3$ alkyl, allyl, $CH_2CH_2OCH_3$ or $CH_2CH_2Cl$; and
   $R_{10}$ is OH, CN or $OSO_2CH_3$.

9. Compounds of Preferred 8 where
   A is A-1;
   X is $CH_3$, $OCH_3$, $OCH_2CH_3$, Cl or $OCH_2CF_3$; and
   Y is $CH_3$, $OCH_3$, $CH_2CH_3$, $CH_2OCH_3$, $NHCH_3$ or $CH(OCH_3)_2$.

10. Compounds of Preferred 9 where Z is CH.
11. Compounds of Preferred 9 where Z is N.
12. Compounds of Preferred 4 where
    $R_7$ is H, $C_2$-$C_3$ cyanoalkyl, allyl or propargyl; and
    $R_8$ is $C_1$-$C_3$ alkyl, allyl, propargyl or cyclopropyl.

13. Compounds of Preferred 12 where
    A is A-1;
    X is $CH_3$, $OCH_3$, $OCH_2CH_3$, Cl or $OCH_2CF_3$; and
    Y is $CH_3$, $OCH_3$, $CH_2CH_3$, $CH_2OCH_3$, $NHCH_3$ or $CH(OCH_3)_2$.

14. Compounds of Preferred 13 where Z is CH.
15. Compounds of Preferred 13 where Z is N.
16. Compounds of Preferred 5 where
    $R_7$ is H, $C_2$-$C_3$ cyanoalkyl, allyl or propargyl; and
    $R_8$ is $C_1$-$C_3$ alkyl, allyl, propargyl or cyclopropyl.

17. Compounds of Preferred 16 where
    A is A-1;
    X is $CH_3$, $OCH_3$, $OCH_2CH_3$, Cl or $OCH_2CF_3$; and
    Y is $CH_3$, $OCH_3$, $CH_2CH_3$, $CH_2OCH_3$, $NHCH_3$ or $CH(OCH_3)_2$.

18. Compounds of Preferred 17 where Z is CH.
19. Compounds of Preferred 17 where Z is N.
20. Compounds of Preferred 6 where
    $R_7$ is H, $C_2$–$C_3$ cyanoalkyl, allyl or propargyl; and
    $R_8$ is $C_1$–$C_3$ alkyl, allyl, propargyl or cyclopropyl.
21. Compounds of preferred 20 where
    A is A-1;
    X is $CH_3$, $OCH_3$, $OCH_2CH_3$, Cl or $OCH_2CF_3$; and
    Y is $CH_3$, $OCH_3$, $CH_2CH_3$, $CH_2OCH_3$, $NHCH_3$ or $CH(OCH_3)_2$.
22. Compounds of Preferred 21 where Z is CH.
23. Compounds of Preferred 21 where Z is N.
24. Compounds of Preferred 7 where
    $R_6$ is $C_1$–$C_2$ alkylthio, $C_1$–$C_2$ alkylsulfinyl, $C_1$–$C_2$ haloalkylthio, $C_1$–$C_2$ haloalkylsulfinyl, $C_1$–$C_2$ haloalkylsulfonyl, $SO_2N(OCH_3)CH_3$ or $SO_2NR_7R_8$;
    $R_7$ is H, $C_2$–$C_3$ cyanoalkyl, allyl or propargyl;
    $R_8$ is $C_1$–$C_3$ alkyl, allyl, propargyl or cyclopropyl.
25. Compounds of Preferred 24 where
    A is A-1;
    X is $CH_3$, $OCH_3$, $OCH_2CH_3$, Cl or $OCH_2CF_3$; and
    Y is $CH_3$, $OCH_3$, $CH_2CH_3$, $CH_2OCH_3$, $NHCH_3$ or $CH(OCH_3)_2$.
26. Compounds of Preferred 25 where Z is CH.
27. Compounds of Preferred 25 where Z is N.
28. Compounds of Preferred 1 where
    J is J-1;
    A is A-1;
    Z is CH;
    W is O;
    $R_2$ is $C_1$–$C_4$ alkylsulfinyl or $C_1$–$C_4$ alkylsulfonyl; and
    $R_f$ is H, $C_1$–$C_2$ alkyl, $C_1$ haloalkyl, $C_1$–$C_2$ alkoxy or $C_1$–$C_2$ thioalkyl.
29. Compounds of Preferred 28 where
    $R_f$ is H;
    $R_2$ is $C_1$–$C_4$ alkylsulfonyl;
    X is $OCH_3$; and
    Y is $OCH_3$.

Specifically Preferred for reasons of greatest ease of synthesis and/or greatest herbicidal efficacy are:
N-[(4,6-dimethoxypyrimidin-2-yl)aminocarbonyl]-3-(1-propylsulfonyl)-2-pyridinesulfonamide;
N-[(4,6-dimethoxypyrimidin-2-yl)aminocarbonyl]-3-(1-propylsulfinyl)-2-pyridinesulfonamide;
N-[(4,6-dimethoxypyrimidin-2-yl)aminocarbonyl]-3-(ethylsulfonyl)-2-pyridinesulfonamide;
N2-[(4,6-dimethoxypyrimidin-2-yl)aminocarbonyl]-N3-ethyl-2,3-pyridinedisulfonamide;
N-[(4,6-dimethoxypyrimidin-2-yl)aminocarbonyl]-3-(methylsulfonyloxy)-2-pyridinesulfonamide; and
N2-[(4,6-dimethoxypyrimidin-2-yl)aminocarbonyl]-N3-methyl-2,3-pyridinedisulfonamide.

This invention also pertains to novel compounds of the following formulas

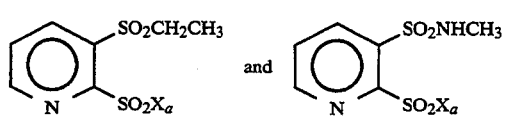

wherein $X_a$ is Cl, $NH_2$, $HNC(CH_3)_3$ and

which are useful as intermediates to herbicidal sulfonylureas.

Specifically preferred are:
3-ethylsulfonyl-2-pyridinesulfonamide and N3-methyl-2,3-pyridinedisulfonamide.

DETAILED DESCRIPTION OF THE INVENTION

Synthesis

Compounds of Formula I can be synthesized either by one or more of the methods described in U.S. Pat. No. 4,456,469, or by the reaction of sulfonamides II with the phenyl ester of the appropriate carbamic acid III in the presence of an equimolar quantity of a tertiary amine base such as 1,8-diazabicyclo[5.4.0]undec-7-ene (DBU) as shown in Equation 1.

Equation 1

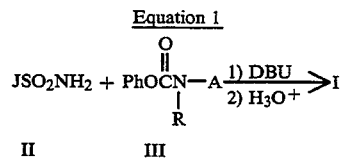

wherein
J, R, and A are as previously defined.

The reaction shown in Equation 1 is best carried out at 25° C. in a solvent such as dioxane or acetonitrile for 1–2 hours under an inert atmosphere as described in European Patent Application No. 70,804 (published Jan. 26, 1983). The desired products of Formula I can be conveniently isolated by acidifying the reaction solution with aqueous hydrochloric acid. Alternatively, the aqueous layer can be extracted with a solvent such as methylene chloride or ethyl acetate. Drying and evaporation of the solvent affords the desired products. The phenyl carbamates can be synthesized by treatment of the corresponding heterocyclic amines of Formula A-NHR with diphenyl carbonate or phenyl chloroformate in the presence of a base such as sodium hydride, pyridine, or potassium carbonate with a catalytic amount of 4-dimethylaminopyridine. The mixture is stirred at temperatures between 25° and 65° C. in a suitable solvent such as tetrahydrofuran for 12–36 hours.

The required sulfonamides of Formula II can be synthesized by either one of the methods shown below in Equations 2 and 3.

Equation 2 depicts the reaction of sulfonyl chlorides of Formula IV with ammonia to give sulfonamides of Formula II.

Equation 2

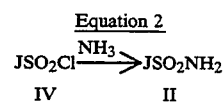

wherein
J is as previously defined.

The amination of Equation 2 is conveniently effected by adding at least two molar equivalents of either anhydrous ammonia or concentrated ammonium hydroxide to a solution of the sulfonyl chloride IV in a suitable solvent such as diethyl ether, tetrahydrofuran or methylene chloride at temperatures between −30° and 25° C. The desired sulfonamides of Formula II are isolated either by filtration, in which case the by-product ammonium chloride is removed by washing with water, or extraction into a suitable organic solvent such as methylene chloride or ethyl acetate. Drying and evaporation of the solvent then affords the products II which are usually sufficiently pure to be carried directly on to the next step.

Sulfonamides of Formula II can also be prepared as shown in Equation 3 by treatment of the corresponding N-t-butylsulfonamides VI with an appropriate acid such as trifluoroacetic (TFA), polyphosphoric (PPA), or p-toluenesulfonic acid (p-TSA).

Equation 3

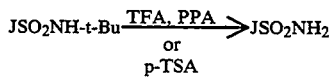

$$\begin{array}{cc} \text{VI} & \text{II} \end{array}$$

wherein
J is as previously defined.

The reaction of Equation 3 is conveniently carried out by stirring a solution of the compound of Formula VI in excess trifluoroacetic acid (approximately 0.3M) at about 25° C. for 1–72 hours. The desired sulfonamides of Formula II are then isolated by removal of the volatiles in vacuo and crystallization from a suitable solvent such as diethyl ether, 1-chlorobutane, or ethyl acetate. Alternatively, the N-t-butylsulfonamides of Formula VI can be treated with a catalytic amount of p-toluenesulfonic acid monohydrate in a solvent such as toluene or xylenes at reflux temperature for 1–6 hours. The desired products are then isolated in a manner analogous to the one described above. For use of polyphosphoric acid in the deprotection of N-t-butylsulfonamides, see J. G. Lombardino, *J. Org. Chem.*, 36, 1843 (1971); for use of trifluoroacetic acid, see J. D. Catt and W. L. Matier, *J. Org. Chem.*, 38, 1974 (1973).

Sulfonamides of Formula VI can be prepared by the reaction of sulfonyl chlorides of Formula IV with excess t-butyl amine as shown in Equation 4.

Equation 4

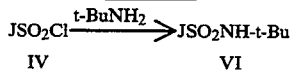

$$\begin{array}{cc} \text{IV} & \text{VI} \end{array}$$

wherein
J is as previously defined.

Sulfonyl chlorides of Formula IV can be prepared according to the procedures described in U.S. Pat. No. 4,456,469. Alternatively, the procedures of South African Patent Application 84/8844 may be utilized which describe the conversion of mercapto or arylmethylthio compounds to sulfonyl chlorides via treatment with hypochlorite solution.

Sulfonyl chlorides of Formula IVa may also be prepared via metallation of 2-fluoropyridine derivatives with lithium diisopropyl amide (LDA) according to the procedure of T. Gungot, F. Marsais and G. Queguiner, *J. Organomet. Chem.*, 1981, 215, 139–150, followed by treatment with sulfur dioxide and N-chlorosuccinimide (NCS) as shown in Equation 5.

Equation 5

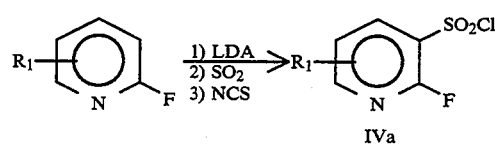

IVa wherein
$R_1$ is as previously defined.

Sulfonyl chlorides of Formula IVb can be prepared from compounds of Formula VII as shown in Equation 6 and described in U.S. Pat. No. 4,420,325.

Equation 6

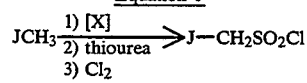

$$\begin{array}{cc} \text{VII} & \text{IVb} \end{array}$$

wherein
J is as previously defined; and
[X] is a suitable halogenating reagent which would be obvious to one skilled in the art.

The sulfides of Formula VIII can be prepared by the reaction of a halo pyridine compound of Formula IX with an appropriate mercaptan in the presence of a base as described in U.S. Pat. No. 4,456,469 and shown in Equation 7.

Equation 7

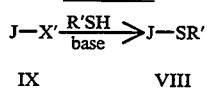

$$\begin{array}{cc} \text{IX} & \text{VIII} \end{array}$$

wherein
X′ is F, Cl, or Br; and
R′ is $C_1$–$C_4$ alkyl or benzyl.

The sulfides of Formula VIIIa can be prepared by metallation of the pyridine compound of Formula X with two equivalents of a strong base such as n-butyllithium or lithium diisopropylamide (LDA) as described by P. Breant, F. Marsais, and G. Queguiner, *Synthesis*, 1983, 822–824, followed by treatment with the appropriate disulfide as shown in Equation 8.

Equation 8

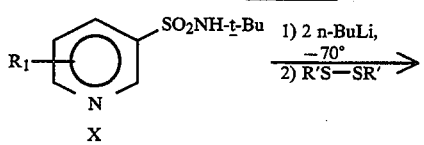

X

VIIIa wherein
R′ is $C_1$–$C_4$ alkyl, $C_3$–$C_5$ cycloalkyl or benzyl; and
$R_1$ is as previously defined.

In an analogous manner, sulfides of Formula VIIIb can be prepared as shown in Equation 9.

Equation 9

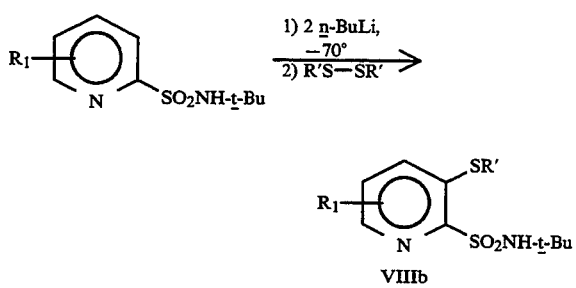

wherein

R' is $C_1$–$C_4$ alkyl, $C_3$–$C_5$ cycloalkyl, or benzyl; and
$R_1$ is as previously defined.

Sulfides of Formula VIIIc can be prepared by the metallation of a 2-fluoropyridine derivative as described previously and again followed by treatment with an appropriate disulfide as shown in Equation 10.

Equation 10

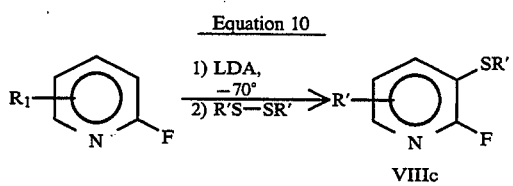

wherein

R' is $C_1$–$C_4$ alkyl, $C_3$–$C_5$ cycloalkyl, or benzyl; and
$R_1$ is as previously defined.

The sulfones and Sulfoxides of General Formula XI can be prepared from the corresponding sulfides of Formula VIIId by any one of the numerous oxidation reagents [O] known in the art such as hydrogen peroxide or peracids, as shown in Equation 11.

Equation 11

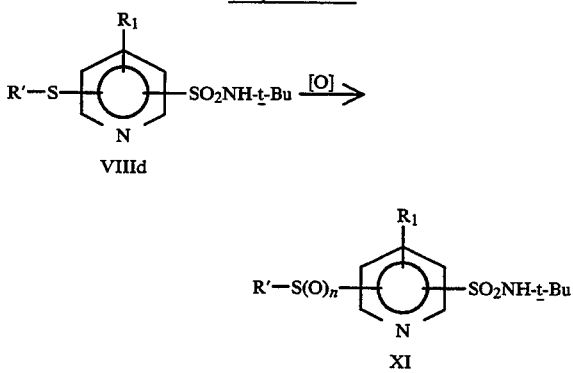

wherein $R_1$ is as previously defined;
R' is $C_1$–$C_4$ alkyl or $C_3$–$C_5$ cycloalkyl; and
n is 1 or 2.

The chloropyridine of Formula IXa can be prepared by diazotization of 3-amino-2-chloropyridine followed by displacement with cuprous cyanide as shown in Equation 12. The diazonium group can also be replaced by other groups such as $SO_2Cl$ and $N_3$ by those skilled in the art via methods known in the literature.

Equation 12

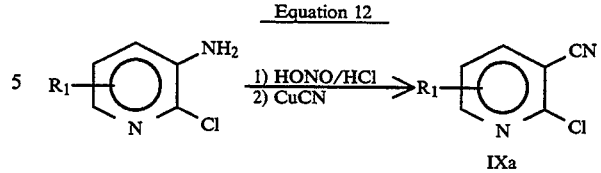

wherein $R_1$ is as previously defined.

The sulfides of General Formula VIIIf can be prepared as shown in Equation 13. Alkylation of a 3-hydroxy-2-mercaptopyridine derivative with alkyl halides utilizing a variety of bases such as potassium carbonate or potassium t-butoxide afforded the sulfides of Formula VIIIe which were then treated with the appropriate sulfonyl chlorides in the presence of an acid acceptor such as triethylamine to afford sulfides of Formula VIIIf.

Equation 13

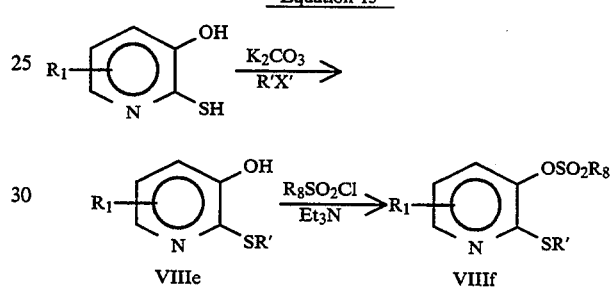

wherein

R' is $C_1$–$C_4$ alkyl or benzyl;
X' is Cl, Br, or I; and
$R_1$ and $R_8$ are as previously defined.

The esters of Formula VIIIg, VIIIh, and VIIIj can be prepared by either of the two methods shown in Equation 14. The first method involves metallation of a 2-fluoropyridine derivative as previously described in Equation 5, followed by treatment with ethyl or methyl chloroformate which afforded esters of Formula XIII. Mercaptide displacement as described in Equation 7 resulted in esters of Formula VIIIg. Acid catalyzed transesterification using the appropriate alcohol as the solvent afforded esters of Formula VIIIh.

The second method involves the alkylation of a 2-mercaptonicotinic acid derivative VIIIi with alkyl halides utilizing a variety of bases such as potassium carbonate or potassium t-butoxide, followed by conversion to the acid halides by any number of standard reagents such as thionyl chloride, phosphorous trichloride or pentachloride, or oxalyl chloride. The acid chlorides were then treated with the appropriate alcohols in the presence of an acid acceptor such as triethylamine, to afford esters of Formula VIIIh. Conversion of the sulfides VIIIh to the sulfonamides VIIIj was carried out as previously described.

Equation 14

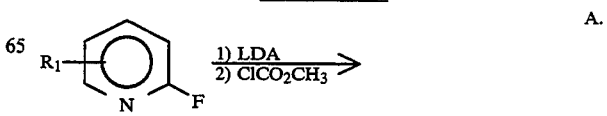

A.

-continued
Equation 14

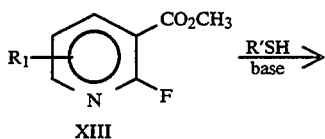
XIII

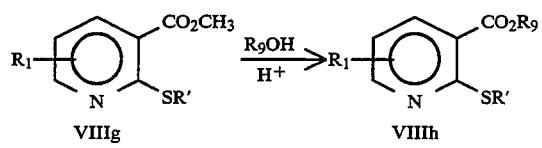
VIIIg      VIIIh

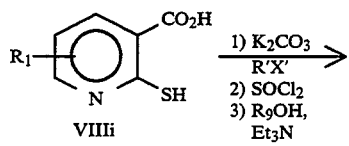
VIIIi

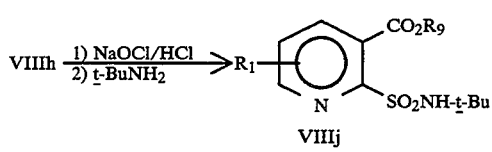
VIIIj wherein $R_9$ can also be $R'_9$; and $X'$, $R'$, $R_1$, $R_9$ and $R'_9$ are as previously defined.

The sulfonamides of General Formula XIIa can be prepared as shown in Equation 15. However, for the preparation of primary or unhindered secondary sulfonamides, a protective group is needed for a later stage in the synthetic sequence. A representative example is shown in Equation 16 where a t-butyl protective group is utilized for the synthesis of sulfonamide IIa.

Equation 15

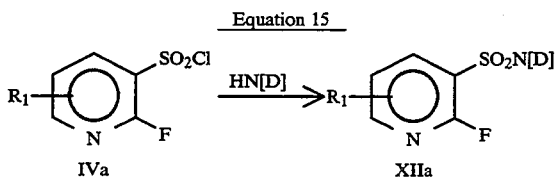
IVa      XIIa wherein

[D] is $R_dR_e$, $R_7R_8$, $R'_7R_8$, or $H_2$; and $R_1$, $R_d$, $R_e$, $R_7$, $R_8$ and $R'_7$ are as previously defined.

Equation 16

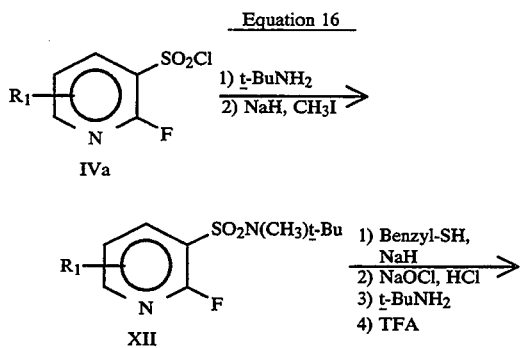
IVa

XII

-continued
Equation 16

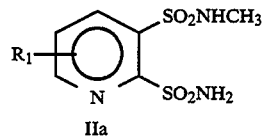
IIa wherein $R_1$ is as previously defined.

The difluoro compounds of Formula XIVa in Equation 17 can be prepared using the reactions previously described. Treatment with one equivalent of various $R_1$ nucleophiles (those that are available in the art) results in a mixture of products which can be separated. An example of the use of sodium methoxide as the reactive nucleophile is shown. Intermediates XIVb and XIVc can be separated and further derivatized as previously described.

Equation 17

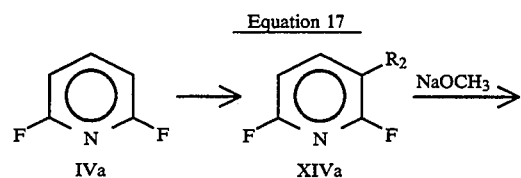
IVa      XIVa

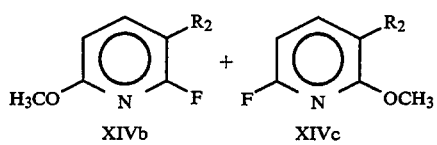
XIVb      XIVc wherein $R_2$ is as previously defined.

An alternative method to prepare esters of Formula XVd is shown in Equation 18. Mercaptide displacement of a 2,6-dihalopyridine can be achieved followed by conversion to the sulfonamide XVa as previously described. Treatment with two equivalents of a strong base such as n-butyllithium in a similar manner to that described by P. Breant, F. Marsails, and G. Queguiner, *Synthesis*, 1983, 822–824, followed by treatment with carbon dioxide affords the acids of Formula XVb. The acids can then be treated with various $R_1$ nucleophiles such as alkoxides, mercaptides or amines to afford the acids of Formula XVc (using sodium methoxide as an example) which can then be esterified with the appropriate alcohols utilizing standard 1,3-dicyclohexylcarbodiimide (DCC) coupling conditions to afford esters of Formula XVd.

Equation 18

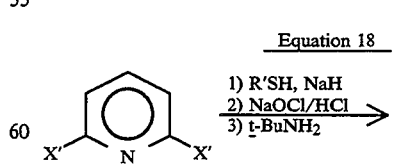

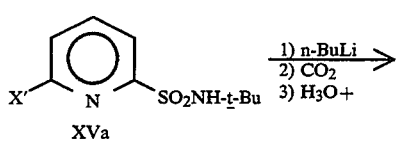
XVa

-continued
Equation 18

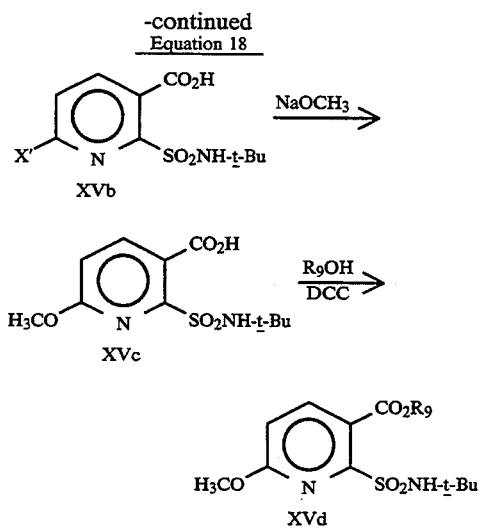

wherein
R$_9$ can also be R'$_9$;
X' is F or Cl; and
R', R$_9$ and R'$_9$ are as previously defined.

In an analogous manner, sulfonamides of General Formula XVIb can be prepared as shown in Equation 19. Treatment of XVa with strong base followed by an appropriate disulfide affords sulfides of Formula XVIa. Further elaboration utilizing chemistry previously described affords sulfonamides of Formula XVIb.

Equation 19

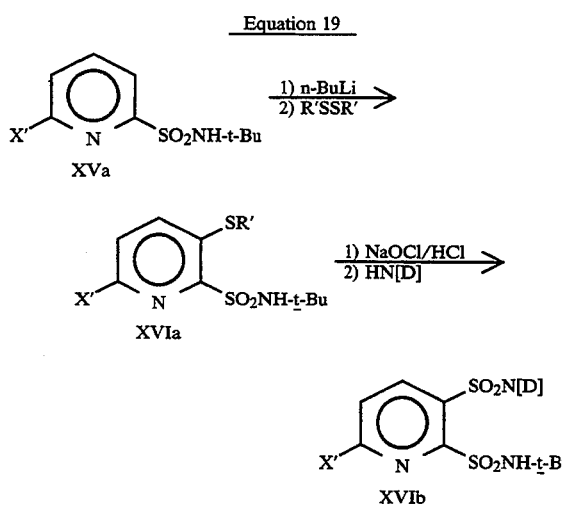

wherein
X' is F or Cl; and
R' and [D] are as previously defined.

A choice by one skilled in the art of the appropriate methods for preparing compounds of Formula I must take into account the nature of the substituents R$_1$ through R$_{11}$, and R$_d$ through R$_g$, and their chemical compatibility with the reaction conditions of Equations 1 through 19.

The heterocyclic amines of Formula A-NHR in Equation 1 above can be prepared by methods known in the literature, or simple modifications thereof, by those skilled in the art. For instance, EP-A No. 84,224 (published Jul. 27, 1983) and W. Braker et al., *J. Chem. Soc.*, 69, 3072 (1947) describes methods for preparing aminopyridines and triazines substituted by acetal groups such as dialkoxymethyl or 1,3-dioxolan-2-yl, among other groups. Also, for example, South African patent application Nos. 82/5045 and 82/5671 describe methods for preparing aminopyrimidines and triazines substituted by haloalkyl or haloalkylthio groups such as OCH$_2$CH$_2$F, OCH$_2$CF$_3$, SCF$_2$H, or OCF$_2$H, among other groups. South African patent application No. 83/7434 (published Oct. 5, 1983) describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2.3-d]pyrimidine-2-amines, the cyclopenta[d]pyrimidine-2-amines (A is A-2) and the 6,7-dihydro-5H-pyrano[2.3-d]pyrimidin-2-amines (A is A-3) can be prepared as described in EP-A No. 15,683. The furo[2.3-d]pyrimidin-2-amines (A is A-4) are described in EP-A No. 46,677.

Compounds of Formula A-NHR where A is A-5 are described in EP-A-73,562. Compounds where A is A-6 are described in EP-A-94,260.

In addition, general methods for preparing aminopyrimidines and triazines have been reviewed in the following publications:

The Chemistry of Heterocyclic Compounds", a series published by Interscience Publishers, Inc., New York and London;

"Pyrimidines", Vol. 16 of the same series by D. J. Brown;

"s-Triazines and Derivatives", Vol. 13 of the same series by E. M. Smolin and L. Rappoport; and F. C. Schaefer, U.S. Pat. No. 3,154,547 and K. R. Huffman and F. C. Schaefer, *J. Org. Chem.*, 28, 1812 (1963), which describes the synthesis of triazines.

Preparation in view of the above would be obvious to one skilled in the art. Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples.

Temperatures are reported in degrees Celsius; abbreviations for nuclear magnetic resonance (NMR) are: s=singlet, d=doublet, t=triplet, m=multiplat, and peak positions are reported as parts per million downfield from internal tetramethylsilane. Infrared (IR) peak positions are given in reciprocal centimeters (cm$^{-1}$).

EXAMPLE 1

Preparation of 2-Fluoro-3-(propylthio)pyridine

To a stirred solution of 59 ml (0.113 mol) of 1.9 molar lithium diisopropyl amide (in hexanes) in 150 mls dry tetrahydrofuran cooled to $-70°$ under nitrogen was added dropwise a solution of 10.0 g of 2-fluoropyridine (0.103 mol) in 30 mls dry tetrahydrofuran such that the temperature was maintained below $-65°$. The solution was stirred at $-70°$ for 4 hours and a solution 17 g of n-propyldisulfide (0.113 mol) in 45 mls dry tetrahydrofuran was added dropwise while maintaining the temperature below $-65°$. After stirring another hour at $-70°$ the solution was poured into water and extracted with ether. The combined organic phases were washed with brine, dried over magnesium sulfate, and evaporated to afford 14.5 g (82%) of a red oil: NMR (CDCl$_3$, 200 MHz), 1.0 (3H, m), 1.7 (2H, m), 2.9 (2H, m), 7.1 (1H, m), 7.7 (1H, m), 8.0 (1H, m); IR (neat) 1585, 1560, 1410, 1245 cm$^{-1}$.

EXAMPLE 2

Preparation of 2-(Phenylmethylthio)-3-(propylthio)pyridine

To a stirred suspension of 0.62 g (0.013 mol) of 50% sodium hydride (in mineral oil), which had been washed with hexanes, in 20 mls dry dimethylformamide cooled to $-5°$ under nitrogen was added dropwise 1.6 g (0.013 mol) benzyl mercaptan such that the temperature was maintained below 5°. The suspension was stirred at room temperature for 1 hour, cooled to 0°, and a solution of 2.0 g (0.012 mol) of the product from Example 1 was added dropwise while maintaining the temperature between 0° and 5°. After warming to room temperature, the solution was poured into water and extracted with ether. The combined organic layers were washed with water and with brine, dried over magnesium sulfate, and evaporated to an oil which was purified by flash chromatography to afford 0.9 g (27%) oil: NMR (CDCl$_3$, 200 MHz), 1.02 (3H, t, J=7 Hz), 1.6 (2H, m), 2.9 (2H, t, J=7 Hz), 4.45 (2H, s), 6.9–7.6 (7H, m), 8.3 (1H, m); IR (neat) 1560, 1370 cm$^{-1}$.

EXAMPLE 3

Preparation of N-(1,1-Dimethylethyl)-3-(propylsulfinyl)-2-pyridinesulfonamide To a vigorously stirred mixture of 0.5 g (0.0018 mol) of the product from Example 2 in 9 mls methylene chloride and 4 mls water cooled to 0° was added 0.7 mls (0.008 mol) concentrated hydrochloric acid followed by the dropwise addition of 8.9 mls (0.006 mol) of a 5% sodium hypochlorite solution such that the temperature was maintained between 0° and 5°. After the mixture was stirred for an additional 30 minutes at 0° the reaction was poured into water and extracted with methylene chloride. The combined organic layers were washed with brine, dried over magnesium sulfate, and filtered. The filtrate was stirred and cooled to $-70°$ under nitrogen and 0.53 g (0.0072 mol) of t-butyl amine was added dropwise and the mixture was allowed to warm to room temperature. The reaction was poured into water and extracted with methylene chloride. The organic layers were combined and washed with brine, dried over magnesium sulfate, and evaporated to a mixture which was purified by flash chromatography to afford 0.4 g (69%) white solid: m.p. 138°–140°; NMR (CDCl$_3$, 200 MHz) 1.09 (3H, m), 1.7 (1H, m), 2.0 (1H, m), 2.8 (1H, m), 3.3 (1H, m), 5.2 (NH), 7.7 (1H, m), 8.6 (1H, m), 8.8 (1H, m); IR (nujol) 3400, 1375, 1325, 1160, 1065, 1015 cm$^{-1}$.

EXAMPLE 4

Preparation of 3-(Propylsulfonyl)-2-pyridinesulfonamide

To a stirred solution of 8.8 g (0.029 mol) of the product from Example 3 in 400 mls methylene chloride cooled to $-5°$, under nitrogen, was added 6.6 g (0.038 mol) of 3-chloroperbenzoic acid and stirred at room temperature for 20 hours. The reaction mixture was poured into water and extracted with methylene chloride. The organic layers were combined and washed with saturated sodium bisulfite and brine, dried over magnesium sulfate, and evaporated to a solid mixture which was washed with hexanes to afford a white solid. The solid was dissolved and stirred in 150 mls trifluoroacetic acid for 72 hours. The solution was evaporated and triturated with ether to afford 5.3 g (46%) white solid: m.p. 153°–157°; NMR (CDCl$_3$, 200 MHz) 1.06 (3H, t, J=7 Hz), 1.8 (2H, m), 3.7 (2H, m) 5.8 (NH$_2$), 7.8 (1H, m), 8.6 (1H, m), 8.95 (1H, m); IR (nujol) 3390, 3180, 1360, 1310, 1175, 1150 cm$^{-1}$.

EXAMPLE 5

Preparation of N-[(4,6-Dimethoxypyrimidin-2-yl)aminocarbonyl]-3-(propylsulfonyl)-2-pyridinesulfonamide To a stirred suspension of 0.4 g (0.0015 mol) of the product from Example 4 and 0.63 g (0.0023 mol) of phenyl (4,6-dimethoxypyrimidin-2-yl)carbamate in 4 mls acetonitrile was added 0.35 g (0.0023 mol) of 1,8-diazabicyclo[5.4.0]undec-7-ene and stirred for 30 minutes. The solution was diluted with water and acidified with 1 normal hydrochloric acid. The resulting precipitate was collected and washed with water and ether to afford 0.45 g (67%) white solid: m.p. 168°–170°; NMR (CDCl$_3$, 200 MHz), 1.07 (3H, t, J=7 Hz), 1.85 (2H, m), 3.7 (2H, m), 3.97 (6H, s), 5.8 (1H, s), 7.26 (NH), 7.8 (1H, m), 8.6 (1H, m), 8.9 (1H, m), 12.9 (NH); IR (nujol) 3320, 1740, 1610, 1580, 1375, 1195, 1170 cm$^{-1}$.

EXAMPLE 6

Preparation of 3-ethylthio-2-fluoropyridine

Using the procedure of Example 1, 40.0 g of 2-fluoropyridine (0.412 mol) was converted to 46.5 g (72%) of the title compound as an oil: NMR(CDCl$_3$, 200 MHz) 1.3 (3H, t, J=7 Hz), 2.95 (2H, q, J=7 Hz), 7.1 (1H, m), 7.7 (1H, m), 8.0 (1H, m); IR (neat) 1585, 1565, 1410, 1230 cm$^{-1}$.

EXAMPLE 7

Preparation of 3-ethylthio-2-(phenylmethylthio)pyridine

Using the procedure of Example 2, 25.0 g (0.160 mol) of the product from Example 6 was converted to 44.8 g (100%) of the title compound as a yellow liquid: NMR (CDCl$_3$, 200 MHz) 1.28 (3H, t, J=7 Hz), 2.9 (2H, q, J=7 Hz), 4.45 (2H, s), 7.0–7.6 (7H, m), 8.35 (1H, m); IR (neat) 1610, 1405 cm$^{-1}$.

EXAMPLE 8

Preparation of
N-(1,1-Dimethylethyl)-3-ethylsulfinyl-2-pyridinesulfonamide

Using the procedure of Example 3, 35.0 g (0.134 mol) of the product from Example 7 was converted to 21.2 g (56%) of the title compound: m.p. 129°–131°; NMR (CDCl$_3$, 200 MHz) 1.23 (9H, s), 1.28 (3H, t, J=7 Hz), 2.9 (1H, m), 3.3 (1H, m), 5.2 (NH), 7.7 (1H, m), 8.55 (1H, m), 8.75 (1H, m); IR (nujol) 3100, 1320, 1155 cm$^{-1}$.

EXAMPLE 9

Preparation of
N-(1,1-Dimethylethyl)-3-ethylsulfonyl-2-pyridinesulfonamide

Using the first half of the procedure of Example 4 (i.e., the 3-chloroperbenzoic acid reaction), 9.0 g (0.033 mol) of the product from Example 9 was converted to 10.1 g (100%) of the title compound: m.p. 58°–63°; NMR (CDCl$_3$, 200 MHz) 1.2 (3H, t, J=7 Hz), 1.2 (9H, s), 3.7 (2H, q, J=7 Hz), 6.1 (NH), 7.7 (1H, m), 8.55 (1H, m), 8.95 (1H, m); IR (nujol) 3300, 1560, 1350, 1300, 1170, 1140 cm$^{-1}$.

EXAMPLE 10

Preparation of 3-ethylsulfonyl-2-pyridinesulfonamide

Using the second half of the procedure of Example 4 (i.e., the trifluoroacetic acid reaction), 9.0 g (0.029 mol) of t-he product from Example 9 was converted to 4.2 g (58%) of the title compound: m.p. 211°–212.5°; NMR (DMSO-d$_6$, 200 MHz) 1.15 (3H, t, J=7 Hz), 3.4 (NH$_2$), 3.7 (2H, q, J=7 Hz), 7.9 (1H, m), 8.5 (1H, m), 8.95 (1H, m); IR (nujol) 3370, 3190, 1350, 1310, 1180 cm$^{-1}$.

EXAMPLE 11

Preparation of
N-[(4,6-dimethoxypyrimidin-2-yl)aminocarbonyl]-3-ethylsulfonyl-2-pyridinesulfonamide Using the procedure of Example 5, 0.60 g (0.0024 mol) of the product from Example 10 was converted to 0.70 g (70%) of the title compound: m.p. 160°–162°; NMR (CDCl$_3$, 200 MHz) 1.35 (3H, t, J=7 Hz), 3.7 (2H, q, J=7 Hz), 3.97 (6H, s), 5.8 (1H, s), 7.3 (NH), 7.75 (1H, m), 8.6 (1H, m), 8.9 (1H, m), 12.95 (NH); IR (nujol) 3260, 1740, 1610, 1360, 1195, 1175 cm$^{-1}$.

EXAMPLE 12

Preparation of 2,6-Difluoro-3-pyridinecarboxylic acid, methyl ester

To a stirred solution of 91 ml (0.182 mol) of 2.0 molar lithium diisopropylamide (in hexanes) in 200 mL dry tetrahydrofuran cooled to −70° under nitrogen was added dropwise a solution of 20.0 g of 2,6-difluoropyridine (0.174 mol) in 75 mL dry tetrahydrofuran such that the temperature was maintained below −60°. The solution was stirred at −70° for 3 hours and was then added via a cannula to a solution 21.7 g (0.230 mol) of methyl chloroformate in 100 mL dry tetrahydrofuran cooled to −70° under nitrogen. After stirring another hour at −70°, the mixture was poured into water and extracted with ether. The combined organic layers were washed with brine, dried over magnesium sulfate, and evaporated to a semisolid which was purified by flash chromatography to afford 13.0 g (43%) orange oil: NMR (CDCl$_3$, 200 MHz) 3.95 (3H, s), 6.9 (1H, m), 8.5 (1H, m); IR (neat) 1745, 1730, 1610, 1415, 1290 cm$^{-1}$.

EXAMPLE 13

Preparation of
2-Fluoro-6-Methoxy-3-Pyridinecarboxylic Acid, Methyl Ester

To a stirred solution of 15.0 g (0.0867 mol) of the product from Example 12 in 240 mL dry tetrahydrofuran cooled to −78° was added dropwise 22.7 mL (0.0993 mol) of 25% sodium methoxide in methanol solution over 45 minutes. After warming to −20°, the mixture was poured into ice water, acidified with 1 normal hydrochloric acid and extracted with ether. The combined organic layers were washed with brine, dried over magnesium sulfate, and evaporated to a semisolid which was purified by flash chromatography to afford 3.2 g (17%) light yellow solid: m.p. 81°–82°; NMR (CDCl$_3$, 200 MHz) 3.9 (3H, s), 3.98 (3H, s), 6.67 (1H, d, J=9 Hz), 8.25 (1H, m); IR (nujol) 1715, 1615, 1290 cm$^{-1}$.

EXAMPLE 14

Preparation of
6-Methoxy-2-(Phenylmethylthio)-3-Pyridinecarboxylic Acid, Methyl Ester To a stirred mixture of 0.8 g (0.0161 mol) of 50% sodium hydride (in mineral oil), which had been washed with hexanes, in 20 mL dry dimethylformamide cooled to −5° under nitrogen was added dropwise 1.9 mL (0.0161 mol) benzyl mercaptan. The suspension was stirred at room temperature for 1 hour, cooled to 0°, and a solution of 3.2 g (0.0147 mol) of the product of Example 13 in 20 mL dry dimethylformamide was added dropwise. After warming to room temperature, the solution was poured into water and extracted with ether. The combined organic layers were washed with water and with brine, dried over magnesium sulfate, and evaporated to an oil which was purified by flash chromatography to afford 3.0 g (64%) of a yellow solid: m.p. 67°–71°; NMR (CDCl$_3$, 200 MHz) 3.88 (3H, s), 3.96 (3H, s), 4.46 (2H, s), 6.44 (1H, d, J=9Hz ), 7.2–7.5 ( 5H, m), 8.1 ( 1H, d, J=9Hz ); IR (nujol) 1700, 1580, 1305, 1255 cm$^{-1}$.

EXAMPLE 15

Preparation of
2-[1,1-Dimethylethyl)Aminosulfonyl]-6-Methoxy-3-Pyridinecarboxylic Acid, Methyl Ester To a vigorously stirred mixture of 3.7 g (0.0129 mol) of the product from Example 14 in 79 mL methylene chloride and 41 mL water cooled to 0° was added 6.3 mL (0.0759 mol) concentrated-hydrochloric acid followed by the dropwise addition of 79 mL (0.053 mol) of a 5% sodium hypochlorite solution such that the temperature was maintained below 5°. After the mixture was stirred for an additional 30 minutes at 0° the reaction was poured into water and extracted with methylene chloride. The combined organic layers were washed with brine, dried over magnesium sulfate, and filtered. The filtrate was stirred and cooled to −70° under nitrogen, and 4.7 (0.0645 mol) of t-butyl amine was added dropwise. The reaction mixture was allowed to warm to −20°, poured into water, acidified with 1 normal hydrochloric acid, and extracted with methylene chloride. The combined organic layers were washed with brine, dried over magnesium sulfate, and evaporated to a semisolid which was purified by flash chromatography to afford 3.0 g (77%) yellow solid: m.p. 128°-130°; NMR (CDCl$_3$, 200 MHz) 1.27 (9H, s), 3.94 (3H, s), 4.05 (3H, s) 5.75 (NH), 6.9 (1H, d, J=9 Hz), 7.95 (1H, d, J=9 HZ); IR (nujol) 3260, 1740, 1605, 1325, 1125 cm$^{-1}$.

EXAMPLE 16

Preparation of 2-(Aminosulfonyl)-6-Methoxy-3-Pyridine-Carboxylic Acid, Methyl Ester A solution of 2.9 g (0.0096 mol) of the product from Example 15 was stirred in 50 mL trifluoroacetic acid at room temperature for 20 hours. The solution was evaporated to afford 2.4 g (100%) white solid: m.p. 142.5°-144.5°; NMR (CDCl, 200 MHz) 3.97 (3H, s), 4.1 (3H, s), 5.6 (NH$_2$), 6.9 (1H, d, J=9Hz), 8.1 (1H, d, J=9Hz); IR (nujol) 3305, 3205, 1715, 1590, 1355, 1320, 1175 cm$^{-1}$.

EXAMPLE 17

Preparation of 2-[[(4,6-Dimethoxypyrimidin-2-yl)aminocarbonyl]aminosulfonyl]-6-Methoxy-3-Pyridinecarboxylic Acid, Methyl Ester To a stirred suspension of 0.4 g (0.0016 mol) of the product from Example 16 and 0.54 g (0.002 mol) of phenyl(4,6-dimethoxypyrimidin-2-yl) carbamate in 4 mL acetonitrile was added dropwise 0.30 g (0.002 mol) of 1,8-diazobicyclo[5.4.0]undec-7-ene and stirred for 30 minutes. The solution was diluted with water and acidified with 1 normal hydrochloric acid. The resulting precipitate was collected and washed with water and with ether to afford 0.57 g (84%) white solid: m.p. 194°-196°; NMR (CDCl$_3$, 200 MHz), 3.83 (3H, s), 3.95 (9H, s), 5.8 (1H, s), 6.95 (1H, d, J=9 Hz), 7.4 (NH), 8.1 (1H, d, J=9 Hz), 12.8 (NH); IR (nujol) 3140, 1740, 1720, 1640, 1360, 1195, 1140 cm$^{-1}$.

EXAMPLE 18

Preparation of N-(1,1-Dimethylethyl)-2-Fluoro-3-Pyridinesulfonamide

To a stirred solution of 396 mL (0.740 mol) of 1.9 molar lithium diisopropylamide (in hexanes) in 1.5 L dry tetrahydrofuran cooled to −70° under nitrogen was added dropwise a solution of 65 g (0.670 mol) of 2-fluoropyridine in 150 mL dry tetrahydrofuran such that the temperature was maintained below −65°. The suspension was stirred at −70° for another 3.5 hours and 86 g (1.34 mol) of sulfur dioxide was added while maintaining the temperature below −65°. After stirring another 15 minutes at −70°, the reaction was allowed to warm to 0° and evaporated to half the original volume and diluted with ether. The white precipitate was collected under nitrogen, washed with ether, and dried. The solid was dissolved in 800 mL acetic acid and cooled to 10°-20°. To this stirred solution was added portionwise 99.4 g (0.740 mol) of N-chlorosuccinimide while maintaining the temperature below 20°. After stirring another 30 minutes, the suspension was evaporated, diluted with water and extracted with methylene chloride. The combined organic phases were washed with saturated aqueous sodium bicarbonate solution until no more gas evolution, washed with brine, dried over magnesium sulfate, and filtered. The filtrate was cooled to −70° under nitrogen and to this stirred solution was added dropwise 199 g (2.7 mol) of t-butylamine. The suspension was poured into ice water, acidified with concentrated hydrochloric acid, and extracted with methylene chloride. The combined organic layers were washed with brine, dried over magnesium sulfate, and evaporated to an oil which was purified by flash chromatography to afford 29.1 g (19%) of a brown solid which was further washed with cold n-butylchloride to afford 22.4 g (14.5%) of a white solid: m.p. 95°-97°; NMR (CDCl$_3$, 200 MHz) 1.25 (9H, s), 4.9 (NH), 7.35 (1H, m), 8.3-8.5 (2H, m).

EXAMPLE 19

Preparation of N-(1,1-Dimethylethyl)-2-Fluoro-N-Methyl-3-Pyridinesulfonamide To a stirred suspension of 3.4 g (0.071 mol) of 50% sodium hydride (in mineral oil), which had been washed with hexanes, in 120 mL dry dimethyldormamide cooled to 0° under nitrogen was added dropwise a solution of 15.0 g (0.065 mol) of the product from Example 18 in 120 mL dry dimethylformamide. After stirring at room temperature for 1 hour, the mixture was cooled to 0° and 12.2 g (0.086 mol) of methyl iodide was added dropwise. After warming to room temperature the reaction was poured into ice water and extracted with ether. The combined organic layers were washed with brine, dried over magnesium sulfate, and evaporated to 15.9 g (99%) oil; NMR (CDCl$_3$, 200 MHz), 1.32 (9H, s), 3.1 (3H, s), 7.3 (1H, m), 8.3-8.4 (2H, m); IR (neat) 1590, 1570, 1335, 1155 cm$^{-1}$.

EXAMPLE 20

Preparation of N-(1,1-Dimethylethyl)-N-Methyl-2-(Phenylmethylthio)-3-Pyridinesulfonamide Using the same procedure as in Example 14, 15.9 g (0.065 mol) of the product from Example 19 was converted to 19.5 g (86%) yellow solid: m.p. 92°-94°; NMR (CDCl$_3$), 200 MHz) 1.26 (9H, s), 3.1 (3H, s), 4.5 (2H, s), 7.0-7.5 (6H, m), 8.2 (1H, m); IR (nujol) 1570, 1385, 1315, 1150, 1120 cm$^{-1}$.

EXAMPLE 21

Preparation of N2, N3=Bis(1,1-Dimethylethyl)-N3-Methyl-2,3-Pyridinedisulfonamide Using the same procedure as in Example 15, 19.5 g (0.056 mol) of the product from Example 20 was converted to a tan solid which was washed with n-butylchloride to afford 13.1 g (66%) white solid: m.p. 155°-156.5°; NMR (CDCl$_3$, 200 MHz) 1.23 (9H, s), 1.33 (9H, s), 3.1 (3H, s), 6.0 (NH), 1H, m), 8.5 (1H, m), 8.8 (1H, m); IR (nujol) 3320, 1340, 1325, 1160, 1120 cm$^{-1}$.

EXAMPLE 22

Preparation of N3-Methyl-2,3-Pyridinedisulfonamide

A stirred solution of 13.1 g (0.036 mol) of the product from Example 21 in 150 mL trifluoroacetic acid was refluxed for 5 hours. After cooling to room temperature, the solution was evaporated to a solid which was washed with ether to afford 9.6 g (100%) white solid: m.p. 220°-223°; NMR (DMSO-d$_6$, 200 MHz), 2.5 (3H, d), 6.9 (NH), 7.65 (NH$_2$), 7.85 (1H, m), 8.45 (1H, m), 8.9 (1H, m); IR (nujol) 3380, 3320, 3180, 1355, 1170 cm$^{-1}$.

EXAMPLE 23

Preparation of N2-[(4,6-Dimethoxypyrimidin-2-yl)aminocarbonyl]-N3-Methyl-2,3-Pyridinedisulfonamide To a stirred suspension of 4.15 g (0.0165 mol) of the product from Example 22 and 5.0 g (0.018 mol) of phenyl (4,6-dimethoxypyrimidin-2-yl)carbamate in 50 mL acetonitrile was added dropwise 2.8 g (0.018 mol) of 1,8-diazabicyclo[5.4.0]undec-4-ene and stirred for 30 minutes. The solution was diluted with water and acidified with 1 normal hydrochloric acid. The resulting precipitate was collected and washed with water and with ether to afford 6.4 g (82%) white solid: m.p. 147°–148.5°; NMR (CDCl$_3$, 200 MHz) 2.7 (3H, d, J=7 Hz), 3.97 (6H, s), 5.8 (1H, s), 6.15 (1H, m), 7.3 (NH), 7.7 (1H, m), 8.55 (1H, m), 8.8 (1H, m), 13.1 (NH); IR (nujol) 3310, 1740, 1610, 1340, 1190, 1165 cm$^{-1}$.

By applying the procedures of Examples 1 through 23 and Equations 1 through 19, the compounds in Tables I through X can be prepared by one skilled in the art.

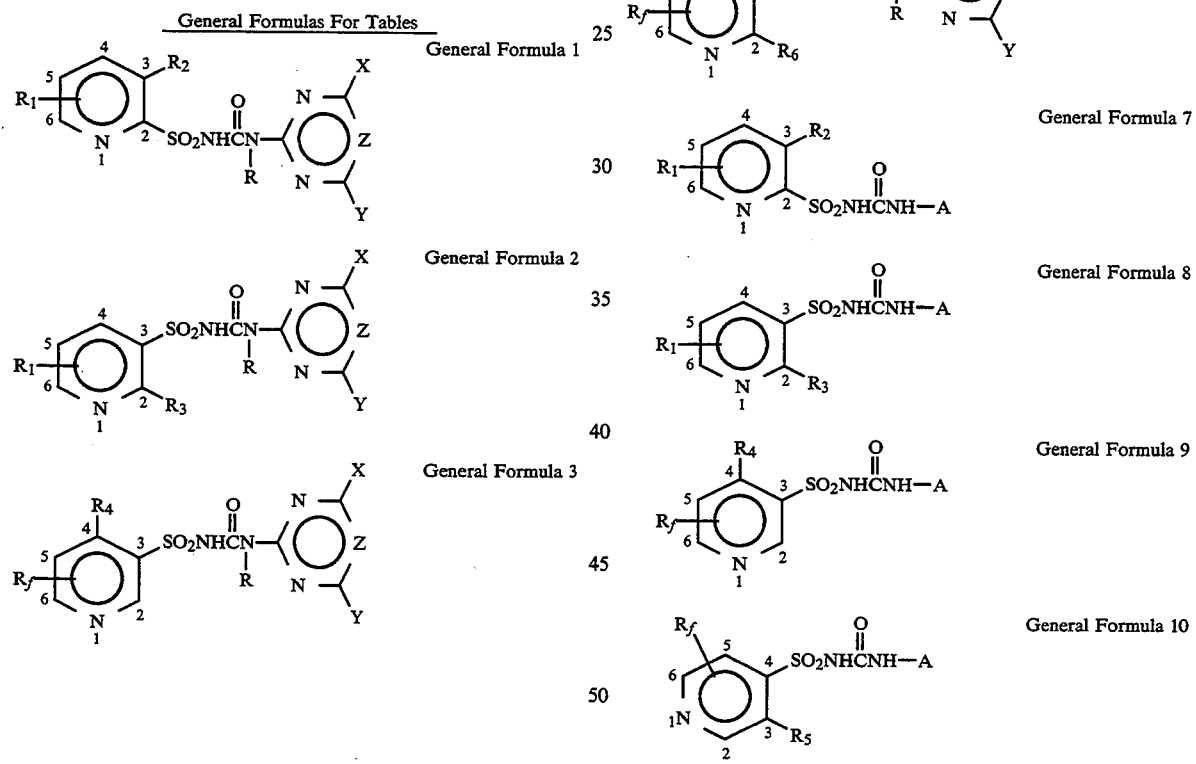

TABLE I

| | | General Formula 1 | | | | |
|---|---|---|---|---|---|---|
| R$_1$ | R$_2$ | R | X | Y | Z | m.p.(°C.) |
| H | SOCH$_3$ | H | OCH$_3$ | OCH$_3$ | CH | 170–174 |
| H | SOCH$_3$ | H | OCH$_3$ | CH$_3$ | CH | 138–140 |
| H | SOCH$_3$ | H | Cl | OCH$_3$ | CH | 124–126 |
| H | SOCH$_3$ | H | CH$_3$ | CH$_3$ | CH | 126–127.5 |
| H | SOCH$_3$ | H | OCH$_3$ | OCH$_3$ | N | |
| H | SOCH$_3$ | H | OCH$_3$ | CH$_3$ | N | 165–167 |
| H | SOCH$_3$ | H | OCH$_2$CH$_3$ | NHCH$_3$ | N | |
| H | SOCH$_3$ | CH$_3$ | OCH$_3$ | CH$_3$ | N | 133–137 |
| 4-CH$_3$ | SOCH$_3$ | H | OCH$_3$ | OCH$_3$ | CH | |
| 4-OCH$_3$ | SOCH$_3$ | H | OCH$_3$ | OCH$_3$ | CH | |
| 6-CH$_3$ | SOCH$_3$ | H | OCH$_3$ | OCH$_3$ | CH | |
| 6-OCH$_3$ | SOCH$_3$ | H | OCH$_3$ | OCH$_3$ | CH | |
| 6-F | SOCH$_3$ | H | OCH$_3$ | OCH$_3$ | CH | |

TABLE I-continued

General Formula 1

| R₁ | R₂ | R | X | Y | Z | m.p.(°C.) |
|---|---|---|---|---|---|---|
| 6-Cl | SOCH₃ | H | OCH₃ | OCH₃ | CH | |
| H | SO₂CH₃ | H | OCH₃ | OCH₃ | CH | 170-172 |
| H | SO₂CH₃ | H | Cl | OCH₃ | CH | 158-160 |
| H | SO₂CH₃ | H | CH₃ | CH₃ | CH | 162-164 |
| H | SO₂CH₃ | H | OCH₃ | OCH₃ | N | 180-184 |
| H | SO₂CH₃ | H | OCH₃ | CH₃ | N | 154-156.5 |
| H | SO₂CH₃ | H | OCH₂CH₃ | NHCH₃ | N | |
| H | SO₂CH₃ | CH₃ | OCH₃ | CH₃ | N | |
| 4-CH₃ | SO₂CH₃ | H | OCH₃ | OCH₃ | CH | |
| 4-OCH₃ | SO₂CH₃ | H | OCH₃ | OCH₃ | CH | |
| 6-CH₃ | SO₂CH₃ | H | OCH₃ | OCH₃ | CH | |
| 6-OCH₃ | SO₂CH₃ | H | OCH₃ | OCH₃ | CH | |
| 6-F | SO₂CH₃ | H | OCH₃ | OCH₃ | CH | |
| 6-Cl | SO₂CH₃ | H | OCH₃ | OCH₃ | CH | |
| H | SOCH₂CH₃ | H | OCH₃ | OCH₃ | CH | 132-136 |
| H | SOCH₂CH₃ | H | OCH₃ | CH₃ | CH | 141-144 |
| H | SOCH₂CH₃ | H | Cl | OCH₃ | CH | 105-107.5 |
| H | SOCH₂CH₃ | H | CH₃ | CH₃ | CH | 153-156.5 |
| H | SOCH₂CH₃ | H | OCH₃ | OCH₃ | N | 154-158 |
| H | SOCH₂CH₃ | H | OCH₃ | CH₃ | N | 172-174 |
| H | SOCH₂CH₃ | H | OCH₂CH₃ | NHCH₃ | N | |
| H | SOCH₂CH₃ | CH₃ | OCH₃ | CH₃ | N | |
| 4-CH₃ | SOCH₂CH₃ | H | OCH₃ | OCH₃ | CH | |
| 4-OCH₃ | SOCH₂CH₃ | H | OCH₃ | OCH₃ | CH | |
| 6-CH₃ | SOCH₂CH₃ | H | OCH₃ | OCH₃ | CH | |
| 6-OCH₃ | SOCH₂CH₃ | H | OCH₃ | OCH₃ | CH | |
| 6-F | SOCH₂CH₃ | H | OCH₃ | OCH₃ | CH | |
| 6-Cl | SOCH₂CH₃ | H | OCH₃ | OCH₃ | CH | |
| H | SO₂CH₂CH₃ | H | OCH₃ | OCH₃ | CH | 160-162 |
| H | SO₂CH₂CH₃ | H | OCH₃ | CH₃ | CH | 160-162 |
| H | SO₂CH₂CH₃ | H | Cl | OCH₃ | CH | 163-164.5 |
| H | SO₂CH₂CH₃ | H | CH₃ | CH₃ | CH | 167-169 |
| H | SO₂CH₂CH₃ | H | OCH₃ | OCH₃ | N | 155-158 |
| H | SO₂CH₂CH₃ | H | OCH₃ | CH₃ | N | 165.5-168 |
| H | SO₂CH₂CH₃ | H | OCH₂CH₃ | NHCH₃ | N | |
| H | SO₂CH₂CH₃ | CH₃ | OCH₃ | CH₃ | N | 137-138 |
| 4-CH₃ | SO₂CH₂CH₃ | H | OCH₃ | OCH₃ | CH | |
| 4-OCH₃ | SO₂CH₂CH₃ | H | OCH₃ | OCH₃ | CH | |
| 6-CH₃ | SO₂CH₂CH₃ | H | OCH₃ | OCH₃ | CH | 178-180 |
| 6-CH₃ | SO₂CH₂CH₃ | H | OCH₃ | CH₃ | CH | 169.5-172 |
| 6-CH₃ | SO₂CH₂CH₃ | H | CH₃ | CH₃ | CH | 172-173.5 |
| 6-CH₃ | SO₂CH₂CH₃ | CH₃ | OCH₃ | CH₃ | N | 133-135 |
| 6-OCH₃ | SO₂CH₂CH₃ | H | OCH₃ | OCH₃ | CH | 210-213 |
| 6-F | SO₂CH₂CH₃ | H | OCH₃ | OCH₃ | CH | 157-160 |
| 6-F | SO₂CH₂CH₃ | H | CH₃ | CH₃ | CH | 176-177 |
| 6-Cl | SO₂CH₂CH₃ | H | OCH₃ | OCH₃ | CH | 187-189 |
| 6-Cl | SO₂CH₂CH₃ | H | Cl | OCH₃ | CH | 171-174 |
| 6-Cl | SO₂CH₂CH₃ | H | CH₃ | CH₃ | CH | 181-182 |
| 6-SCH₃ | SO₂CH₂CH₃ | H | OCH₃ | OCH₃ | CH | |
| 6-SCH₃ | SO₂CH₂CH₃ | H | Cl | OCH₃ | CH | |
| 5-CH₃ | SO₂CH₂CH₃ | H | OCH₃ | OCH₃ | CH | 159-160 |
| 5-CH₃ | SO₂CH₂CH₃ | H | Cl | OCH₃ | CH | 176-177 |
| 5-CH₃ | SO₂CH₂CH₃ | H | OCH₃ | OCH₃ | N | 155-156 |
| 5-CH₃ | SO₂CH₂CH₃ | H | OCH₃ | CH₃ | N | 159-161 |
| H | SOCH₂CH₂CH₃ | H | OCH₃ | OCH₃ | CH | 111-115 |
| H | SOCH₂CH₂CH₃ | H | OCH₃ | CH₃ | CH | 141-145 |
| H | SOCH₂CH₂CH₃ | H | Cl | OCH₃ | CH | 111-113 |
| H | SOCH₂CH₂CH₃ | H | CH₃ | CH₃ | CH | 173-175 |
| H | SOCH₂CH₂CH₃ | H | OCH₃ | OCH₃ | N | 186-189 |
| H | SOCH₂CH₂CH₃ | H | OCH₃ | CH₃ | N | 164-166 |
| H | SOCH₂CH₂CH₃ | H | OCH₂CH₃ | NHCH₃ | N | 121-123 |
| H | SOCH₂CH₂CH₃ | CH₃ | OCH₃ | CH₃ | N | |
| 4-CH₃ | SOCH₂CH₂CH₃ | H | OCH₃ | OCH₃ | CH | |
| 4-OCH₃ | SOCH₂CH₂CH₃ | H | OCH₃ | OCH₃ | CH | |
| 6-CH₃ | SOCH₂CH₂CH₃ | H | OCH₃ | OCH₃ | CH | |
| 6-OCH₃ | SOCH₂CH₂CH₃ | H | OCH₃ | OCH₃ | CH | |
| 6-F | SOCH₂CH₂CH₃ | H | OCH₃ | OCH₃ | CH | |
| 6-Cl | SOCH₂CH₂CH₃ | H | OCH₃ | OCH₃ | CH | |
| H | SO₂CH₂CH₂CH₃ | H | OCH₃ | OCH₃ | CH | 168-170 |
| H | SO₂CH₂CH₂CH₃ | H | OCH₃ | CH₃ | CH | 157-159 |
| H | SO₂CH₂CH₂CH₃ | H | Cl | OCH₃ | CH | 165-167 |
| H | SO₂CH₂CH₂CH₃ | H | CH₃ | CH₃ | CH | 158-160 |
| H | SO₂CH₂CH₂CH₃ | H | OCH₃ | OCH₃ | N | 164-166 |
| H | SO₂CH₂CH₂CH₃ | H | OCH₃ | CH₃ | N | 165-168 |
| H | SO₂CH₂CH₂CH₃ | H | OCH₂CH₃ | NHCH₃ | N | 148-152 |
| H | SO₂CH₂CH₂CH₃ | CH₃ | OCH₃ | CH₃ | N | |
| 4-CH₃ | SO₂CH₂CH₂CH₃ | H | OCH₃ | OCH₃ | CH | |
| 4-OCH₃ | SO₂CH₂CH₂CH₃ | H | OCH₃ | OCH₃ | CH | |
| 6-CH₃ | SO₂CH₂CH₂CH₃ | H | OCH₃ | OCH₃ | CH | |

TABLE I-continued

General Formula 1

| R₁ | R₂ | R | X | Y | Z | m.p.(°C.) |
|---|---|---|---|---|---|---|
| 6-OCH₃ | SO₂CH₂CH₂CH₃ | H | OCH₃ | OCH₃ | CH | |
| 6-F | SO₂CH₂CH₂CH₃ | H | OCH₃ | OCH₃ | CH | |
| 6-Cl | SO₂CH₂CH₂CH₃ | H | OCH₃ | OCH₃ | CH | |
| H | SOCH(CH₃)₂ | H | OCH₃ | OCH₃ | CH | 144–147 |
| H | SOCH(CH₃)₂ | H | OCH₃ | CH₃ | CH | 143–145.5 |
| H | SOCH(CH₃)₂ | H | Cl | OCH₃ | CH | 133–135 |
| H | SOCH(CH₃)₂ | H | CH₃ | CH₃ | CH | 150–153 |
| H | SOCH(CH₃)₂ | H | OCH₃ | OCH₃ | N | 155–159 |
| H | SOCH(CH₃)₂ | H | OCH₃ | CH₃ | N | 150–153 |
| H | SOCH(CH₃)₂ | H | OCH₂CH₃ | NHCH₃ | N | |
| H | SOCH(CH₃)₂ | CH₃ | OCH₃ | CH₃ | N | |
| 4-CH₃ | SOCH(CH₃)₂ | H | OCH₃ | OCH₃ | CH | |
| 4-OCH₃ | SOCH(CH₃)₂ | H | OCH₃ | OCH₃ | CH | |
| 6-CH₃ | SOCH(CH₃)₂ | H | OCH₃ | OCH₃ | CH | |
| 6-OCH₃ | SOCH(CH₃)₂ | H | OCH₃ | OCH₃ | CH | |
| 6-F | SOCH(CH₃)₂ | H | OCH₃ | OCH₃ | CH | |
| 6-Cl | SOCH(CH₃)₂ | H | OCH₃ | OCH₃ | CH | |
| H | SO₂CH(CH₃)₂ | H | OCH₃ | OCH₃ | CH | 140–146 |
| H | SO₂CH(CH₃)₂ | H | OCH₃ | CH₃ | CH | 159–160.5 |
| H | SO₂CH(CH₃)₂ | H | Cl | OCH₃ | CH | 164–165.5 |
| H | SO₂CH(CH₃)₂ | H | CH₃ | CH₃ | CH | 161–163 |
| H | SO₂CH(CH₃)₂ | H | OCH₃ | OCH₃ | N | 164–166 |
| H | SO₂CH(CH₃)₂ | H | OCH₃ | CH₃ | N | 165–167 |
| H | SO₂CH(CH₃)₂ | H | OCH₂CH₃ | NHCH₃ | N | |
| H | SO₂CH(CH₃)₂ | CH₃ | OCH₃ | CH₃ | N | 145–149 |
| 4-CH₃ | SO₂CH(CH₃)₂ | H | OCH₃ | OCH₃ | CH | |
| 4-OCH₃ | SO₂CH(CH₃)₂ | H | OCH₃ | OCH₃ | CH | |
| 6-CH₃ | SO₂CH(CH₃)₂ | H | OCH₃ | OCH₃ | CH | |
| 6-OCH₃ | SO₂CH(CH₃)₂ | H | OCH₃ | OCH₃ | CH | |
| 6-F | SO₂CH(CH₃)₂ | H | OCH₃ | OCH₃ | CH | |
| 6-Cl | SO₂CH(CH₃)₂ | H | OCH₃ | OCH₃ | CH | |
| H | SOCH₂CH₂CH₂CH₃ | H | OCH₃ | OCH₃ | CH | |
| H | SOCH₂CH₂CH₂CH₃ | H | OCH₃ | CH₃ | CH | |
| H | SOCH₂CH₂CH₂CH₃ | H | Cl | OCH₃ | CH | |
| H | SOCH₂CH₂CH₂CH₃ | H | CH₃ | CH₃ | CH | |
| H | SOCH₂CH₂CH₂CH₃ | H | OCH₃ | OCH₃ | N | |
| H | SOCH₂CH₂CH₂CH₃ | H | OCH₃ | CH₃ | N | |
| H | SOCH₂CH₂CH₂CH₃ | H | OCH₂CH₃ | NHCH₃ | N | |
| H | SOCH₂CH₂CH₂CH₃ | CH₃ | OCH₃ | CH₃ | N | |
| 4-CH₃ | SOCH₂CH₂CH₂CH₃ | H | OCH₃ | OCH₃ | CH | |
| 4-OCH₃ | SOCH₂CH₂CH₂CH₃ | H | OCH₃ | OCH₃ | CH | |
| 6-CH₃ | SOCH₂CH₂CH₂CH₃ | H | OCH₃ | OCH₃ | CH | |
| 6-OCH₃ | SOCH₂CH₂CH₂CH₃ | H | OCH₃ | OCH₃ | CH | |
| 6-F | SOCH₂CH₂CH₂CH₃ | H | OCH₃ | OCH₃ | CH | |
| 6-Cl | SOCH₂CH₂CH₂CH₃ | H | OCH₃ | OCH₃ | CH | |
| H | SO₂CH₂CH₂CH₂CH₃ | H | OCH₃ | OCH₃ | CH | 155–157 |
| H | SO₂CH₂CH₂CH₂CH₃ | H | OCH₃ | CH₃ | CH | 142–144 |
| H | SO₂CH₂CH₂CH₂CH₃ | H | Cl | OCH₃ | CH | 151–153 |
| H | SO₂CH₂CH₂CH₂CH₃ | H | CH₃ | CH₃ | CH | 142–143 |
| H | SO₂CH₂CH₂CH₂CH₃ | H | OCH₃ | OCH₃ | N | 153.5–155 |
| H | SO₂CH₂CH₂CH₂CH₃ | H | OCH₃ | CH₃ | N | 142.5–145.5 |
| H | SO₂CH₂CH₂CH₂CH₃ | H | OCH₂CH₃ | NHCH₃ | N | |
| H | SO₂CH₂CH₂CH₂CH₃ | CH₃ | OCH₃ | CH₃ | N | |
| H | SO₂CH₂CH₂CH₂CH₃ | CH₃ | OCH₃ | OCH₃ | N | 133–136 |
| 4-CH₃ | SO₂CH₂CH₂CH₂CH₃ | H | OCH₃ | OCH₃ | CH | |
| 4-OCH₃ | SO₂CH₂CH₂CH₂CH₃ | H | OCH₃ | OCH₃ | CH | |
| 6-CH₃ | SO₂CH₂CH₂CH₂CH₃ | H | OCH₃ | OCH₃ | CH | |
| 6-OCH₃ | SO₂CH₂CH₂CH₂CH₃ | H | OCH₃ | OCH₃ | CH | |
| 6-F | SO₂CH₂CH₂CH₂CH₃ | H | OCH₃ | OCH₃ | CH | |
| 6-Cl | SO₂CH₂CH₂CH₂CH₃ | H | OCH₃ | OCH₃ | CH | |
| H | S-cyclopropyl | H | OCH₃ | OCH₃ | CH | |
| H | S-cyclopropyl | H | OCH₃ | CH₃ | CH | |
| H | S-cyclopropyl | H | Cl | OCH₃ | CH | |
| H | S-cyclopropyl | H | CH₃ | CH₃ | CH | |
| H | S-cyclopropyl | H | OCH₃ | OCH₃ | N | |
| H | S-cyclopropyl | H | OCH₃ | CH₃ | N | |
| H | S-cyclopropyl | H | OCH₂CH₃ | NHCH₃ | N | |
| H | S-cyclopropyl | CH₃ | OCH₃ | CH₃ | N | |
| 4-CH₃ | S-cyclopropyl | H | OCH₃ | OCH₃ | CH | |
| 4-OCH₃ | S-cyclopropyl | H | OCH₃ | OCH₃ | CH | |
| 6-CH₃ | S-cyclopropyl | H | OCH₃ | OCH₃ | CH | |
| 6-OCH₃ | S-cyclopropyl | H | OCH₃ | OCH₃ | CH | |
| 6-F | S-cyclopropyl | H | OCH₃ | OCH₃ | CH | |
| 6-Cl | S-cyclopropyl | H | OCH₃ | OCH₃ | CH | |
| H | SO-cyclopropyl | H | OCH₃ | OCH₃ | CH | |
| H | SO-cyclopropyl | H | OCH₃ | CH₃ | CH | |
| H | SO-cyclopropyl | H | Cl | OCH₃ | CH | |
| H | SO-cyclopropyl | H | CH₃ | CH₃ | CH | |
| H | SO-cyclopropyl | H | OCH₃ | OCH₃ | N | |
| H | SO-cyclopropyl | H | OCH₃ | CH₃ | N | |

TABLE I-continued

General Formula 1

| R₁ | R₂ | R | X | Y | Z | m.p.(°C.) |
|---|---|---|---|---|---|---|
| H | SO-cyclopropyl | H | OCH₂CH₃ | NHCH₃ | N | |
| H | SO-cyclopropyl | CH₃ | OCH₃ | CH₃ | N | |
| 4-CH₃ | SO-cyclopropyl | H | OCH₃ | OCH₃ | CH | |
| 4-OCH₃ | SO-cyclopropyl | H | OCH₃ | OCH₃ | CH | |
| 6-CH₃ | SO-cyclopropyl | H | OCH₃ | OCH₃ | CH | |
| 6-OCH₃ | SO-cyclopropyl | H | OCH₃ | OCH₃ | CH | |
| 6-F | SO-cyclopropyl | H | OCH₃ | OCH₃ | CH | |
| 6-Cl | SO-cyclopropyl | H | OCH₃ | OCH₃ | CH | |
| H | SO₂-cyclopropyl | H | OCH₃ | OCH₃ | CH | |
| H | SO₂-cyclopropyl | H | OCH₃ | CH₃ | CH | |
| H | SO₂-cyclopropyl | H | Cl | OCH₃ | CH | |
| H | SO₂-cyclopropyl | H | CH₃ | CH₃ | CH | |
| H | SO₂-cyclopropyl | H | OCH₃ | OCH₃ | N | |
| H | SO₂-cyclopropyl | H | OCH₃ | CH₃ | N | |
| H | SO₂-cyclopropyl | H | OCH₂CH₃ | NHCH₃ | N | |
| H | SO₂-cyclopropyl | CH₃ | OCH₃ | CH₃ | N | |
| 4-CH₃ | SO₂-cyclopropyl | H | OCH₃ | OCH₃ | CH | |
| 4-OCH₃ | SO₂-cyclopropyl | H | OCH₃ | OCH₃ | CH | |
| 6-CH₃ | SO₂-cyclopropyl | H | OCH₃ | OCH₃ | CH | |
| 6-OCH₃ | SO₂-cyclopropyl | H | OCH₃ | OCH₃ | CH | |
| 6-F | SO₂-cyclopropyl | H | OCH₃ | OCH₃ | CH | |
| 6-Cl | SO₂-cyclopropyl | H | OCH₃ | OCH₃ | CH | |
| H | OSO₂CH₃ | H | OCH₃ | OCH₃ | CH | 169–171 |
| H | OSO₂CH₃ | H | OCH₃ | CH₃ | CH | 172–173.5 |
| H | OSO₂CH₃ | H | Cl | OCH₃ | CH | 171–173 |
| H | OSO₂CH₃ | H | CH₃ | CH₃ | CH | 161.5–165 |
| H | OSO₂CH₃ | H | OCH₃ | OCH₃ | N | |
| H | OSO₂CH₃ | H | OCH₃ | CH₃ | N | 155–158 |
| H | OSO₂CH₃ | H | OCH₂CH₃ | NHCH₃ | N | |
| H | OSO₂CH₃ | CH₃ | OCH₃ | CH₃ | N | |
| 4-CH₃ | OSO₂CH₃ | H | OCH₃ | OCH₃ | CH | |
| 4-OCH₃ | OSO₂CH₃ | H | OCH₃ | OCH₃ | CH | |
| 6-CH₃ | OSO₂CH₃ | H | OCH₃ | OCH₃ | CH | |
| 6-OCH₃ | OSO₂CH₃ | H | OCH₃ | OCH₃ | CH | |
| 6-F | OSO₂CH₃ | H | OCH₃ | OCH₃ | CH | |
| 6-Cl | OSO₂CH₃ | H | OCH₃ | OCH₃ | CH | |
| H | OSO₂CH₂CH₃ | H | OCH₃ | OCH₃ | CH | 162–163.5 |
| H | OSO₂CH₂CH₃ | H | OCH₃ | CH₃ | CH | 160–162 |
| H | OSO₂CH₂CH₃ | H | Cl | OCH₃ | CH | 139–143 |
| H | OSO₂CH₂CH₃ | H | CH₃ | CH₃ | CH | 132–138 |
| H | OSO₂CH₂CH₃ | H | OCH₃ | OCH₃ | N | 171.5–173 |
| H | OSO₂CH₂CH₃ | H | OCH₃ | CH₃ | N | 147–149 |
| H | OSO₂CH₂CH₃ | H | OCH₂CH₃ | NHCH₃ | N | |
| H | OSO₂CH₂CH₃ | CH₃ | OCH₃ | CH₃ | N | |
| 4-CH₃ | OSO₂CH₂CH₃ | H | OCH₃ | OCH₃ | CH | |
| 4-OCH₃ | OSO₂CH₂CH₃ | H | OCH₃ | OCH₃ | CH | |
| 6-CH₃ | OSO₂CH₂CH₃ | H | OCH₃ | OCH₃ | CH | |
| 6-OCH₃ | OSO₂CH₂CH₃ | H | OCH₃ | OCH₃ | CH | |
| 6-F | OSO₂CH₂CH₃ | H | OCH₃ | OCH₃ | CH | |
| 6-Cl | OSO₂CH₂CH₃ | H | OCH₃ | OCH₃ | CH | |
| H | OSO₂CH₂CH₂CH₃ | H | OCH₃ | OCH₃ | CH | 156–157 |
| H | OSO₂CH₂CH₂CH₃ | H | OCH₃ | CH₃ | CH | 131–133 |
| H | OSO₂CH₂CH₂CH₃ | H | Cl | OCH₃ | CH | 127–132 |
| H | OSO₂CH₂CH₂CH₃ | H | CH₃ | CH₃ | CH | 152–153 |
| H | OSO₂CH₂CH₂CH₃ | H | OCH₃ | OCH₃ | N | 154–155 |
| H | OSO₂CH₂CH₂CH₃ | H | OCH₃ | CH₃ | N | |
| H | OSO₂CH₂CH₂CH₃ | H | OCH₂CH₃ | NHCH₃ | N | |
| H | OSO₂CH₂CH₂CH₃ | CH₃ | OCH₃ | CH₃ | N | |
| 4-CH₃ | OSO₂CH₂CH₂CH₃ | H | OCH₃ | OCH₃ | CH | |
| 4-OCH₃ | OSO₂CH₂CH₂CH₃ | H | OCH₃ | OCH₃ | CH | |
| 6-CH₃ | OSO₂CH₂CH₂CH₃ | H | OCH₃ | OCH₃ | CH | |
| 6-OCH₃ | OSO₂CH₂CH₂CH₃ | H | OCH₃ | OCH₃ | CH | |
| 6-F | OSO₂CH₂CH₂CH₃ | H | OCH₃ | OCH₃ | CH | |
| 6-Cl | OSO₂CH₂CH₂CH₃ | H | OCH₃ | OCH₃ | CH | |
| H | OSO₂CH(CH₃)₂ | H | OCH₃ | OCH₃ | CH | |
| H | OSO₂CH(CH₃)₂ | H | OCH₃ | CH₃ | CH | |
| H | OSO₂CH(CH₃)₂ | H | Cl | OCH₃ | CH | |
| H | OSO₂CH(CH₃)₂ | H | CH₃ | CH₃ | CH | |
| H | OSO₂CH(CH₃)₂ | H | OCH₃ | OCH₃ | N | |
| H | OSO₂CH(CH₃)₂ | H | OCH₃ | CH₃ | N | |
| H | OSO₂CH(CH₃)₂ | H | OCH₂CH₃ | NHCH₃ | N | |
| H | OSO₂CH(CH₃)₂ | CH₃ | OCH₃ | CH₃ | N | |
| 4-CH₃ | OSO₂CH(CH₃)₂ | H | OCH₃ | OCH₃ | CH | |
| 4-OCH₃ | OSO₂CH(CH₃)₂ | H | OCH₃ | OCH₃ | CH | |
| 6-CH₃ | OSO₂CH(CH₃)₂ | H | OCH₃ | OCH₃ | CH | |
| 6-OCH₃ | OSO₂CH(CH₃)₂ | H | OCH₃ | OCH₃ | CH | |
| 6-F | OSO₂CH(CH₃)₂ | H | OCH₃ | OCH₃ | CH | |
| 6-Cl | OSO₂CH(CH₃)₂ | H | OCH₃ | OCH₃ | CH | |
| H | OSO₂CH₂CH₂CH₂CH₃ | H | OCH₃ | OCH₃ | CH | |
| H | OSO₂CH₂CH₂CH₂CH₃ | H | OCH₃ | CH₃ | CH | |

TABLE I-continued

General Formula 1

| R$_1$ | R$_2$ | R | X | Y | Z | m.p.(°C.) |
|---|---|---|---|---|---|---|
| H | OSO$_2$CH$_2$CH$_2$CH$_2$CH$_3$ | H | Cl | OCH$_3$ | CH | |
| H | OSO$_2$CH$_2$CH$_2$CH$_2$CH$_3$ | H | CH$_3$ | CH$_3$ | CH | |
| H | OSO$_2$CH$_2$CH$_2$CH$_2$CH$_3$ | H | OCH$_3$ | OCH$_3$ | N | |
| H | OSO$_2$CH$_2$CH$_2$CH$_2$CH$_3$ | H | OCH$_3$ | CH$_3$ | N | |
| H | OSO$_2$CH$_2$CH$_2$CH$_2$CH$_3$ | H | OCH$_2$CH$_3$ | NHCH$_3$ | N | |
| H | OSO$_2$CH$_2$CH$_2$CH$_2$CH$_3$ | CH$_3$ | OCH$_3$ | CH$_3$ | N | |
| 4-CH$_3$ | OSO$_2$CH$_2$CH$_2$CH$_2$CH$_3$ | H | OCH$_3$ | OCH$_3$ | CH | |
| 4-OCH$_3$ | OSO$_2$CH$_2$CH$_2$CH$_2$CH$_3$ | H | OCH$_3$ | OCH$_3$ | CH | |
| 6-CH$_3$ | OSO$_2$CH$_2$CH$_2$CH$_2$CH$_3$ | H | OCH$_3$ | OCH$_3$ | CH | |
| 6-OCH$_3$ | OSO$_2$CH$_2$CH$_2$CH$_2$CH$_3$ | H | OCH$_3$ | OCH | CH | |
| 6-F | OSO$_2$CH$_2$CH$_2$CH$_2$CH$_3$ | H | OCH$_3$ | OCH$_3$ | CH | |
| 6-Cl | OSO$_2$CH$_2$CH$_2$CH$_2$CH$_3$ | H | OCH$_3$ | OCH$_3$ | CH | |
| H | OSO$_2$CF$_3$ | H | OCH$_3$ | OCH$_3$ | CH | 140–142 |
| H | OSO$_2$CF$_3$ | H | OCH$_3$ | CH$_3$ | CH | |
| H | OSO$_2$CF$_3$ | H | Cl | OCH$_3$ | CH | 154–156 |
| H | OSO$_2$CF$_3$ | H | CH$_3$ | CH$_3$ | CH | 157–160 |
| H | OSO$_2$CF$_3$ | H | OCH$_3$ | OCH$_3$ | N | 164–166 |
| H | OSO$_2$CF$_3$ | H | OCH$_3$ | CH$_3$ | N | 157–159 |
| H | OSO$_2$CF$_3$ | H | OCH$_2$CH$_3$ | NHCH$_3$ | N | |
| H | OSO$_2$CF$_3$ | CH$_3$ | OCH$_3$ | CH$_3$ | N | |
| 4-CH$_3$ | OSO$_2$CF$_3$ | H | OCH$_3$ | OCH$_3$ | CH | |
| 4-OCH$_3$ | OSO$_2$CF$_3$ | H | OCH$_3$ | OCH$_3$ | CH | |
| 6-CH$_3$ | OSO$_2$CF$_3$ | H | OCH$_3$ | OCH$_3$ | CH | |
| 6-OCH$_3$ | OSO$_2$CF$_3$ | H | OCH$_3$ | OCH$_3$ | CH | |
| 6-F | OSO$_2$CF$_3$ | H | OCH$_3$ | OCH$_3$ | CH | |
| 6-Cl | OSO$_2$CF$_3$ | H | OCH$_3$ | OCH$_3$ | CH | |
| H | OSO$_2$CCl$_3$ | H | OCH$_3$ | OCH$_3$ | CH | |
| H | OSO$_2$CCl$_3$ | H | OCH$_3$ | CH$_3$ | CH | |
| H | OSO$_2$CCl$_3$ | H | Cl | OCH$_3$ | CH | |
| H | OSO$_2$CCl$_3$ | H | CH$_3$ | CH$_3$ | CH | |
| H | OSO$_2$CCl$_3$ | H | OCH$_3$ | OCH$_3$ | N | |
| H | OSO$_2$CCl$_3$ | H | OCH$_3$ | CH$_3$ | N | |
| H | OSO$_2$CCl$_3$ | H | OCH$_2$CH$_3$ | NHCH$_3$ | N | |
| H | OSO$_2$CCl$_3$ | CH$_3$ | OCH$_3$ | CH$_3$ | N | |
| 4-CH$_3$ | OSO$_2$CCl$_3$ | H | OCH$_3$ | OCH$_3$ | CH | |
| 4-OCH$_3$ | OSO$_2$CCl$_3$ | H | OCH$_3$ | OCH$_3$ | CH | |
| 6-CH$_3$ | OSO$_2$CCl$_3$ | H | OCH$_3$ | OCH$_3$ | CH | |
| 6-OCH$_3$ | OSO$_2$CCl$_3$ | H | OCH$_3$ | OCH$_3$ | CH | |
| 6-F | OSO$_2$CCl$_3$ | H | OCH$_3$ | OCH$_3$ | CH | |
| 6-Cl | OSO$_2$CCl$_3$ | H | OCH$_3$ | OCH$_3$ | CH | |
| H | OSO$_2$CH$_2$CH$_2$CH$_2$Cl | H | OCH$_3$ | OCH$_3$ | CH | |
| H | OSO$_2$CH$_2$CH$_2$CH$_2$Cl | H | OCH$_3$ | CH$_3$ | CH | |
| H | OSO$_2$CH$_2$CH$_2$CH$_2$Cl | H | Cl | OCH$_3$ | CH | |
| H | OSO$_2$CH$_2$CH$_2$CH$_2$Cl | H | CH$_3$ | CH$_3$ | CH | |
| H | OSO$_2$CH$_2$CH$_2$CH$_2$Cl | H | OCH$_3$ | OCH$_3$ | N | |
| H | OSO$_2$CH$_2$CH$_2$CH$_2$Cl | H | OCH$_3$ | CH$_3$ | N | |
| H | OSO$_2$CH$_2$CH$_2$CH$_2$Cl | H | OCH$_2$CH$_3$ | NHCH$_3$ | N | |
| H | OSO$_2$CH$_2$CH$_2$CH$_2$Cl | CH$_3$ | OCH$_3$ | CH$_3$ | N | |
| 4-CH$_3$ | OSO$_2$CH$_2$CH$_2$CH$_2$Cl | H | OCH$_3$ | OCH$_3$ | CH | |
| 4-OCH$_3$ | OSO$_2$CH$_2$CH$_2$CH$_2$Cl | H | OCH$_3$ | OCH$_3$ | CH | |
| 6-CH$_3$ | OSO$_2$CH$_2$CH$_2$CH$_2$Cl | H | OCH$_3$ | OCH$_3$ | CH | |
| 6-OCH$_3$ | OSO$_2$CH$_2$CH$_2$CH$_2$Cl | H | OCH$_3$ | OCH$_3$ | CH | |
| 6-F | OSO$_2$CH$_2$CH$_2$CH$_2$Cl | H | OCH$_3$ | OCH$_3$ | CH | |
| 6-Cl | OSO$_2$CH$_2$CH$_2$CH$_2$Cl | H | OCH$_3$ | OCH$_3$ | CH | |
| H | SO$_2$OCH$_2$CF$_3$ | H | OCH$_3$ | OCH$_3$ | CH | |
| H | SO$_2$OCH$_2$CF$_3$ | H | OCH$_3$ | CH$_3$ | CH | |
| H | SO$_2$OCH$_2$CF$_3$ | H | Cl | OCH$_3$ | CH | |
| H | SO$_2$OCH$_2$CF$_3$ | H | CH$_3$ | CH$_3$ | CH | |
| H | SO$_2$OCH$_2$CF$_3$ | H | OCH$_3$ | OCH$_3$ | N | |
| H | SO$_2$OCH$_2$CF$_3$ | H | OCH$_3$ | CH$_3$ | N | |
| H | SO$_2$OCH$_2$CF$_3$ | H | OCH$_2$CH$_3$ | NHCH$_3$ | N | |
| H | SO$_2$OCH$_2$CF$_3$ | CH$_3$ | OCH$_3$ | CH$_3$ | N | |
| 4-CH$_3$ | SO$_2$OCH$_2$CF$_3$ | H | OCH$_3$ | OCH$_3$ | CH | |
| 4-OCH$_3$ | SO$_2$OCH$_2$CF$_3$ | H | OCH$_3$ | OCH$_3$ | CH | |
| 6-CH$_3$ | SO$_2$OCH$_2$CF$_3$ | H | OCH$_3$ | OCH$_3$ | CH | |
| 6-OCH$_3$ | SO$_2$OCH$_2$CF$_3$ | H | OCH$_3$ | OCH$_3$ | CH | |
| 6-F | SO$_2$OCH$_2$CF$_3$ | H | OCH$_3$ | OCH$_3$ | CH | |
| 6-Cl | SO$_2$OCH$_2$CF$_3$ | H | OCH$_3$ | OCH$_3$ | CH | |
| H | SO$_2$OCH$_3$ | H | OCH$_3$ | OCH$_3$ | CH | |
| H | SO$_2$OCH$_3$ | H | OCH$_3$ | CH$_3$ | CH | |
| H | SO$_2$OCH$_3$ | H | Cl | OCH$_3$ | CH | |
| H | SO$_2$OCH$_3$ | H | CH$_3$ | CH$_3$ | CH | |
| H | SO$_2$OCH$_3$ | H | OCH$_3$ | OCH$_3$ | N | |
| H | SO$_2$OCH$_3$ | H | OCH$_3$ | CH$_3$ | N | |
| H | SO$_2$OCH$_3$ | H | OCH$_2$CH$_3$ | NHCH$_3$ | N | |
| H | SO$_2$OCH$_3$ | CH$_3$ | OCH$_3$ | CH$_3$ | N | |
| 4-CH$_3$ | SO$_2$OCH$_3$ | H | OCH$_3$ | OCH$_3$ | CH | |
| 4-OCH$_3$ | SO$_2$OCH$_3$ | H | OCH$_3$ | OCH$_3$ | CH | |
| 6-CH$_3$ | SO$_2$OCH$_3$ | H | OCH$_3$ | OCH$_3$ | CH | |
| 6-OCH$_3$ | SO$_2$OCH$_3$ | H | OCH$_3$ | OCH$_3$ | CH | |

TABLE I-continued

General Formula 1

| R₁ | R₂ | R | X | Y | Z | m.p.(°C.) |
|---|---|---|---|---|---|---|
| 6-F | SO₂OCH₃ | H | OCH₃ | OCH₃ | CH | |
| 6-Cl | SO₂OCH₃ | H | OCH₃ | OCH₃ | CH | |
| H | SO₂OCH₂CH₃ | H | OCH₃ | OCH₃ | CH | |
| H | SO₂OCH₂CH₃ | H | OCH₃ | CH₃ | CH | |
| H | SO₂OCH₂CH₃ | H | Cl | OCH₃ | CH | |
| H | SO₂OCH₂CH₃ | H | CH₃ | CH₃ | CH | |
| H | SO₂OCH₂CH₃ | H | OCH₃ | OCH₃ | N | |
| H | SO₂OCH₂CH₃ | H | OCH₃ | CH₃ | N | |
| H | SO₂OCH₂CH₃ | H | OCH₂CH₃ | NHCH₃ | N | |
| H | SO₂OCH₂CH₃ | CH₃ | OCH₃ | CH₃ | N | |
| 4-CH₃ | SO₂OCH₂CH₃ | H | OCH₃ | OCH₃ | CH | |
| 4-OCH₃ | SO₂OCH₂CH₃ | H | OCH₃ | OCH₃ | CH | |
| 6-CH₃ | SO₂OCH₂CH₃ | H | OCH₃ | OCH₃ | CH | |
| 6-OCH₃ | SO₂OCH₂CH₃ | H | OCH₃ | OCH₃ | CH | |
| 6-F | SO₂OCH₂CH₃ | H | OCH₃ | OCH₃ | CH | |
| 6-Cl | SO₂OCH₂CH₃ | H | OCH₃ | OCH₃ | CH | |
| H | N₃ | H | OCH₃ | OCH₃ | CH | |
| H | N₃ | H | OCH₃ | CH₃ | CH | |
| H | N₃ | H | Cl | OCH₃ | CH | |
| H | N₃ | H | CH₃ | CH₃ | CH | |
| H | N₃ | H | OCH₃ | OCH₃ | N | |
| H | N₃ | H | OCH₃ | CH₃ | N | |
| H | N₃ | H | OCH₂CH₃ | NHCH₃ | N | |
| H | N₃ | CH₃ | OCH₃ | CH₃ | N | |
| 4-CH₃ | N₃ | H | OCH₃ | OCH₃ | CH | |
| 4-OCH₃ | N₃ | H | OCH₃ | OCH₃ | CH | |
| 6-CH₃ | N₃ | H | OCH₃ | OCH₃ | CH | |
| 6-OCH₃ | N₃ | H | OCH₃ | OCH₃ | CH | |
| 6-F | N₃ | H | OCH₃ | OCH₃ | CH | |
| 6-Cl | N₃ | H | OCH₃ | OCH₃ | CH | |
| H | CN | H | OCH₃ | OCH₃ | CH | |
| H | CN | H | OCH₃ | CH₃ | CH | |
| H | CN | H | Cl | OCH₃ | CH | |
| H | CN | H | CH₃ | CH₃ | CH | |
| H | CN | H | OCH₃ | OCH₃ | N | |
| H | CN | H | OCH₃ | CH₃ | N | |
| H | CN | H | OCH₂CH₃ | NHCH₃ | N | |
| H | CN | CH₃ | OCH₃ | CH₃ | N | |
| 4-CH₃ | CN | H | OCH₃ | OCH₃ | CH | |
| 4-OCH₃ | CN | H | OCH₃ | OCH₃ | CH | |
| 6-CH₃ | CN | H | OCH₃ | OCH₃ | CH | |
| 6-OCH₃ | CN | H | OCH₃ | OCH₃ | CH | |
| 6-F | CN | H | OCH₃ | OCH₃ | CH | |
| 6-Cl | CN | H | OCH₃ | OCH₃ | CH | |
| H | P(O)(OCH₃)₂ | H | OCH₃ | OCH₃ | CH | |
| H | P(O)(OCH₃)₂ | H | OCH₃ | CH₃ | CH | |
| H | P(O)(OCH₃)₂ | H | Cl | OCH₃ | CH | |
| H | P(O)(OCH₃)₂ | H | CH₃ | CH₃ | CH | |
| H | P(O)(OCH₃)₂ | H | OCH₃ | OCH₃ | N | |
| H | P(O)(OCH₃)₂ | H | OCH₃ | CH₃ | N | |
| H | P(O)(OCH₃)₂ | H | OCH₂CH₃ | NHCH₃ | N | |
| H | P(O)(OCH₃)₂ | CH₃ | OCH₃ | CH₃ | N | |
| 4-CH₃ | P(O)(OCH₃)₂ | H | OCH₃ | OCH₃ | CH | |
| 4-OCH₃ | P(O)(OCH₃)₂ | H | OCH₃ | OCH₃ | CH | |
| 6-CH₃ | P(O)(OCH₃)₂ | H | OCH₃ | OCH₃ | CH | |
| 6-OCH₃ | P(O)(OCH₃)₂ | H | OCH₃ | OCH₃ | CH | |
| 6-F | P(O)(OCH₃)₂ | H | OCH₃ | OCH₃ | CH | |
| 6-Cl | P(O)(OCH₃)₂ | H | OCH₃ | OCH₃ | CH | |
| H | P(O)(OCH₂CH₃)₂ | H | OCH₃ | OCH₃ | CH | 108–111 |
| H | P(O)(OCH₂CH₃)₂ | H | OCH₃ | CH₃ | CH | |
| H | P(O)(OCH₂CH₃)₂ | H | Cl | OCH₃ | CH | |
| H | P(O)(OCH₂CH₃)₂ | H | CH₃ | CH₃ | CH | 110–114 |
| H | P(O)(OCH₂CH₃)₂ | H | OCH₃ | OCH₃ | N | |
| H | P(O)(OCH₂CH₃)₂ | H | OCH₃ | CH₃ | N | |
| H | P(O)(OCH₂CH₃)₂ | H | OCH₂CH₃ | NHCH₃ | N | |
| H | P(O)(OCH₂CH₃)₂ | CH₃ | OCH₃ | CH₃ | N | |
| 4-CH₃ | P(O)(OCH₂CH₃)₂ | H | OCH₃ | OCH₃ | CH | |
| 4-OCH₃ | P(O)(OCH₂CH₃)₂ | H | OCH₃ | OCH₃ | CH | |
| 6-CH₃ | P(O)(OCH₂CH₃)₂ | H | OCH₃ | OCH₃ | CH | |
| 6-OCH₃ | P(O)(OCH₂CH₃)₂ | H | OCH₃ | OCH₃ | CH | |
| 6-F | P(O)(OCH₂CH₃)₂ | H | OCH₃ | OCH₃ | CH | |
| 6-Cl | P(O)(OCH₂CH₃)₂ | H | OCH₃ | OCH₃ | CH | |
| H | P(S)(OCH₃)₂ | H | OCH₃ | OCH₃ | CH | |
| H | P(S)(OCH₃)₂ | H | OCH₃ | CH₃ | CH | |
| H | P(S)(OCH₃)₂ | H | Cl | OCH₃ | CH | |
| H | P(S)(OCH₃)₂ | H | CH₃ | CH₃ | CH | |
| H | P(S)(OCH₃)₂ | H | OCH₃ | OCH₃ | N | |
| H | P(S)(OCH₃)₂ | H | OCH₃ | CH₃ | N | |
| H | P(S)(OCH₃)₂ | H | OCH₂CH₃ | NHCH₃ | N | |
| H | P(S)(OCH₃)₂ | CH₃ | OCH₃ | CH₃ | N | |

TABLE I-continued

General Formula 1

| R₁ | R₂ | R | X | Y | Z | m.p.(°C.) |
|---|---|---|---|---|---|---|
| 4-CH₃ | P(S)(OCH₃)₂ | H | OCH₃ | OCH₃ | CH | |
| 4-OCH₃ | P(S)(OCH₃)₂ | H | OCH₃ | OCH₃ | CH | |
| 6-CH₃ | P(S)(OCH₃)₂ | H | OCH₃ | OCH₃ | CH | |
| 6-OCH₃ | P(S)(OCH₃)₂ | H | OCH₃ | OCH₃ | CH | |
| 6-F | P(S)(OCH₃)₂ | H | OCH₃ | OCH₃ | CH | |
| 6-Cl | P(S)(OCH₃)₂ | H | OCH₃ | OCH₃ | CH | |
| H | P(S)(OCH₂CH₃)₂ | H | OCH₃ | OCH₃ | CH | |
| H | P(S)(OCH₂CH₃)₂ | H | OCH₃ | CH₃ | CH | |
| H | P(S)(OCH₂CH₃)₂ | H | Cl | OCH₃ | CH | |
| H | P(S)(OCH₂CH₃)₂ | H | CH₃ | CH₃ | CH | |
| H | P(S)(OCH₂CH₃)₂ | H | OCH₃ | OCH₃ | N | |
| H | P(S)(OCH₂CH₃)₂ | H | OCH₃ | CH₃ | N | |
| H | P(S)(OCH₂CH₃)₂ | H | OCH₂CH₃ | NHCH₃ | N | |
| H | P(S)(OCH₂CH₃)₂ | CH₃ | OCH₃ | CH₃ | N | |
| 4-CH₃ | P(S)(OCH₂CH₃)₂ | H | OCH₃ | OCH₃ | CH | |
| 4-OCH₃ | P(S)(OCH₂CH₃)₂ | H | OCH₃ | OCH₃ | CH | |
| 6-CH₃ | P(S)(OCH₂CH₃)₂ | H | OCH₃ | OCH₃ | CH | |
| 6-OCH₃ | P(S)(OCH₂CH₃)₂ | H | OCH₃ | OCH₃ | CH | |
| 6-F | P(S)(OCH₂CH₃)₂ | H | OCH₃ | OCH₃ | CH | |
| 6-Cl | P(S)(OCH₂CH₃)₂ | H | OCH₃ | OCH₃ | CH | |
| H | CH₂F | H | OCH₃ | OCH₃ | CH | |
| H | CH₂F | H | OCH₃ | CH₃ | CH | |
| H | CH₂F | H | Cl | OCH₃ | CH | |
| H | CH₂F | H | CH₃ | CH₃ | CH | |
| H | CH₂F | H | OCH₃ | OCH₃ | N | |
| H | CH₂F | H | OCH₃ | CH₃ | N | |
| H | CH₂F | H | OCH₂CH₃ | NHCH₃ | N | |
| H | CH₂F | CH₃ | OCH₃ | CH₃ | N | |
| 4-CH₃ | CH₂F | H | OCH₃ | OCH₃ | CH | |
| 4-OCH₃ | CH₂F | H | OCH₃ | OCH₃ | CH | |
| 6-CH₃ | CH₂F | H | OCH₃ | OCH₃ | CH | |
| 6-OCH₃ | CH₂F | H | OCH₃ | OCH₃ | CH | |
| 6-F | CH₂F | H | OCH₃ | OCH₃ | CH | |
| 6-Cl | CH₂F | H | OCH₃ | OCH₃ | CH | |
| H | CF₂H | H | OCH₃ | OCH₃ | CH | |
| H | CF₂H | H | OCH₃ | CH₃ | CH | |
| H | CF₂H | H | Cl | OCH₃ | CH | |
| H | CF₂H | H | CH₃ | CH₃ | CH | |
| H | CF₂H | H | OCH₃ | OCH₃ | N | |
| H | CF₂H | H | OCH₃ | CH₃ | N | |
| H | CF₂H | H | OCH₂CH₃ | NHCH₃ | N | |
| H | CF₂H | CH₃ | OCH₃ | CH₃ | N | |
| 4-CH₃ | CF₂H | H | OCH₃ | OCH₃ | CH | |
| 4-OCH₃ | CF₂H | H | OCH₃ | OCH₃ | CH | |
| 6-CH₃ | CF₂H | H | OCH₃ | OCH₃ | CH | |
| 6-OCH₃ | CF₂H | H | OCH₃ | OCH₃ | CH | |
| 6-F | CF₂H | H | OCH₃ | OCH₃ | CH | |
| 6-Cl | CF₂H | H | OCH₃ | OCH₃ | CH | |
| H | CH₂Cl | H | OCH₃ | OCH₃ | CH | |
| H | CH₂Cl | H | OCH₃ | CH₃ | CH | |
| H | CH₂Cl | H | Cl | OCH₃ | CH | |
| H | CH₂Cl | H | CH₃ | CH₃ | CH | |
| H | CH₂Cl | H | OCH₃ | OCH₃ | N | |
| H | CH₂Cl | H | OCH₃ | CH₃ | N | |
| H | CH₂Cl | H | OCH₂CH₃ | NHCH₃ | N | |
| H | CH₂Cl | CH₃ | OCH₃ | CH₃ | N | |
| 4-CH₃ | CH₂Cl | H | OCH₃ | OCH₃ | CH | |
| 4-OCH₃ | CH₂Cl | H | OCH₃ | OCH₃ | CH | |
| 6-CH₃ | CH₂Cl | H | OCH₃ | OCH₃ | CH | |
| 6-OCH₃ | CH₂Cl | H | OCH₃ | OCH₃ | CH | |
| 6-F | CH₂Cl | H | OCH₃ | OCH₃ | CH | |
| 6-Cl | CH₂Cl | H | OCH₃ | OCH₃ | CH | |
| H | CCl₂H | H | OCH₃ | OCH₃ | CH | |
| H | CCl₂H | H | OCH₃ | CH₃ | CH | |
| H | CCl₂H | H | Cl | OCH₃ | CH | |
| H | CCl₂H | H | CH₃ | CH₃ | CH | |
| H | CCl₂H | H | OCH₃ | OCH₃ | N | |
| H | CCl₂H | H | OCH₃ | CH₃ | N | |
| H | CCl₂H | H | OCH₂CH₃ | NHCH₃ | N | |
| H | CCl₂H | CH₃ | OCH₃ | CH₃ | N | |
| 4-CH₃ | CCl₂H | H | OCH₃ | OCH₃ | CH | |
| 4-OCH₃ | CCl₂H | H | OCH₃ | OCH₃ | CH | |
| 6-CH₃ | CCl₂H | H | OCH₃ | OCH₃ | CH | |
| 6-OCH₃ | CCl₂H | H | OCH₃ | OCH₃ | CH | |
| 6-F | CCl₂H | H | OCH₃ | OCH₃ | CH | |
| 6-Cl | CCl₂H | H | OCH₃ | OCH₃ | CH | |
| H | CH₂CH₂Cl | H | OCH₃ | OCH₃ | CH | |
| H | CH₂CH₂Cl | H | OCH₃ | CH₃ | CH | |
| H | CH₂CH₂Cl | H | Cl | OCH₃ | CH | |
| H | CH₂CH₂Cl | H | CH₃ | CH₃ | CH | |

TABLE I-continued

General Formula 1

| R₁ | R₂ | R | X | Y | Z | m.p.(°C.) |
|---|---|---|---|---|---|---|
| H | CH₂CH₂Cl | H | OCH₃ | OCH₃ | N | |
| H | CH₂CH₂Cl | H | OCH₃ | CH₃ | N | |
| H | CH₂CH₂Cl | H | OCH₂CH₃ | NHCH₃ | N | |
| H | CH₂CH₂Cl | CH₃ | OCH₃ | CH₃ | N | |
| 4-CH₃ | CH₂CH₂Cl | H | OCH₃ | OCH₃ | CH | |
| 4-OCH₃ | CH₂CH₂Cl | H | OCH₃ | OCH₃ | CH | |
| 6-CH₃ | CH₂CH₂Cl | H | OCH₃ | OCH₃ | CH | |
| 6-OCH₃ | CH₂CH₂Cl | H | OCH₃ | OCH₃ | CH | |
| 6-F | CH₂CH₂Cl | H | OCH₃ | OCH₃ | CH | |
| 6-Cl | CH₂CH₂Cl | H | OCH₃ | OCH₃ | CH | |
| H | CH₂CH₂Br | H | OCH₃ | OCH₃ | CH | |
| H | CH₂CH₂Br | H | OCH₃ | CH₃ | CH | |
| H | CH₂CH₂Br | H | Cl | OCH₃ | CH | |
| H | CH₂CH₂Br | H | CH₃ | CH₃ | CH | |
| H | CH₂CH₂Br | H | OCH₃ | OCH₃ | N | |
| H | CH₂CH₂Br | H | OCH₃ | CH₃ | N | |
| H | CH₂CH₂Br | H | OCH₂CH₃ | NHCH₃ | N | |
| H | CH₂CH₂Br | CH₃ | OCH₃ | CH₃ | N | |
| 4-CH₃ | CH₂CH₂Br | H | OCH₃ | OCH₃ | CH | |
| 4-OCH₃ | CH₂CH₂Br | H | OCH₃ | OCH₃ | CH | |
| 6-CH₃ | CH₂CH₂Br | H | OCH₃ | OCH₃ | CH | |
| 6-OCH₃ | CH₂CH₂Br | H | OCH₃ | OCH₃ | CH | |
| 6-F | CH₂CH₂Br | H | OCH₃ | OCH₃ | CH | |
| 6-Cl | CH₂CH₂Br | H | OCH₃ | OCH₃ | CH | |
| H | CHFCH₃ | H | OCH₃ | OCH₃ | CH | |
| H | CRFCH₃ | H | OCH₃ | CH₃ | CH | |
| H | CHFCH₃ | H | Cl | OCH₃ | CH | |
| H | CHFCH₃ | H | CH₃ | CH₃ | CH | |
| H | CHFCH₃ | H | OCH₃ | OCH₃ | N | |
| H | CHFCH₃ | H | OCH₃ | CH₃ | N | |
| H | CHFCH₃ | H | OCH₂CH₃ | NHCH₃ | N | |
| H | CHFCH₃ | CH₃ | OCH₃ | CH₃ | N | |
| 4-CH₃ | CHFCH₃ | H | OCH₃ | OCH₃ | CH | |
| 4-OCH₃ | CHFCH₃ | H | OCH₃ | OCH₃ | CH | |
| 6-CH₃ | CHFCH₃ | H | OCH₃ | OCH₃ | CH | |
| 6-OCH₃ | CHFCH₃ | H | OCH₃ | OCH₃ | CH | |
| 6-F | CHFCH₃ | H | OCH₃ | OCH₃ | CH | |
| 6-Cl | CHFCH₃ | H | OCH₃ | OCH₃ | CH | |
| H | CHClCH₃ | H | OCH₃ | OCH₃ | CH | |
| H | CHClCH₃ | H | OCH₃ | CH₃ | CH | |
| H | CHClCH₃ | H | Cl | OCH₃ | CH | |
| H | CHClCH₃ | H | CH₃ | CH₃ | CH | |
| H | CHClCH₃ | H | OCH₃ | OCH₃ | N | |
| H | CHClCH₃ | H | OCH₃ | CH₃ | N | |
| H | CHClCH₃ | H | OCH₂CH₃ | NHCH₃ | N | |
| H | CHClCH₃ | CH₃ | OCH₃ | CH₃ | N | |
| 4-CH₃ | CHClCH₃ | H | OCH₃ | OCH₃ | CH | |
| 4-OCH₃ | CHClCH₃ | H | OCH₃ | OCH₃ | CH | |
| 6-CH₃ | CHClCH₃ | H | OCH₃ | OCH₃ | CH | |
| 6-OCH₃ | CHClCH₃ | H | OCH₃ | OCH₃ | CH | |
| 6-F | CHClCH₃ | H | OCH₃ | OCH₃ | CH | |
| 6-Cl | CHClCH₃ | H | OCH₃ | OCH₃ | CH | |
| H | CF₂CF₂H | H | OCH₃ | OCH₃ | CH | |
| H | CF₂CF₂H | H | OCH₃ | CH₃ | CH | |
| H | CF₂CF₂H | H | Cl | OCH₃ | CH | |
| H | CF₂CF₂H | H | CH₃ | CH₃ | CH | |
| H | CF₂CF₂H | H | OCH₃ | OCH₃ | N | |
| H | CF₂CF₂H | H | OCH₃ | CH₃ | N | |
| H | CF₂CF₂H | H | OCH₂CH₃ | NHCH₃ | N | |
| H | CF₂CF₂H | CH₃ | OCH₃ | CH₃ | N | |
| 4-CH₃ | CF₂CF₂H | H | OCH₃ | OCH₃ | CH | |
| 4-OCH₃ | CF₂CF₂H | H | OCH₃ | OCH₃ | CH | |
| 6-CH₃ | CF₂CF₂H | H | OCH₃ | OCH₃ | CH | |
| 6-OCH₃ | CF₂CF₂H | H | OCH₃ | OCH₃ | CH | |
| 6-F | CF₂CF₂H | H | OCH₃ | OCH₃ | CH | |
| 6-Cl | CF₂CF₂H | H | OCH₃ | OCH₃ | CH | |
| 6-CH₂CH₃ | SO₂N(CH₃)₂ | H | OCH₃ | OCH₃ | CH | |
| 6-CH₂CH₃ | SO₂N(CH₃)₂ | H | OCH₃ | CH₃ | CH | |
| 6-CH₂CH₃ | SO₂N(CH₃)₂ | H | Cl | OCH₃ | CH | |
| 6-CH₂CH₃ | SO₂N(CH₃)₂ | H | CH₃ | CH₃ | CH | |
| 6-CH₂CH₃ | SO₂N(CH₃)₂ | H | OCH₃ | OCH₃ | N | |
| 6-CH₂CH₃ | SO₂N(CH₃)₂ | H | OCH₃ | CH₃ | N | |
| 6-CH₂CH₃ | SO₂N(CH₃)₂ | H | OCH₂CH₃ | NHCH₃ | N | |
| 6-CH₂CH₃ | SO₂N(CH₃)₂ | CH₃ | OCH₂CH₃ | CH₃ | N | |
| 6-OCH₃ | SO₂N(CH₃)₂ | H | OCH₃ | OCH₃ | CH | |
| 6-OCH₃ | SO₂N(CH₃)₂ | H | OCH₃ | CH₃ | CH | |
| 6-OCH₃ | SO₂N(CH₃)₂ | H | Cl | OCH₃ | CH | |
| 6-OCH₃ | SO₂N(CH₃)₂ | H | CH₃ | CH₃ | CH | |
| 6-OCH₃ | SO₂N(CH₃)₂ | H | OCH₃ | OCH₃ | N | |
| 6-OCH₃ | SO₂N(CH₃)₂ | H | OCH₃ | CH₃ | N | |

TABLE I-continued

General Formula 1

| R₁ | R₂ | R | X | Y | Z | m.p.(°C.) |
|---|---|---|---|---|---|---|
| 6-OCH₃ | SO₂N(CH₃)₂ | H | OCH₂CH₃ | NHCH₃ | N | |
| 6-OCH₃ | SO₂N(CH₃)₂ | CH₃ | OCH₃ | CH₃ | N | |
| 6-OCH₂CH₃ | SO₂N(CH₃)₂ | H | OCH₃ | OCH₃ | CH | |
| 6-OCH₂CH₃ | SO₂N(CH₃)₂ | H | OCH₃ | CH₃ | CH | |
| 6-OCH₂CH₃ | SO₂N(CH₃)₂ | H | Cl | OCH₃ | CH | |
| 6-OCH₂CH₃ | SO₂N(CH₃)₂ | H | CH₃ | CH₃ | CH | |
| 6-OCH₂CH₃ | SO₂N(CH₃)₂ | H | OCH₃ | OCH₃ | N | |
| 6-OCH₂CH₃ | SO₂N(CH₃)₂ | H | OCH₃ | CH₃ | N | |
| 6-OCH₂CH₃ | SO₂N(CH₃)₂ | H | OCH₂CH₃ | NHCH₃ | N | |
| 6-OCH₂CH₃ | SO₂N(CH₃)₂ | CH₃ | OCH₃ | CH₃ | N | |
| 6-SCH₂CH₃ | SO₂N(CH₃)₂ | H | OCH₃ | OCH₃ | CH | |
| 6-SCH₂CH₃ | SO₂N(CH₃)₂ | H | OCH₃ | CH₃ | CH | |
| 6-SCH₂CH₃ | SO₂N(CH₃)₂ | H | Cl | OCH₃ | CH | |
| 6-SCH₂CH₃ | SO₂N(CH₃)₂ | H | CH₃ | CH₃ | CH | |
| 6-SCH₂CH₃ | SO₂N(CH₃)₂ | H | OCH₃ | OCH₃ | N | |
| 6-SCH₂CH₃ | SO₂N(CH₃)₂ | H | OCH₃ | CH₃ | N | |
| 6-SCH₂CH₃ | SO₂N(CH₃)₂ | H | OCH₂CH₃ | NHCH₃ | N | |
| 6-SCH₂CH₃ | SO₂N(CH₃)₂ | CH₃ | OCH₃ | CH₃ | N | |
| 6-SCH₃ | SO₂N(CH₃)₂ | H | OCH₃ | OCH₃ | CH | |
| 6-SCH₃ | SO₂N(CH₃)₂ | H | OCH₃ | CH₃ | CH | |
| 6-SCH₃ | SO₂N(CH₃)₂ | H | Cl | OCH₃ | CH | |
| 6-SCH₃ | SO₂N(CH₃)₂ | H | CH₃ | CH₃ | CH | |
| 6-SCH₃ | SO₂N(CH₃)₂ | H | OCH₃ | OCH₃ | N | |
| 6-SCH₃ | SO₂N(CH₃)₂ | H | OCH₃ | CH₃ | N | |
| 6-SCH₃ | SO₂N(CH₃)₂ | H | OCH₂CH₃ | NHCH₃ | N | |
| 6-SCH₃ | SO₂N(CH₃)₂ | CH₃ | OCH₃ | CH₃ | N | |
| 6-N(CH₃)₂ | SO₂N(CH₃)₂ | H | OCH₃ | OCH₃ | CH | |
| 6-N(CH₃)₂ | SO₂N(CH₃)₂ | H | OCH₃ | CH₃ | CH | |
| 6-N(CH₃)₂ | SO₂N(CH₃)₂ | H | Cl | OCH₃ | CH | |
| 6-N(CH₃)₂ | SO₂N(CH₃)₂ | H | CH₃ | CH₃ | CH | |
| 6-N(CH₃)₂ | SO₂N(CH₃)₂ | H | OCH₃ | OCH₃ | N | |
| 6-N(CH₃)₂ | SO₂N(CH₃)₂ | H | OCH₃ | CH₃ | N | |
| 6-N(CH₃)₂ | SO₂N(CH₃)₂ | H | OCH₂CH₃ | NHCH₃ | N | |
| 6-N(CH₃)₂ | SO₂N(CH₃)₂ | CH₃ | OCH₃ | CH₃ | N | |
| 6-NHCH₃ | SO₂N(CH₃)₂ | H | OCH₃ | OCH₃ | CH | |
| 6-NHCH₃ | SO₂N(CH₃)₂ | H | OCH₃ | CH₃ | CH | |
| 6-NHCH₃ | SO₂N(CH₃)₂ | H | Cl | OCH₃ | CH | |
| 6-NHCH₃ | SO₂N(CH₃)₂ | H | CH₃ | CH₃ | CH | |
| 6-NHCH₃ | SO₂N(CH₃)₂ | H | OCH₃ | OCH₃ | N | |
| 6-NHCH₃ | SO₂N(CH₃)₂ | H | OCH₃ | CH₃ | N | |
| 6-NHCH₃ | SO₂N(CH₃)₂ | H | OCH₂CH₃ | NHCH₃ | N | |
| 6-NHCH₃ | SO₂N(CH₃)₂ | CH₃ | OCH₃ | CH₃ | N | |
| 6-OCH₃ | SO₂N(CH₂CH₃)₂ | H | OCH₃ | OCH₃ | CH | |
| 6-OCH₃ | SO₂N(CH₂CH₃)₂ | H | OCH₃ | CH₃ | CH | |
| 6-OCH₃ | SO₂N(CH₂CH₃)₂ | H | Cl | OCH₃ | CH | |
| 6-OCH₃ | SO₂N(CH₂CH₃)₂ | H | CH₃ | CH₃ | CH | |
| 6-OCH₃ | SO₂N(CH₂CH₃)₂ | H | OCH₃ | OCH₃ | N | |
| 6-OCH₃ | SO₂N(CH₂CH₃)₂ | H | OCH₃ | CH₃ | N | |
| 6-OCH₃ | SO₂N(CH₂CH₃)₂ | H | OCH₂CH₃ | NHCH₃ | N | |
| 6-OCH₃ | SO₂N(CH₂CH₃)₂ | CH₃ | OCH₃ | CH₃ | N | |
| 6-SCH₃ | SO₂N(CH₂CH₃)₂ | H | OCH₃ | OCH₃ | CH | |
| 6-SCH₃ | SO₂N(CH₂CH₃)₂ | H | OCH₃ | CH₃ | CH | |
| 6-SCH₃ | SO₂N(CH₂CH₃)₂ | H | Cl | OCH₃ | CH | |
| 6-SCH₃ | SO₂N(CH₂CH₃)₂ | H | CH₃ | CH₃ | CH | |
| 6-SCH₃ | SO₂N(CH₂CH₃)₂ | H | OCH₃ | OCH₃ | N | |
| 6-SCH₃ | SO₂N(CH₂CH₃)₂ | H | OCH₃ | CH₃ | N | |
| 6-SCH₃ | SO₂N(CH₂CH₃)₂ | H | OCH₂CH₃ | NHCH₃ | N | |
| 6-SCH₃ | SO₂N(CH₂CH₃)₂ | CH₃ | OCH₃ | CH₃ | N | |
| 6-N(CH₃)₂ | SO₂N(CH₂CH₃)₂ | H | OCH₃ | OCH₃ | CH | |
| 6-N(CH₃)₂ | SO₂N(CH₂CH₃)₂ | H | OCH₃ | CH₃ | CH | |
| 6-N(CH₃)₂ | SO₂N(CH₂CH₃)₂ | H | Cl | OCH₃ | CH | |
| 6-N(CH₃)₂ | SO₂N(CH₂CH₃)₂ | H | CH₃ | CH₃ | CH | |
| 6-N(CH₃)₂ | SO₂N(CH₂CH₃)₂ | H | OCH₃ | OCH₃ | N | |
| 6-N(CH₃)₂ | SO₂N(CH₂CH₃)₂ | H | OCH₃ | CH₃ | N | |
| 6-N(CH₃)₂ | SO₂N(CH₂CH₃)₂ | H | OCH₂CH₃ | NHCH₃ | N | |
| 6-N(CH₃)₂ | SO₂N(CH₂CH₃)₂ | CH₃ | OCH₃ | CH₃ | N | |
| 6-SCH₃ | SO₂NHOCH₃ | H | OCH₃ | OCH₃ | CH | |
| 6-SCH₃ | SO₂NHOCH₃ | H | OCH₃ | CH₃ | CH | |
| 6-SCH₃ | SO₂NHOCH₃ | H | Cl | OCH₃ | CH | |
| 6-SCH₃ | SO₂NHOCH₃ | H | CH₃ | CH₃ | CH | |
| 6-SCH₃ | SO₂NHOCH₃ | H | OCH₃ | OCH₃ | N | |
| 6-SCH₃ | SO₂NHOCH₃ | H | OCH₃ | CH₃ | N | |
| 6-SCH₃ | SO₂NHOCH₃ | H | OCH₂CH₃ | NHCH₃ | N | |
| 6-SCH₃ | SO₂NHOCH₃ | CH₃ | OCH₃ | CH₃ | N | |
| 6-SCH₂CH₃ | SO₂NHOCH₃ | H | OCH₃ | OCH₃ | CH | |
| 6-SCH₂CH₃ | SO₂NHOCH₃ | H | OCH₃ | CH₃ | CH | |
| 6-SCH₂CH₃ | SO₂NHOCH₃ | H | Cl | OCH₃ | CH | |
| 6-SCH₂CH₃ | SO₂NHOCH₃ | H | CH₃ | CH₃ | CH | |
| 6-SCH₂CH₃ | SO₂NHOCH₃ | H | OCH₃ | OCH₃ | N | |
| 6-SCH₂CH₃ | SO₂NHOCH₃ | H | OCH₃ | CH₃ | N | |

TABLE I-continued

General Formula 1

| R₁ | R₂ | R | X | Y | Z | m.p.(°C.) |
|---|---|---|---|---|---|---|
| 6-SCH₂CH₃ | SO₂NHOCH₃ | H | OCH₂CH₃ | NHCH₃ | N | |
| 6-SCH₂CH₃ | SO₂NHOCH₃ | CH₃ | OCH₃ | CH₃ | N | |
| 6-N(CH₃)₂ | SO₂NHOCH₃ | H | OCH₃ | OCH₃ | CH | |
| 6-N(CH₃)₂ | SO₂NHOCH₃ | H | OCH₃ | CH₃ | CH | |
| 6-N(CH₃)₂ | SO₂NHOCH₃ | H | Cl | OCH₃ | CH | |
| 6-N(CH₃)₂ | SO₂NHOCH₃ | H | CH₃ | CH₃ | CH | |
| 6-N(CH₃)₂ | SO₂NHOCH₃ | H | OCH₃ | OCH₃ | N | |
| 6-N(CH₃)₂ | SO₂NHOCH₃ | H | OCH₃ | CH₃ | N | |
| 6-N(CH₃)₂ | SO₂NHOCH₃ | H | OCH₂CH₃ | NHCH₃ | N | |
| 6-N(CH₃)₂ | SO₂NHOCH₃ | CH₃ | OCH₃ | CH₃ | N | |
| 6-OCH₃ | SO₂NHOCH₃ | H | OCH₃ | OCH₃ | CH | |
| 6-OCH₃ | SO₂NHOCH₃ | H | OCH₃ | CH₃ | CH | |
| 6-OCH₃ | SO₂NHOCH₃ | H | Cl | OCH₃ | CH | |
| 6-OCH₃ | SO₂NHOCH₃ | H | CH₃ | CH₃ | CH | |
| 6-OCH₃ | SO₂NHOCH₃ | H | OCH₃ | OCH₃ | N | |
| 6-OCH₃ | SO₂NHOCH₃ | H | OCH₃ | CH₃ | N | |
| 6-OCH₃ | SO₂NHOCH₃ | H | OCH₂CH₃ | NHCH₃ | N | |
| 6-OCH₃ | SO₂NHOCH₃ | CH₃ | OCH₃ | CH₃ | N | |
| 6-OCH₃ | SO₂NHCH₃ | H | OCH₃ | OCH₃ | CH | |
| 6-OCH₃ | SO₂NHCH₃ | H | OCH₃ | CH₃ | CH | |
| 6-OCH₃ | SO₂NHCH₃ | H | Cl | OCH₃ | CH | |
| 6-OCH₃ | SO₂NHCH₃ | H | CH₃ | CH₃ | CH | |
| 6-OCH₃ | SO₂NHCH₃ | H | OCH₃ | OCH₃ | N | |
| 6-OCH₃ | SO₂NHCH₃ | H | OCH₃ | CH₃ | N | |
| 6-OCH₃ | SO₂NHCH₃ | H | OCH₂CH₃ | NHCH₃ | N | |
| 6-OCH₃ | SO₂NHCH₃ | CH₃ | OCH₃ | CH₃ | N | |
| 6-SCH₃ | SO₂NHCH₃ | H | OCH₃ | OCH₃ | CH | |
| 6-SCH₃ | SO₂NHCH₃ | H | OCH₃ | CH₃ | CH | |
| 6-SCH₃ | SO₂NHCH₃ | H | Cl | OCH₃ | CH | |
| 6-SCH₃ | SO₂NHCH₃ | H | CH₃ | CH₃ | CH | |
| 6-SCH₃ | SO₂NHCH₃ | H | OCH₃ | OCH₃ | N | |
| 6-SCH₃ | SO₂NHCH₃ | H | OCH₃ | CH₃ | N | |
| 6-SCH₃ | SO₂NHCH₃ | H | OCH₂CH₃ | NHCH₃ | N | |
| 6-SCH₃ | SO₂NHCH₃ | CH₃ | OCH₃ | CH₃ | N | |
| H | SO₂NHCH₃ | H | OCH₃ | OCH₃ | CH | 147–148.5 |
| H | SO₂NHCH₃ | H | OCH₃ | CH₃ | CH | |
| H | SO₂NHCH₃ | H | Cl | OCH₃ | CH | 155–157 |
| H | SO₂NHCH₃ | H | CH₃ | CH₃ | CH | 150–152 |
| H | SO₂NHCH₃ | H | OCH₃ | OCH₃ | N | |
| H | SO₂NHCH₃ | H | OCH₃ | CH₃ | N | 153.5–155 |
| H | SO₂NHCH₃ | H | OCH₂CH₃ | NHCH₃ | N | |
| H | SO₂NHCH₃ | CH₃ | OCH₃ | CH₃ | N | |
| 4-CH₃ | SO₂NHCH₃ | H | OCH₃ | OCH₃ | CH | |
| 4-OCH₃ | SO₂NHCH₃ | H | OCH₃ | OCH₃ | CH | |
| 6-CH₃ | SO₂NHCH₃ | H | OCH₃ | OCH₃ | CH | |
| 6-F | SO₂NHCH₃ | H | OCH₃ | OCH₃ | CH | |
| 6-Cl | SO₂NHCH₃ | H | OCH₃ | OCH₃ | CH | |
| H | SO₂NHCH₂CH₃ | H | OCH₃ | OCH₃ | CH | 163–165.5 |
| H | SO₂NHCH₂CH₃ | H | OCH₃ | CH₃ | CH | |
| H | SO₂NHCH₂CH₃ | H | Cl | OCH₃ | CH | 158.5–161 |
| H | SO₂NHCH₂CH₃ | H | CH₃ | CH₃ | CH | 118–121.5 |
| H | SO₂NHCH₂CH₃ | H | OCH₃ | OCH₃ | N | 162–164 |
| H | SO₂NHCH₂CH₃ | H | OCH₃ | CH₃ | N | 158–160 |
| H | SO₂NHCH₂CH₃ | H | OCH₂CH₃ | NHCH₃ | N | |
| H | SO₂NHCH₂CH₃ | CH₃ | OCH₃ | CH₃ | N | 122–125.5 |
| 4-CH₃ | SO₂NHCH₂CH₃ | H | OCH₃ | OCH₃ | CH | |
| 4-OCH₃ | SO₂NHCH₂CH₃ | H | OCH₃ | OCH₃ | CH | |
| 6-CH₃ | SO₂NHCH₂CH₃ | H | OCH₃ | OCH₃ | CH | |
| 6-OCH₃ | SO₂NHCH₂CH₃ | H | OCH₃ | OCH₃ | CH | |
| 6-F | SO₂NHCH₂CH₃ | H | OCH₃ | OCH₃ | CH | |
| 6-Cl | SO₂NHCH₂CH₃ | H | OCH₃ | OCH₃ | CH | |
| H | SO₂NHCH₂CH₂CH₃ | H | OCH₃ | OCH₃ | CH | 138.5–141 |
| H | SO₂NHCH₂CH₂CH₃ | H | OCH₃ | CH₃ | CH | 117–120 |
| H | SO₂NHCH₂CH₂CH₃ | H | Cl | OCH₃ | CH | 125–129 |
| H | SO₂NHCH₂CH₂CH₃ | H | CH₃ | CH₃ | CH | |
| H | SO₂NHCH₂CH₂CH₃ | H | OCH₃ | OCH₃ | N | 132–135 |
| H | SO₂NHCH₂CH₂CH₃ | H | OCH₃ | CH₃ | N | |
| H | SO₂NHCH₂CH₂CH₃ | H | OCH₂CH₃ | NHCH₃ | N | |
| H | SO₂NHCH₂CH₂CH₃ | CH₃ | OCH₃ | CH₃ | N | |
| 4-CH₃ | SO₂NHCH₂CH₂CH₃ | H | OCH₃ | OCH₃ | CH | |
| 4-OCH₃ | SO₂NHCH₂CH₂CH₃ | H | OCH₃ | OCH₃ | CH | |
| 6-CH₃ | SO₂NHCH₂CH₂CH₃ | H | OCH₃ | OCH₃ | CH | |
| 6-OCH₃ | SO₂NHCH₂CH₂CH₃ | H | OCH₃ | OCH₃ | CH | |
| 6-F | SO₂NHCH₂CH₂CH₃ | H | OCH₃ | OCH₃ | CH | |
| 6-Cl | SO₂NHCH₂CH₂CH₃ | H | OCH₃ | OCH₃ | CH | |
| H | SO₂NHCH(CH₃)₂ | H | OCH₃ | OCH₃ | CH | 164–166 |
| H | SO₂NHCH(CH₃)₂ | H | OCH₃ | CH₃ | CH₃ | |
| H | SO₂NHCH(CH₃)₂ | H | Cl | OCH₃ | CH | 153.5–156 |
| H | SO₂NHCH(CH₃)₂ | H | CH₃ | CH₃ | CH | |
| H | SO₂NHCH(CH₃)₂ | H | OCH₃ | OCH₃ | N | 149–152 |

TABLE I-continued

General Formula 1

| R₁ | R₂ | R | X | Y | Z | m.p.(°C.) |
|---|---|---|---|---|---|---|
| H | SO₂NHCH(CH₃)₂ | H | OCH₃ | OCH₃ | N | 149–151 |
| H | SO₂NHCH(CH₃)₂ | H | OCH₂CH₃ | NHCH₃ | N | |
| H | SO₂NHCH(CH₃)₂ | CH₃ | OCH₃ | CH₃ | N | 141–143 |
| 4-CH₃ | SO₂NHCH(CH₃)₂ | H | OCH₃ | OCH₃ | CH | |
| 4-OCH₃ | SO₂NHCH(CH₃)₂ | H | OCH₃ | OCH₃ | CH | |
| 6-CH₃ | SO₂NHCH(CH₃)₂ | H | OCH₃ | OCH₃ | CH | |
| 6-OCH₃ | SO₂NHCH(CH₃)₂ | H | OCH₃ | OCH₃ | CH | |
| 6-F | SO₂NHCH(CH₃)₂ | H | OCH₃ | OCH₃ | CH | |
| 6-Cl | SO₂NHCH(CH₃)₂ | H | OCH₃ | OCH₃ | CH | |
| H | SO₂NHcyclopropyl | H | OCH₃ | OCH₃ | CH | |
| H | SO₂NHcyclopropyl | H | OCH₃ | CH₃ | CH | |
| H | SO₂NHcyclopropyl | H | Cl | OCH₃ | CH | |
| H | SO₂NHcyclopropyl | H | CH₃ | CH₃ | CH | |
| H | SO₂NHcyclopropyl | H | OCH₃ | OCH₃ | N | |
| H | SO₂NHcyclopropyl | H | OCH₃ | CH₃ | N | |
| H | SO₂NHcyclopropyl | H | OCH₂CH₃ | NHCH₃ | N | |
| H | SO₂NHcyclopropyl | CH₃ | OCH₃ | CH₃ | N | |
| 4-CH₃ | SO₂NHcyclopropyl | H | OCH₃ | OCH₃ | CH | |
| 4-OCH₃ | SO₂NHcyclopropyl | H | OCH₃ | OCH₃ | CH | |
| 6-CH₃ | SO₂NHcyclopropyl | H | OCH₃ | OCH₃ | CH | |
| 6-OCH₃ | SO₂NHcyclopropyl | H | OCH₃ | OCH₃ | CH | |
| 6-F | SO₂NHcyclopropyl | H | OCH₃ | OCH₃ | CH | |
| 6-Cl | SO₂NHcyclopropyl | H | OCH₃ | OCH₃ | CH | |
| H | SO₂NHCH₂CH=CH₂ | H | OCH₃ | OCH₃ | CH | |
| H | SO₂NHCH₂CH=CH₂ | H | OCH₃ | CH₃ | CH | |
| H | SO₂NHCH₂CH=CH₂ | H | CL | OCH₃ | CH | |
| H | SO₂NHCH₂CH=CH₂ | H | CH₃ | CH₃ | CH | |
| H | SO₂NHCH₂CH=CH₂ | H | OCH₃ | OCH₃ | N | |
| H | SO₂NHCH₂CH=CH₂ | H | OCH₃ | CH₃ | N | |
| H | SO₂NHCH₂CH=CH₂ | H | OCH₂CH₃ | NHCH₃ | N | |
| H | SO₂NHCH₂CH=CH₂ | CH₃ | OCH₃ | CH₃ | N | |
| 4-CH₃ | SO₂NHCH₂CH=CH₂ | H | OCH₃ | OCH₃ | CH | |
| 4-OCH₃ | SO₂NHCH₂CH=CH₂ | H | OCH₃ | OCH₃ | CH | |
| 6-CH₃ | SO₂NHCH₂CH=CH₂ | H | OCH₃ | OCH₃ | CH | |
| 6-OCH₃ | SO₂NHCH₂CH=CH₂ | H | OCH₃ | OCH₃ | CH | |
| 6-F | SO₂NHCH₂CH=CH₂ | H | OCH₃ | OCH₃ | CH | |
| 6-Cl | SO₂NHCH₂CH=CH₂ | H | OCH₃ | OCH₃ | CH | |
| H | SO₂NHCH₂C≡CH | H | OCH₃ | OCH₃ | CH | |
| H | SO₂NHCH₂C≡CH | H | OCH₃ | CH₃ | CH | |
| H | SO₂NHCH₂C≡CH | H | Cl | OCH₃ | CH | |
| H | SO₂NHCH₂C≡CH | H | CH₃ | CH₃ | CH | |
| H | SO₂NHCH₂C≡CH | H | OCH₃ | OCH₃ | N | |
| H | SO₂NHCH₂C≡CH | H | OCH₃ | CH₃ | N | |
| H | SO₂NHCH₂C≡CH | H | OCH₂CH₃ | NHCH₃ | N | |
| H | SO₂NHCH₂C≡CH | CH₃ | OCH₃ | CH₃ | N | |
| 4-CH₃ | SO₂NHCH₂C≡CH | H | OCH₃ | OCH₃ | CH | |
| 4-OCH₃ | SO₂NHCH₂C≡CH | H | OCH₃ | OCH₃ | CH | |
| 6-CH₃ | SO₂NHCH₂C≡CH | H | OCH₃ | OCH₃ | CH | |
| 6-OCH | SO₂NHCH₂C≡CH | H | OCH₃ | OCH₃ | CH | |
| 6-F | SO₂NHCH₂C≡CH | H | OCH₃ | OCH₃ | CH | |
| 6-Cl | SO₂NHCH₂C≡CH | H | OCH₃ | OCH₃ | CH | |
| H | SO₂NHCH₂OCH₃ | H | OCH₃ | OCH₃ | CH | |
| H | SO₂NHCH₂OCH₃ | H | OCH₃ | CH₃ | CH | |
| H | SO₂NHCH₂OCH₃ | H | CL | OCH₃ | CH | |
| H | SO₂NHCH₂OCH₃ | H | CH₃ | CH₃ | CH | |
| H | SO₂NHCH₂OCH₃ | H | OCH₃ | OCH₃ | N | |
| H | SO₂NHCH₂OCH₃ | H | OCH₃ | CH₃ | N | |
| H | SO₂NHCH₂OCH₃ | H | OCH₂CH₃ | NHCH₃ | N | |
| H | SO₂NHCH₂OCH₃ | CH₃ | OCH₃ | CH₃ | N | |
| 4-CH₃ | SO₂NHCH₂OCH₃ | H | OCH₃ | OCH₃ | CH | |
| 4-OCH₃ | SO₂NHCH₂OCH₃ | H | OCH₃ | OCH₃ | CH | |
| 6-CH₃ | SO₂NHCH₂OCH₃ | H | OCH₃ | OCH₃ | CH | |
| 6-OCH₃ | SO₂NHCH₂OCH₃ | H | OCH₃ | OCH₃ | CH | |
| 6-F | SO₂NHCH₂OCH₃ | H | OCH₃ | OCH₃ | CH | |
| 6-Cl | SO₂NHCH₂OCH₃ | H | OCH₃ | OCH₃ | CH | |
| H | SO₂NHCH₂CF₃ | H | OCH₃ | OCH₃ | CH | |
| H | SO₂NHCH₂CF₃ | H | OCH₃ | CH₃ | CH | |
| H | SO₂NHCH₂CF₃ | H | Cl | OCH₃ | CH | |
| H | SO₂NHCH₂CF₃ | H | CH₃ | CH₃ | CH | |
| H | SO₂NHCH₂CF₃ | H | OCH₃ | OCH₃ | N | |
| H | SO₂NHCH₂CF₃ | H | OCH₃ | CH₃ | N | |
| H | SO₂NHCH₂CF₃ | H | OCH₂CH₃ | NHCH₃ | N | |
| H | SO₂NHCH₂CF₃ | CH₃ | OCH₃ | CH₃ | N | |
| 4-CH₃ | SO₂NHCH₂CF₃ | H | OCH₃ | OCH₃ | CH | |
| 4-OCH₃ | SO₂NHCH₂CF₃ | H | OCH₃ | OCH₃ | CH | |
| 6-CH₃ | SO₂NHCH₂CF₃ | H | OCH₃ | OCH₃ | CH | |
| 6-OCH | SO₂NHCH₂CF₃ | H | OCH₃ | OCH₃ | CH | |
| 6-F | SO₂NHCH₂CF₃ | H | OCH₃ | OCH₃ | CH | |
| 6-Cl | SO₂NHCH₂CN | H | OCH₃ | OCH₃ | CH | |
| H | SO₂NHCH₂CN | H | OCH₃ | OCH₃ | CH | |

TABLE I-continued

General Formula 1

| R₁ | R₂ | R | X | Y | Z | m.p.(°C.) |
|---|---|---|---|---|---|---|
| H | SO₂NHCH₂CN | H | OCH₃ | CH₃ | CH | |
| H | SO₂NHCH₂CN | H | CL | OCH₃ | CH | |
| H | SO₂NHCH₂CN | H | CH₃ | CH₃ | CH | |
| H | SO₂NHCH₂CN | H | OCH₃ | OCH₃ | N | |
| H | SO₂NHCH₂CN | H | OCH₃ | CH₃ | N | |
| H | SO₂NHCH₂CN | H | OCH₂CH₃ | NHCH₃ | N | |
| H | SO₂NHCH₂CN | CH₃ | OCH₃ | CH₃ | N | |
| 4-CH₃ | SO₂NHCH₂CN | H | OCH₃ | OCH₃ | CH | |
| 4-OCH₃ | SO₂NHCH₂CN | H | OCH₃ | OCH₃ | CH | |
| 6-CH₃ | SO₂NHCH₂CN | H | OCH₃ | OCH₃ | CH | |
| 6-OCH₃ | SO₂NHCH₂CN | H | OCH₃ | OCH₃ | CH | |
| 6-F | SO₂NHCH₂CN | H | OCH₃ | OCH₃ | CH | |
| 6-Cl | SO₂NHCH₂CN | H | OCH₃ | OCH₃ | CH | |
| H | SO₂N(CH₂CH=CH₂)₂ | H | OCH₃ | OCH₃ | CH | |
| H | SO₂N(CH₂CH=CH₂)₂ | H | OCH₃ | CH₃ | CH | |
| H | SO₂N(CH₂CH=CH₂)₂ | H | Cl | OCH₃ | CH | |
| H | SO₂N(CH₂CH=CH₂)₂ | H | CH₃ | CH₃ | CH | |
| H | SO₂N(CH₂CH=CH₂)₂ | H | OCH₃ | OCH₃ | N | |
| H | SO₂N(CH₂CH=CH₂)₂ | H | OCH₃ | CH₃ | N | |
| H | SO₂N(CH₂CH=CH₂)₂ | H | OCH₂CH₃ | NHCH₃ | N | |
| H | SO₂N(CH₂CH=CH₂)₂ | CH₃ | OCH₃ | CH₃ | N | |
| 4-CH₃ | SO₂N(CH₂CH=CH₂)₂ | H | OCH₃ | OCH₃ | CH | |
| 4-OCH₃ | SO₂N(CH₂CH=CH₂)₂ | H | OCH₃ | OCH₃ | CH | |
| 6-CH₃ | SO₂N(CH₂CH=CH₂)₂ | H | OCH₃ | OCH₃ | CH | |
| 6-OCH₃ | SO₂N(CH₂CH=CH₂)₂ | H | OCH₃ | OCH₃ | CH | |
| 6-F | SO₂N(CH₂CH=CH₂)₂ | H | OCH₃ | OCH₃ | CH | |
| 6-Cl | SO₂-pyrrolidino | H | OCH₃ | OCH₃ | CH | |
| H | SO₂-pyrrolidino | H | OCH₃ | OCH₃ | CH | |
| H | SO₂-pyrrolidino | H | OCH₃ | CH₃ | CH | |
| H | SO₂-pyrrolidino | H | CL | OCH₃ | CH | |
| H | SO₂-pyrrolidino | H | CH₃ | CH₃ | CH | |
| H | SO₂-pyrrolidino | H | OCH₃ | OCH₃ | N | |
| H | SO₂-pyrrolidino | H | OCH₃ | CH₃ | N | |
| H | SO₂-pyrrolidino | H | OCH₂CH₃ | NHCH₃ | N | |
| H | SO₂-pyrrolidino | CH₃ | OCH₃ | CH₃ | N | |
| 4-CH₃ | SO₂-pyrrolidino | H | OCH₃ | OCH₃ | CH | |
| 4-OCH₃ | SO₂-pyrrolidino | H | OCH₃ | OCH₃ | CH | |
| 6-CH₃ | SO₂-pyrrolidino | H | OCH₃ | OCH₃ | CH | |
| 6-OCH₃ | SO₂-pyrrolidino | H | OCH₃ | OCH₃ | CH | |
| 6-F | SO₂-pyrrolidino | H | OCH₃ | OCH₃ | CH | |
| 6-Cl | SO₂-pyrrolidino | H | OCH₃ | OCH₃ | CH | |
| H | SO₂NHCH₂CH₂OCH₃ | H | OCH₃ | OCH₃ | CH | |
| H | SO₂NHCH₂CH₂OCH₃ | H | OCH₃ | CH₃ | CH | |
| H | SO₂NHCH₂CH₂OCH₃ | H | Cl | OCH₃ | CH | |
| H | SO₂NHCH₂CH₂OCH₃ | H | CH₃ | CH₃ | CH | |
| H | SO₂NHCH₂CH₂OCH₃ | H | OCH₃ | OCH₃ | N | |
| H | SO₂NHCH₂CH₂OCH₃ | H | OCH₃ | CH₃ | N | |
| H | SO₂NHCH₂CH₂OCH₃ | H | OCH₂CH₃ | NHCH₃ | N | |
| H | SO₂NHCH₂CH₂OCH₃ | CH₃ | OCH₃ | CH₃ | N | |
| 4-CH₃ | SO₂NHCH₂CH₂OCH₃ | H | OCH₃ | OCH₃ | CH | |
| 4-OCH₃ | SO₂NHCH₂CH₂OCH₃ | H | OCH₃ | OCH₃ | CH | |
| 6-CH₃ | SO₂NHCH₂CH₂OCH₃ | H | OCH₃ | OCH₃ | CH | |
| 6-OCH₃ | SO₂NHCH₂CH₂OCH₃ | H | OCH₃ | OCH₃ | CH | |
| 6-F | SO₂NHCH₂CH₂OCH₃ | H | OCH₃ | OCH₃ | CH | |
| 6-Cl | SO₂NHCH₂CH₂OCH₃ | H | OCH₃ | OCH₃ | CH | |
| H | SO₂-pyrrolidino | H | OCH₃ | OCH₃ | CH | 146–149 |
| H | SO₂-pyrrolidino | H | CH₃ | CH₃ | CH | 169–171 |
| 6-CH₂CH₃ | CO₂CH₃ | H | OCH₃ | OCH₃ | CH | |
| 6-CH₂CH₃ | CO₂CH₃ | H | OCH₃ | CH₃ | CH | |
| 6-CH₂CH₃ | CO₂CH₃ | H | Cl | OCH₃ | CH | |
| 6-CH₂CH₃ | CO₂CH₃ | H | CH₃ | CH₃ | CH | |
| 6-CH₂CH₃ | CO₂CH₃ | H | OCH₃ | OCH₃ | N | |
| 6-CH₂CH₃ | CO₂CH₃ | H | OCH₃ | CH₃ | N | |
| 6-CH₂CH₃ | CO₂CH₃ | H | OCH₂CH₃ | NHCH₃ | N | |
| 6-CH₂CH₃ | CO₂CH₃ | CH₃ | OCH₃ | CH₃ | N | |
| 6-OCH₃ | CO₂CH₃ | H | OCH₃ | OCH₃ | CH | 194–196 |
| 6-OCH₃ | CO₂CH₃ | H | OCH₃ | CH₃ | CH | 165–167 |
| 6-OCH₃ | CO₂CH₃ | H | Cl | OCH₃ | CH | 173–175 |
| 6-OCH₃ | CO₂CH₃ | H | CH₃ | CH₃ | CH | 138.5–145 |
| 6-OCH₃ | CO₂CH₃ | H | OCH₃ | OCH₃ | N | 173–176 |
| 6-OCH₃ | CO₂CH₃ | H | OCH₃ | CH₃ | N | 158–161 |
| 6-OCH₃ | CO₂CH₃ | H | OCH₂CH₃ | NHCH₃ | N | |
| 6-OCH₃ | CO₂CH₃ | CH₃ | OCH₃ | CH₃ | N | |
| 6-OCH₂CH₃ | CO₂CH₃ | H | OCH₃ | OCH₃ | CH | 154–157 |
| 6-OCH₂CH₃ | CO₂CH₃ | H | OCH₃ | CH₃ | CH | 160–162 |
| 6-OCH₂CH₃ | CO₂CH₃ | H | Cl | OCH₃ | CH | 130–132 |
| 6-OCH₂CH₃ | CO₂CH₃ | H | CH₃ | CH₃ | CH | 140–141 |
| 6-OCH₂CH₃ | CO₂CH₃ | H | OCH₃ | OCH₃ | N | 160–162 |
| 6-OCH₂CH₃ | CO₂CH₃ | H | OCH₃ | CH₃ | N | 152–153 |
| 6-OCH₂CH₃ | CO₂CH₃ | H | OCH₂CH₃ | NHCH₃ | N | |

TABLE I-continued

General Formula 1

| R₁ | R₂ | R | X | Y | Z | m.p.(°C.) |
|---|---|---|---|---|---|---|
| 6-OCH₂CH₃ | CO₂CH₃ | CH₃ | OCH₃ | CH₃ | N | |
| 6-OCF₃ | CO₂CH₃ | H | OCH₃ | OCH₃ | CH | |
| 6-OCF₃ | CO₂CH₃ | H | OCH₃ | CH₃ | CH | |
| 6-OCF₃ | CO₂CH₃ | H | Cl | OCH₃ | CH | |
| 6-OCF₃ | CO₂CH₃ | H | CH₃ | CH₃ | CH | |
| 6-OCF₃ | CO₂CH₃ | H | OCH₃ | OCH₃ | N | |
| 6-OCF₃ | CO₂CH₃ | H | OCH₃ | CH₃ | N | |
| 6-OCH₂CF₃ | CO₂CH₃ | H | OCH₃ | OCH₃ | CH | 158–162 |
| 6-OCH₂CF₃ | CO₂CH₃ | H | OCH₃ | CH₃ | CH | 168–170 |
| 6-OCH₂CF₃ | CO₂CH₃ | H | Cl | OCH₃ | CH | 149–150 |
| 6-OCH₂CF₃ | CO₂CH₃ | H | CH₃ | CH₃ | CH | 150–152 |
| 6-OCH₂CF₃ | CO₂CH₃ | H | OCH₃ | OCH₃ | N | |
| 6-OCH₂CF₃ | CO₂CH₃ | H | OCH₃ | CH₃ | N | |
| 6-OCH₂CF₃ | CO₂CH₃ | H | OCH₂CH₃ | NHCH₃ | N | |
| 6-OCH₂CF₃ | CO₂CH₃ | CH₃ | OCH₃ | CH₃ | N | |
| 6-OCF₃ | CO₂CH₃ | H | OCH₂CH₃ | NHCH₃ | N | |
| 6-OCF₃ | CO₂CH₃ | CH₃ | OCH₃ | CH₃ | N | |
| 6-OCF₂H | CO₂CH₃ | H | OCH₃ | OCH₃ | CH | |
| 6-OCF₂H | CO₂CH₃ | H | OCH₃ | CH₃ | CH | |
| 6-OCF₂H | CO₂CH₃ | H | Cl | OCH₃ | CH | |
| 6-OCF₂H | CO₂CH₃ | H | CH₃ | CH₃ | CH | |
| 6-OCF₂H | CO₂CH₃ | H | OCH₃ | OCH₃ | N | |
| 6-OCF₂H | CO₂CH₃ | H | OCH₃ | CH₃ | N | |
| 6-OCF₂H | CO₂CH₃ | H | OCH₂CH₃ | NHCH₃ | N | |
| 6-OCF₂H | CO₂CH₃ | CH₃ | OCH₃ | CH₃ | N | |
| 6-SCH₃ | CO₂CH₃ | H | OCH₃ | OCH₃ | CH | |
| 6-SCH₃ | CO₂CH₃ | H | OCH₃ | CH₃ | CH | |
| 6-SCH₃ | CO₂CH₃ | H | Cl | OCH₃ | CH | |
| 6-SCH₃ | CO₂CH₃ | H | CH₃ | CH₃ | CH | |
| 6-SCH₃ | CO₂CH₃ | H | OCH₃ | OCH₃ | N | |
| 6-SCH₃ | CO₂CH₃ | H | OCH₃ | CH₃ | N | |
| 6-SCH₃ | CO₂CH₃ | H | OCH₂CH₃ | NHCH₃ | N | |
| 6-SCH₃ | CO₂CH₃ | CH₃ | OCH₃ | CH₃ | N | |
| 6-SCH₂CH₃ | CO₂CH₃ | H | OCH₃ | OCH₃ | CH | |
| 6-SCH₂CH₃ | CO₂CH₃ | H | OCH₃ | CH₃ | CH | |
| 6-SCH₂CH₃ | CO₂CH₃ | H | Cl | OCH₃ | CH | |
| 6-SCH₂CH₃ | CO₂CH₃ | H | CH₃ | CH₃ | CH | |
| 6-SCH₂CH₃ | CO₂CH₃ | H | OCH₃ | OCH₃ | N | |
| 6-SCH₂CH₃ | CO₂CH₃ | H | OCH₃ | CH₃ | N | |
| 6-SCH₂CH₃ | CO₂CH₃ | H | OCH₂CH₃ | NHCH₃ | N | |
| 6-SCH₂CH₃ | CO₂CH₃ | CH₃ | OCH₃ | CH₃ | N | |
| 6-N(CH₃)₂ | CO₂CH₃ | H | OCH₃ | OCH₃ | CH | 164–167 |
| 6-N(CH₃)₂ | CO₂CH₃ | H | OCH₃ | CH₃ | CH | 178–179 |
| 6-N(CH₃)₂ | CO₂CH₃ | H | Cl | OCH₃ | CH | 147–150 |
| 6-N(CH₃)₂ | CO₂CH₃ | H | CH₃ | CH₃ | CH | 164–165 |
| 6-N(CH₃)₂ | CO₂CH₃ | H | OCH₃ | OCH₃ | N | 171–172 |
| 6-N(CH₃)₂ | CO₂CH₃ | H | OCH₃ | CH₃ | N | 132–134 |
| 6-N(CH₃)₂ | CO₂CH₃ | H | OCH₂CH₃ | NHCH₃ | N | 152–155 |
| 6-N(CH₃)₂ | CO₂CH₃ | CH₃ | OCH₃ | CH₃ | N | |
| 6-NHCH₃ | CO₂CH₃ | H | OCH₃ | OCH₃ | CH | |
| 6-NHCH₃ | CO₂CH₃ | H | OCH₃ | CH₃ | CH | |
| 6-NHCH₃ | CO₂CH₃ | H | Cl | OCH₃ | CH | |
| 6-NHCH₃ | CO₂CH₃ | H | CH₃ | CH₃ | CH | |
| 6-NHCH₃ | CO₂CH₃ | H | OCH₃ | OCH₃ | N | |
| 6-NHCH₃ | CO₂CH₃ | H | OCH₃ | CH₃ | N | |
| 6-NHCH₃ | CO₂CH₃ | H | OCH₂CH₃ | NHCH₃ | N | |
| 6-NHCH₃ | CO₂CH₃ | CH₃ | OCH₃ | CH₃ | N | |
| 6-CH₂CH₃ | CO₂CH₂CH₃ | H | OCH₃ | OCH₃ | CH | |
| 6-CH₂CH₃ | CO₂CH₂CH₃ | H | OCH₃ | CH₃ | CH | |
| 6-CH₂CH₃ | CO₂CH₂CH₃ | H | Cl | OCH₃ | CH | |
| 6-CH₂CH₃ | CO₂CH₂CH₃ | H | CH₃ | CH₃ | CH | |
| 6-CH₂CH₃ | CO₂CH₂CH₃ | H | OCH₃ | OCH₃ | N | |
| 6-CH₂CH₃ | CO₂CH₂CH₃ | H | OCH₃ | CH₃ | N | |
| 6-CH₂CH₃ | CO₂CH₂CH₃ | H | OCH₂CH₃ | NHCH₃ | N | |
| 6-CH₂CH₃ | CO₂CH₂CH₃ | CH₃ | OCH₃ | CH₃ | N | |
| 6-OCH₃ | CO₂CH₂CH₃ | H | OCH₃ | OCH₃ | CH | 158–161 |
| 6-OCH₃ | CO₂CH₂CH₃ | H | OCH₃ | CH₃ | CH | 147–149 |
| 6-OCH₃ | CO₂CH₂CH₃ | H | Cl | OCH₃ | CH | 124–127 |
| 6-OCH₃ | CO₂CH₂CH₃ | H | CH₃ | CH₃ | CH | 149–151 |
| 6-OCH₃ | CO₂CH₂CH₃ | H | OCH₃ | OCH₃ | N | 164–165 |
| 6-OCH₃ | CO₂CH₂CH₃ | H | OCH₃ | CH₃ | N | 131–132 |
| 6-OCH₃ | CO₂CH₂CH₃ | H | OCH₂CH₃ | NHCH₃ | N | |
| 6-OCH₃ | CO₂CH₂CH₃ | CH₃ | OCH₃ | CH₃ | N | |
| 6-OCH₂CH₃ | CO₂CH₂CH₃ | H | OCH₃ | OCH₃ | CH | 152–154 |
| 6-OCH₂CH₃ | CO₂CH₂CH₃ | H | OCH₃ | CH₃ | CH | 134–135 |
| 6-OCH₂CH₃ | CO₂CH₂CH₃ | H | Cl | OCH₃ | CH | 153–160 |
| 6-OCH₂CH₃ | CO₂CH₂CH₃ | H | CH₃ | CH₃ | CH | 159–163 |
| 6-OCH₂CH₃ | CO₂CH₂CH₃ | H | OCH₃ | OCH₃ | N | 320–330 |
| 6-OCH₂CH₃ | CO₂CH₂CH₃ | H | OCH₃ | CH₃ | N | |
| 6-OCH₂CH₃ | CO₂CH₂CH₃ | H | OCH₂CH₃ | NHCH₃ | N | |

TABLE I-continued

General Formula 1

| $R_1$ | $R_2$ | R | X | Y | Z | m.p.(°C.) |
|---|---|---|---|---|---|---|
| 6-OCH$_2$CH$_3$ | CO$_2$CH$_2$CH$_3$ | CH$_3$ | OCH$_3$ | CH$_3$ | N | |
| 6-OCH$_2$CF$_3$ | CO$_2$CH$_2$CH$_3$ | H | OCH$_3$ | OCH$_3$ | CH | 173–175 |
| 6-OCH$_2$CF$_3$ | CO$_2$CH$_2$CH$_3$ | H | OCH$_3$ | CH$_3$ | CH | 166–167 |
| 6-OCH$_2$CF$_3$ | CO$_2$CH$_2$CH$_3$ | H | Cl | OCH$_3$ | CH | 150–152 |
| 6-OCH$_2$CF$_3$ | CO$_2$CH$_2$CH$_3$ | H | CH$_3$ | CH$_3$ | CH | 142–144 |
| 6-OCH$_2$CF$_3$ | CO$_2$CH$_2$CH$_3$ | H | OCH$_3$ | OCH$_3$ | N | 138–141 |
| 6-OCH$_2$CF$_3$ | CO$_2$CH$_2$CH$_3$ | H | OCH$_3$ | CH$_3$ | N | 122–126 |
| 6-OCH$_2$CF$_3$ | CO$_2$CH$_2$CH$_3$ | H | OCH$_2$CH$_3$ | NHCH$_3$ | N | |
| 6-OCH$_2$CF$_3$ | CO$_2$CH$_2$CH$_3$ | CH$_3$ | OCH$_3$ | CH$_3$ | N | |
| 6-OCF$_3$ | CO$_2$CH$_2$CH$_3$ | H | OCH$_3$ | OCH$_3$ | CH | |
| 6-OCF$_3$ | CO$_2$CH$_2$CH$_3$ | H | OCH$_3$ | CH$_3$ | CH | |
| 6-OCF$_3$ | CO$_2$CH$_2$CH$_3$ | H | Cl | OCH$_3$ | CH | |
| 6-OCF$_3$ | CO$_2$CH$_2$CH$_3$ | H | CH$_3$ | CH$_3$ | CH | |
| 6-OCF$_3$ | CO$_2$CH$_2$CH$_3$ | H | OCH$_3$ | OCH$_3$ | N | |
| 6-OCF$_3$ | CO$_2$CH$_2$CH$_3$ | H | OCH$_3$ | CH$_3$ | N | |
| 6-OCF$_3$ | CO$_2$CH$_2$CH$_3$ | H | OCH$_2$CH$_3$ | NHCH$_3$ | N | |
| 6-OCF$_3$ | CO$_2$CH$_2$CH$_3$ | CH$_3$ | OCH$_3$ | CH$_3$ | N | |
| 6-OCF$_2$H | CO$_2$CH$_2$CH$_3$ | H | OCH$_3$ | OCH$_3$ | CH | |
| 6-OCF$_2$H | CO$_2$CH$_2$CH$_3$ | H | OCH$_3$ | CH$_3$ | CH | |
| 6-OCF$_2$H | CO$_2$CH$_2$CH$_3$ | H | Cl | OCH$_3$ | CH | |
| 6-OCF$_2$H | CO$_2$CH$_2$CH$_3$ | H | CH$_3$ | CH$_3$ | CH | |
| 6-OCF$_2$H | CO$_2$CH$_2$CH$_3$ | H | OCH$_3$ | OCH$_3$ | N | |
| 6-OCF$_2$H | CO$_2$CH$_2$CH$_3$ | H | OCH$_3$ | CH$_3$ | N | |
| 6-OCF$_2$H | CO$_2$CH$_2$CH$_3$ | H | OCH$_2$CH$_3$ | NHCH$_3$ | N | |
| 6-OCF$_2$H | CO$_2$CH$_2$CH$_3$ | CH$_3$ | OCH$_3$ | CH$_3$ | N | |
| 6-SCH$_3$ | CO$_2$CH$_2$CH$_3$ | H | OCH$_3$ | OCH$_3$ | CH | |
| 6-SCH$_3$ | CO$_2$CH$_2$CH$_3$ | H | OCH$_3$ | CH$_3$ | CH | |
| 6-SCH$_3$ | CO$_2$CH$_2$CH$_3$ | H | Cl | OCH$_3$ | CH | |
| 6-SCH$_3$ | CO$_2$CH$_2$CH$_3$ | H | CH$_3$ | CH$_3$ | CH | |
| 6-SCH$_3$ | CO$_2$CH$_2$CH$_3$ | H | OCH$_3$ | OCH$_3$ | N | |
| 6-SCH$_3$ | CO$_2$CH$_2$CH$_3$ | H | OCH$_3$ | CH$_3$ | N | |
| 6-SCH$_3$ | CO$_2$CH$_2$CH$_3$ | H | OCH$_2$CH$_3$ | NHCH$_3$ | N | |
| 6-SCH$_3$ | CO$_2$CH$_2$CH$_3$ | CH$_3$ | OCH$_3$ | CH$_3$ | N | |
| 6-SCH$_2$CH$_3$ | CO$_2$CH$_2$CH$_3$ | H | OCH$_3$ | OCH$_3$ | CH | |
| 6-SCH$_2$CH$_3$ | CO$_2$CH$_2$CH$_3$ | H | OCH$_3$ | CH$_3$ | CH | |
| 6-SCH$_2$CH$_3$ | CO$_2$CH$_2$CH$_3$ | H | Cl | OCH$_3$ | CH | |
| 6-SCH$_2$CH$_3$ | CO$_2$CH$_2$CH$_3$ | H | CH$_3$ | CH$_3$ | CH | |
| 6-SCH$_2$CH$_3$ | CO$_2$CH$_2$CH$_3$ | H | OCH$_3$ | OCH$_3$ | N | |
| 6-SCH$_2$CH$_3$ | CO$_2$CH$_2$CH$_3$ | H | OCH$_3$ | CH$_3$ | N | |
| 6-SCH$_2$CH$_3$ | CO$_2$CH$_2$CH$_3$ | H | OCH$_2$CH$_3$ | NHCH$_3$ | N | |
| 6-SCH$_2$CH$_3$ | CO$_2$CH$_2$CH$_3$ | CH$_3$ | OCH$_3$ | CH$_3$ | N | |
| 6-N(CH$_3$)$_2$ | CO$_2$CH$_2$CH$_3$ | H | OCH$_3$ | OCH$_3$ | CH | 147–149 |
| 6-N(CH$_3$)$_2$ | CO$_2$CH$_2$CH$_3$ | H | OCH$_3$ | CH$_3$ | CH | 149–150 |
| 6-N(CH$_3$)$_2$ | CO$_2$CH$_2$CH$_3$ | H | Cl | OCH$_3$ | CH | 150–151 |
| 6-N(CH$_3$)$_2$ | CO$_2$CH$_2$CH$_3$ | H | CH$_3$ | CH$_3$ | CH | 172–175 |
| 6-N(CH$_3$)$_2$ | CO$_2$CH$_2$CH$_3$ | H | OCH$_3$ | OCH$_3$ | N | 152–153 |
| 6-N(CH$_3$)$_2$ | CO$_2$CH$_2$CH$_3$ | H | OCH$_3$ | CH$_3$ | N | 148–150 |
| 6-N(CH$_3$)$_2$ | CO$_2$CH$_2$CH$_3$ | H | OCH$_2$CH$_3$ | NHCH$_3$ | N | |
| 6-N(CH$_3$)$_2$ | CO$_2$CH$_2$CH$_3$ | CH$_3$ | OCH$_3$ | CH$_3$ | N | |
| 6-NHCH$_3$ | CO$_2$CH$_2$CH$_3$ | H | OCH$_3$ | OCH$_3$ | CH | |
| 6-NHCH$_3$ | CO$_2$CH$_2$CH$_3$ | H | OCH$_3$ | CH$_3$ | CH | |
| 6-NHCH$_3$ | CO$_2$CH$_2$CH$_3$ | H | Cl | OCH$_3$ | CH | |
| 6-NHCH$_3$ | CO$_2$CH$_2$CH$_3$ | H | CH$_3$ | CH$_3$ | CH | |
| 6-NHCH$_3$ | CO$_2$CH$_2$CH$_3$ | H | OCH$_3$ | OCH$_3$ | N | |
| 6-NHCH$_3$ | CO$_2$CH$_2$CH$_3$ | H | OCH$_3$ | CH$_3$ | N | |
| 6-NHCH$_3$ | CO$_2$CH$_2$CH$_3$ | H | OCH$_2$CH$_3$ | NHCH$_3$ | N | |
| 6-NHCH$_3$ | CO$_2$CH$_2$CH$_3$ | CH$_3$ | OCH$_3$ | CH$_3$ | N | |
| H | CO$_2$CH$_2$CH$_2$OH | H | OCH$_3$ | OCH$_3$ | CH | |
| H | CO$_2$CH$_2$CH$_2$OH | H | OCH$_3$ | CH$_3$ | CH | |
| H | CO$_2$CH$_2$CH$_2$OH | H | Cl | OCH$_3$ | CH | |
| H | CO$_2$CH$_2$CH$_2$OH | H | CH$_3$ | CH$_3$ | CH | |
| H | CO$_2$CH$_2$CH$_2$OH | H | OCH$_3$ | OCH$_3$ | N | |
| H | CO$_2$CH$_2$CH$_2$OH | H | OCH$_3$ | CH$_3$ | N | |
| H | CO$_2$CH$_2$CH$_2$OH | H | OCH$_2$CH$_3$ | NHCH$_3$ | N | |
| H | CO$_2$CH$_2$CH$_2$OH | CH$_3$ | OCH$_3$ | CH$_3$ | N | |
| 4-CH$_3$ | CO$_2$CH$_2$CH$_2$OH | H | OCH$_3$ | OCH$_3$ | CH | |
| 4-OCH$_3$ | CO$_2$CH$_2$CH$_2$OH | H | OCH$_3$ | OCH$_3$ | CH | |
| 6-CH$_3$ | CO$_2$CH$_2$CH$_2$OH | H | OCH$_3$ | OCH$_3$ | CH | |
| 6-OCH$_3$ | CO$_2$CH$_2$CH$_2$OH | H | OCH$_3$ | OCH$_3$ | CH | |
| 6-F | CO$_2$CH$_2$CH$_2$OH | H | OCH$_3$ | OCH$_3$ | CH | |
| 6-Cl | CO$_2$CH$_2$CH$_2$OH | H | OCH$_3$ | OCH$_3$ | CH | |
| H | CO$_2$CH$_2$CH$_2$CN | H | OCH$_3$ | OCH$_3$ | CH | |
| H | CO$_2$CH$_2$CH$_2$CN | H | OCH$_3$ | CH$_3$ | CH | |
| H | CO$_2$CH$_2$CH$_2$CN | H | Cl | OCH$_3$ | CH | |
| H | CO$_2$CH$_2$CH$_2$CN | H | CH$_3$ | CH$_3$ | CH | |
| H | CO$_2$CH$_2$CH$_2$CN | H | OCH$_3$ | OCH$_3$ | N | |
| H | CO$_2$CH$_2$CH$_2$CN | H | OCH$_3$ | CH$_3$ | N | |
| H | CO$_2$CH$_2$CH$_2$CN | H | OCH$_2$CH$_3$ | NHCH$_3$ | N | |
| H | CO$_2$CH$_2$CH$_2$CN | CH$_3$ | OCH$_3$ | CH$_3$ | N | |
| 4-CH$_3$ | CO$_2$CH$_2$CH$_2$CN | H | OCH$_3$ | OCH$_3$ | CH | |

TABLE I-continued

General Formula 1

| R₁ | R₂ | R | X | Y | Z | m.p.(°C.) |
|---|---|---|---|---|---|---|
| 4-OCH₃ | CO₂CH₂CH₂CN | H | OCH₃ | OCH₃ | CH | |
| 6-CH₃ | CO₂CH₂CH₂CN | H | OCH₃ | OCH₃ | CH | |
| 6-OCH₃ | CO₂CH₂CH₂CN | H | OCH₃ | OCH₃ | CH | |
| 6-F | CO₂CH₂CH₂CN | H | OCH₃ | OCH₃ | CH | |
| 6-Cl | CO₂CH₂CH₂CN | H | OCH₃ | OCH₃ | CH | |
| H | CO₂CH₂CH₂OSO₂CH₃ | H | OCH₃ | OCH₃ | CH | |
| H | CO₂CH₂CH₂OSO₂CH₃ | H | OCH₃ | CH₃ | CH | |
| H | CO₂CH₂CH₂OSO₂CH₃ | H | Cl | OCH₃ | CH | |
| H | CO₂CH₂CH₂OSO₂CH₃ | H | CH₃ | CH₃ | CH | |
| H | CO₂CH₂CH₂OSO₂CH₃ | H | OCH₃ | OCH₃ | N | |
| H | CO₂CH₂CH₂OSO₂CH₃ | H | OCH₃ | CH₃ | N | |
| H | CO₂CH₂CH₂OSO₂CH₃ | H | OCH₂CH₃ | NHCH₃ | N | |
| H | CO₂CH₂CH₂OSO₂CH₃ | CH₃ | OCH₃ | CH₃ | N | |
| 4-CH₃ | CO₂CH₂CH₂OSO₂CH₃ | H | OCH₃ | OCH₃ | CH | |
| 4-OCH₃ | CO₂CH₂CH₂OSO₂CH₃ | H | OCH₃ | OCH₃ | CH | |
| 6-CH₃ | CO₂CH₂CH₂OSO₂CH₃ | H | OCH₃ | OCH₃ | CH | |
| 6-OCH₃ | CO₂CH₂CH₂OSO₂CH₃ | H | OCH₃ | OCH₃ | CH | |
| 6-F | CO₂CH₂CH₂OSO₂CH₃ | H | OCH₃ | OCH₃ | CH | |
| 6-Cl | CO₂CH₂CH₂OSO₂CH₃ | H | OCH₃ | OCH₃ | CH | |
| H | CO₂CH₂CH₂OSO₂CF₃ | H | OCH₃ | OCH₃ | CH | |
| H | CO₂CH₂CH₂OSO₂CF₃ | H | OCH₃ | CH₃ | CH | |
| H | CO₂CH₂CH₂OSO₂CF₃ | H | Cl | OCH₃ | CH | |
| H | CO₂CH₂CH₂OSO₂CF₃ | H | CH₃ | CH₃ | CH | |
| H | CO₂CH₂CH₂OSO₂CF₃ | H | OCH₃ | OCH₃ | N | |
| H | CO₂CH₂CH₂OSO₂CF₃ | H | OCH₃ | CH₃ | N | |
| H | CO₂CH₂CH₂OSO₂CF₃ | H | OCH₂CH₃ | NHCH₃ | N | |
| H | CO₂CH₂CH₂OSO₂CF₃ | CH₃ | OCH₃ | CH₃ | N | |
| 4-CH₃ | CO₂CH₂CH₂OSO₂CF₃ | H | OCH₃ | OCH₃ | CH | |
| 4-OCH₃ | CO₂CH₂CH₂OSO₂CF₃ | H | OCH₃ | OCH₃ | CH | |
| 6-CH₃ | CO₂CH₂CH₂OSO₂CF₃ | H | OCH₃ | OCH₃ | CH | |
| 6-OCH₃ | CO₂CH₂CH₂OSO₂CF₃ | H | OCH₃ | OCH₃ | CH | |
| 6-F | CO₂CH₂CH₂OSO₂CF₃ | H | OCH₃ | OCH₃ | CH | |
| 6-Cl | CO₂CH₂CH₂OSO₂CF₃ | H | OCH₃ | OCH₃ | CH | |
| H | CO₂CH₂CF₃ | H | OCH₃ | OCH₃ | CH | |
| H | CO₂CH₂CF₃ | H | OCH₃ | CH₃ | CH | |
| H | CO₂CH₂CF₃ | H | Cl | OCH₃ | CH | |
| H | CO₂CH₂CF₃ | H | CH₃ | CH₃ | CH | |
| H | CO₂CH₂CF₃ | H | OCH₃ | OCH₃ | N | |
| H | CO₂CH₂CF₃ | H | OCH₃ | CH₃ | N | |
| H | CO₂CH₂CF₃ | H | OCH₂CH₃ | NHCH₃ | N | |
| H | CO₂CH₂CF₃ | CH₃ | OCH₃ | CH₃ | N | |
| 4-CH₃ | CO₂CH₂CF₃ | H | OCH₃ | OCH₃ | CH | |
| 4-OCH₃ | CO₂CH₂CF₃ | H | OCH₃ | OCH₃ | CH | |
| 6-CH₃ | CO₂CH₂CF₃ | H | OCH₃ | OCH₃ | CH | |
| 6-OCH₃ | CO₂CH₂CF₃ | H | OCH₃ | OCH₃ | CH | |
| 6-F | CO₂CH₂CF₃ | H | OCH₃ | OCH₃ | CH | |
| 6-Cl | CO₂CH₂CF₃ | H | OCH₃ | OCH₃ | CH | |
| H | CO₂CH₂C≡CH | H | OCH₃ | OCH₃ | CH | 127–128 |
| H | CO₂CH₂C≡CH | H | OCH₃ | CH₃ | CH | 142–144 |
| H | CO₂CH₂C≡CH | H | Cl | OCH₃ | CH | 154–156 |
| H | CO₂CH₂C≡CH | H | CH₃ | CH₃ | CH | 141–142 |
| H | CO₂CH₂C≡CH | H | OCH₃ | OCH₃ | N | 137–138 |
| H | CO₂CH₂C≡CH | H | OCH₃ | CH₃ | N | 136–137 |
| H | CO₂CH₂C≡CH | H | OCH₂CH₃ | NHCH₃ | N | |
| H | CO₂CH₂C≡CH | CH₃ | OCH₃ | CH₃ | N | |
| 4-CH₃ | CO₂CH₂C≡CH | H | OCH₃ | OCH₃ | CH | |
| 4-OCH₃ | CO₂CH₂C≡CH | H | OCH₃ | OCH₃ | CH | |
| 6-CH₃ | CO₂CH₂C≡CH | H | OCH₃ | OCH₃ | CH | |
| 6-OCH₃ | CO₂CH₂C≡CH | H | OCH₃ | OCH₃ | CH | |
| 6-F | CO₂CH₂C≡CH | H | OCH₃ | OCH₃ | CH | |
| 6-Cl | CO₂CH₂C≡CH | H | OCH₃ | OCH₃ | CH | |
| H | CO₂CH₂CH₂CH₂Cl | H | OCH₃ | OCH₃ | CH | |
| H | CO₂CH₂CH₂CH₂Cl | H | OCH₃ | CH₃ | CH | |
| H | CO₂CH₂CH₂CH₂Cl | H | Cl | OCH₃ | CH | |
| H | CO₂CH₂CH₂CH₂Cl | H | CH₃ | CH₃ | CH | |
| H | CO₂CH₂CH₂CH₂Cl | H | OCH₃ | OCH₃ | N | |
| H | CO₂CH₂CH₂CH₂Cl | H | OCH₃ | CH₃ | N | |
| H | CO₂CH₂CH₂CH₂Cl | H | OCH₂CH₃ | NHCH₃ | N | |
| H | CO₂CH₂CH₂CH₂Cl | CH₃ | OCH₃ | CH₃ | N | |
| 4-CH₃ | CO₂CH₂CH₂CH₂Cl | H | OCH₃ | OCH₃ | CH | |
| 4-OCH₃ | CO₂CH₂CH₂CH₂Cl | H | OCH₃ | OCH₃ | CH | |
| 6-CH₃ | CO₂CH₂CH₂CH₂Cl | H | OCH₃ | OCH₃ | CH | |
| 6-OCH₃ | CO₂CH₂CH₂CH₂Cl | H | OCH₃ | OCH₃ | CH | |
| 6-F | CO₂CH₂CH₂CH₂Cl | H | OCH₃ | OCH₃ | CH | |
| 6-Cl | CO₂CH₂CH₂CH₂Cl | H | OCH₃ | OCH₃ | CH | |
| H | CO₂CH₂CH₂SCH₃ | H | OCH₃ | OCH₃ | CH | |
| H | CO₂CH₂CH₂SCH₃ | H | OCH₃ | CH₃ | CH | |
| H | CO₂CH₂CH₂SCH₃ | H | Cl | OCH₃ | CH | |
| H | CO₂CH₂CH₂SCH₃ | H | CH₃ | CH₃ | CH | |
| H | CO₂CH₂CH₂SCH₃ | H | OCH₃ | OCH₃ | N | |

TABLE I-continued

General Formula 1

| R₁ | R₂ | R | X | Y | Z | m.p.(°C.) |
|---|---|---|---|---|---|---|
| H | CO₂CH₂CH₂SCH₃ | H | OCH₃ | CH₃ | N | |
| H | CO₂CH₂CH₂SCH₃ | H | OCH₂CH₃ | NHCH₃ | N | |
| H | CO₂CH₂CH₂SCH₃ | CH₃ | OCH₃ | CH₃ | N | |
| 4-CH₃ | CO₂CH₂CH₂SCH₃ | H | OCH₃ | OCH₃ | CH | |
| 4-OCH₃ | CO₂CH₂CH₂SCH₃ | H | OCH₃ | OCH₃ | CH | |
| 6-CH₃ | CO₂CH₂CH₂SCH₃ | H | OCH₃ | OCH₃ | CH | |
| 6-OCH₃ | CO₂CH₂CH₂SCH₃ | H | OCH₃ | OCH₃ | CH | |
| 6-F | CO₂CH₂CH₂SCH₃ | H | OCH₃ | OCH₃ | CH | |
| 6-Cl | CO₂CH₂CH₂SCH₃ | H | OCH₃ | OCH₃ | CH | |
| H | CO₂CH₂-cyclopropyl | H | OCH₃ | OCH₃ | CH | 143–145 |
| H | CO₂CH₂-cyclopropyl | H | Cl | OCH₃ | CH | 124–128 |
| H | CO₂CH₂-cyclopropyl | H | CH₃ | CH₃ | CH | 134–138 |
| H | CO₂CH₂-cyclopropyl | H | OCH₃ | OCH₃ | N | 154–161 |

TABLE II

General Formula 2

| R₁ | R₃ | R | X | Y | Z | m.p. (°C.) |
|---|---|---|---|---|---|---|
| H | SOCH₃ | H | OCH₃ | OCH₃ | CH | |
| H | SOCH₃ | H | OCH₃ | CH₃ | CH | |
| H | SOCH₃ | H | Cl | OCH₃ | CH | |
| H | SOCH₃ | H | CH₃ | CH₃ | CH | |
| H | SOCH₃ | H | OCH₃ | OCH₃ | N | |
| H | SOCH₃ | H | OCH₃ | CH₃ | N | |
| H | SOCH₃ | CH₃ | OCH₃ | CH₃ | N | |
| 4-CH₃ | SOCH₃ | H | OCH₃ | OCH₃ | CH | |
| 4-Cl | SOCH₃ | H | OCH₃ | OCH₃ | CH | |
| 6-CH₃ | SOCH₃ | H | OCH₃ | OCH₃ | CH | |
| 6-OCH₃ | SOCH₃ | H | OCH₃ | OCH₃ | CH | |
| 6-F | SOCH₃ | H | OCH₃ | OCH₃ | CH | |
| 6-Cl | SOCH₃ | H | OCH₃ | OCH₃ | CH | |
| H | SOCH₂CH₃ | H | OCH₃ | OCH₃ | CH | |
| H | SOCH₂CH₃ | H | OCH₃ | CH₃ | CH | |
| H | SOCH₂CH₃ | H | Cl | OCH₃ | CH | |
| H | SOCH₂CH₃ | H | CH₃ | CH₃ | CH | |
| H | SOCH₂CH₃ | H | OCH₃ | OCH₃ | N | |
| H | SOCH₂CH₃ | H | OCH₃ | CH₃ | N | |
| H | SOCH₂CH₃ | CH₃ | OCH₃ | CH₃ | N | |
| 4-CH₃ | SOCH₂CH₃ | H | OCH₃ | OCH₃ | CH | |
| 4-Cl | SOCH₂CH₃ | H | OCH₃ | OCH₃ | CH | |
| 6-CH₃ | SOCH₂CH₃ | H | OCH₃ | OCH₃ | CH | |
| 6-OCH₃ | SOCH₂CH₃ | H | OCH₃ | OCH₃ | CH | |
| 6-F | SOCH₂CH₃ | H | OCH₃ | OCH₃ | CH | |
| 6-Cl | SOCH₂CH₃ | H | OCH₃ | OCH₃ | CH | |
| H | SOCH₂CH₂CH₃ | H | OCH₃ | OCH₃ | CH | |
| H | SOCH₂CH₂CH₃ | H | OCH₃ | CH₃ | CH | |
| H | SOCH₂CH₂CH₃ | H | Cl | OCH₃ | CH | |
| H | SOCH₂CH₂CH₃ | H | CH₃ | CH₃ | CH | |
| H | SOCH₂CH₂CH₃ | H | OCH₃ | OCH₃ | N | |
| H | SOCH₂CH₂CH₃ | H | OCH₃ | CH₃ | N | |
| H | SOCH₂CH₂CH₃ | CH₃ | OCH₃ | CH₃ | N | |
| 4-CH₃ | SOCH₂CH₂CH₃ | H | OCH₃ | OCH₃ | CH | |
| 4-Cl | SOCH₂CH₂CH₃ | H | OCH₃ | OCH₃ | CH | |
| 6-CH₃ | SOCH₂CH₂CH₃ | H | OCH₃ | OCH₃ | CH | |
| 6-OCH₃ | SOCH₂CH₂CH₃ | H | OCH₃ | OCH₃ | CH | |
| 6-F | SOCH₂CH₂CH₃ | H | OCH₃ | OCH₃ | CH | |
| 6-Cl | SOCH₂CH₂CH₃ | H | OCH₃ | OCH₃ | CH | |
| H | SOCH₂CH₂CH₂CH₃ | H | OCH₃ | OCH₃ | CH | |
| H | SOCH₂CH₂CH₂CH₃ | H | OCH₃ | CH₃ | CH | |
| H | SOCH₂CH₂CH₂CH₃ | H | Cl | OCH₃ | CH | |
| H | SOCH₂CH₂CH₂CH₃ | H | CH₃ | CH₃ | CH | |
| H | SOCH₂CH₂CH₂CH₃ | H | OCH₃ | OCH₃ | N | |
| H | SOCH₂CH₂CH₂CH₃ | H | OCH₃ | CH₃ | N | |
| H | SOCH₂CH₂CH₂CH₃ | CH₃ | OCH₃ | CH₃ | N | |
| 4-CH₃ | SOCH₂CH₂CH₂CH₃ | H | OCH₃ | OCH₃ | CH | |
| 4-Cl | SOCH₂CH₂CH₂CH₃ | H | OCH₃ | OCH₃ | CH | |
| 6-CH₃ | SOCH₂CH₂CH₂CH₃ | H | OCH₃ | OCH₃ | CH | |
| 6-OCH₃ | SOCH₂CH₂CH₂CH₃ | H | OCH₃ | OCH₃ | CH | |
| 6-F | SOCH₂CH₂CH₂CH₃ | H | OCH₃ | OCH₃ | CH | |
| 6-Cl | SOCH₂CH₂CH₂CH₃ | H | OCH₃ | OCH₃ | CH | |
| H | SOCH(CH₃)₂ | H | OCH₃ | OCH₃ | CH | |
| H | SOCH(CH₃)₂ | H | OCH₃ | CH₃ | CH | |
| H | SOCH(CH₃)₂ | H | Cl | OCH₃ | CH | |
| H | SOCH(CH₃)₂ | H | CH₃ | CH₃ | CH | |
| H | SOCH(CE₃)₂ | H | OCH₃ | OCH₃ | N | |
| H | SOCH(CH₃)₂ | H | OCH₃ | CH₃ | N | |
| H | SOCH(CH₃)₂ | CH₃ | OCH₃ | CH₃ | N | |
| 4-CH₃ | SOCH(CH₃)₂ | H | OCH₃ | OCH₃ | CH | |

TABLE II-continued

General Formula 2

| R₁ | R₃ | R | X | Y | Z | m.p. (°C.) |
|---|---|---|---|---|---|---|
| 4-Cl | SOCH(CH₃)₂ | H | OCH₃ | OCH₃ | CH | |
| 6-CH₃ | SOCH(CH₃)₂ | H | OCH₃ | OCH₃ | CH | |
| 6-OCH₃ | SOCH(CH₃)₂ | H | OCH₃ | OCH₃ | CH | |
| 6-F | SOCH(CH₃)₂ | H | OCH₃ | OCH₃ | CH | |
| 6-Cl | SOCH(CH₃)₂ | H | OCH₃ | OCH₃ | CH | |
| H | S-cyclopropyl | H | OCH₃ | OCH₃ | CH | |
| H | S-cyclopropyl | H | OCH₃ | CH₃ | CH | |
| H | S-cyclopropyl | H | Cl | OCH₃ | CH | |
| H | S-cyclopropyl | H | CH₃ | CH₃ | CH | |
| H | S-cyclopropyl | H | OCH₃ | OCH₃ | N | |
| H | S-cyclopropyl | H | OCH₃ | CH₃ | N | |
| H | S-cyclopropyl | H | OCH₂CH₃ | NHCH₃ | N | |
| H | S-cyclopropyl | CH₃ | OCH₃ | CH₃ | N | |
| 4-CH₃ | S-cyclopropyl | H | OCH₃ | OCH₃ | CH | |
| 4-Cl | S-cyclopropyl | H | OCH₃ | OCH₃ | CH | |
| 6-CH₃ | S-cyclopropyl | H | OCH₃ | OCH₃ | CH | |
| 6-OCH₃ | S-cyclopropyl | H | OCH₃ | OCH₃ | CH | |
| 6-F | S-cyclopropyl | H | OCH₃ | OCH₃ | CH | |
| 6-Cl | S-cyclopropyl | H | OCH₃ | OCH₃ | CH | |
| H | SO-cyclopropyl | H | OCH₃ | OCH₃ | CH | |
| H | SO-cyclopropyl | H | OCH₃ | CH₃ | CH | |
| H | SO-cyclopropyl | H | Cl | OCH₃ | CH | |
| H | SO-cyclopropyl | H | CH₃ | CH₃ | CH | |
| H | SO-cyclopropyl | H | OCH₃ | OCH₃ | N | |
| H | SO-cyclopropyl | H | OCH₃ | CH₃ | N | |
| H | SO-cyclopropyl | H | OCH₂CH₃ | NHCH₃ | N | |
| H | SO-cyclopropyl | CH₃ | OCH₃ | CH₃ | N | |
| 4-CH₃ | SO-cyclopropyl | H | OCH₃ | OCH₃ | CH | |
| 4-Cl | SO-cyclopropyl | H | OCH₃ | OCH₃ | CH | |
| 6-CH₃ | SO-cyclopropyl | H | OCH₃ | OCH₃ | CH | |
| 6-OCH₃ | SO-cyclopropyl | H | OCH₃ | OCH₃ | CH | |
| 6-F | SO-cyclopropyl | H | OCH₃ | OCH₃ | CH | |
| 6-Cl | SO-cyclopropyl | H | OCH₃ | OCH₃ | CH | |
| H | SO₂-cyclopropyl | H | OCH₃ | OCH₃ | CH | |
| H | SO₂-cyclopropyl | H | OCH₃ | CH₃ | CH | |
| H | SO₂-cyclopropyl | H | Cl | OCH₃ | CH | |
| H | SO₂-cyclopropyl | H | CH₃ | CH₃ | CH | |
| H | SO₂-cyclopropyl | H | OCH₃ | OCH₃ | N | |
| H | SO₂-cyclopropyl | H | OCH₃ | CH₃ | N | |
| H | SO₂-cyclopropyl | H | OCH₂CH₃ | NHCH₃ | N | |
| H | SO₂-cyclopropyl | CH₃ | OCH₃ | CH₃ | N | |
| 4-CH₃ | SO₂-cyclopropyl | H | OCH₃ | OCH₃ | CH | |
| 4-Cl | SO₂-cyclopropyl | H | OCH₃ | OCH₃ | CH | |
| 6-CH₃ | SO₂-cyclopropyl | H | OCH₃ | OCH₃ | CH | |
| 6-OCH₃ | SO₂-cyclopropyl | H | OCH₃ | OCH₃ | CH | |
| 6-F | SO₂-cyclopropyl | H | OCH₃ | OCH₃ | CH | |
| 6-Cl | SO₂-cyclopropyl | H | OCH₃ | OCH₃ | CH | |
| H | OSO₂CH₃ | H | OCH₃ | OCH₃ | CH | |
| H | OSO₂CH₃ | H | OCH₃ | CH₃ | CH | |
| H | OSO₂CH₃ | H | Cl | OCH₃ | CH | |
| H | OSO₂CH₃ | H | CH₃ | CH₃ | CH | |
| H | OSO₂CH₃ | H | OCH₃ | OCH₃ | N | |
| H | OSO₂CH₃ | H | OCH₃ | CH₃ | N | |
| H | OSO₂CH₃ | H | OCH₂CH₃ | NHCH₃ | N | |
| H | OSO₂CH₃ | CH₃ | OCH₃ | CH₃ | N | |
| 4-CH₃ | OSO₂CH₃ | H | OCH₃ | OCH₃ | CH | |
| 4-Cl | OSO₂CH₃ | H | OCH₃ | OCH₃ | CH | |
| 6-CH₃ | OSO₂CH₃ | H | OCH₃ | OCH₃ | CH | |
| 6-OCH₃ | OSO₂CH₃ | H | OCH₃ | OCH₃ | CH | |
| 6-F | OSO₂CH₃ | H | OCH₃ | OCH₃ | CH | |
| 6-Cl | OSO₂CH₃ | H | OCH₃ | OCH₃ | CH | |
| H | OSO₂CH₂CH₃ | H | OCH₃ | OCH₃ | CH | |
| H | OSO₂CH₂CH₃ | H | OCH₃ | CH₃ | CH | |
| H | OSO₂CH₂CH₃ | H | Cl | OCH₃ | CH | |
| H | OSO₂CH₂CH₃ | H | CH₃ | CH₃ | CH | |
| H | OSO₂CH₂CH₃ | H | OCH₃ | OCH₃ | N | |
| H | OSO₂CH₂CH₃ | H | OCH₃ | CH₃ | N | |
| H | OSO₂CH₂CH₃ | H | OCH₂CH₃ | NHCH₃ | N | |
| H | OSO₂CH₂CH₃ | CH₃ | OCH₃ | CH₃ | N | |
| 4-CH₃ | OSO₂CH₂CH₃ | H | OCH₃ | OCH₃ | CH | |
| 4-Cl | OSO₂CH₂CH₃ | H | OCH₃ | OCH₃ | CH | |
| 6-CH₃ | OSO₂CH₂CH₃ | H | OCH₃ | OCH₃ | CH | |
| 6-OCH₃ | OSO₂CH₂CH₃ | H | OCH₃ | OCH₃ | CH | |
| 6-F | OSO₂CH₂CH₃ | H | OCH₃ | OCH₃ | CH | |
| 6-Cl | OSO₂CH₂CH₃ | H | OCH₃ | OCH₃ | CH | |
| H | OSO₂CF₃ | H | OCH₃ | OCH₃ | CH | |
| H | OSO₂CF₃ | H | OCH₃ | CH₃ | CH | |
| H | OSO₂CF₃ | H | Cl | OCH₃ | CH | |
| H | OSO₂CF₃ | H | CH₃ | CH₃ | CH | |
| H | OSO₂CF₃ | H | OCH₃ | OCH₃ | N | |

TABLE II-continued

General Formula 2

| $R_1$ | $R_3$ | R | X | Y | Z | m.p. (°C.) |
|---|---|---|---|---|---|---|
| H | $OSO_2CF_3$ | H | $OCH_3$ | $CH_3$ | N | |
| H | $OSO_2CF_3$ | H | $OCH_2CH_3$ | $NHCH_3$ | N | |
| H | $OSO_2CF_3$ | $CH_3$ | $OCH_3$ | $CH_3$ | N | |
| 4-$CH_3$ | $OSO_2CF_3$ | H | $OCH_3$ | $OCH_3$ | CH | |
| 4-Cl | $OSO_2CF_3$ | H | $OCH_3$ | $OCH_3$ | CH | |
| 6-$CH_3$ | $OSO_2CF_3$ | H | $OCH_3$ | $OCH_3$ | CH | |
| 6-$OCH_3$ | $OSO_2CF_3$ | H | $OCH_3$ | $OCH_3$ | CH | |
| 6-F | $OSO_2CF_3$ | H | $OCH_3$ | $OCH_3$ | CH | |
| 6-Cl | $OSO_2CF_3$ | H | $OCO_3$ | $OCH_3$ | CH | |
| H | $OSO_2CCl_3$ | H | $OCH_3$ | $OCH_3$ | CH | |
| H | $OSO_2CCl_3$ | H | $OCH_3$ | $CH_3$ | CH | |
| H | $OSO_2CCl_3$ | H | Cl | $OCH_3$ | CH | |
| H | $OSO_2CCl_3$ | H | $CH_3$ | $CH_3$ | CH | |
| H | $OSO_2CCl_3$ | H | $OCH_3$ | $OCH_3$ | N | |
| H | $OSO_2CCl_3$ | H | $OCH_3$ | $CH_3$ | N | |
| H | $OSO_2CCl_3$ | H | $OCH_2CH_3$ | $NHCH_3$ | N | |
| H | $OSO_2CCl_3$ | $CH_3$ | $OCH_3$ | $CH_3$ | N | |
| 4-$CH_3$ | $OSO_2CCl_3$ | H | $OCH_3$ | $OCH_3$ | CH | |
| 4-Cl | $OSO_2CCl_3$ | H | $OCH_3$ | $OCH_3$ | CH | |
| 6-$CH_3$ | $OSO_2CCl_3$ | H | $OCH_3$ | $OCH_3$ | CH | |
| 6-$OCH_3$ | $OSO_2CCl_3$ | H | $OCH_3$ | $OCH_3$ | CH | |
| 6-F | $OSO_2CCl_3$ | H | $OCH_3$ | $OCH_3$ | CH | |
| 6-Cl | $OSO_2CCl_3$ | H | $OCH_3$ | $OCH_3$ | CH | |
| H | $OSO_2CH_2CH_2CH_3$ | H | $OCH_3$ | $OCH_3$ | CH | |
| H | $OSO_2CH_2CH_2CH_3$ | H | $OCH_3$ | $CH_3$ | CH | |
| H | $OSO_2CH_2CH_2CH_3$ | H | Cl | $OCH_3$ | CH | |
| H | $OSO_2CH_2CH_2CH_3$ | H | $CH_3$ | $CH_3$ | CH | |
| H | $OSO_2CH_2CH_2CH_3$ | H | $OCH_3$ | $OCH_3$ | N | |
| H | $OSO_2CH_2CH_2CH_3$ | H | $OCH_3$ | $CH_3$ | N | |
| H | $OSO_2CH_2CH_2CH_3$ | H | $OCH_2CH_3$ | $NHCH_3$ | N | |
| H | $OSO_2CH_2CH_2CH_3$ | $CH_3$ | $OCH_3$ | $CH_3$ | N | |
| 4-$CH_3$ | $OSO_2CH_2CH_2CH_3$ | H | $OCH_3$ | $OCH_3$ | CH | |
| 4-Cl | $OSO_2CH_2CH_2CH_3$ | H | $OCH_3$ | $OCH_3$ | CH | |
| 6-$CH_3$ | $OSO_2CH_2CH_2CH_3$ | H | $OCH_3$ | $OCH_3$ | CH | |
| 6-$OCH_3$ | $OSO_2CH_2CH_2CH_3$ | H | $OCH_3$ | $OCH_3$ | CH | |
| 6-F | $OSO_2CH_2CH_2CH_3$ | H | $OCH_3$ | $OCH_3$ | CH | |
| 6-Cl | $OSO_2CH_2CH_2CH_3$ | H | $OCO_3$ | $OCH_3$ | CH | |
| H | $SO_2OCH_2CF_3$ | H | $OCH_3$ | $OCH_3$ | CH | |
| H | $SO_2OCH_2CF_3$ | H | $OCH_3$ | $CH_3$ | CH | |
| H | $SO_2OCH_2CF_3$ | H | Cl | $OCH_3$ | CH | |
| H | $SO_2OCH_2CF_3$ | H | $CH_3$ | $CH_3$ | CH | |
| H | $SO_2OCH_2CF_3$ | H | $OCH_3$ | $OCH_3$ | N | |
| H | $SO_2OCH_2CF_3$ | H | $OCH_3$ | $CH_3$ | N | |
| H | $SO_2OCH_2CF_3$ | H | $OCH_2CH_3$ | $NHCH_3$ | N | |
| H | $SO_2OCH_2CF_3$ | $CH_3$ | $OCH_3$ | $CH_3$ | N | |
| 4-$CH_3$ | $SO_2OCH_2CF_3$ | H | $OCH_3$ | $OCH_3$ | CH | |
| 4-Cl | $SO_2OCH_2CF_3$ | H | $OCH_3$ | $OCH_3$ | CH | |
| 6-$CH_3$ | $SO_2OCH_2CF_3$ | H | $OCH_3$ | $OCH_3$ | CH | |
| 6-$OCH_3$ | $SO_2OCH_2CF_3$ | H | $OCH_3$ | $OCH_3$ | CH | |
| 6-F | $SO_2OCH_2CF_3$ | H | $OCH_3$ | $OCH_3$ | CH | |
| 6-Cl | $SO_2OCH_2CF_3$ | H | $OCH_3$ | $OCH_3$ | CH | |
| H | $P(O)(OCH_3)_2$ | H | $OCH_3$ | $OCH_3$ | CH | |
| H | $P(O)(OCH_3)_2$ | H | $OCH_3$ | $CH_3$ | CH | |
| H | $P(O)(OCH_3)_2$ | H | Cl | $OCH_3$ | CH | |
| H | $P(O)(OCH_3)_2$ | H | $CH_3$ | $CH_3$ | CH | |
| H | $P(O)(OCH_3)_2$ | H | $OCH_3$ | $OCH_3$ | N | |
| H | $P(O)(OCH_3)_2$ | H | $OCH_3$ | $CH_3$ | N | |
| H | $P(O)(OCH_3)_2$ | H | $OCH_2CH_3$ | $NHCH_3$ | N | |
| H | $P(O)(OCH_3)_2$ | $CH_3$ | $OCH_3$ | $CH_3$ | N | |
| 4-$CH_3$ | $P(O)(OCH_3)_2$ | H | $OCH_3$ | $OCH_3$ | CH | |
| 4-Cl | $P(O)(OCH_3)_2$ | H | $OCH_3$ | $OCH_3$ | CH | |
| 6-$CH_3$ | $P(O)(OCH_3)_2$ | H | $OCH_3$ | $OCH_3$ | CH | |
| 6-$OCH_3$ | $P(O)(OCH_3)_2$ | H | $OCH_3$ | $OCH_3$ | CH | |
| 6-F | $P(O)(OCH_3)_2$ | H | $OCH_3$ | $OCH_3$ | CH | |
| 6-Cl | $P(O)(OCH_3)_2$ | H | $OCO_3$ | $OCH_3$ | CH | |
| H | CN | H | $OCH_3$ | $OCH_3$ | CH | |
| H | CN | H | $OCH_3$ | $CH_3$ | CH | |
| H | CN | H | Cl | $OCH_3$ | CH | |
| H | CN | H | $CH_3$ | $CH_3$ | CH | |
| H | CN | H | $OCH_3$ | $OCH_3$ | N | |
| H | CN | H | $OCH_3$ | $CH_3$ | N | |
| H | CN | H | $OCH_2CH_3$ | $NHCH_3$ | N | |
| H | CN | $CH_3$ | $OCH_3$ | $CH_3$ | N | |
| 4-$CH_3$ | CN | H | $OCH_3$ | $OCH_3$ | CH | |
| 4-Cl | CN | H | $OCH_3$ | $OCH_3$ | CH | |
| 6-$CH_3$ | CN | H | $OCH_3$ | $OCH_3$ | CH | |
| 6-$OCH_3$ | CN | H | $OCH_3$ | $OCH_3$ | CH | |
| 6-F | CN | H | $OCH_3$ | $OCH_3$ | CH | |
| 6-Cl | CN | H | $OCH_3$ | $OCH_3$ | CH | |
| H | $CH_2F$ | H | $OCH_3$ | $OCH_3$ | CH | |

TABLE II-continued

General Formula 2

| $R_1$ | $R_3$ | R | X | Y | Z | m.p. (°C.) |
|---|---|---|---|---|---|---|
| H | $CH_2F$ | H | $OCH_3$ | $CH_3$ | CH | |
| H | $CH_2F$ | H | Cl | $OCH_3$ | CH | |
| H | $CH_2F$ | H | $CH_3$ | $CH_3$ | CH | |
| H | $CH_2F$ | H | $OCH_3$ | $OCH_3$ | N | |
| H | $CH_2F$ | H | $OCH_3$ | $CH_3$ | N | |
| H | $CH_2F$ | H | $OCH_2CH_3$ | $NHCH_3$ | N | |
| H | $CH_2F$ | $CH_3$ | $OCH_3$ | $CH_3$ | N | |
| 4-$CH_3$ | $CH_2F$ | H | $OCH_3$ | $OCH_3$ | CH | |
| 4-Cl | $CH_2F$ | H | $OCH_3$ | $OCH_3$ | CH | |
| 6-$CH_3$ | $CH_2F$ | H | $OCH_3$ | $OCH_3$ | CH | |
| 6-$OCH_3$ | $CH_2F$ | H | $OCH_3$ | $OCH_3$ | CH | |
| 6-F | $CH_2F$ | H | $OCH_3$ | $OCH_3$ | CH | |
| 6-Cl | $CH_2F$ | H | $OCO_3$ | $OCH_3$ | CH | |
| H | $CF_2H$ | H | $OCH_3$ | $OCH_3$ | CH | |
| H | $CH_2H$ | H | $OCH_3$ | $CH_3$ | CH | |
| H | $CF_2H$ | H | Cl | $OCH_3$ | CH | |
| H | $CF_2H$ | H | $CH_3$ | $CH_3$ | CH | |
| H | $CF_2H$ | H | $OCH_3$ | $OCH_3$ | N | |
| H | $CF_2H$ | H | $OCH_3$ | $CH_3$ | N | |
| H | $CF_2H$ | H | $OCH_2CH_3$ | $NHCH_3$ | N | |
| H | $CF_2H$ | $CH_3$ | $OCH_3$ | $CH_3$ | N | |
| 4-$CH_3$ | $CF_2H$ | H | $OCH_3$ | $OCH_3$ | CH | |
| 4-Cl | $CF_2H$ | H | $OCH_3$ | $OCH_3$ | CH | |
| 6-$CH_3$ | $CF_2H$ | H | $OCH_3$ | $OCH_3$ | CH | |
| 6-$OCH_3$ | $CF_2H$ | H | $OCH_3$ | $OCH_3$ | CH | |
| 6-F | $CF_2H$ | H | $OCH_3$ | $OCH_3$ | CH | |
| 6-Cl | $CF_2H$ | H | $OCH_3$ | $OCH_3$ | CH | |
| H | $SO_2NHCH_3$ | H | $OCH_3$ | $OCH_3$ | CH | |
| H | $SO_2NHCH_3$ | H | $OCH_3$ | $CH_3$ | CH | |
| H | $SO_2NHCH_3$ | H | Cl | $OCH_3$ | CH | |
| H | $SO_2NHCH_3$ | H | $CH_3$ | $CH_3$ | CH | |
| H | $SO_2NHCH_3$ | H | $OCH_3$ | $OCH_3$ | N | |
| H | $SO_2NHCH_3$ | H | $OCH_3$ | $CH_3$ | N | |
| H | $SO_2NHCH_3$ | H | $OCH_2CH_3$ | $NHCH_3$ | N | |
| H | $SO_2NHCH_3$ | $CH_3$ | $OCH_3$ | $CH_3$ | N | |
| 4-$CH_3$ | $SO_2NHCH_3$ | H | $OCH_3$ | $OCH_3$ | CH | |
| 4-Cl | $SO_2NHCH_3$ | H | $OCH_3$ | $OCH_3$ | CH | |
| 6-$CH_3$ | $SO_2NHCH_3$ | H | $OCH_3$ | $OCH_3$ | CH | |
| 6-$OCH_3$ | $SO_2NHCH_3$ | H | $OCH_3$ | $OCH_3$ | CH | |
| 6-F | $SO_2NHCH_3$ | H | $OCH_3$ | $OCH_3$ | CH | |
| 6-Cl | $SO_2NHCH_3$ | H | $OCH_3$ | $OCH_3$ | CH | |
| H | $SO_2NHCH_2CH_3$ | H | $OCH_3$ | $OCH_3$ | CH | |
| H | $SO_2NHCH_2CH_3$ | H | $OCH_3$ | $CH_3$ | CH | |
| H | $SO_2NHCH_2CH_3$ | H | Cl | $OCH_3$ | CH | |
| H | $SO_2NHCH_2CH_3$ | H | $CH_3$ | $CH_3$ | CH | |
| H | $SO_2NHCH_2CH_3$ | H | $OCH_3$ | $OCH_3$ | N | |
| H | $SO_2NHCH_2CH_3$ | H | $OCH_3$ | $CH_3$ | N | |
| H | $SO_2NHCH_2CH_3$ | H | $OCH_2CH_3$ | $NHCH_3$ | N | |
| H | $SO_2NHCH_2CH_3$ | $CH_3$ | $OCH_3$ | $CH_3$ | N | |
| 4-$CH_3$ | $SO_2NHCH_2CH_3$ | H | $OCH_3$ | $OCH_3$ | CH | |
| 4-Cl | $SO_2NHCH_2CH_3$ | H | $OCH_3$ | $OCH_3$ | CH | |
| 6-$CH_3$ | $SO_2NHCH_2CH_3$ | H | $OCH_3$ | $OCH_3$ | CH | |
| 6-$OCH_3$ | $SO_2NHCH_2CH_3$ | H | $OCH_3$ | $OCH_3$ | CH | |
| 6-F | $SO_2NHCH_2CH_3$ | H | $OCH_3$ | $OCH_3$ | CH | |
| 6-Cl | $SO_2NHCH_2CH_3$ | H | $OCH_3$ | $OCH_3$ | CH | |
| H | $SO_2NHCH_2CH_2CH_3$ | H | $OCH_3$ | $OCH_3$ | CH | |
| H | $SO_2NHCH_2CH_2CH_3$ | H | $OCH_3$ | $CH_3$ | CH | |
| H | $SO_2NHCH_2CH_2CH_3$ | H | Cl | $OCH_3$ | CH | |
| H | $SO_2NHCH_2CH_2CH_3$ | H | $CH_3$ | $CH_3$ | CH | |
| H | $SO_2NHCH_2CH_2CH_3$ | H | $OCH_3$ | $OCH_3$ | N | |
| H | $SO_2NHCH_2CH_2CH_3$ | H | $OCH_3$ | $CH_3$ | N | |
| H | $SO_2NHCH_2CH_2CH_3$ | H | $OCH_2CH_3$ | $NHCH_3$ | N | |
| H | $SO_2NHCH_2CH_2CH_3$ | $CH_3$ | $OCH_3$ | $CH_3$ | N | |
| 4-$CH_3$ | $SO_2NHCH_2CH_2CH_3$ | H | $OCH_3$ | $OCH_3$ | CH | |
| 4-Cl | $SO_2NHCH_2CH_2CH_3$ | H | $OCH_3$ | $OCH_3$ | CH | |
| 6-$CH_3$ | $SO_2NHCH_2CH_2CH_3$ | H | $OCH_3$ | $OCH_3$ | CH | |
| 6-$OCH_3$ | $SO_2NHCH_2CH_2CH_3$ | H | $OCH_3$ | $OCH_3$ | CH | |
| 6-F | $SO_2NHCH_2CH_2CH_3$ | H | $OCH_3$ | $OCH_3$ | CH | |
| 6-Cl | $SO_2NHCH_2CH_2CH_3$ | H | $OCH_3$ | $OCH_3$ | CH | |
| H | $SO_2NHCH(CH_3)_2$ | H | $OCH_3$ | $OCH_3$ | CH | |
| H | $SO_2NHCH(CH_3)_2$ | H | $OCH_3$ | $CH_3$ | CH | |
| H | $SO_2NHCH(CH_3)_2$ | H | Cl | $OCH_3$ | CH | |
| H | $SO_2NHCH(CH_3)_2$ | H | $CH_3$ | $CH_3$ | CH | |
| H | $SO_2NHCH(CH_3)_2$ | H | $OCH_3$ | $OCH_3$ | N | |
| H | $SO_2NHCH(CH_3)_2$ | H | $OCH_3$ | $CH_3$ | N | |
| H | $SO_2NHCH(CH_3)_2$ | H | $OCH_2CH_3$ | $NHCH_3$ | N | |
| H | $SO_2NHCH(CH_3)_2$ | $CH_3$ | $OCH_3$ | $CH_3$ | N | |
| 4-$CH_3$ | $SO_2NHCH(CH_3)_2$ | H | $OCH_3$ | $OCH_3$ | CH | |
| 4-Cl | $SO_2NHCH(CH_3)_2$ | H | $OCH_3$ | $OCH_3$ | CH | |
| 6-$CH_3$ | $SO_2NHCH(CH_3)_2$ | H | $OCH_3$ | $OCH_3$ | CH | |

TABLE II-continued

General Formula 2

| R₁ | R₃ | R | X | Y | Z | m.p. (°C.) |
|---|---|---|---|---|---|---|
| 6-OCH₃ | SO₂NHCH(CH₃)₂ | H | OCH₃ | OCH₃ | CH | |
| 6-F | SO₂NHCH(CH₃)₂ | H | OCH₃ | OCH₃ | CH | |
| 6-Cl | SO₂NHCH(CH₃)₂ | H | OCH₃ | OCH₃ | CH | |
| H | SO₂NH-cyclopropyl | H | OCH₃ | OCH₃ | CH | |
| H | SO₂NH-cyclopropyl | H | OCH₃ | CH₃ | CH | |
| H | SO₂NH-cyclopropyl | H | Cl | OCH₃ | CH | |
| H | SO₂NH-cyclopropyl | H | CH₃ | CH₃ | CH | |
| H | SO₂NH-cyclopropyl | H | OCH₃ | OCH₃ | N | |
| H | SO₂NH-cyclopropyl | H | OCH₃ | CH₃ | N | |
| H | SO₂NH-cyclopropyl | H | OCH₂CH₃ | NHCH₃ | N | |
| H | SO₂NH-cyclopropyl | CH₃ | OCH₃ | CH₃ | N | |
| 4-CH₃ | SO₂NH-cyclopropyl | H | OCH₃ | OCH₃ | CH | |
| 4-Cl | SO₂NH-cyclopropyl | H | OCH₃ | OCH₃ | CH | |
| 6-CH₃ | SO₂NH-cyclopropyl | H | OCH₃ | OCH₃ | CH | |
| 6-OCH₃ | SO₂NH-cyclopropyl | H | OCH₃ | OCH₃ | CH | |
| 6-F | SO₂NH-cyclopropyl | H | OCH₃ | OCH₃ | CH | |
| 6-Cl | SO₂NH-cyclopropyl | H | OCH₃ | OCH₃ | CH | |
| H | SO₂NHCH₂CH=CH₂ | H | OCH₃ | OCH₃ | CH | |
| H | SO₂NHCH₂CH=CH₂ | H | OCH₃ | CH₃ | CH | |
| H | SO₂NHCH₂CH=CH₂ | H | Cl | OCH₃ | CH | |
| H | SO₂NHCH₂CH=CH₂ | H | CH₃ | CH₃ | CH | |
| H | SO₂NHCH₂CH=CH₂ | H | OCH₃ | OCH₃ | N | |
| H | SO₂NHCH₂CH=CH₂ | H | OCH₃ | CH₃ | N | |
| H | SO₂NHCH₂CH=CH₂ | H | OCH₂CH₃ | NHCH₃ | N | |
| H | SO₂NHCH₂CH=CH₂ | CH₃ | OCH₃ | CH₃ | N | |
| 4-CH₃ | SO₂NHCH₂CH=CH₂ | H | OCH₃ | OCH₃ | CH | |
| 4-Cl | SO₂NHCH₂CH=CH₂ | H | OCH₃ | OCH₃ | CH | |
| 6-CH₃ | SO₂NHCH₂CH=CH₂ | H | OCH₃ | OCH₃ | CH | |
| 6-OCH₃ | SO₂NHCH₂CH=CH₂ | H | OCH₃ | OCH₃ | CH | |
| 6-F | SO₂NHCH₂CH=CH₂ | H | OCH₃ | OCH₃ | CH | |
| 6-Cl | SO₂NHCH₂CH=CH₂ | H | OCH₃ | OCH₃ | CH | |
| H | SO₂NHCH₂CF₃ | H | OCH₃ | OCH₃ | CH | |
| H | SO₂NHCH₂CF₃ | H | OCH₃ | CH₃ | CH | |
| H | SO₂NHCH₂CF₃ | H | Cl | OCH₃ | CH | |
| H | SO₂NHCH₂CF₃ | H | CH₃ | CH₃ | CH | |
| H | SO₂NHCH₂CF₃ | H | OCH₃ | OCH₃ | N | |
| H | SO₂NHCH₂CF₃ | H | OCH₃ | CH₃ | N | |
| H | SO₂NHCH₂CF₃ | H | OCH₂CH₃ | NHCH₃ | N | |
| H | SO₂NHCH₂CF₃ | CH₃ | OCH₃ | CH₃ | N | |
| 4-CH₃ | SO₂NHCH₂CF₃ | H | OCH₃ | OCH₃ | CH | |
| 4-Cl | SO₂NHCH₂CF₃ | H | OCH₃ | OCH₃ | CH | |
| 6-CH₃ | SO₂NHCH₂CF₃ | H | OCH₃ | OCH₃ | CH | |
| 6-OCH₃ | SO₂NHCH₂CF₃ | H | OCH₃ | OCH₃ | CH | |
| 6-F | SO₂NHCH₂CF₃ | H | OCH₃ | OCH₃ | CH | |
| 6-Cl | SO₂NHCH₂CF₃ | H | OCH₃ | OCH₃ | CH | |
| H | SO₂NHCH₂CN | H | OCH₃ | OCH₃ | CH | |
| H | SO₂NHCH₂CN | H | OCH₃ | CH₃ | CH | |
| H | SO₂NHCH₂CN | H | Cl | OCH₃ | CH | |
| H | SO₂NHCH₂CN | H | CH₃ | CH₃ | CH | |
| H | SO₂NHCH₂CN | H | OCH₃ | OCH₃ | N | |
| H | SO₂NHCH₂CN | H | OCH₃ | CH₃ | N | |
| H | SO₂NHCH₂CN | H | OCH₂CH₃ | NHCH₃ | N | |
| H | SO₂NHCH₂CN | CH₃ | OCH₃ | CH₃ | N | |
| 4-CH₃ | SO₂NHCH₂CN | H | OCH₃ | OCH₃ | CH | |
| 4-Cl | SO₂NHCH₂CN | H | OCH₃ | OCH₃ | CH | |
| 6-CH₃ | SO₂NHCH₂CN | H | OCH₃ | OCH₃ | CH | |
| 6-OCH₃ | SO₂NHCH₂CN | H | OCH₃ | OCH₃ | CH | |
| 6-F | SO₂NHCH₂CN | H | OCH₃ | OCH₃ | CH | |
| 6-Cl | SO₂NHCH₂CN | H | OCH₃ | OCH₃ | CH | |
| H | SO₂N(CH₂CH=CH₂)₂ | H | OCH₃ | OCH₃ | CH | |
| H | SO₂N(CH₂CH=CH₂)₂ | H | OCH₃ | CH₃ | CH | |
| H | SO₂N(CH₂CH=CH₂)₂ | H | Cl | OCH₃ | CH | |
| H | SO₂N(CH₂CH=CH₂)₂ | H | CH₃ | CH₃ | CH | |
| H | SO₂N(CH₂CH=CH₂)₂ | H | OCH₃ | OCH₃ | N | |
| H | SO₂N(CH₂CH=CH₂)₂ | H | OCH₃ | CH₃ | N | |
| H | SO₂N(CH₂CH=CH₂)₂ | H | OCH₂CH₃ | NHCH₃ | N | |
| H | SO₂N(CH₂CH=CH₂)₂ | CH₃ | OCH₃ | CH₃ | N | |
| 4-CH₃ | SO₂N(CH₂CH=CH₂)₂ | H | OCH₃ | OCH₃ | CH | |
| 4-Cl | SO₂N(CH₂CH=CH₂)₂ | H | OCH₃ | OCH₃ | CH | |
| 6-CH₃ | SO₂N(CH₂CH=CH₂)₂ | H | OCH₃ | OCH₃ | CH | |
| 6-OCH₃ | SO₂N(CH₂CH=CH₂)₂ | H | OCH₃ | OCH₃ | CH | |
| 6-F | SO₂N(CH₂CH=CH₂)₂ | H | OCH₃ | OCH₃ | CH | |
| 6-Cl | SO₂N(CH₂CH=CH₂)₂ | H | OCH₃ | OCH₃ | CH | |
| H | SO₂-pyrrolidino | H | OCH₃ | OCH₃ | CH | |
| H | SO₂-pyrrolidino | H | OCH₃ | CH₃ | CH | |
| H | SO₂-pyrrolidino | H | Cl | OCH₃ | CH | |
| H | SO₂-pyrrolidino | H | CH₃ | CH₃ | CH | |
| H | SO₂-pyrrolidino | H | OCH₃ | OCH₃ | N | |
| H | SO₂-pyrrolidino | H | OCH₃ | CH₃ | N | |
| H | SO₂-pyrrolidino | H | OCH₂CH₃ | NHCH₃ | N | |

TABLE II-continued

General Formula 2

| $R_1$ | $R_3$ | R | X | Y | Z | m.p. (°C.) |
|---|---|---|---|---|---|---|
| H | $SO_2$-pyrrolidino | $CH_3$ | $OCH_3$ | $CH_3$ | N | |
| 4-$CH_3$ | $SO_2$-pyrrolidino | H | $OCH_3$ | $OCH_3$ | CH | |
| 4-Cl | $SO_2$-pyrrolidino | H | $OCH_3$ | $OCH_3$ | CH | |
| 6-$CH_3$ | $SO_2$-pyrrolidino | H | $OCH_3$ | $OCH_3$ | CH | |
| 6-$OCH_3$ | $SO_2$-pyrrolidino | H | $OCH_3$ | $OCH_3$ | CH | |
| 6-F | $SO_2$-pyrrolidino | H | $OCH_3$ | $OCH_3$ | CH | |
| 6-Cl | $SO_2$-pyrrolidino | H | $OCH_3$ | $OCH_3$ | CH | |
| H | $SO_2NHCH_2CH_2OCH_3$ | H | $OCH_3$ | $OCH_3$ | CH | |
| H | $SO_2NHCH_2CH_2OCH_3$ | H | $OCH_3$ | $CH_3$ | CH | |
| H | $SO_2NHCH_2CH_2OCH_3$ | H | Cl | $OCH_3$ | CH | |
| H | $SO_2NHCH_2CH_2OCH_3$ | H | $CH_3$ | $CH_3$ | CH | |
| H | $SO_2NHCH_2CH_2OCH_3$ | H | $OCH_3$ | $OCH_3$ | N | |
| H | $SO_2NHCH_2CH_2OCH_3$ | H | $OCH_3$ | $CH_3$ | N | |
| H | $SO_2NHCH_2CH_2OCH_3$ | H | $OCH_2CH_3$ | $NHCH_3$ | N | |
| H | $SO_2NHCH_2CH_2OCH_3$ | $CH_3$ | $OCH_3$ | $CH_3$ | N | |
| 4-$CH_3$ | $SO_2NHCH_2CH_2OCH_3$ | H | $OCH_3$ | $OCH_3$ | CH | |
| 4-Cl | $SO_2NHCH_2CH_2OCH_3$ | H | $OCH_3$ | $OCH_3$ | CH | |
| 6-$CH_3$ | $SO_2NHCH_2CH_2OCH_3$ | H | $OCH_3$ | $OCH_3$ | CH | |
| 6-$OCH_3$ | $SO_2NHCH_2CH_2OCH_3$ | H | $OCH_3$ | $OCH_3$ | CH | |
| 6-F | $SO_2NHCH_2CH_2OCH_3$ | H | $OCH_3$ | $OCH_3$ | CH | |
| 6-Cl | $SO_2NHCH_2CH_2OCH_3$ | H | $OCH_3$ | $OCH_3$ | CH | |
| H | $SO_2NH_2$ | H | $OCH_3$ | $OCH_3$ | CH | |
| H | $SO_2NH_2$ | H | $OCH_3$ | $CH_3$ | CH | |
| H | $SO_2NH_2$ | H | Cl | $OCH_3$ | CH | |
| H | $SO_2NH_2$ | H | $CH_3$ | $CH_3$ | CH | |
| H | $SO_2NH_2$ | H | $OCH_3$ | $OCH_3$ | N | |
| H | $SO_2NH_2$ | H | $OCH_3$ | $CH_3$ | N | |
| H | $SO_2NH_2$ | H | $OCH_2CH_3$ | $NHCH_3$ | N | |
| H | $SO_2NH_2$ | $CH_3$ | $OCH_3$ | $CH_3$ | N | |
| 4-$CH_3$ | $SO_2NH_2$ | H | $OCH_3$ | $OCH_3$ | CH | |
| 4-Cl | $SO_2NH_2$ | H | $OCH_3$ | $OCH_3$ | CH | |
| 6-$CH_3$ | $SO_2NH_2$ | H | $OCH_3$ | $OCH_3$ | CH | |
| 6-$OCH_3$ | $SO_2NH_2$ | H | $OCH_3$ | $OCH_3$ | CH | |
| 6-F | $SO_2NH_2$ | H | $OCH_3$ | $OCH_3$ | CH | |
| 6-Cl | $SO_2NH_2$ | H | $OCH_3$ | $OCH_3$ | CH | |
| H | $CO_2CH_2CH_2OH$ | H | $OCH_3$ | $OCH_3$ | CH | |
| H | $CO_2CH_2CH_2OH$ | H | $OCH_3$ | $CH_3$ | CH | |
| H | $CO_2CH_2CH_2OH$ | H | Cl | $OCH_3$ | CH | |
| H | $CO_2CH_2CH_2OH$ | H | $CH_3$ | $CH_3$ | CH | |
| H | $CO_2CH_2CH_2OH$ | H | $OCH_3$ | $OCH_3$ | N | |
| H | $CO_2CH_2CH_2OH$ | H | $OCH_3$ | $CH_3$ | N | |
| H | $CO_2CH_2CH_2OH$ | H | $OCH_2CH_3$ | $NHCH_3$ | N | |
| H | $CO_2CH_2CH_2OH$ | $CH_3$ | $OCH_3$ | $CH_3$ | N | |
| 4-$CH_3$ | $CO_2CH_2CH_2OH$ | H | $OCH_3$ | $OCH_3$ | CH | |
| 4-Cl | $CO_2CH_2CH_2OH$ | H | $OCH_3$ | $OCH_3$ | CH | |
| 6-$CH_3$ | $CO_2CH_2CH_2OH$ | H | $OCH_3$ | $OCH_3$ | CH | |
| 6-$OCH_3$ | $CO_2CH_2CH_2OH$ | H | $OCH_3$ | $OCH_3$ | CH | |
| 6-F | $CO_2CH_2CH_2OH$ | H | $OCH_3$ | $OCH_3$ | CH | |
| 6-Cl | $CO_2CH_2CH_2OH$ | H | $OCO_3$ | $OCH_3$ | CH | |
| H | $CO_2CH_2CH_2CN$ | H | $OCH_3$ | $OCH_3$ | CH | |
| H | $CO_2CH_2CH_2CN$ | H | $OCH_3$ | $CH_3$ | CH | |
| H | $CO_2CH_2CH_2CN$ | H | Cl | $OCH_3$ | CH | |
| H | $CO_2CH_2CH_2CN$ | H | $CH_3$ | $CH_3$ | CH | |
| H | $CO_2CH_2CH_2CN$ | H | $OCH_3$ | $OCH_3$ | N | |
| H | $CO_2CH_2CH_2CN$ | H | $OCH_3$ | $CH_3$ | N | |
| H | $CO_2CH_2CH_2CN$ | H | $OCH_2CH_3$ | $NHCH_3$ | N | |
| H | $CO_2CH_2CH_2CN$ | $CH_3$ | $OCH_3$ | $CH_3$ | N | |
| 4-$CH_3$ | $CO_2CH_2CH_2CN$ | H | $OCH_3$ | $OCH_3$ | CH | |
| 4-Cl | $CO_2CH_2CH_2CN$ | H | $OCH_3$ | $OCH_3$ | CH | |
| 6-$CH_3$ | $CO_2CH_2CH_2CN$ | H | $OCH_3$ | $OCH_3$ | CH | |
| 6-$OCH_3$ | $CO_2CH_2CH_2CN$ | H | $OCH_3$ | $OCH_3$ | CH | |
| 6-F | $CO_2CH_2CH_2CN$ | H | $OCH_3$ | $OCH_3$ | CH | |
| 6-Cl | $CO_2CH_2CH_2CN$ | H | $OCH_3$ | $OCH_3$ | CH | |
| H | $CO_2CH_2CH_2OSO_2CH_3$ | H | $OCH_3$ | $OCH_3$ | CH | |
| H | $CO_2CH_2CH_2OSO_2CH_3$ | H | $OCH_3$ | $CH_3$ | CH | |
| H | $CO_2CH_2CH_2OSO_2CH_3$ | H | Cl | $OCH_3$ | CH | |
| H | $CO_2CH_2CH_2OSO_2CH_3$ | H | $CH_3$ | $CH_3$ | CH | |
| H | $CO_2CH_2CH_2OSO_2CH_3$ | H | $OCH_3$ | $OCH_3$ | N | |
| H | $CO_2CH_2CH_2OSO_2CH_3$ | H | $OCH_3$ | $CH_3$ | N | |
| H | $CO_2CH_2CH_2OSO_2CH_3$ | H | $OCH_2CH_3$ | $NHCH_3$ | N | |
| H | $CO_2CH_2CH_2OSO_2CH_3$ | $CH_3$ | $OCH_3$ | $CH_3$ | N | |
| 4-$CH_3$ | $CO_2CH_2CH_2OSO_2CH_3$ | H | $OCH_3$ | $OCH_3$ | CH | |
| 4-Cl | $CO_2CH_2CH_2OSO_2CH_3$ | H | $OCH_3$ | $OCH_3$ | CH | |
| 6-$CH_3$ | $CO_2CH_2CH_2OSO_2CH_3$ | H | $OCH_3$ | $OCH_3$ | CH | |
| 6-$OCH_3$ | $CO_2CH_2CH_2OSO_2CH_3$ | H | $OCH_3$ | $OCH_3$ | CH | |
| 6-F | $CO_2CH_2CH_2OSO_2CH_3$ | H | $OCH_3$ | $OCH_3$ | CH | |
| 6-Cl | $CO_2CH_2CH_2OSO_2CH_3$ | H | $OCO_3$ | $OCH_3$ | CH | |
| H | $CO_2CH_2CF_3$ | H | $OCH_3$ | $OCH_3$ | CH | |
| H | $CO_2CH_2CF_3$ | H | $OCH_3$ | $CH_3$ | CH | |
| H | $CO_2CH_2CF_3$ | H | Cl | $OCH_3$ | CH | |

TABLE II-continued

General Formula 2

| R₁ | R₃ | R | X | Y | Z | m.p. (°C.) |
|---|---|---|---|---|---|---|
| H | CO₂CH₂CF₃ | H | CH₃ | CH₃ | CH | |
| H | CO₂CH₂CF₃ | H | OCH₃ | OCH₃ | N | |
| H | CO₂CH₂CF₃ | H | OCH₃ | CH₃ | N | |
| H | CO₂CH₂CF₃ | H | OCH₂CH₃ | NHCH₃ | N | |
| H | CO₂CH₂CF₃ | CH₃ | OCH₃ | CH₃ | N | |
| 4-CH₃ | CO₂CH₂CF₃ | H | OCH₃ | OCH₃ | CH | |
| 4-Cl | CO₂CH₂CF₃ | H | OCH₃ | OCH₃ | CH | |
| 6-CH₃ | CO₂CH₂CF₃ | H | OCH₃ | OCH₃ | CH | |
| 6-OCH₃ | CO₂CH₂CF₃ | H | OCH₃ | OCH₃ | CH | |
| 6-F | CO₂CH₂CF₃ | H | OCH₃ | OCH₃ | CH | |
| 6-Cl | CO₂CH₂CF₃ | H | OCH₃ | OCH₃ | CH | |

TABLE III

General Formula 3

| R₁ | R₄ | R | X | Y | Z | m.p.(°C.) |
|---|---|---|---|---|---|---|
| H | SOCH₃ | H | OCH₃ | OCH₃ | CH | |
| H | SOCH₃ | H | OCH₃ | CH₃ | CH | |
| H | SOCH₃ | H | Cl | OCH₃ | CH | |
| H | SOCH₃ | H | CH₃ | CH₃ | CH | |
| H | SOCH₃ | H | OCH₃ | OCH₃ | N | |
| H | SOCH₃ | H | OCH₃ | CH₃ | N | |
| H | SOCH₃ | CH₃ | OCH₃ | CH₃ | N | |
| 2-Cl | SOCH₃ | H | OCH₃ | OCH₃ | CH | |
| 2-F | SOCH₃ | H | OCH₃ | OCH₃ | CH | |
| 6-CH₃ | SOCH₃ | H | OCH₃ | OCH₃ | CH | |
| 6-OCH₃ | SOCH₃ | H | OCH₃ | OCH₃ | CH | |
| 6-F | SOCH₃ | H | OCH₃ | OCH₃ | CH | |
| 6-Cl | SOCH₃ | H | OCH₃ | OCH₃ | CH | |
| H | SOCH₂CH₃ | H | OCH₃ | OCH₃ | CH | |
| H | SOCH₂CH₃ | H | OCH₃ | CH₃ | CH | |
| H | SOCH₂CH₃ | H | Cl | OCH₃ | CH | |
| H | SOCH₂CH₃ | H | CH₃ | CH₃ | CH | |
| H | SOCH₂CH₃ | H | OCH₃ | OCH₃ | N | |
| H | SOCH₂CH₃ | H | OCH₃ | CH₃ | N | |
| H | SOCH₂CH₃ | CH₃ | OCH₃ | CH₃ | N | |
| 2-Cl | SOCH₂CH₃ | H | OCH₃ | OCH₃ | CH | |
| 2-F | SOCH₂CH₃ | H | OCH₃ | OCH₃ | CH | |
| 6-CH₃ | SOCH₂CH₃ | H | OCH₃ | OCH₃ | CH | |
| 6-OCH₃ | SOCH₂CH₃ | H | OCH₃ | OCH₃ | CH | |
| 6-F | SOCH₂CH₃ | H | OCH₃ | OCH₃ | CH | |
| 6-Cl | SOCH₂CH₃ | H | OCH₃ | OCH₃ | CH | |
| H | SOCH₂CH₂CH₃ | H | OCH₃ | OCH₃ | CH | |
| H | SOCH₂CH₂CH₃ | H | OCH₃ | CH₃ | CH | |
| H | SOCH₂CH₂CH₃ | H | Cl | OCH₃ | CH | |
| H | SOCH₂CH₂CH₃ | H | CH₃ | CH₃ | CH | |
| H | SOCH₂CH₂CH₃ | H | OCH₃ | OCH₃ | N | |
| H | SOCH₂CH₂CH₃ | H | OCH₃ | CH₃ | N | |
| H | SOCH₂CH₂CH₃ | CH₃ | OCH₃ | CH₃ | N | |
| 2-Cl | SOCH₂CH₂CH₃ | H | OCH₃ | OCH₃ | CH | |
| 2-F | SOCH₂CH₂CH₃ | H | OCH₃ | OCH₃ | CH | |
| 6-CH₃ | SOCH₂CH₂CH₃ | H | OCH₃ | OCH₃ | CH | |
| 6-OCH₃ | SOCH₂CH₂CH₃ | H | OCH₃ | OCH₃ | CH | |
| 6-F | SOCH₂CH₂CH₃ | H | OCH₃ | OCH₃ | CH | |
| 6-Cl | SOCH₂CH₂CH₃ | H | OCH₃ | OCH₃ | CH | |
| H | SOCH₂CH₂CH₂CH₃ | H | OCH₃ | OCH₃ | CH | |
| H | SOCH₂CH₂CH₂CH₃ | H | OCH₃ | CH₃ | CH | |
| H | SOCH₂CH₂CH₂CH₃ | H | Cl | OCH₃ | CH | |
| H | SOCH₂CH₂CH₂CH₃ | H | CH₃ | CH₃ | CH | |
| H | SOCH₂CH₂CH₂CH₃ | H | OCH₃ | OCH₃ | N | |
| H | SOCH₂CH₂CH₂CH₃ | H | OCH₃ | CH₃ | N | |
| H | SOCH₂CH₂CH₂CH₃ | CH₃ | OCH₃ | CH₃ | N | |
| 2-Cl | SOCH₂CH₂CH₂CH₃ | H | OCH₃ | OCH₃ | CH | |
| 2-F | SOCH₂CH₂CH₂CH₃ | H | OCH₃ | OCH₃ | CH | |
| 6-CH₃ | SOCH₂CH₂CH₂CH₃ | H | OCH₃ | OCH₃ | CH | |
| 6-OCH₃ | SOCH₂CH₂CH₂CH₃ | H | OCH₃ | OCH₃ | CH | |
| 6-F | SOCH₂CH₂CH₂CH₃ | H | OCH₃ | OCH₃ | CH | |
| 6-Cl | SOCH₂CH₂CH₂CH₃ | H | OCH₃ | OCH₃ | CH | |
| H | SOCH(CH₃)₂ | H | OCH₃ | OCH₃ | CH | |
| H | SOCH(CH₃)₂ | H | OCH₃ | CH₃ | CH | |
| H | SOCH(CH₃)₂ | H | Cl | OCH₃ | CH | |
| H | SOCH(CH₃)₂ | H | CH₃ | CH₃ | CH | |
| H | SOCH(CH₃)₂ | H | OCH₃ | OCH₃ | N | |
| H | SOCH(CH₃)₂ | H | OCH₃ | CH₃ | N | |
| H | SOCH(CH₃)₂ | CH₃ | OCH₃ | CH₃ | N | |
| 2-Cl | SOCH(CH₃)₂ | H | OCH₃ | OCH₃ | CH | |
| 2-F | SOCH(CH₃)₂ | H | OCH₃ | OCH₃ | CH | |
| 6-CH₃ | SOCH(CH₃)₂ | H | OCH₃ | OCH₃ | CH | |

TABLE III-continued

General Formula 3

| $R_f$ | $R_4$ | R | X | Y | Z | m.p.(°C.) |
|---|---|---|---|---|---|---|
| 6-OCH$_3$ | SOCH(CH$_3$)$_2$ | H | OCH$_3$ | OCH$_3$ | CH | |
| 6-F | SOCH(CH$_3$)$_2$ | H | OCH$_3$ | OCH$_3$ | CH | |
| 6-Cl | SOCH(CH$_3$)$_2$ | H | OCH$_3$ | OCH$_3$ | CH | |
| H | S-cyclopropyl | H | OCH$_3$ | OCH$_3$ | CH | |
| H | S-cyclopropyl | H | OCH$_3$ | CH$_3$ | CH | |
| H | S-cyclopropyl | H | Cl | OCH$_3$ | CH | |
| H | S-cyclopropyl | H | CH$_3$ | CH$_3$ | CH | |
| H | S-cyclopropyl | H | OCH$_3$ | OCH$_3$ | N | |
| H | S-cyclopropyl | H | OCH$_3$ | CH$_3$ | N | |
| H | S-cyclopropyl | H | OCH$_2$CH$_3$ | NHCH$_3$ | N | |
| H | S-cyclopropyl | CH$_3$ | OCH$_3$ | CH$_3$ | N | |
| 2-Cl | S-cyclopropyl | H | OCH$_3$ | OCH$_3$ | CH | |
| 2-F | S-cyclopropyl | H | OCH$_3$ | OCH$_3$ | CH | |
| 6-CH$_3$ | S-cyclopropyl | H | OCH$_3$ | OCH$_3$ | CH | |
| 6-OCH$_3$ | S-cyclopropyl | H | OCH$_3$ | OCH$_3$ | CH | |
| 6-F | S-cyclopropyl | H | OCH$_3$ | OCH$_3$ | CH | |
| 6-Cl | S-cyclopropyl | H | OCH$_3$ | OCH$_3$ | CH | |
| H | SO-cyclopropyl | H | OCH$_3$ | OCH$_3$ | CH | |
| H | SO-cyclopropyl | H | OCH$_3$ | CH$_3$ | CH | |
| H | SO-cyclopropyl | H | Cl | OCH$_3$ | CH | |
| H | SO-cyclopropyl | H | CH$_3$ | CH$_3$ | CH | |
| H | SO-cyclopropyl | H | OCH$_3$ | OCH$_3$ | N | |
| H | SO-cyclopropyl | H | OCH$_3$ | CH$_3$ | N | |
| H | SO-cyclopropyl | H | OCH$_2$CH$_3$ | NHCH$_3$ | N | |
| H | SO-cyclopropyl | CH$_3$ | OCH$_3$ | CH$_3$ | N | |
| 2-Cl | SO-cyclopropyl | H | OCH$_3$ | OCH$_3$ | CH | |
| 2-F | SO-cyclopropyl | H | OCH$_3$ | OCH$_3$ | CH | |
| 6-CH$_3$ | SO-cyclopropyl | H | OCH$_3$ | OCH$_3$ | CH | |
| 6-OCH$_3$ | SO-cyclopropyl | H | OCH$_3$ | OCH$_3$ | CH | |
| 6-F | SO-cyclopropyl | H | OCH$_3$ | OCH$_3$ | CH | |
| 6-Cl | SO-cyclopropyl | H | OCH$_3$ | OCH$_3$ | CH | |
| H | SO$_2$-cyclopropyl | H | OCH$_3$ | OCH$_3$ | CH | |
| H | SO$_2$-cyclopropyl | H | OCH$_3$ | CH$_3$ | CH | |
| H | SO$_2$-cyclopropyl | H | Cl | OCH$_3$ | CH | |
| H | SO$_2$-cyclopropyl | H | CH$_3$ | CH$_3$ | CH | |
| H | SO$_2$-cyclopropyl | H | OCH$_3$ | OCH$_3$ | N | |
| H | SO$_2$-cyclopropyl | H | OCH$_3$ | CH$_3$ | N | |
| H | SO$_2$-cyclopropyl | H | OCH$_2$CH$_3$ | NHCH$_3$ | N | |
| H | SO$_2$-cyclopropyl | CH$_3$ | OCH$_3$ | CH$_3$ | N | |
| 2-Cl | SO$_2$-cyclopropyl | H | OCH$_3$ | OCH$_3$ | CH | |
| 2-F | SO$_2$-cyclopropyl | H | OCH$_3$ | OCH$_3$ | CH | |
| 6-CH$_3$ | SO$_2$-cyclopropyl | H | OCH$_3$ | OCH$_3$ | CH | |
| 6-OCH$_3$ | SO$_2$-cyclopropyl | H | OCH$_3$ | OCH$_3$ | CH | |
| 6-F | SO$_2$-cyclopropyl | H | OCH$_3$ | OCH$_3$ | CH | |
| 6-Cl | SO$_2$-cyclopropyl | H | OCH$_3$ | OCH$_3$ | CH | |
| H | OSO$_2$CH$_3$ | H | OCH$_3$ | OCH$_3$ | CH | |
| H | OSO$_2$CH$_3$ | H | OCH$_3$ | CH$_3$ | CH | |
| H | OSO$_2$CH$_3$ | H | Cl | OCH$_3$ | CH | |
| H | OSO$_2$CH$_3$ | H | CH$_3$ | CH$_3$ | CH | |
| H | OSO$_2$CH$_3$ | H | OCH$_3$ | OCH$_3$ | N | |
| H | OSO$_2$CH$_3$ | H | OCH$_3$ | CH$_3$ | N | |
| H | OSO$_2$CH$_3$ | H | OCH$_2$CH$_3$ | NHCH$_3$ | N | |
| H | OSO$_2$CH$_3$ | CH$_3$ | OCH$_3$ | CH$_3$ | N | |
| 2-Cl | OSO$_2$CH$_3$ | H | OCH$_3$ | OCH$_3$ | CH | |
| 2-F | OSO$_2$CH$_3$ | H | OCH$_3$ | OCH$_3$ | CH | |
| 6-CH$_3$ | OSO$_2$CH$_3$ | H | OCH$_3$ | OCH$_3$ | CH | |
| 6-OCH$_3$ | OSO$_2$CH$_3$ | H | OCH$_3$ | OCH$_3$ | CH | |
| 6-F | OSO$_2$CH$_3$ | H | OCH$_3$ | OCH$_3$ | CH | |
| 6-Cl | OSO$_2$CH$_3$ | H | OCH$_3$ | OCH$_3$ | CH | |
| H | OSO$_2$CH$_2$CH$_3$ | H | OCH$_3$ | OCH$_3$ | CH | |
| H | OSO$_2$CH$_2$CH$_3$ | H | OCH$_3$ | CH$_3$ | CH | |
| H | OSO$_2$CH$_2$CH$_3$ | H | Cl | OCH$_3$ | CH | |
| H | OSO$_2$CH$_2$CH$_3$ | H | CH$_3$ | CH$_3$ | CH | |
| H | OSO$_2$CH$_2$CH$_3$ | H | OCH$_3$ | OCH$_3$ | N | |
| H | OSO$_2$CH$_2$CH$_3$ | H | OCH$_3$ | CH$_3$ | N | |
| H | OSO$_2$CH$_2$CH$_3$ | H | OCH$_2$CH$_3$ | NHCH$_3$ | N | |
| H | OSO$_2$CH$_2$CH$_3$ | CH$_3$ | OCH$_3$ | CH$_3$ | N | |
| 2-Cl | OSO$_2$CH$_2$CH$_3$ | H | OCH$_3$ | OCH$_3$ | CH | |
| 2-F | OSO$_2$CH$_2$CH$_3$ | H | OCH$_3$ | OCH$_3$ | CH | |
| 6-CH$_3$ | OSO$_2$CH$_2$CH$_3$ | H | OCH$_3$ | OCH$_3$ | CH | |
| 6-OCH$_3$ | OSO$_2$CH$_2$CH$_3$ | H | OCH$_3$ | OCH$_3$ | CH | |
| 6-F | OSO$_2$CH$_2$CH$_3$ | H | OCH$_3$ | OCH$_3$ | CH | |
| 6-Cl | OSO$_2$CH$_2$CH$_3$ | H | OCH$_3$ | OCH$_3$ | CH | |
| H | OSO$_2$CH$_2$CH$_2$CH$_3$ | H | OCH$_3$ | OCH$_3$ | CH | |
| H | OSO$_2$CH$_2$CH$_2$CH$_3$ | H | OCH$_3$ | CH$_3$ | CH | |
| H | OSO$_2$CH$_2$CH$_2$CH$_3$ | H | Cl | OCH$_3$ | CH | |
| H | OSO$_2$CH$_2$CH$_2$CH$_3$ | H | CH$_3$ | CH$_3$ | CH | |
| H | OSO$_2$CH$_2$CH$_2$CH$_3$ | H | OCH$_3$ | OCH$_3$ | N | |
| H | OSO$_2$CH$_2$CH$_2$CH$_3$ | H | OCH$_3$ | CH$_3$ | N | |
| H | OSO$_2$CH$_2$CH$_2$CH$_3$ | H | OCH$_2$CH$_3$ | NHCH$_3$ | N | |

TABLE III-continued

General Formula 3

| $R_f$ | $R_4$ | R | X | Y | Z | m.p.(°C.) |
|---|---|---|---|---|---|---|
| H | OSO$_2$CH$_2$CH$_2$CH$_3$ | CH$_3$ | OCH$_3$ | CH$_3$ | N | |
| 2-Cl | OSO$_2$CH$_2$CH$_2$CH$_3$ | H | OCH$_3$ | OCH$_3$ | CH | |
| 2-F | OSO$_2$CH$_2$CH$_2$CH$_3$ | H | OCH$_3$ | OCH$_3$ | CH | |
| 6-CH$_3$ | OSO$_2$CH$_2$CH$_2$CH$_3$ | H | OCH$_3$ | OCH$_3$ | CH | |
| 6-OCH$_3$ | OSO$_2$CH$_2$CH$_2$CH$_3$ | H | OCH$_3$ | OCH$_3$ | CH | |
| 6-F | OSO$_2$CH$_2$CH$_2$CH$_3$ | H | OCH$_3$ | OCH$_3$ | CH | |
| 6-Cl | OSO$_2$CH$_2$CH$_2$CH$_3$ | H | OCH$_3$ | OCH$_3$ | CH | |
| H | OSO$_2$CF$_3$ | H | OCH$_3$ | OCH$_3$ | CH | |
| H | OSO$_2$CF$_3$ | H | OCH$_3$ | CH$_3$ | CH | |
| H | OSO$_2$CF$_3$ | H | Cl | OCH$_3$ | CH | |
| H | OSO$_2$CF$_3$ | H | CH$_3$ | CH$_3$ | CH | |
| H | OSO$_2$CF$_3$ | H | OCH$_3$ | OCH$_3$ | N | |
| H | OSO$_2$CF$_3$ | H | OCH$_3$ | CH$_3$ | N | |
| H | OSO$_2$CF$_3$ | H | OCH$_2$CH$_3$ | NHCH$_3$ | N | |
| H | OSO$_2$CF$_3$ | CH$_3$ | OCH$_3$ | CH$_3$ | N | |
| 2-Cl | OSO$_2$CF$_3$ | H | OCH$_3$ | OCH$_3$ | CH | |
| 2-F | OSO$_2$CF$_3$ | H | OCH$_3$ | OCH$_3$ | CH | |
| 6-CH$_3$ | OSO$_2$CF$_3$ | H | OCH$_3$ | OCH$_3$ | CH | |
| 6-OCH$_3$ | OSO$_2$CF$_3$ | H | OCH$_3$ | OCH$_3$ | CH | |
| 6-F | OSO$_2$CF$_3$ | H | OCH$_3$ | OCH$_3$ | CH | |
| 6-Cl | OSO$_2$CF$_3$ | H | OCH$_3$ | OCH$_3$ | CH | |
| H | OSO$_2$CCl$_3$ | H | OCH$_3$ | OCH$_3$ | CH | |
| H | OSO$_2$CCl$_3$ | H | OCH$_3$ | CH$_3$ | CH | |
| H | OSO$_2$CCl$_3$ | H | Cl | OCH$_3$ | CH | |
| H | OSO$_2$CCl$_3$ | H | CH$_3$ | CH$_3$ | CH | |
| H | OSO$_2$CCl$_3$ | H | OCH$_3$ | OCH$_3$ | N | |
| H | OSO$_2$CCl$_3$ | H | OCH$_3$ | CH$_3$ | N | |
| H | OSO$_2$CCl$_3$ | H | OCH$_2$CH$_3$ | NHCH$_3$ | N | |
| H | OSO$_2$CCl$_3$ | CH$_3$ | OCH$_3$ | CH$_3$ | N | |
| 2-Cl | OSO$_2$CCl$_3$ | H | OCH$_3$ | OCH$_3$ | CH | |
| 2-F | OSO$_2$CCl$_3$ | H | OCH$_3$ | OCH$_3$ | CH | |
| 6-CH$_3$ | OSO$_2$CCl$_3$ | H | OCH$_3$ | OCH$_3$ | CH | |
| 6-OCH$_3$ | OSO$_2$CCl$_3$ | H | OCH$_3$ | OCH$_3$ | CH | |
| 6-F | OSO$_2$CCl$_3$ | H | OCH$_3$ | OCH$_3$ | CH | |
| 6-Cl | OSO$_2$CCl$_3$ | H | OCH$_3$ | OCH$_3$ | CH | |
| H | N$_3$ | H | OCH$_3$ | OCH$_3$ | CH | |
| H | N$_3$ | H | OCH$_3$ | CH$_3$ | CH | |
| H | N$_3$ | H | Cl | OCH$_3$ | CH | |
| H | N$_3$ | H | CH$_3$ | CH$_3$ | CH | |
| H | N$_3$ | H | OCH$_3$ | OCH$_3$ | N | |
| H | N$_3$ | H | OCH$_3$ | CH$_3$ | N | |
| H | N$_3$ | H | OCH$_2$CH$_3$ | NRCH$_3$ | N | |
| H | N$_3$ | CH$_3$ | OCH$_3$ | CH$_3$ | N | |
| 2-Cl | N$_3$ | H | OCH$_3$ | OCH$_3$ | CH | |
| 2-F | N$_3$ | H | OCH$_3$ | OCH$_3$ | CH | |
| 6-CH$_3$ | N$_3$ | H | OCH$_3$ | OCH$_3$ | CH | |
| 6-OCH$_3$ | N$_3$ | H | OCH$_3$ | OCH$_3$ | CH | |
| 6-F | N$_3$ | H | OCH$_3$ | OCH$_3$ | CH | |
| 6-Cl | N$_3$ | H | OCH$_3$ | OCH$_3$ | CH | |
| H | P(O)(OCH$_3$)$_2$ | H | OCH$_3$ | OCH$_3$ | CH | |
| H | P(O)(OCH$_3$)$_2$ | H | OCH$_3$ | CH$_3$ | CH | |
| H | P(O)(OCH$_3$)$_2$ | H | Cl | OCH$_3$ | CH | |
| H | P(O)(OCH$_3$)$_2$ | H | CH$_3$ | CH$_3$ | CH | |
| H | P(O)(OCH$_3$)$_2$ | H | OCH$_3$ | OCH$_3$ | N | |
| H | P(O)(OCH$_3$)$_2$ | H | OCH$_3$ | CH$_3$ | N | |
| H | P(O)(OCH$_3$)$_2$ | H | OCH$_2$CH$_3$ | NHCH$_3$ | N | |
| H | P(O)(OCH$_3$)$_2$ | CH$_3$ | OCH$_3$ | CH$_3$ | N | |
| 2-Cl | P(O)(OCH$_3$)$_2$ | H | OCH$_3$ | OCH$_3$ | CH | |
| 2-F | P(O)(OCH$_3$)$_2$ | H | OCH$_3$ | OCH$_3$ | CH | |
| 6-CH$_3$ | P(O)(OCH$_3$)$_2$ | H | OCH$_3$ | OCH$_3$ | CH | |
| 6-OCH$_3$ | P(O)(OCH$_3$)$_2$ | H | OCH$_3$ | OCH$_3$ | CH | |
| 6-F | P(O)(OCH$_3$)$_2$ | H | OCH$_3$ | OCH$_3$ | CH | |
| 6-Cl | P(O)(OCH$_3$)$_2$ | H | OCH$_3$ | OCH$_3$ | CH | |
| H | CN | H | OCH$_3$ | OCH$_3$ | CH | |
| H | CN | H | OCH$_3$ | CH$_3$ | CH | |
| H | CN | H | Cl | OCH$_3$ | CH | |
| H | CN | H | CH$_3$ | CH$_3$ | CH | |
| H | CN | H | OCH$_3$ | OCH$_3$ | CN | |
| H | CN | H | OCH$_3$ | CH$_3$ | CN | |
| H | CN | H | OCH$_2$CH$_3$ | NHCH$_3$ | CN | |
| H | CN | CH$_3$ | OCH$_3$ | CH$_3$ | CN | |
| 2-Cl | CN | H | OCH$_3$ | OCH$_3$ | CH | |
| 2-F | CN | H | OCH$_3$ | OCH$_3$ | CH | |
| 6-CH$_3$ | CN | H | OCH$_3$ | OCH$_3$ | CH | |
| 6-OCH$_3$ | CN | H | OCH$_3$ | OCH$_3$ | CH | |
| 6-F | CN | H | OCH$_3$ | OCH$_3$ | CH | |
| 6-Cl | CN | H | OCH$_3$ | OCH$_3$ | CH | |
| H | CH$_2$F | H | OCH$_3$ | OCH$_3$ | CH | |
| H | CH$_2$F | H | OCH$_3$ | CH$_3$ | CH | |
| H | CH$_2$F | H | Cl | OCH$_3$ | CH | |

TABLE III-continued

General Formula 3

| $R_f$ | $R_4$ | R | X | Y | Z | m.p.(°C.) |
|---|---|---|---|---|---|---|
| H | CH$_2$F | H | CH$_3$ | CH$_3$ | CH | |
| H | CH$_2$F | H | OCH$_3$ | OCH$_3$ | N | |
| H | CH$_2$F | H | OCH$_3$ | CH$_3$ | N | |
| H | CH$_2$F | H | OCH$_2$CH$_3$ | NHCH$_3$ | N | |
| H | CH$_2$F | CH$_3$ | OCH$_3$ | CH$_3$ | N | |
| 2-Cl | CH$_2$F | H | OCH$_3$ | OCH$_3$ | CH | |
| 2-F | CH$_2$F | H | OCH$_3$ | OCH$_3$ | CH | |
| 6-CH$_3$ | CH$_2$F | H | OCH$_3$ | OCH$_3$ | CH | |
| 6-OCH$_3$ | CH$_2$F | H | OCH$_3$ | OCH$_3$ | CH | |
| 6-F | CH$_2$F | H | OCH$_3$ | OCH$_3$ | CH | |
| 6-Cl | CH$_2$F | H | OCH$_3$ | OCH$_3$ | CH | |
| H | CF$_2$H | H | OCH$_3$ | OCH$_3$ | CH | |
| H | CF$_2$H | H | OCH$_3$ | CH$_3$ | CH | |
| H | CF$_2$H | H | Cl | OCH$_3$ | CH | |
| H | CF$_2$H | H | CH$_3$ | CH$_3$ | CH | |
| H | CF$_2$H | H | OCH$_3$ | OCH$_3$ | N | |
| H | CF$_2$H | H | OCH$_3$ | CH$_3$ | N | |
| H | CF$_2$H | H | OCH$_2$CH$_3$ | NHCH$_3$ | N | |
| H | CF$_2$H | CH$_3$ | OCH$_3$ | CH$_3$ | N | |
| 2-Cl | CF$_2$H | H | OCH$_3$ | OCH$_3$ | CH | |
| 2-F | CF$_2$H | H | OCH$_3$ | OCH$_3$ | CH | |
| 6-CH$_3$ | CF$_2$H | H | OCH$_3$ | OCH$_3$ | CH | |
| 6-OCH$_3$ | CF$_2$H | H | OCH$_3$ | OCH$_3$ | CH | |
| 6-F | CF$_2$H | H | OCH$_3$ | OCH$_3$ | CH | |
| 6-Cl | CF$_2$H | H | OCH$_3$ | OCH$_3$ | CH | |
| H | SO$_2$N(OCH$_3$)CH$_3$ | H | OCH$_3$ | OCH$_3$ | CH | |
| H | SO$_2$N(OCH$_3$)CH$_3$ | H | OCH$_3$ | CH$_3$ | CH | |
| H | SO$_2$N(OCH$_3$)CH$_3$ | H | Cl | OCH$_3$ | CH | |
| H | SO$_2$N(OCH$_3$)CH$_3$ | H | CH$_3$ | CH$_3$ | CH | |
| H | SO$_2$N(OCH$_3$)CH$_3$ | H | OCH$_3$ | OCH$_3$ | N | |
| H | SO$_2$N(OCH$_3$)CH$_3$ | H | OCH$_3$ | CH$_3$ | N | |
| H | SO$_2$N(OCH$_3$)CH$_3$ | H | OCH$_2$CH$_3$ | NHCH$_3$ | N | |
| H | SO$_2$N(OCH$_3$)CH$_3$ | CH$_3$ | OCH$_3$ | CH$_3$ | N | |
| 2-Cl | SO$_2$N(OCH$_3$)CH$_3$ | H | OCH$_3$ | OCH$_3$ | CH | |
| 2-F | SO$_2$N(OCH$_3$)CH$_3$ | H | OCH$_3$ | OCH$_3$ | CH | |
| 6-CH$_3$ | SO$_2$N(OCH$_3$)CH$_3$ | H | OCH$_3$ | OCH$_3$ | CH | |
| 6-OCH$_3$ | SO$_2$N(OCH$_3$)CH$_3$ | H | OCH$_3$ | OCH$_3$ | CH | |
| 6-F | SO$_2$N(OCH$_3$)CH$_3$ | H | OCH$_3$ | OCH$_3$ | CH | |
| 6-Cl | SO$_2$N(OCH$_3$)CH$_3$ | H | OCH$_3$ | OCH$_3$ | CH | |
| H | SO$_2$NHCH$_3$ | H | OCH$_3$ | OCH$_3$ | CH | |
| H | SO$_2$NHCH$_3$ | H | OCH$_3$ | CH$_3$ | CH | |
| H | SO$_2$NHCH$_3$ | H | Cl | OCH$_3$ | CH | |
| H | SO$_2$NHCH$_3$ | H | CH$_3$ | CH$_3$ | CH | |
| H | SO$_2$NHCH$_3$ | H | OCH$_3$ | OCH$_3$ | N | |
| H | SO$_2$NHCH$_3$ | H | OCH$_3$ | CH$_3$ | N | |
| H | SO$_2$NHCH$_3$ | H | OCH$_2$CH$_3$ | NHCH$_3$ | N | |
| H | SO$_2$NHCH$_3$ | CH$_3$ | OCH$_3$ | CH$_3$ | N | |
| 2-Cl | SO$_2$NHCH$_3$ | H | OCH$_3$ | OCH$_3$ | CH | |
| 2-F | SO$_2$NHCH$_3$ | H | OCH$_3$ | OCH$_3$ | CH | |
| 6-CH$_3$ | SO$_2$NHCH$_3$ | H | OCH$_3$ | OCH$_3$ | CH | |
| 6-OCH$_3$ | SO$_2$NHCH$_3$ | H | OCH$_3$ | OCH$_3$ | CH | |
| 6-F | SO$_2$NHCH$_3$ | H | OCH$_3$ | OCH$_3$ | CH | |
| 6-Cl | SO$_2$NHCH$_3$ | H | OCH$_3$ | OCH$_3$ | CH | |
| H | SO$_2$NHCH$_2$CH$_3$ | H | OCH$_3$ | OCH$_3$ | CH | |
| H | SO$_2$NHCH$_2$CH$_3$ | H | OCH$_3$ | CH$_3$ | CH | |
| H | SO$_2$NHCH$_2$CH$_3$ | H | Cl | OCH$_3$ | CH | |
| H | SO$_2$NHCH$_2$CH$_3$ | H | CH$_3$ | CH$_3$ | CH | |
| H | SO$_2$NHCH$_2$CH$_3$ | H | OCH$_3$ | OCH$_3$ | N | |
| H | SO$_2$NHCH$_2$CH$_3$ | H | OCH$_3$ | CH$_3$ | N | |
| H | SO$_2$NHCH$_2$CH$_3$ | H | OCH$_2$CH$_3$ | NHCH$_3$ | N | |
| H | SO$_2$NHCH$_2$CH$_3$ | CH$_3$ | OCH$_3$ | CH$_3$ | N | |
| 2-Cl | SO$_2$NHCH$_2$CH$_3$ | H | OCH$_3$ | OCH$_3$ | CH | |
| 2-F | SO$_2$NHCH$_2$CH$_3$ | H | OCH$_3$ | OCH$_3$ | CH | |
| 6-CH$_3$ | SO$_2$NHCH$_2$CH$_3$ | H | OCH$_3$ | OCH$_3$ | CH | |
| 6-OCH$_3$ | SO$_2$NHCH$_2$CH$_3$ | H | OCH$_3$ | OCH$_3$ | CH | |
| 6-F | SO$_2$NHCH$_2$CH$_3$ | H | OCH$_3$ | OCH$_3$ | CH | |
| 6-Cl | SO$_2$NHCH$_2$CH$_3$ | H | OCH$_3$ | OCH$_3$ | CH | |
| H | SO$_2$NHCH$_2$CH$_2$OCH$_3$ | H | OCH$_3$ | OCH$_3$ | CH | |
| H | SO$_2$NHCH$_2$CH$_2$OCH$_3$ | H | OCH$_3$ | CH$_3$ | CH | |
| H | SO$_2$NHCH$_2$CH$_2$OCH$_3$ | H | Cl | OCH$_3$ | CH | |
| H | SO$_2$NHCH$_2$CH$_2$OCH$_3$ | H | CH$_3$ | CH$_3$ | CH | |
| H | SO$_2$NHCH$_2$CH$_2$OCH$_3$ | H | OCH$_3$ | OCH$_3$ | N | |
| H | SO$_2$NHCH$_2$CH$_2$OCH$_3$ | H | OCH$_3$ | CH$_3$ | N | |
| H | SO$_2$NHCH$_2$CH$_2$OCH$_3$ | H | OCH$_2$CH$_3$ | NHCH$_3$ | N | |
| H | SO$_2$NHCH$_2$CH$_2$OCH$_3$ | CH$_3$ | OCH$_3$ | CH$_3$ | N | |
| 2-Cl | SO$_2$NHCH$_2$CH$_2$OCH$_3$ | H | OCH$_3$ | OCH$_3$ | CH | |
| 2-F | SO$_2$NHCH$_2$CH$_2$OCH$_3$ | H | OCH$_3$ | OCH$_3$ | CH | |
| 6-CH$_3$ | SO$_2$NHCH$_2$CH$_2$OCH$_3$ | H | OCH$_3$ | OCH$_3$ | CH | |
| 6-OCH$_3$ | SO$_2$NHCH$_2$CH$_2$OCH$_3$ | H | OCH$_3$ | OCH$_3$ | CH | |
| 6-F | SO$_2$NHCH$_2$CH$_2$OCH$_3$ | H | OCH$_3$ | OCH$_3$ | CH | |

TABLE III-continued

General Formula 3

| $R_f$ | $R_4$ | R | X | Y | Z | m.p.(°C.) |
|---|---|---|---|---|---|---|
| 6-Cl | SO$_2$NHCH$_2$CH$_2$OCH$_3$ | H | OCH$_3$ | OCH$_3$ | CH | |
| H | CO$_2$CH$_2$CH$_2$OH | H | OCH$_3$ | OCH$_3$ | CH | |
| H | CO$_2$CH$_2$CH$_2$OH | H | OCH$_3$ | CH$_3$ | CH | |
| H | CO$_2$CH$_2$CH$_2$OH | H | Cl | OCH$_3$ | CH | |
| H | CO$_2$CH$_2$CH$_2$OH | H | CH$_3$ | CH$_3$ | CH | |
| H | CO$_2$CH$_2$CH$_2$OH | H | OCH$_3$ | OCH$_3$ | N | |
| H | CO$_2$CH$_2$CH$_2$OH | H | OCH$_3$ | CH$_3$ | N | |
| H | CO$_2$CH$_2$CH$_2$OH | H | OCH$_2$CH$_3$ | NHCH$_3$ | N | |
| H | CO$_2$CH$_2$CH$_2$OH | CH$_3$ | OCH$_3$ | CH$_3$ | N | |
| 2-Cl | CO$_2$CH$_2$CH$_2$OH | H | OCH$_3$ | OCH$_3$ | CH | |
| 2-F | CO$_2$CH$_2$CH$_2$OH | H | OCH$_3$ | OCH$_3$ | CH | |
| 6-CH$_3$ | CO$_2$CH$_2$CH$_2$OH | H | OCH$_3$ | OCH$_3$ | CH | |
| 6-OCH$_3$ | CO$_2$CH$_2$CH$_2$OH | H | OCH$_3$ | OCH$_3$ | CH | |
| 6-F | CO$_2$CH$_2$CH$_2$OH | H | OCH$_3$ | OCH$_3$ | CH | |
| 6-Cl | CO$_2$CH$_2$CH$_2$OH | H | OCH$_3$ | OCH$_3$ | CH | |
| H | CO$_2$CH$_2$CH$_2$CN | H | OCH$_3$ | OCH$_3$ | CH | |
| H | CO$_2$CH$_2$CH$_2$CN | H | OCH$_3$ | CH$_3$ | CH | |
| H | CO$_2$CH$_2$CH$_2$CN | H | Cl | OCH$_3$ | CH | |
| H | CO$_2$CH$_2$CH$_2$CN | H | CH$_3$ | CH$_3$ | CH | |
| H | CO$_2$CH$_2$CH$_2$CN | H | OCH$_3$ | OCH$_3$ | N | |
| H | CO$_2$CH$_2$CH$_2$CN | H | OCH$_3$ | CH$_3$ | N | |
| H | CO$_2$CH$_2$CH$_2$CN | H | OCH$_3$ | OCH$_3$ | N | |
| H | CO$_2$CH$_2$CH$_2$CN | CH$_3$ | OCH$_3$ | CH$_3$ | N | |
| 2-Cl | CO$_2$CH$_2$CH$_2$CN | H | OCH$_3$ | OCH$_3$ | CH | |
| 2-F | CO$_2$CH$_2$CH$_2$CN | H | OCH$_3$ | OCH$_3$ | CH | |
| 6-CH$_3$ | CO$_2$CH$_2$CH$_2$CN | H | OCH$_3$ | OCH$_3$ | CH | |
| 6-OCH$_3$ | CO$_2$CH$_2$CH$_2$CN | H | OCH$_3$ | OCH$_3$ | CH | |
| 6-F | CO$_2$CH$_2$CH$_2$CN | H | OCH$_3$ | OCH$_3$ | CH | |
| 6-Cl | CO$_2$CH$_2$CH$_2$CN | H | OCH$_3$ | OCH$_3$ | CH | |
| H | CO$_2$CH$_2$CH$_2$OSO$_2$CH$_3$ | H | OCH$_3$ | OCH$_3$ | CH | |
| H | CO$_2$CH$_2$CH$_2$OSO$_2$CH$_3$ | H | OCH$_3$ | CH$_3$ | CH | |
| H | CO$_2$CH$_2$CH$_2$OSO$_2$CH$_3$ | H | Cl | OCH$_3$ | CH | |
| H | CO$_2$CH$_2$CH$_2$OSO$_2$CH$_3$ | H | CH$_3$ | CH$_3$ | CH | |
| H | CO$_2$CH$_2$CH$_2$OSO$_2$CH$_3$ | H | OCH$_3$ | OCH$_3$ | N | |
| H | CO$_2$CH$_2$CH$_2$OSO$_2$CH$_3$ | H | OCH$_3$ | CH$_3$ | N | |
| H | CO$_2$CH$_2$CH$_2$OSO$_2$CH$_3$ | H | OCH$_2$CH$_3$ | NHCH$_3$ | N | |
| H | CO$_2$CH$_2$CH$_2$OSO$_2$CH$_3$ | CH$_3$ | OCH$_3$ | CH$_3$ | N | |
| 2-Cl | CO$_2$CH$_2$CH$_2$OSO$_2$CH$_3$ | H | OCH$_3$ | OCH$_3$ | CH | |
| 2-F | CO$_2$CH$_2$CH$_2$OSO$_2$CH$_3$ | H | OCH$_3$ | OCH$_3$ | CH | |
| 6-CH$_3$ | CO$_2$CH$_2$CH$_2$OSO$_2$CH$_3$ | H | OCH$_3$ | OCH$_3$ | CH | |
| 6-OCH$_3$ | CO$_2$CH$_2$CH$_2$OSO$_2$CH$_3$ | H | OCH$_3$ | OCH$_3$ | CH | |
| 6-F | CO$_2$CH$_2$CH$_2$OSO$_2$CH$_3$ | H | OCH$_3$ | OCH$_3$ | CH | |
| 6-Cl | CO$_2$CH$_2$CH$_2$OSO$_2$CH$_3$ | H | OCH$_3$ | OCH$_3$ | CH | |
| H | CO$_2$CH$_2$CF$_3$ | H | OCH$_3$ | OCH$_3$ | CH | |
| H | CO$_2$CH$_2$CF$_3$ | H | OCH$_3$ | CH$_3$ | CH | |
| H | CO$_2$CH$_2$CF$_3$ | H | Cl | OCH$_3$ | CH | |
| H | CO$_2$CH$_2$CF$_3$ | H | CH$_3$ | CH$_3$ | CH | |
| H | CO$_2$CH$_2$CF$_3$ | H | OCH$_3$ | OCH$_3$ | N | |
| H | CO$_2$CH$_2$CF$_3$ | H | OCH$_3$ | CH$_3$ | N | |
| H | CO$_2$CH$_2$CF$_3$ | H | OCH$_3$ | OCH$_3$ | N | |
| H | CO$_2$CH$_2$CF$_3$ | CH$_3$ | OCH$_3$ | CH$_3$ | N | |
| 2-Cl | CO$_2$CH$_2$CF$_3$ | H | OCH$_3$ | OCH$_3$ | CH | |
| 2-F | CO$_2$CH$_2$CF$_3$ | H | OCH$_3$ | OCH$_3$ | CH | |
| 6-CH$_3$ | CO$_2$CH$_2$CF$_3$ | H | OCH$_3$ | OCH$_3$ | CH | |
| 6-OCH$_3$ | CO$_2$CH$_2$CF$_3$ | H | OCH$_3$ | OCH$_3$ | CH | |
| 6-F | CO$_2$CH$_2$CF$_3$ | H | OCH$_3$ | OCH$_3$ | CH | |
| 6-Cl | CO$_2$CH$_2$CF$_3$ | H | OCH$_3$ | OCH$_3$ | CH | |

TABLE IV

General Formula 4

| $R_f$ | $R_5$ | R | X | Y | Z | m.p. (°C.) |
|---|---|---|---|---|---|---|
| H | SOCH$_3$ | H | OCH$_3$ | OCH$_3$ | CH | |
| H | SOCH$_3$ | H | OCH$_3$ | CH$_3$ | CH | |
| H | SOCH$_3$ | H | Cl | OCH$_3$ | CH | |
| H | SOCH$_3$ | H | CH$_3$ | CH$_3$ | CH | |
| H | SOCH$_3$ | H | OCH$_3$ | OCH$_3$ | N | |
| H | SOCH$_3$ | H | OCH$_3$ | CH$_3$ | N | |
| H | SOCH$_3$ | H | OCH$_2$CH$_3$ | NHCH$_3$ | N | |
| H | SOCH$_3$ | CH$_3$ | OCH$_3$ | CH$_3$ | N | |
| 5-CH$_3$ | SOCH$_3$ | H | OCH$_3$ | OCH$_3$ | CH | |
| 5-OCH$_3$ | SOCH$_3$ | H | OCH$_3$ | OCH$_3$ | CH | |
| 6-CH$_3$ | SOCH$_3$ | H | OCH$_3$ | OCH$_3$ | CH | |
| 6-OCH$_3$ | SOCH$_3$ | H | OCH$_3$ | OCH$_3$ | CH | |
| 6-F | SOCH$_3$ | H | OCH$_3$ | OCH$_3$ | CH | |
| 6-Cl | SOCH$_3$ | H | OCH$_3$ | OCH$_3$ | CH | |
| H | SO$_2$CH$_3$ | H | OCH$_3$ | OCH$_3$ | CH | |
| H | SO$_2$CH$_3$ | H | OCH$_3$ | CH$_3$ | CH | |

TABLE IV-continued

General Formula 4

| $R_f$ | $R_5$ | R | X | Y | Z | m.p. (°C.) |
|---|---|---|---|---|---|---|
| H | SO$_2$CH$_3$ | H | Cl | OCH$_3$ | CH | |
| H | SO$_2$CH$_3$ | H | CH$_3$ | CH$_3$ | CH | |
| H | SO$_2$CH$_3$ | H | OCH$_3$ | OCH$_3$ | N | |
| H | SO$_2$CH$_3$ | H | OCH$_3$ | CH$_3$ | N | |
| H | SO$_2$CH$_3$ | H | OCH$_2$CH$_3$ | NHCH$_3$ | N | |
| H | SO$_2$CH$_3$ | CH$_3$ | OCH$_3$ | CH$_3$ | N | |
| 5-CH$_3$ | SO$_2$CH$_3$ | H | OCH$_3$ | OCH$_3$ | CH | |
| 5-OCH$_3$ | SO$_2$CH$_3$ | H | OCH$_3$ | OCH$_3$ | CH | |
| 6-CH$_3$ | SO$_2$CH$_3$ | H | OCH$_3$ | OCH$_3$ | CH | |
| 6-OCH$_3$ | SO$_2$CH$_3$ | H | OCH$_3$ | OCH$_3$ | CH | |
| 6-F | SO$_2$CH$_3$ | H | OCH$_3$ | OCH$_3$ | CH | |
| 6-Cl | SO$_2$CH$_3$ | H | OCH$_3$ | OCH$_3$ | CH | |
| H | SOCH$_2$CH$_3$ | H | OCH$_3$ | OCH$_3$ | CH | |
| H | SOCH$_2$CH$_3$ | H | OCH$_3$ | CH$_3$ | CH | |
| H | SOCH$_2$CH$_3$ | H | Cl | OCH$_3$ | CH | |
| H | SOCH$_2$CH$_3$ | H | CH$_3$ | CH$_3$ | CH | |
| H | SOCH$_2$CH$_3$ | H | OCH$_3$ | OCH$_3$ | N | |
| H | SOCH$_2$CH$_3$ | H | OCH$_3$ | CH$_3$ | N | |
| H | SOCH$_2$CH$_3$ | H | OCH$_2$CH$_3$ | NHCH$_3$ | N | |
| H | SOCH$_2$CH$_3$ | CH$_3$ | OCH$_3$ | CH$_3$ | N | |
| 5-CH$_3$ | SOCH$_2$CH$_3$ | H | OCH$_3$ | OCH$_3$ | CH | |
| 5-OCH$_3$ | SOCH$_2$CH$_3$ | H | OCH$_3$ | OCH$_3$ | CH | |
| 6-CH$_3$ | SOCH$_2$CH$_3$ | H | OCH$_3$ | OCH$_3$ | CH | |
| 6-OCH$_3$ | SOCH$_2$CH$_3$ | H | OCH$_3$ | OCH$_3$ | CH | |
| 6-F | SOCH$_2$CH$_3$ | H | OCH$_3$ | OCH$_3$ | CH | |
| 6-Cl | SOCH$_2$CH$_3$ | H | OCH$_3$ | OCH$_3$ | CH | |
| H | SO$_2$CH$_2$CH$_3$ | H | OCH$_3$ | OCH$_3$ | CH | |
| H | SO$_2$CH$_2$CH$_3$ | H | OCH$_3$ | CH$_3$ | CH | |
| H | SO$_2$CH$_2$CH$_3$ | H | Cl | OCH$_3$ | CH | |
| H | SO$_2$CH$_2$CH$_3$ | H | CH$_3$ | CH$_3$ | CH | |
| H | SO$_2$CH$_2$CH$_3$ | H | OCH$_3$ | OCH$_3$ | N | |
| H | SO$_2$CH$_2$CH$_3$ | H | OCH$_3$ | CH$_3$ | N | |
| H | SO$_2$CH$_2$CH$_3$ | H | OCH$_2$CH$_3$ | NHCH$_3$ | N | |
| H | SO$_2$CH$_2$CH$_3$ | CH$_3$ | OCH$_3$ | CH$_3$ | N | |
| 5-CH$_3$ | SO$_2$CH$_2$CH$_3$ | H | OCH$_3$ | OCH$_3$ | CH | |
| 5-OCH$_3$ | SO$_2$CH$_2$CH$_3$ | H | OCH$_3$ | OCH$_3$ | CH | |
| 6-CH$_3$ | SO$_2$CH$_2$CH$_3$ | H | OCH$_3$ | OCH$_3$ | CH | |
| 6-OCH$_3$ | SO$_2$CH$_2$CH$_3$ | H | OCH$_3$ | OCH$_3$ | CH | |
| 6-F | SO$_2$CH$_2$CH$_3$ | H | OCH$_3$ | OCH$_3$ | CH | |
| 6-Cl | SO$_2$CH$_2$CH$_3$ | H | OCH$_3$ | OCH$_3$ | CH | |
| H | SOCH$_2$CH$_2$CH$_3$ | H | OCH$_3$ | OCH$_3$ | CH | |
| H | SOCH$_2$CH$_2$CH$_3$ | H | OCH$_3$ | CH$_3$ | CH | |
| H | SOCH$_2$CH$_2$CH$_3$ | H | Cl | OCH$_3$ | CH | |
| H | SOCH$_2$CH$_2$CH$_3$ | H | CH$_3$ | CH$_3$ | CH | |
| H | SOCH$_2$CH$_2$CH$_3$ | H | OCH$_3$ | OCH$_3$ | N | |
| H | SOCH$_2$CH$_2$CH$_3$ | H | OCH$_3$ | CH$_3$ | N | |
| H | SOCH$_2$CH$_2$CH$_3$ | H | OCH$_2$CH$_3$ | NHCH$_3$ | N | |
| H | SOCH$_2$CH$_2$CH$_3$ | CH$_3$ | OCH$_3$ | CH$_3$ | N | |
| 5-CH$_3$ | SOCH$_2$CH$_2$CH$_3$ | H | OCH$_3$ | OCH$_3$ | CH | |
| 5-OCH$_3$ | SOCH$_2$CH$_2$CH$_3$ | H | OCH$_3$ | OCH$_3$ | CH | |
| 6-CH$_3$ | SOCH$_2$CH$_2$CH$_3$ | H | OCH$_3$ | OCH$_3$ | CH | |
| 6-OCH$_3$ | SOCH$_2$CH$_2$CH$_3$ | H | OCH$_3$ | OCH$_3$ | CH | |
| 6-F | SOCH$_2$CH$_2$CH$_3$ | H | OCH$_3$ | OCH$_3$ | CH | |
| 6-Cl | SOCH$_2$CH$_2$CH$_3$ | H | OCH$_3$ | OCH$_3$ | CH | |
| H | SO$_2$CH$_2$CH$_2$CH$_3$ | H | OCH$_3$ | OCH$_3$ | CH | |
| H | SO$_2$CH$_2$CH$_2$CH$_3$ | H | OCH$_3$ | CH$_3$ | CH | |
| H | SO$_2$CH$_2$CH$_2$CH$_3$ | H | Cl | OCH$_3$ | CH | |
| H | SO$_2$CH$_2$CH$_2$CH$_3$ | H | CH$_3$ | CH$_3$ | CH | |
| H | SO$_2$CH$_2$CH$_2$CH$_3$ | H | OCH$_3$ | OCH$_3$ | N | |
| H | SO$_2$CH$_2$CH$_2$CH$_3$ | H | OCH$_3$ | CH$_3$ | N | |
| H | SO$_2$CH$_2$CH$_2$CH$_3$ | H | OCH$_2$CH$_3$ | NHCH$_3$ | N | |
| H | SO$_2$CH$_2$CH$_2$CH$_3$ | CH$_3$ | OCH$_3$ | CH$_3$ | N | |
| 5-CH$_3$ | SO$_2$CH$_2$CH$_2$CH$_3$ | H | OCH$_3$ | OCH$_3$ | CH | |
| 5-OCH$_3$ | SO$_2$CH$_2$CH$_2$CH$_3$ | H | OCH$_3$ | OCH$_3$ | CH | |
| 6-CH$_3$ | SO$_2$CH$_2$CH$_2$CH$_3$ | H | OCH$_3$ | OCH$_3$ | CH | |
| 6-OCH$_3$ | SO$_2$CH$_2$CH$_2$CH$_3$ | H | OCH$_3$ | OCH$_3$ | CH | |
| 6-F | SO$_2$CH$_2$CH$_2$CH$_3$ | H | OCH$_3$ | OCH$_3$ | CH | |
| 6-Cl | SO$_2$CH$_2$CH$_2$CH$_3$ | H | OCH$_3$ | OCH$_3$ | CH | |
| H | SOCH$_2$CH$_2$CH$_2$CH$_3$ | H | OCH$_3$ | OCH$_3$ | CH | |
| H | SOCH$_2$CH$_2$CH$_2$CH$_3$ | H | OCH$_3$ | CH$_3$ | CH | |
| H | SOCH$_2$CH$_2$CH$_2$CH$_3$ | H | Cl | OCH$_3$ | CH | |
| H | SOCH$_2$CH$_2$CH$_2$CH$_3$ | H | CH$_3$ | CH$_3$ | CH | |
| H | SOCH$_2$CH$_2$CH$_2$CH$_3$ | H | OCH$_3$ | OCH$_3$ | N | |
| H | SOCH$_2$CH$_2$CH$_2$CH$_3$ | H | OCH$_3$ | CH$_3$ | N | |
| H | SOCH$_2$CH$_2$CH$_2$CH$_3$ | H | OCH$_2$CH$_3$ | NHCH$_3$ | N | |
| H | SOCH$_2$CH$_2$CH$_2$CH$_3$ | CH$_3$ | OCH$_3$ | CH$_3$ | N | |
| 5-CH$_3$ | SOCH$_2$CH$_2$CH$_2$CH$_3$ | H | OCH$_3$ | OCH$_3$ | CH | |
| 5-OCH$_3$ | SOCH$_2$CH$_2$CH$_2$CH$_3$ | H | OCH$_3$ | OCH$_3$ | CH | |
| 6-CH$_3$ | SOCH$_2$CH$_2$CH$_2$CH$_3$ | H | OCH$_3$ | OCH$_3$ | CH | |
| 6-OCH$_3$ | SOCH$_2$CH$_2$CH$_2$CH$_3$ | H | OCH$_3$ | OCH$_3$ | CH | |

TABLE IV-continued

General Formula 4

| R$_f$ | R$_5$ | R | X | Y | Z | m.p. (°C.) |
|---|---|---|---|---|---|---|
| 6-F | SOCH$_2$CH$_2$CH$_2$CH$_3$ | H | OCH$_3$ | OCH$_3$ | CH | |
| 6-Cl | SOCH$_2$CH$_2$CH$_2$CH$_3$ | H | OCH$_3$ | OCH$_3$ | CH | |
| H | SO$_2$CH$_2$CH$_2$CH$_2$CH$_3$ | H | OCH$_3$ | OCH$_3$ | CH | |
| H | SO$_2$CH$_2$CH$_2$CH$_2$CH$_3$ | H | OCH$_3$ | CH$_3$ | CH | |
| H | SO$_2$CH$_2$CH$_2$CH$_2$CH$_3$ | H | Cl | OCH$_3$ | CH | |
| H | SO$_2$CH$_2$CH$_2$CH$_2$CH$_3$ | H | CH$_3$ | CH$_3$ | CH | |
| H | SO$_2$CH$_2$CH$_2$CH$_2$CH$_3$ | H | OCH$_3$ | OCH$_3$ | N | |
| H | SO$_2$CH$_2$CH$_2$CH$_2$CH$_3$ | H | OCH$_3$ | CH$_3$ | N | |
| H | SO$_2$CH$_2$CH$_2$CH$_2$CH$_3$ | H | OCH$_2$CH$_3$ | NHCH$_3$ | N | |
| H | SO$_2$CH$_2$CH$_2$CH$_2$CH$_3$ | CH$_3$ | OCH$_3$ | CH$_3$ | N | |
| 5-CH$_3$ | SO$_2$CH$_2$CH$_2$CH$_2$CH$_3$ | H | OCH$_3$ | OCH$_3$ | CH | |
| 5-OCH$_3$ | SO$_2$CH$_2$CH$_2$CH$_2$CH$_3$ | H | OCH$_3$ | OCH$_3$ | CH | |
| 6-CH$_3$ | SO$_2$CH$_2$CH$_2$CH$_2$CH$_3$ | H | OCH$_3$ | OCH$_3$ | CH | |
| 6-OCH$_3$ | SO$_2$CH$_2$CH$_2$CH$_2$CH$_3$ | H | OCH$_3$ | OCH$_3$ | CH | |
| 6-F | SO$_2$CH$_2$CH$_2$CH$_2$CH$_3$ | H | OCH$_3$ | OCH$_3$ | CH | |
| 6-Cl | SO$_2$CH$_2$CH$_2$CH$_2$CH$_3$ | H | OCH$_3$ | OCH$_3$ | CH | |
| H | SOCH(CH$_3$)$_2$ | H | OCH$_3$ | OCH$_3$ | CH | |
| H | SOCH(CH$_3$)$_2$ | H | OCH$_3$ | CH$_3$ | CH | |
| H | SOCH(CH$_3$)$_2$ | H | Cl | OCH$_3$ | CH | |
| H | SOCH(CH$_3$)$_2$ | H | CH$_3$ | CH$_3$ | CH | |
| H | SOCH(CH$_3$)$_2$ | H | OCH$_3$ | OCH$_3$ | N | |
| H | SOCH(CH$_3$)$_2$ | H | OCH$_3$ | CH$_3$ | N | |
| H | SOCH(CH$_3$)$_2$ | H | OCH$_2$CH$_3$ | NHCH$_3$ | N | |
| H | SOCH(CH$_3$)$_2$ | CH$_3$ | OCH$_3$ | CH$_3$ | N | |
| 5-CH$_3$ | SOCH(CH$_3$)$_2$ | H | OCH$_3$ | OCH$_3$ | CH | |
| 5-OCH$_3$ | SOCH(CH$_3$)$_2$ | H | OCH$_3$ | OCH$_3$ | CH | |
| 6-CH$_3$ | SOCH(CH$_3$)$_2$ | H | OCH$_3$ | OCH$_3$ | CH | |
| 6-OCH$_3$ | SOCH(CH$_3$)$_2$ | H | OCH$_3$ | OCH$_3$ | CH | |
| 6-F | SOCH(CH$_3$)$_2$ | H | OCH$_3$ | OCH$_3$ | CH | |
| 6-Cl | SOCH(CH$_3$)$_2$ | H | OCH$_3$ | OCH$_3$ | CH | |
| H | SO$_2$CH(CH$_3$)$_2$ | H | OCH$_3$ | OCH$_3$ | CH | |
| H | SO$_2$CH(CH$_3$)$_2$ | H | OCH$_3$ | CH$_3$ | CH | |
| H | SO$_2$CH(CH$_3$)$_2$ | H | Cl | OCH$_3$ | CH | |
| H | SO$_2$CH(CH$_3$)$_2$ | H | CH$_3$ | CH$_3$ | CH | |
| H | SO$_2$CH(CH$_3$)$_2$ | H | OCH$_3$ | OCH$_3$ | N | |
| H | SO$_2$CH(CH$_3$)$_2$ | H | OCH$_3$ | CH$_3$ | N | |
| H | SO$_2$CH(CH$_3$)$_2$ | H | OCH$_2$CH$_3$ | NHCH$_3$ | N | |
| H | SO$_2$CH(CH$_3$)$_2$ | CH$_3$ | OCH$_3$ | CH$_3$ | N | |
| 5-CH$_3$ | SO$_2$CH(CH$_3$)$_2$ | H | OCH$_3$ | OCH$_3$ | CH | |
| 5-OCH$_3$ | SO$_2$CH(CH$_3$)$_2$ | H | OCH$_3$ | OCH$_3$ | CH | |
| 6-CH$_3$ | SO$_2$CH(CH$_3$)$_2$ | H | OCH$_3$ | OCH$_3$ | CH | |
| 6-OCH$_3$ | SO$_2$CH(CH$_3$)$_2$ | H | OCH$_3$ | OCH$_3$ | CH | |
| 6-F | SO$_2$CH(CH$_3$)$_2$ | H | OCH$_3$ | OCH$_3$ | CH | |
| 6-Cl | SO$_2$CH(CH$_3$)$_2$ | H | OCH$_3$ | OCH$_3$ | CH | |
| H | S-cyclopropyl | H | OCH$_3$ | OCH$_3$ | CH | |
| H | S-cyclopropyl | H | OCH$_3$ | CH$_3$ | CH | |
| H | S-cyclopropyl | H | Cl | OCH$_3$ | CH | |
| H | S-cyclopropyl | H | CH$_3$ | CH$_3$ | CH | |
| H | S-cyclopropyl | H | OCH$_3$ | OCH$_3$ | N | |
| H | S-cyclopropyl | H | OCH$_3$ | CH$_3$ | N | |
| H | S-cyclopropyl | H | OCH$_2$CH$_3$ | NHCH$_3$ | N | |
| H | S-cyclopropyl | CH$_3$ | OCH$_3$ | CH$_3$ | N | |
| 5-CH$_3$ | S-cyclopropyl | H | OCH$_3$ | OCH$_3$ | CH | |
| 5-OCH$_3$ | S-cyclopropyl | H | OCH$_3$ | OCH$_3$ | CH | |
| 6-CH$_3$ | S-cyclopropyl | H | OCH$_3$ | OCH$_3$ | CH | |
| 6-OCH$_3$ | S-cyclopropyl | H | OCH$_3$ | OCH$_3$ | CH | |
| 6-F | S-cyclopropyl | H | OCH$_3$ | OCH$_3$ | CH | |
| 6-Cl | S-cyclopropyl | H | OCH$_3$ | OCH$_3$ | CH | |
| H | SO-cyclopropyl | H | OCH$_3$ | OCH$_3$ | CH | |
| H | SO-cyclopropyl | H | OCH$_3$ | CH$_3$ | CH | |
| H | SO-cyclopropyl | H | Cl | OCH$_3$ | CH | |
| H | SO-cyclopropyl | H | CH$_3$ | CH$_3$ | CH | |
| H | SO-cyclopropyl | H | OCH$_3$ | OCH$_3$ | N | |
| H | SO-cyclopropyl | H | OCH$_3$ | CH$_3$ | N | |
| H | SO-cyclopropyl | H | OCH$_2$CH$_3$ | NHCH$_3$ | N | |
| H | SO-cyclopropyl | CH$_3$ | OCH$_3$ | CH$_3$ | N | |
| 5-CH$_3$ | SO-cyclopropyl | H | OCH$_3$ | OCH$_3$ | CH | |
| 5-OCH$_3$ | SO-cyclopropyl | H | OCH$_3$ | OCH$_3$ | CH | |
| 6-CH$_3$ | SO-cyclopropyl | H | OCH$_3$ | OCH$_3$ | CH | |
| 6-OCH$_3$ | SO-cyclopropyl | H | OCH$_3$ | OCH$_3$ | CH | |
| 6-F | SO-cyclopropyl | H | OCH$_3$ | OCH$_3$ | CH | |
| 6-Cl | SO-cyclopropyl | H | OCH$_3$ | OCH$_3$ | CH | |
| H | SO$_2$-cyclopropyl | H | OCH$_3$ | OCH$_3$ | CH | |
| H | SO$_2$-cyclopropyl | H | OCH$_3$ | CH$_3$ | CH | |
| H | SO$_2$-cyclopropyl | H | Cl | OCH$_3$ | CH | |
| H | SO$_2$-cyclopropyl | H | CH$_3$ | CH$_3$ | CH | |
| H | SO$_2$-cyclopropyl | H | OCH$_3$ | OCH$_3$ | N | |
| H | SO$_2$-cyclopropyl | H | OCH$_3$ | CH$_3$ | N | |
| H | SO$_2$-cyclopropyl | H | OCH$_2$CH$_3$ | NHCH$_3$ | N | |
| H | SO$_2$-cyclopropyl | CH$_3$ | OCH$_3$ | CH$_3$ | N | |

TABLE IV-continued

General Formula 4

| $R_f$ | $R_5$ | R | X | Y | Z | m.p. (°C.) |
|---|---|---|---|---|---|---|
| 5-CH$_3$ | SO$_2$-cyclopropyl | H | OCH$_3$ | OCH$_3$ | CH | |
| 5-OCH$_3$ | SO$_2$-cyclopropyl | H | OCH$_3$ | OCH$_3$ | CH | |
| 6-CH$_3$ | SO$_2$-cyclopropyl | H | OCH$_3$ | OCH$_3$ | CH | |
| 6-OCH$_3$ | SO$_2$-cyclopropyl | H | OCH$_3$ | OCH$_3$ | CH | |
| 6-F | SO$_2$-cyclopropyl | H | OCH$_3$ | OCH$_3$ | CH | |
| 6-Cl | SO$_2$-cyclopropyl | H | OCH$_3$ | OCH$_3$ | CH | |
| H | OSO$_2$CH$_3$ | H | OCH$_3$ | OCH$_3$ | CH | |
| H | OSO$_2$CH$_3$ | H | OCH$_3$ | CH$_3$ | CH | |
| H | OSO$_2$CH$_3$ | H | Cl | OCH$_3$ | CH | |
| H | OSO$_2$CH$_3$ | H | CH$_3$ | CH$_3$ | CH | |
| H | OSO$_2$CH$_3$ | H | OCH$_3$ | OCH$_3$ | N | |
| H | OSO$_2$CH$_3$ | H | OCH$_3$ | CH$_3$ | N | |
| H | OSO$_2$CH$_3$ | H | OCH$_2$CH$_3$ | NHCH$_3$ | N | |
| H | OSO$_2$CH$_3$ | CH$_3$ | OCH$_3$ | CH$_3$ | N | |
| 5-CH$_3$ | OSO$_2$CH$_3$ | H | OCH$_3$ | OCH$_3$ | CH | |
| 5-OCH$_3$ | OSO$_2$CH$_3$ | H | OCH$_3$ | OCH$_3$ | CH | |
| 6-CH$_3$ | OSO$_2$CH$_3$ | H | OCH$_3$ | OCH$_3$ | CH | |
| 6-OCH$_3$ | OSO$_2$CH$_3$ | H | OCH$_3$ | OCH$_3$ | CH | |
| 6-F | OSO$_2$CH$_3$ | H | OCH$_3$ | OCH$_3$ | CH | |
| 6-Cl | OSO$_2$CH$_3$ | H | OCH$_3$ | OCH$_3$ | CH | |
| H | OSO$_2$CF$_3$ | H | OCH$_3$ | OCH$_3$ | CH | |
| H | OSO$_2$CF$_3$ | H | OCH$_3$ | CH$_3$ | CH | |
| H | OSO$_2$CF$_3$ | H | Cl | OCH$_3$ | CH | |
| H | OSO$_2$CF$_3$ | H | CH$_3$ | CH$_3$ | CH | |
| H | OSO$_2$CF$_3$ | H | OCH$_3$ | OCH$_3$ | N | |
| H | OSO$_2$CF$_3$ | H | OCH$_3$ | CH$_3$ | N | |
| H | OSO$_2$CF$_3$ | H | OCH$_2$CH$_3$ | NHCH$_3$ | N | |
| H | OSO$_2$CF$_3$ | CH$_3$ | OCH$_3$ | CH$_3$ | N | |
| 5-CH$_3$ | OSO$_2$CF$_3$ | H | OCH$_3$ | OCH$_3$ | CH | |
| 5-OCH$_3$ | OSO$_2$CF$_3$ | H | OCH$_3$ | OCH$_3$ | CH | |
| 6-CH$_3$ | OSO$_2$CF$_3$ | H | OCH$_3$ | OCH$_3$ | CH | |
| 6-OCH$_3$ | OSO$_2$CF$_3$ | H | OCH$_3$ | OCH$_3$ | CH | |
| 6-F | OSO$_2$CF$_3$ | H | OCH$_3$ | OCH$_3$ | CH | |
| 6-Cl | OSO$_2$CF$_3$ | H | OCH$_3$ | OCH$_3$ | CH | |
| H | OSO$_2$CH$_2$CH$_3$ | H | OCH$_3$ | OCH$_3$ | CH | |
| H | OSO$_2$CH$_2$CH$_3$ | H | OCH$_3$ | CH$_3$ | CH | |
| H | OSO$_2$CH$_2$CH$_3$ | H | Cl | OCH$_3$ | CH | |
| H | OSO$_2$CH$_2$CH$_3$ | H | CH$_3$ | CH$_3$ | CH | |
| H | OSO$_2$CH$_2$CH$_3$ | H | OCH$_3$ | OCH$_3$ | N | |
| H | OSO$_2$CH$_2$CH$_3$ | H | OCH$_3$ | CH$_3$ | N | |
| H | OSO$_2$CH$_2$CH$_3$ | H | OCH$_2$CH$_3$ | NHCH$_3$ | N | |
| H | OSO$_2$CH$_2$CH$_3$ | CH$_3$ | OCH$_3$ | CH$_3$ | N | |
| 5-CH$_3$ | OSO$_2$CH$_2$CH$_3$ | H | OCH$_3$ | OCH$_3$ | CH | |
| 5-OCH$_3$ | OSO$_2$CH$_2$CH$_3$ | H | OCH$_3$ | OCH$_3$ | CH | |
| 6-CH$_3$ | OSO$_2$CH$_2$CH$_3$ | H | OCH$_3$ | OCH$_3$ | CH | |
| 6-OCH$_3$ | OSO$_2$CH$_2$CH$_3$ | H | OCH$_3$ | OCH$_3$ | CH | |
| 6-F | OSO$_2$CH$_2$CH$_3$ | H | OCH$_3$ | OCH$_3$ | CH | |
| 6-Cl | OSO$_2$CH$_2$CH$_3$ | H | OCH$_3$ | OCH$_3$ | CH | |
| H | N$_3$ | H | OCH$_3$ | OCH$_3$ | CH | |
| H | N$_3$ | H | OCH$_3$ | CH$_3$ | CH | |
| H | N$_3$ | H | Cl | OCH$_3$ | CH | |
| H | N$_3$ | H | CH$_3$ | CH$_3$ | CH | |
| H | N$_3$ | H | OCH$_3$ | OCH$_3$ | N | |
| H | N$_3$ | H | OCH$_3$ | CH$_3$ | N | |
| H | N$_3$ | H | OCH$_2$CH$_3$ | NHCH$_3$ | N | |
| H | N$_3$ | CH$_3$ | OCH$_3$ | CH$_3$ | N | |
| 5-CH$_3$ | N$_3$ | H | OCH$_3$ | OCH$_3$ | CH | |
| 5-OCH$_3$ | N$_3$ | H | OCH$_3$ | OCH$_3$ | CH | |
| 6-CH$_3$ | N$_3$ | H | OCH$_3$ | OCH$_3$ | CH | |
| 6-OCH$_3$ | N$_3$ | H | OCH$_3$ | OCH$_3$ | CH | |
| 6-F | N$_3$ | H | OCH$_3$ | OCH$_3$ | CH | |
| 6-Cl | N$_3$ | H | OCH$_3$ | OCH$_3$ | CH | |
| H | CN | H | OCH$_3$ | OCH$_3$ | CH | |
| H | CN | H | OCH$_3$ | CH$_3$ | CH | |
| H | CN | H | Cl | OCH$_3$ | CH | |
| H | CN | H | CH$_3$ | CH$_3$ | CH | |
| H | CN | H | OCH$_3$ | OCH$_3$ | N | |
| H | CN | H | OCH$_3$ | CH$_3$ | N | |
| H | CN | H | OCH$_2$CH$_3$ | NHCH$_3$ | N | |
| H | CN | CH$_3$ | OCH$_3$ | CH$_3$ | N | |
| 5-CH$_3$ | CN | H | OCH$_3$ | OCH$_3$ | CH | |
| 5-OCH$_3$ | CN | H | OCH$_3$ | OCH$_3$ | CH | |
| 6-CH$_3$ | CN | H | OCH$_3$ | OCH$_3$ | CH | |
| 6-OCH$_3$ | CN | H | OCH$_3$ | OCH$_3$ | CH | |
| 6-F | CN | H | OCH$_3$ | OCH$_3$ | CH | |
| 6-Cl | CN | H | OCH$_3$ | OCH$_3$ | CH | |
| H | CH$_2$F | H | OCH$_3$ | OCH$_3$ | CH | |
| H | CH$_2$F | H | OCH$_3$ | CH$_3$ | CH | |
| H | CH$_2$F | H | Cl | OCH$_3$ | CH | |
| H | CH$_2$F | H | CH$_3$ | CH$_3$ | CH | |

TABLE IV-continued

General Formula 4

| $R_f$ | $R_5$ | R | X | Y | Z | m.p. (°C.) |
|---|---|---|---|---|---|---|
| H | $CH_2F$ | H | $OCH_3$ | $OCH_3$ | N | |
| H | $CH_2F$ | H | $OCH_3$ | $CH_3$ | N | |
| H | $CH_2F$ | H | $OCH_2CH_3$ | $NHCH_3$ | N | |
| H | $CH_2F$ | $CH_3$ | $OCH_3$ | $CH_3$ | N | |
| 5-$CH_3$ | $CH_2F$ | H | $OCH_3$ | $OCH_3$ | CH | |
| 5-$OCH_3$ | $CH_2F$ | H | $OCH_3$ | $OCH_3$ | CH | |
| 6-$CH_3$ | $CH_2F$ | H | $OCH_3$ | $OCH_3$ | CH | |
| 6-$OCH_3$ | $CH_2F$ | H | $OCH_3$ | $OCH_3$ | CH | |
| 6-F | $CH_2F$ | H | $OCH_3$ | $OCH_3$ | CH | |
| 6-Cl | $CH_2F$ | H | $OCH_3$ | $OCH_3$ | CH | |
| H | $CF_2H$ | H | $OCH_3$ | $OCH_3$ | CH | |
| H | $CF_2H$ | H | $OCH_3$ | $CH_3$ | CH | |
| H | $CF_2H$ | H | Cl | $OCH_3$ | CH | |
| H | $CF_2H$ | H | $CH_3$ | $CH_3$ | CH | |
| H | $CF_2H$ | H | $OCH_3$ | $OCH_3$ | N | |
| R | $CF_2H$ | H | $OCH_3$ | $CH_3$ | N | |
| H | $CF_2H$ | H | $OCH_2CH_3$ | $NHCH_3$ | N | |
| H | $CF_2H$ | $CH_3$ | $OCH_3$ | $CH_3$ | N | |
| 5-$CH_3$ | $CF_2H$ | H | $OCH_3$ | $OCH_3$ | CH | |
| 5-$OCH_3$ | $CF_2H$ | H | $OCH_3$ | $OCH_3$ | CH | |
| 6-$CH_3$ | $CF_2H$ | H | $OCH_3$ | $OCH_3$ | CH | |
| 6-$OCH_3$ | $CF_2H$ | H | $OCH_3$ | $OCH_3$ | CH | |
| 6-F | $CF_2H$ | H | $OCH_3$ | $OCH_3$ | CH | |
| 6-Cl | $CF_2H$ | H | $OCH_3$ | $OCH_3$ | CH | |
| H | $SO_2N(OCH_3)CH_3$ | H | $OCH_3$ | $OCH_3$ | CH | |
| H | $SO_2N(OCH_3)CH_3$ | H | $OCH_3$ | $CH_3$ | CH | |
| H | $SO_2N(OCH_3)CH_3$ | H | Cl | $OCH_3$ | CH | |
| H | $SO_2N(OCH_3)CH_3$ | H | $CH_3$ | $CH_3$ | CH | |
| H | $SO_2N(OCH_3)CH_3$ | H | $OCH_3$ | $OCH_3$ | N | |
| H | $SO_2N(OCH_3)CH_3$ | H | $OCH_3$ | $CH_3$ | N | |
| H | $SO_2N(OCH_3)CH_3$ | H | $OCH_2CH_3$ | $NHCH_3$ | N | |
| H | $SO_2N(OCH_3)CH_3$ | $CH_3$ | $OCH_3$ | $CH_3$ | N | |
| 5-$CH_3$ | $SO_2N(OCH_3)CH_3$ | H | $OCH_3$ | $OCH_3$ | CH | |
| 5-$OCH_3$ | $SO_2N(OCH_3)CH_3$ | H | $OCH_3$ | $OCH_3$ | CH | |
| 6-$CH_3$ | $SO_2N(OCH_3)CH_3$ | H | $OCH_3$ | $OCH_3$ | CH | |
| 6-$OCH_3$ | $SO_2N(OCH_3)CH_3$ | H | $OCH_3$ | $OCH_3$ | CH | |
| 6-F | $SO_2N(OCH_3)CH_3$ | H | $OCH_3$ | $OCH_3$ | CH | |
| 6-Cl | $SO_2N(OCH_3)CH_3$ | H | $OCH_3$ | $OCH_3$ | CH | |
| H | $SO_2NHCH_3$ | H | $OCH_3$ | $OCH_3$ | CH | |
| H | $SO_2NHCH_3$ | H | $OCH_3$ | $CH_3$ | CH | |
| H | $SO_2NHCH_3$ | H | Cl | $OCH_3$ | CH | |
| H | $SO_2NHCH_3$ | H | $CH_3$ | $CH_3$ | CH | |
| H | $SO_2NHCH_3$ | H | $OCH_3$ | $OCH_3$ | N | |
| H | $SO_2NHCH_3$ | H | $OCH_3$ | $CH_3$ | N | |
| H | $SO_2NHCH_3$ | H | $OCH_2CH_3$ | $NHCH_3$ | N | |
| H | $SO_2NHCH_3$ | $CH_3$ | $OCH_3$ | $CH_3$ | N | |
| 5-$CH_3$ | $SO_2NHCH_3$ | H | $OCH_3$ | $OCH_3$ | CH | |
| 5-$OCH_3$ | $SO_2NHCH_3$ | H | $OCH_3$ | $OCH_3$ | CH | |
| 6-$CH_3$ | $SO_2NHCH_3$ | H | $OCH_3$ | $OCH_3$ | CH | |
| 6-$OCH_3$ | $SO_2NHCH_3$ | H | $OCH_3$ | $OCH_3$ | CH | |
| 6-F | $SO_2NHCH_3$ | H | $OCH_3$ | $OCH_3$ | CH | |
| 6-Cl | $SO_2NHCH_3$ | H | $OCH_3$ | $OCH_3$ | CH | |
| H | $SO_2NHCH_2CH_3$ | H | $OCH_3$ | $OCH_3$ | CH | |
| H | $SO_2NHCH_2CH_3$ | H | $OCH_3$ | $CH_3$ | CH | |
| H | $SO_2NHCH_2CH_3$ | H | Cl | $OCH_3$ | CH | |
| H | $SO_2NHCH_2CH_3$ | H | $CH_3$ | $CH_3$ | CH | |
| H | $SO_2NHCH_2CH_3$ | H | $OCH_3$ | $OCH_3$ | N | |
| H | $SO_2NHCH_2CH_3$ | H | $OCH_3$ | $CH_3$ | N | |
| H | $SO_2NHCH_2CH_3$ | H | $OCH_2CH_3$ | $NHCH_3$ | N | |
| H | $SO_2NHCH_2CH_3$ | $CH_3$ | $OCH_3$ | $CH_3$ | N | |
| 5-$CH_3$ | $SO_2NHCH_2CH_3$ | H | $OCH_3$ | $OCH_3$ | CH | |
| 5-$OCH_3$ | $SO_2NHCH_2CH_3$ | H | $OCH_3$ | $OCH_3$ | CH | |
| 6-$CH_3$ | $SO_2NHCH_2CH_3$ | H | $OCH_3$ | $OCH_3$ | CH | |
| 6-$OCH_3$ | $SO_2NHCH_2CH_3$ | H | $OCH_3$ | $OCH_3$ | CH | |
| 6-F | $SO_2NHCH_2CH_3$ | H | $OCH_3$ | $OCH_3$ | CH | |
| 6-Cl | $SO_2NHCH_2CH_3$ | H | $OCH_3$ | $OCH_3$ | CH | |
| H | $CO_2CH_2CH_2OH$ | H | $OCH_3$ | $OCH_3$ | CH | |
| H | $CO_2CH_2CH_2OH$ | H | $OCH_3$ | $CH_3$ | CH | |
| H | $CO_2CH_2CH_2OH$ | H | Cl | $OCH_3$ | CH | |
| H | $CO_2CH_2CH_2OH$ | H | $CH_3$ | $CH_3$ | CH | |
| H | $CO_2CH_2CH_2OH$ | H | $OCH_3$ | $OCH_3$ | N | |
| H | $CO_2CH_2CH_2OH$ | H | $OCH_3$ | $CH_3$ | N | |
| H | $CO_2CH_2CH_2OH$ | H | $OCH_2CH_3$ | $NHCH_3$ | N | |
| H | $CO_2CH_2CH_2OH$ | $CH_3$ | $OCH_3$ | $CH_3$ | N | |
| 5-$CH_3$ | $CO_2CH_2CH_2OH$ | H | $OCH_3$ | $OCH_3$ | CH | |
| 5-$OCH_3$ | $CO_2CH_2CH_2OH$ | H | $OCH_3$ | $OCH_3$ | CH | |
| 6-$CH_3$ | $CO_2CH_2CH_2OH$ | H | $OCH_3$ | $OCH_3$ | CH | |
| 6-$OCH_3$ | $CO_2CH_2CH_2OH$ | H | $OCH_3$ | $OCH_3$ | CH | |
| 6-F | $CO_2CH_2CH_2OH$ | H | $OCH_3$ | $OCH_3$ | CH | |
| 6-Cl | $CO_2CH_2CH_2OH$ | H | $OCH_3$ | $OCH_3$ | CH | |

TABLE IV-continued

General Formula 4

| $R_f$ | $R_5$ | R | X | Y | Z | m.p. (°C.) |
|---|---|---|---|---|---|---|
| H | CO$_2$CH$_2$CH$_2$CN | H | OCH$_3$ | OCH$_3$ | CH | |
| H | CO$_2$CH$_2$CH$_2$CN | H | OCH$_3$ | CH$_3$ | CH | |
| H | CO$_2$CH$_2$CH$_2$CN | H | Cl | OCH$_3$ | CH | |
| H | CO$_2$CH$_2$CH$_2$CN | H | CH$_3$ | CH$_3$ | CH | |
| H | CO$_2$CH$_2$CH$_2$CN | H | OCH$_3$ | OCH$_3$ | N | |
| H | CO$_2$CH$_2$CH$_2$CN | H | OCH$_3$ | CH$_3$ | N | |
| H | CO$_2$CH$_2$CH$_2$CN | H | OCH$_2$CH$_3$ | NHCH$_3$ | N | |
| H | CO$_2$CH$_2$CH$_2$CN | CH$_3$ | OCH$_3$ | CH$_3$ | N | |
| 5-CH$_3$ | CO$_2$CH$_2$CH$_2$CN | H | OCH$_3$ | OCH$_3$ | CH | |
| 5-OCH$_3$ | CO$_2$CH$_2$CH$_2$CN | H | OCH$_3$ | OCH$_3$ | CH | |
| 6-CH$_3$ | CO$_2$CH$_2$CH$_2$CN | H | OCH$_3$ | OCH$_3$ | CH | |
| 6-OCH$_3$ | CO$_2$CH$_2$CH$_2$CN | H | OCH$_3$ | OCH$_3$ | CH | |
| 6-F | CO$_2$CH$_2$CH$_2$CN | H | OCH$_3$ | OCH$_3$ | CH | |
| 6-Cl | CO$_2$CH$_2$CH$_2$CN | H | OCH$_3$ | OCH$_3$ | CH | |
| H | CO$_2$CH$_2$CH$_2$OSO$_2$CH$_3$ | H | OCH$_3$ | OCH$_3$ | CH | |
| H | CO$_2$CH$_2$CH$_2$OSO$_2$CH$_3$ | H | OCH$_3$ | CH$_3$ | CH | |
| H | CO$_2$CH$_2$CH$_2$OSO$_2$CH$_3$ | H | Cl | OCH$_3$ | CH | |
| H | CO$_2$CH$_2$CH$_2$OSO$_2$CH$_3$ | H | CH$_3$ | CH$_3$ | CH | |
| H | CO$_2$CH$_2$CH$_2$OSO$_2$CH$_3$ | H | OCH$_3$ | OCH$_3$ | N | |
| H | CO$_2$CH$_2$CH$_2$OSO$_2$CH$_3$ | H | OCH$_3$ | CH$_3$ | N | |
| H | CO$_2$CH$_2$CH$_2$OSO$_2$CH$_3$ | H | OCH$_2$CH$_3$ | NHCH$_3$ | N | |
| H | CO$_2$CH$_2$CH$_2$OSO$_2$CH$_3$ | CH$_3$ | OCH$_3$ | CH$_3$ | N | |
| 5-CH$_3$ | CO$_2$CH$_2$CH$_2$OSO$_2$CH$_3$ | H | OCH$_3$ | OCH$_3$ | CH | |
| 5-OCH$_3$ | CO$_2$CH$_2$CH$_2$OSO$_2$CH$_3$ | H | OCH$_3$ | OCH$_3$ | CH | |
| 6-CH$_3$ | CO$_2$CH$_2$CH$_2$OSO$_2$CH$_3$ | H | OCH$_3$ | OCH$_3$ | CH | |
| 6-OCH$_3$ | CO$_2$CH$_2$CH$_2$OSO$_2$CH$_3$ | H | OCH$_3$ | OCH$_3$ | CH | |
| 6-F | CO$_2$CH$_2$CH$_2$OSO$_2$CH$_3$ | H | OCH$_3$ | OCH$_3$ | CH | |
| 6-Cl | CO$_2$CH$_2$CH$_2$OSO$_2$CH$_3$ | H | OCH$_3$ | OCH$_3$ | CH | |

TABLE V

General Formula 5

| $R_f$ | $R_6$ | R | X | Y | Z | m.p. (°C.) |
|---|---|---|---|---|---|---|
| H | SCH$_3$ | H | OCH$_3$ | OCH$_3$ | CH | |
| H | SCH$_3$ | H | OCH$_3$ | CH$_3$ | CH | |
| H | SCH$_3$ | H | Cl | OCH$_3$ | CH | |
| H | SCH$_3$ | H | CH$_3$ | CH$_3$ | CH | |
| H | SCH$_3$ | H | OCH$_3$ | OCH$_3$ | N | |
| H | SCH$_3$ | H | OCH$_3$ | CH$_3$ | N | |
| H | SCH$_3$ | H | OCH$_2$CH$_3$ | NHCH$_3$ | N | |
| H | SCH$_3$ | CH$_3$ | OCH$_3$ | CH$_3$ | N | |
| 4-CH$_3$ | SCH$_3$ | H | OCH$_3$ | OCH$_3$ | CH | |
| 4-OCH$_3$ | SCH$_3$ | H | OCH$_3$ | OCH$_3$ | CH | |
| 6-CH$_3$ | SCH$_3$ | H | OCH$_3$ | OCH$_3$ | CH | |
| 6-OCH$_3$ | SCH$_3$ | H | OCH$_3$ | OCH$_3$ | CH | |
| 6-F | SCH$_3$ | H | OCH$_3$ | OCH$_3$ | CH | |
| 6-Cl | SCH$_3$ | H | OCH$_3$ | OCH$_3$ | CH | |
| H | SOCH$_3$ | H | OCH$_3$ | OCH$_3$ | CH | |
| H | SOCH$_3$ | H | OCH$_3$ | CH$_3$ | CH | |
| H | SOCH$_3$ | H | Cl | OCH$_3$ | CH | |
| H | SOCH$_3$ | H | CH$_3$ | CH$_3$ | CH | |
| H | SOCH$_3$ | H | OCH$_3$ | OCH$_3$ | N | |
| H | SOCH$_3$ | H | OCH$_3$ | CH$_3$ | N | |
| H | SOCH$_3$ | H | OCH$_2$CH$_3$ | NHCH$_3$ | N | |
| H | SOCH$_3$ | CH$_3$ | OCH$_3$ | CH$_3$ | N | |
| 4-CH$_3$ | SOCH$_3$ | H | OCH$_3$ | OCH$_3$ | CH | |
| 4-OCH$_3$ | SOCH$_3$ | H | OCH$_3$ | OCH$_3$ | CH | |
| 6-CH$_3$ | SOCH$_3$ | H | OCH$_3$ | OCH$_3$ | CH | |
| 6-OCH$_3$ | SOCH$_3$ | H | OCH$_3$ | OCH$_3$ | CH | |
| 6-F | SOCH$_3$ | H | OCH$_3$ | OCH$_3$ | CH | |
| 6-Cl | SOCH$_3$ | H | OCH$_3$ | OCH$_3$ | CH | |
| H | SO-cyclopropyl | H | OCH$_3$ | OCH$_3$ | CH | |
| H | SO-cyclopropyl | H | OCH$_3$ | CH$_3$ | CH | |
| H | SO-cyclopropyl | H | Cl | OCH$_3$ | CH | |
| H | SO-cyclopropyl | H | CH$_3$ | CH$_3$ | CH | |
| H | SO-cyclopropyl | H | OCH$_3$ | OCH$_3$ | N | |
| H | SO-cyclopropyl | H | OCH$_3$ | CH$_3$ | N | |
| H | SO-cyclopropyl | H | OCH$_2$CH$_3$ | NHCH$_3$ | N | |
| H | SO-cyclopropyl | CH$_3$ | OCH$_3$ | CH$_3$ | N | |
| 4-CH$_3$ | SO-cyclopropyl | H | OCH$_3$ | OCH$_3$ | CH | |
| 4-OCH$_3$ | SO-cyclopropyl | H | OCH$_3$ | OCH$_3$ | CH | |
| 6-CH$_3$ | SO-cyclopropyl | H | OCH$_3$ | OCH$_3$ | CH | |
| 6-OCH$_3$ | SO-cyclopropyl | H | OCH$_3$ | OCH$_3$ | CH | |
| 6-F | SO-cyclopropyl | H | OCH$_3$ | OCH$_3$ | CH | |
| 6-Cl | SO-cyclopropyl | H | OCH$_3$ | OCH$_3$ | CH | |
| H | SO$_2$-cyclopropyl | H | OCH$_3$ | OCH$_3$ | CH | |
| H | SO$_2$-cyclopropyl | H | OCH$_3$ | CH$_3$ | CH | |
| H | SO$_2$-cyclopropyl | H | Cl | OCH$_3$ | CH | |

TABLE V-continued

General Formula 5

| $R_f$ | $R_6$ | R | X | Y | Z | m.p. (°C.) |
|---|---|---|---|---|---|---|
| H | SO₂-cyclopropyl | H | CH₃ | CH₃ | CH | |
| H | SO₂-cyclopropyl | H | OCH₃ | OCH₃ | N | |
| H | SO₂-cyclopropyl | H | OCH₃ | CH₃ | N | |
| H | SO₂-cyclopropyl | H | OCH₂CH₃ | NHCH₃ | N | |
| H | SO₂-cyclopropyl | CH₃ | OCH₃ | CH₃ | N | |
| 4-CH₃ | SO₂-cyclopropyl | H | OCH₃ | OCH₃ | CH | |
| 4-OCH₃ | SO₂-cyclopropyl | H | OCH₃ | OCH₃ | CH | |
| 6-CH₃ | SO₂-cyclopropyl | H | OCH₃ | OCH₃ | CH | |
| 6-OCH₃ | SO₂-cyclopropyl | H | OCH₃ | OCH₃ | CH | |
| 6-F | SO₂-cyclopropyl | H | OCH₃ | OCH₃ | CH | |
| 6-Cl | SO₂-cyclopropyl | H | OCH₃ | OCH₃ | CH | |
| H | OSO₂CH₃ | H | OCH₃ | OCH₃ | CH | |
| H | OSO₂CH₃ | H | OCH₃ | CH₃ | CH | |
| H | OSO₂CH₃ | H | Cl | OCH₃ | CH | |
| H | OSO₂CH₃ | H | CH₃ | CH₃ | CH | |
| H | OSO₂CH₃ | H | OCH₃ | OCH₃ | N | |
| H | OSO₂CH₃ | H | OCH₃ | CH₃ | N | |
| H | OSO₂CH₃ | H | OCH₂CH₃ | NHCH₃ | N | |
| H | OSO₂CH₃ | CH₃ | OCH₃ | CH₃ | N | |
| 4-CH₃ | OSO₂CH₃ | H | OCH₃ | OCH₃ | CH | |
| 4-OCH₃ | OSO₂CH₃ | H | OCH₃ | OCH₃ | CH | |
| 6-CH₃ | OSO₂CH₃ | H | OCH₃ | OCH₃ | CH | |
| 6-OCH₃ | OSO₂CH₃ | H | OCH₃ | OCH₃ | CH | |
| 6-F | OSO₂CH₃ | H | OCH₃ | OCH₃ | CH | |
| 6-Cl | OSO₂CH₃ | H | OCH₃ | OCH₃ | CH | |
| H | CN | H | OCH₃ | OCH₃ | CH | |
| H | CN | H | OCH₃ | CH₃ | CH | |
| H | CN | H | Cl | OCH₃ | CH | |
| H | CN | H | CH₃ | CH₃ | CH | |
| H | CN | H | OCH₃ | OCH₃ | N | |
| H | CN | H | OCH₃ | CH₃ | N | |
| H | CN | H | OCH₂CH₃ | NHCH₃ | N | |
| H | CN | CH₃ | OCH₃ | CH₃ | N | |
| 4-CH₃ | CN | H | OCH₃ | OCH₃ | CH | |
| 4-OCH₃ | CN | H | OCH₃ | OCH₃ | CH | |
| 6-CH₃ | CN | H | OCH₃ | OCH₃ | CH | |
| 6-OCH₃ | CN | H | OCH₃ | OCH₃ | CH | |
| 6-F | CN | H | OCH₃ | OCH₃ | CH | |
| 6-Cl | CN | H | OCH₃ | OCH₃ | CH | |
| H | CH₂F | H | OCH₃ | OCH₃ | CH | |
| H | CH₂F | H | OCH₃ | CH₃ | CH | |
| H | CH₂F | H | Cl | OCH₃ | CH | |
| H | CH₂F | H | CH₃ | CH₃ | CH | |
| H | CH₂F | H | OCH₃ | OCH₃ | N | |
| H | CH₂F | H | OCH₃ | CH₃ | N | |
| H | CH₂F | H | OCH₂CH₃ | NHCH₃ | N | |
| H | CH₂F | CH₃ | OCH₃ | CH₃ | N | |
| 4-CH₃ | CH₂F | H | OCH₃ | OCH₃ | CH | |
| 4-OCH₃ | CH₂F | H | OCH₃ | OCH₃ | CH | |
| 6-CH₃ | CH₂F | H | OCH₃ | OCH₃ | CH | |
| 6-OCH₃ | CH₂F | H | OCH₃ | OCH₃ | CH | |
| 6-F | CH₂F | H | OCH₃ | OCH₃ | CH | |
| 6-Cl | CH₂F | H | OCH₃ | OCH₃ | CH | |
| H | SO₂N(OCH₃)CH₃ | H | OCH₃ | OCH₃ | CH | |
| H | SO₂N(OCH₃)CH₃ | H | OCH₃ | CH₃ | CH | |
| H | SO₂N(OCH₃)CH₃ | H | Cl | OCH₃ | CH | |
| H | SO₂N(OCH₃)CH₃ | H | CH₃ | CH₃ | CH | |
| H | SO₂N(OCH₃)CH₃ | H | OCH₃ | OCH₃ | N | |
| H | SO₂N(OCH₃)CH₃ | H | OCH₃ | CH₃ | N | |
| H | SO₂N(OCH₃)CH₃ | H | OCH₂CH₃ | NHCH₃ | N | |
| H | SO₂N(OCH₃)CH₃ | CH₃ | OCH₃ | CH₃ | N | |
| 4-CH₃ | SO₂N(OCH₃)CH₃ | H | OCH₃ | OCH₃ | CH | |
| 4-OCH₃ | SO₂N(OCH₃)CH₃ | H | OCH₃ | OCH₃ | CH | |
| 6-CH₃ | SO₂N(OCH₃)CH₃ | H | OCH₃ | OCH₃ | CH | |
| 6-OCH₃ | SO₂N(OCH₃)CH₃ | H | OCH₃ | OCH₃ | CH | |
| 6-F | SO₂N(OCH₃)CH₃ | H | OCH₃ | OCH₃ | CH | |
| 6-Cl | SO₂N(OCH₃)CH₃ | H | OCH₃ | OCH₃ | CH | |
| H | CO₂CH₂CH₂OH | H | OCH₃ | OCH₃ | CH | |
| H | CO₂CH₂CH₂OH | H | OCH₃ | CH₃ | CH | |
| H | CO₂CH₂CH₂OH | H | Cl | OCH₃ | CH | |
| H | CO₂CH₂CH₂OH | H | CH₃ | CH₃ | CH | |
| H | CO₂CH₂CH₂OH | H | OCH₃ | OCH₃ | N | |
| H | CO₂CH₂CH₂OH | H | OCH₃ | CH₃ | N | |
| H | CO₂CH₂CH₂OH | H | OCH₂CH₃ | NHCH₃ | N | |
| H | CO₂CH₂CH₂OH | CH₃ | OCH₃ | CH₃ | N | |
| 4-CH₃ | CO₂CH₂CH₂OH | H | OCH₃ | OCH₃ | CH | |
| 4-OCH₃ | CO₂CH₂CH₂OH | H | OCH₃ | OCH₃ | CH | |
| 6-CH₃ | CO₂CH₂CH₂OH | H | OCH₃ | OCH₃ | CH | |
| 6-OCH₃ | CO₂CH₂CH₂OH | H | OCH₃ | OCH₃ | CH | |
| 6-F | CO₂CH₂CH₂OH | H | OCH₃ | OCH₃ | CH | |

TABLE V-continued

General Formula 5

| $R_f$ | $R_6$ | R | X | Y | Z | m.p. (°C.) |
|---|---|---|---|---|---|---|
| 6-Cl | CO₂CH₂CH₂OH | H | OCH₃ | OCH₃ | CH | |
| H | CO₂CH₂CH₂CN | H | OCH₃ | OCH₃ | CH | |
| H | CO₂CH₂CH₂CN | H | OCH₃ | CH₃ | CH | |
| H | CO₂CH₂CH₂CN | H | Cl | OCH₃ | CH | |
| H | CO₂CH₂CH₂CN | H | CH₃ | CH₃ | CH | |
| H | CO₂CH₂CH₂CN | H | OCH₃ | OCH₃ | N | |
| H | CO₂CH₂CH₂CN | H | OCH₃ | CH₃ | N | |
| H | CO₂CH₂CH₂CN | H | OCH₂CH₃ | NHCH₃ | N | |
| H | CO₂CH₂CH₂CN | CH₃ | OCH₃ | CH₃ | N | |
| 4-CH₃ | CO₂CH₂CH₂CN | H | OCH₃ | OCH₃ | CH | |
| 4-OCH₃ | CO₂CH₂CH₂CN | H | OCH₃ | OCH₃ | CH | |
| 6-CH₃ | CO₂CH₂CH₂CN | H | OCH₃ | OCH₃ | CH | |
| 6-OCH₃ | CO₂CH₂CH₂CN | H | OCH₃ | OCH₃ | CH | |
| 6-F | CO₂CH₂CH₂CN | H | OCH₃ | OCH₃ | CH | |
| 6-Cl | CO₂CH₂CH₂CN | H | OCH₃ | OCH₃ | CH | |
| H | CO₂CH₂CF₃ | H | OCH₃ | OCH₃ | CH | |
| H | CO₂CH₂CF₃ | H | OCH₃ | CH₃ | CH | |
| H | CO₂CH₂CF₃ | H | Cl | OCH₃ | CH | |
| H | CO₂CH₂CF₃ | H | CH₃ | CH₃ | CH | |
| H | CO₂CH₂CF₃ | H | OCH₃ | OCH₃ | N | |
| H | CO₂CH₂CF₃ | H | OCH₃ | CH₃ | N | |
| H | CO₂CH₂CF₃ | H | OCH₂CH₃ | NHCH₃ | N | |
| H | CO₂CH₂CF₃ | CH₃ | OCH₃ | CH₃ | N | |
| 4-CH₃ | CO₂CH₂CF₃ | H | OCH₃ | OCH₃ | CH | |
| 4-OCH₃ | CO₂CH₂CF₃ | H | OCH₃ | OCH₃ | CH | |
| 6-CH₃ | CO₂CH₂CF₃ | H | OCH₃ | OCH₃ | CH | |
| 6-OCH₃ | CO₂CH₂CF₃ | H | OCH₃ | OCH₃ | CH | |
| 6-F | CO₂CH₂CF₃ | H | OCH₃ | OCH₃ | CH | |
| 6-Cl | CO₂CH₂CF₃ | H | OCH₃ | OCH₃ | CH | |

TABLE VI

General Formula 6

| $R_f$ | $R_6$ | R | X | Y | Z | m.p.(°C.) |
|---|---|---|---|---|---|---|
| H | SCH₃ | H | OCH₃ | OCH₃ | CH | |
| H | SCH₃ | H | OCH₃ | CH₃ | CH | |
| H | SCH₃ | H | Cl | OCH₃ | CH | |
| H | SCH₃ | H | CH₃ | CH₃ | CH | |
| H | SCH₃ | H | OCH₃ | OCH₃ | N | |
| H | SCH₃ | H | OCH₃ | CH₃ | N | |
| H | SCH₃ | H | OCH₂CH₃ | NHCH₃ | N | |
| H | SCH₃ | CH₃ | OCH₃ | CH₃ | N | |
| 4-CH₃ | SCH₃ | H | OCH₃ | OCH₃ | CH | |
| 4-Cl | SCH₃ | H | OCH₃ | OCH₃ | CH | |
| 6-CH₃ | SCH₃ | H | OCH₃ | OCH₃ | CH | |
| 6-OCH₃ | SCH₃ | H | OCH₃ | OCH₃ | CH | |
| 6-F | SCH₃ | H | OCH₃ | OCH₃ | CH | |
| 6-Cl | SCH₃ | H | OCH₃ | OCH₃ | CH | |
| H | SOCH₃ | H | OCH₃ | OCH₃ | CH | |
| H | SOCH₃ | H | OCH₃ | CH₃ | CH | |
| H | SOCH₃ | H | Cl | OCH₃ | CH | |
| H | SOCH₃ | H | CH₃ | CH₃ | CH | |
| H | SOCH₃ | H | OCH₃ | OCH₃ | N | |
| H | SOCH₃ | H | OCH₃ | CH₃ | N | |
| H | SOCH₃ | H | OCH₂CH₃ | NHCH₃ | N | |
| H | SOCH | CH₃ | OCH₃ | CH₃ | N | |
| 4-CH₃ | SOCH₃ | H | OCH₃ | OCH₃ | CH | |
| 4-Cl | SOCH₃ | H | OCH₃ | OCH₃ | CH | |
| 6-CH₃ | SOCH₃ | H | OCH₃ | OCH₃ | CH | |
| 6-OCH₃ | SOCH₃ | H | OCH₃ | OCH₃ | CH | |
| 6-F | SOCH₃ | H | OCH₃ | OCH₃ | CH | |
| 6-Cl | SOCH₃ | H | OCH₃ | OCH₃ | CH | |
| H | SO-cyclopropyl | H | OCH₃ | OCH₃ | CH | |
| H | SO-cyclopropyl | H | OCH₃ | CH₃ | CH | |
| H | SO-cyclopropyl | H | Cl | OCH₃ | CH | |
| H | SO-cyclopropyl | H | CH₃ | CH₃ | CH | |
| H | SO-cyclopropyl | H | OCH₃ | OCH₃ | N | |
| H | SO-cyclopropyl | H | OCH₃ | CH₃ | N | |
| H | SO-cyclopropyl | H | OCH₂CH₃ | NHCH₃ | N | |
| H | SO-cyclopropyl | CH₃ | OCH₃ | CH₃ | N | |
| 4-CH₃ | SO-cyclopropyl | H | OCH₃ | OCH₃ | CH | |
| 4-Cl | SO-cyclopropyl | H | OCH₃ | OCH₃ | CH | |
| 6-CH₃ | SO-cyclopropyl | H | OCH₃ | OCH₃ | CH | |
| 6-OCH₃ | SO-cyclopropyl | H | OCH₃ | OCH₃ | CH | |
| 6-F | SO-cyclopropyl | H | OCH₃ | OCH₃ | CH | |
| 6-Cl | SO-cyclopropyl | H | OCH₃ | OCH₃ | CH | |
| H | SO₂-cyclopropyl | H | OCH₃ | OCH₃ | CH | |
| H | SO₂-cyclopropyl | H | OCH₃ | CH₃ | CH | |

TABLE VI-continued

General Formula 6

| $R_f$ | $R_6$ | R | X | Y | Z | m.p.(°C.) |
|---|---|---|---|---|---|---|
| H | $SO_2$-cyclopropyl | H | Cl | $OCH_3$ | CH | |
| H | $SO_2$-cyclopropyl | H | $CH_3$ | $CH_3$ | CH | |
| H | $SO_2$-cyclopropyl | H | $OCH_3$ | $OCH_3$ | N | |
| H | $SO_2$-cyclopropyl | H | $OCH_3$ | $CH_3$ | N | |
| H | $SO_2$-cyclopropyl | H | $OCH_2CH_3$ | $NHCH_3$ | N | |
| H | $SO_2$-cyclopropyl | $CH_3$ | $OCH_3$ | $CH_3$ | N | |
| 4-$CH_3$ | $SO_2$-cyclopropyl | H | $OCH_3$ | $OCH_3$ | CH | |
| 4-Cl | $SO_2$-cyclopropyl | H | $OCH_3$ | $OCH_3$ | CH | |
| 6-$CH_3$ | $SO_2$-cyclopropyl | H | $OCH_3$ | $OCH_3$ | CH | |
| 6-$OCH_3$ | $SO_2$-cyclopropyl | H | $OCH_3$ | $OCH_3$ | CH | |
| 6-F | $SO_2$-cyclopropyl | H | $OCH_3$ | $OCH_3$ | CH | |
| 6-Cl | $SO_2$-cyclopropyl | H | $OCH_3$ | $OCH_3$ | CH | |
| H | $OSO_2CH_3$ | H | $OCH_3$ | $OCH_3$ | CH | |
| H | $OSO_2CH_3$ | H | $OCH_3$ | $CH_3$ | CH | |
| H | $OSO_2CH_3$ | H | Cl | $OCH_3$ | CH | |
| H | $OSO_2CH_3$ | H | $CH_3$ | $CH_3$ | CH | |
| H | $OSO_2CH_3$ | H | $OCH_3$ | $OCH_3$ | N | |
| H | $OSO_2CH_3$ | H | $OCH_3$ | $CH_3$ | N | |
| H | $OSO_2CH_3$ | H | $OCH_2CH_3$ | $NHCH_3$ | N | |
| H | $OSO_2CH_3$ | $CH_3$ | $OCH_3$ | $CH_3$ | N | |
| 4-$CH_3$ | $OSO_2CH_3$ | H | $OCH_3$ | $OCH_3$ | CH | |
| 4-Cl | $OSO_2CH_3$ | H | $OCH_3$ | $OCH_3$ | CH | |
| 6-$CH_3$ | $OSO_2CH_3$ | H | $OCH_3$ | $OCH_3$ | CH | |
| 6-$OCH_3$ | $OSO_2CH_3$ | H | $OCH_3$ | $OCH_3$ | CH | |
| 6-F | $OSO_2CH_3$ | H | $OCH_3$ | $OCH_3$ | CH | |
| 6-Cl | $OSO_2CH_3$ | H | $OCH_3$ | $OCH_3$ | CH | |
| H | CN | H | $OCH_3$ | $OCH_3$ | CH | |
| H | CN | H | $OCH_3$ | $CH_3$ | CH | |
| H | CN | H | Cl | $OCH_3$ | CH | |
| H | CN | H | $CH_3$ | $CH_3$ | CH | |
| H | CN | H | $OCH_3$ | $OCH_3$ | N | |
| H | CN | H | $OCH_3$ | $CH_3$ | N | |
| H | CN | H | $OCH_2CH_3$ | $NHCH_3$ | N | |
| H | CN | $CH_3$ | $OCH_3$ | $CH_3$ | N | |
| 4-$CH_3$ | CN | H | $OCH_3$ | $OCH_3$ | CH | |
| 4-Cl | CN | H | $OCH_3$ | $OCH_3$ | CH | |
| 6-$CH_3$ | CN | H | $OCH_3$ | $OCH_3$ | CH | |
| 6-$OCH_3$ | CN | H | $OCH_3$ | $OCH_3$ | CH | |
| 6-F | CN | H | $OCH_3$ | $OCH_3$ | CH | |
| 6-Cl | CN | H | $OCH_3$ | $OCH_3$ | CH | |
| H | $SO_2N(OCH_3)CH_3$ | H | $OCH_3$ | $OCH_3$ | CH | |
| H | $SO_2N(OCH_3)CH_3$ | H | $OCH_3$ | $CH_3$ | CH | |
| H | $SO_2N(OCH_3)CH_3$ | H | Cl | $OCH_3$ | CH | |
| H | $SO_2N(OCH_3)CH_3$ | H | $CH_3$ | $CH_3$ | CH | |
| H | $SO_2N(OCH_3)CH_3$ | H | $OCH_3$ | $OCH_3$ | N | |
| H | $SO_2N(OCH_3)CH_3$ | H | $OCH_3$ | $CH_3$ | N | |
| H | $SO_2N(OCH_3)CH_3$ | H | $OCH_2CH_3$ | $NHCH_3$ | N | |
| H | $SO_2N(OCH_3)CH_3$ | $CH_3$ | $OCH_3$ | $CH_3$ | N | |
| 4-$CH_3$ | $SO_2N(OCH_3)CH_3$ | H | $OCH_3$ | $OCH_3$ | CH | |
| 4-Cl | $SO_2N(OCH_3)CH_3$ | H | $OCH_3$ | $OCH_3$ | CH | |
| 6-$CH_3$ | $SO_2N(OCH_3)CH_3$ | H | $OCH_3$ | $OCH_3$ | CH | |
| 6-$OCH_3$ | $SO_2N(OCH_3)CH_3$ | H | $OCH_3$ | $OCH_3$ | CH | |
| 6-F | $SO_2N(OCH_3)CH_3$ | H | $OCH_3$ | $OCH_3$ | CH | |
| 6-Cl | $SO_2N(OCH_3)CH_3$ | H | $OCH_3$ | $OCH_3$ | CH | |
| H | $CO_2CH_2CH_2OH$ | H | $OCH_3$ | $OCH_3$ | CH | |
| H | $CO_2CH_2CH_2OH$ | H | $OCH_3$ | $CH_3$ | CH | |
| H | $CO_2CH_2CH_2OH$ | H | Cl | $OCH_3$ | CH | |
| H | $CO_2CH_2CH_2OH$ | H | $CH_3$ | $CH_3$ | CH | |
| H | $CO_2CH_2CH_2OH$ | H | $OCH_3$ | $OCH_3$ | N | |
| H | $CO_2CH_2CH_2OH$ | H | $OCH_3$ | $CH_3$ | N | |
| H | $CO_2CH_2CH_2OH$ | H | $OCH_2CH_3$ | $NHCH_3$ | N | |
| H | $CO_2CH_2CH_2OH$ | $CH_3$ | $OCH_3$ | $CH_3$ | N | |
| 4-$CH_3$ | $CO_2CH_2CH_2OH$ | H | $OCH_3$ | $OCH_3$ | CH | |
| 4-Cl | $CO_2CH_2CH_2OH$ | H | $OCH_3$ | $OCH_3$ | CH | |
| 6-$CH_3$ | $CO_2CH_2CH_2OH$ | H | $OCH_3$ | $OCH_3$ | CH | |
| 6-$OCH_3$ | $CO_2CH_2CH_2OH$ | H | $OCH_3$ | $OCH_3$ | CH | |
| 6-F | $CO_2CH_2CH_2OH$ | H | $OCH_3$ | $OCH_3$ | CH | |
| 6-Cl | $CO_2CH_2CH_2OH$ | H | $OCH_3$ | $OCH_3$ | CH | |
| H | $CO_2CH_2CH_2CN$ | H | $OCH_3$ | $OCH_3$ | CH | |
| H | $CO_2CH_2CH_2CN$ | H | $OCH_3$ | $CH_3$ | CH | |
| H | $CO_2CH_2CH_2CN$ | H | Cl | $OCH_3$ | CH | |
| H | $CO_2CH_2CH_2CN$ | H | $CH_3$ | $CH_3$ | CH | |
| H | $CO_2CH_2CH_2CN$ | H | $OCH_3$ | $OCH_3$ | N | |
| H | $CO_2CH_2CH_2CN$ | H | $OCH_3$ | $CH_3$ | N | |
| H | $CO_2CH_2CH_2CN$ | H | $OCH_2CH_3$ | $NHCH_3$ | N | |
| H | $CO_2CH_2CH_2CN$ | $CH_3$ | $OCH_3$ | $CH_3$ | N | |
| 4-$CH_3$ | $CO_2CH_2CH_2CN$ | H | $OCH_3$ | $OCH_3$ | CH | |
| 4-Cl | $CO_2CH_2CH_2CN$ | H | $OCH_3$ | $OCH_3$ | CH | |
| 6-$CH_3$ | $CO_2CH_2CH_2CN$ | H | $OCH_3$ | $OCH_3$ | CH | |
| 6-$OCH_3$ | $CO_2CH_2CH_2CN$ | H | $OCH_3$ | $OCH_3$ | CH | |

TABLE VI-continued

| | | General Formula 6 | | | | |
|---|---|---|---|---|---|---|
| $R_f$ | $R_6$ | R | X | Y | Z | m.p.(°C.) |
| 6-F | $CO_2CH_2CH_2CN$ | H | $OCH_3$ | $OCH_3$ | CH | |
| 6-Cl | $CO_2CH_2CH_2CN$ | H | $OCH_3$ | $OCH_3$ | CH | |

TABLE VII

| | | General Formula 7 | | | |
|---|---|---|---|---|---|
| $R_1$ | $R_7$ | A | X | Y | m.p.(°C.) |
| H | $SOCH_3$ | A-2 | $X_1 = CH_3$ | $Y_1 = CH_2$ | |
| H | $SOCH_3$ | A-3 | $X_1 = CH_3$ | | |
| H | $SOCH_3$ | A-3 | $X_1 = OCH_3$ | | |
| H | $SOCH_3$ | A-4 | $X_3 = OCH_3$ | | |
| H | $SO_2CH_3$ | A-2 | $X_1 = CH_3$ | $Y_1 = CH_2$ | |
| H | $SO_2CH_3$ | A-3 | $X_1 = CH_3$ | | |
| H | $SO_2CH_3$ | A-3 | $X_1 = OCH_3$ | | |
| H | $SO_2CH_3$ | A-4 | $X_3 = OCH_3$ | | |
| H | $SOCH_2CH_3$ | A-2 | $X_1 = CH_3$ | $Y_1 = CH_2$ | |
| H | $SOCH_2CH_3$ | A-3 | $X_1 = CH_3$ | | |
| H | $SOCH_2CH_3$ | A-3 | $X_1 = OCH_3$ | | |
| H | $SOCH_2CH_3$ | A-4 | $X_3 = OCH_3$ | | |
| H | $SO_2CH_2CH_3$ | A-2 | $X_1 = CH_3$ | $Y_1 = CH_2$ | |
| H | $SO_2CH_2CH_3$ | A-3 | $X_1 = CH_3$ | | |
| H | $SO_2CH_2CH_3$ | A-3 | $X_1 = OCH_3$ | | |
| H | $SO_2CH_2CH_3$ | A-4 | $X_3 = OCH_3$ | | |
| H | $SOCH_2CH_2CH_3$ | A-2 | $X_1 = CH_3$ | $Y_1 = CH_2$ | |
| H | $SOCH_2CH_2CH_3$ | A-3 | $X_1 = CH_3$ | | |
| H | $SOCH_2CH_2CH_3$ | A-3 | $X_1 = OCH_3$ | | |
| H | $SOCH_2CH_2CH_3$ | A-4 | $X_3 = OCH_3$ | | |
| H | $SO_2CH_2CH_2CH_3$ | A-2 | $X_1 = CH_3$ | $Y_1 = CH_2$ | |
| H | $SO_2CH_2CH_2CH_3$ | A-3 | $X_1 = CH_3$ | | |
| H | $SO_2CH_2CH_2CH_3$ | A-3 | $X_1 = OCH_3$ | | |
| H | $SO_2CH_2CH_2CH_3$ | A-4 | $X_3 = OCH_3$ | | |
| H | $SOCH(CH_3)_2$ | A-2 | $X_1 = CH_3$ | $Y_1 = CH_2$ | |
| H | $SOCH(CH_3)_2$ | A-3 | $X_1 = CH_3$ | | |
| H | $SOCH(CH_3)_2$ | A-3 | $X_1 = OCH_3$ | | |
| H | $SOCH(CH_3)_2$ | A-4 | $X_3 = OCH_3$ | | |
| H | $SO_2CH(CH_3)_2$ | A-2 | $X_1 = CH_3$ | $Y_1 = CH_2$ | |
| H | $SO_2CH(CH_3)_2$ | A-3 | $X_1 = CH_3$ | | |
| H | $SO_2CH(CH_3)_2$ | A-3 | $X_1 = OCH_3$ | | |
| H | $SO_2CH(CH_3)_2$ | A-4 | $X_3 = OCH_3$ | | |
| H | $SOCH_2CH_2CH_2CH_3$ | A-2 | $X_1 = CH_3$ | $Y_1 = CH2$ | |
| H | $SOCH_2CH_2CH_2CH_3$ | A-3 | $X_1 = CH_3$ | | |
| H | $SOCH_2CH_2CH_2CH_3$ | A-3 | $X_1 = OCH_3$ | | |
| H | $SOCH_2CH_2CH_2CH_3$ | A-4 | $X_1 = OCH_3$ | | |
| H | $SO_2CH_2CH_2CH_2CH_3$ | A-2 | $X_1 = CH_3$ | $Y_1 = CH_2$ | |
| H | $SO_2CH_2CH_2CH_2CH_3$ | A-3 | $X_1 = CH_3$ | | |
| H | $SO_2CH_2CH_2CH_2CH_3$ | A-3 | $X_1 = OCH_3$ | | |
| H | $SO_2CH_2CH_2CH_2CH_3$ | A-4 | $X_3 = OCH_3$ | | |
| H | S-cyclopropyl | A-2 | $X_1 = CH_3$ | $Y_1 = CH_2$ | |
| H | S-cyclopropyl | A-3 | $X_1 = CH_3$ | | |
| H | S-cyclopropyl | A-3 | $X_1 = OCH_3$ | | |
| H | S-cyclopropyl | A-4 | $X_3 = OCH_3$ | | |
| H | $SO_2$-cyclopropyl | A-2 | $X_1 = CH_3$ | $Y_1 = CH_2$ | |
| H | $SO_2$-cyclopropyl | A-3 | $X_1 = CH_3$ | | |
| H | $SO_2$-cyclopropyl | A-3 | $X_1 = OCH_3$ | | |
| H | $SO_2$-cyclopropyl | A-4 | $X_3 = OCH_3$ | | |
| H | $OSO_2CH_3$ | A-2 | $X_1 = CH_3$ | $Y_1 = CH_2$ | |
| H | $OSO_2CH_3$ | A-3 | $X_1 = CH_3$ | | |
| H | $OSO_2CH_3$ | A-3 | $X_1 = OCH_3$ | | |
| H | $OSO_2CH_3$ | A-4 | $X_3 = OCH_3$ | | |
| H | $OSO_2CH_3$ | A-7 | $X_4 = OCH_3$ | $Y_4 = OCH_3$ | |
| H | $OSO_2CH_2CH_3$ | A-2 | $X_1 = CH_3$ | $Y_1 = CH_2$ | |
| H | $OSO_2CH_2CH_3$ | A-3 | $X_1 = CH_3$ | | |
| H | $OSO_2CH_2CH_3$ | A-3 | $X_1 = OCH_3$ | | |
| H | $OSO_2CH_2CH_3$ | A-4 | $X_3 = OCH_3$ | | |
| H | $OSO_2CF_3$ | A-2 | $X_1 = CH_3$ | $Y_1 = CH_2$ | |
| H | $OSO_2CF_3$ | A-3 | $X_1 = CH_3$ | | |
| H | $OSO_2CF_3$ | A-3 | $X_1 = OCH_3$ | | |
| H | $OSO_2CF_3$ | A-4 | $X_3 = OCH_3$ | | |
| H | $OSO_2CCl_3$ | A-2 | $X_1 = CH_3$ | $Y_1 = CH_2$ | |
| H | $OSO_2CCl_3$ | A-3 | $X_1 = CH_3$ | | |
| H | $OSO_2CCl_3$ | A-3 | $X_1 = OCH_3$ | | |
| H | $OSO_2CCl_3$ | A-4 | $X_3 = OCH_3$ | | |
| H | CN | A-2 | $X_1 = CH_3$ | $Y_1 = CH_2$ | |
| H | CN | A-3 | $X_1 = CH_3$ | | |
| H | CN | A-3 | $X_1 = OCH_3$ | | |
| H | CN | A-4 | $X_3 = OCH_3$ | | |
| H | $CH_2F$ | A-2 | $X_1 = CH_3$ | $Y_1 = CH_2$ | |
| H | $CH_2F$ | A-3 | $X_1 = CH_3$ | | |

TABLE VII-continued

General Formula 7

| $R_1$ | $R_7$ | A | X | Y | m.p.(°C.) |
|---|---|---|---|---|---|
| H | $CH_2F$ | A-3 | $X_1 = OCH_3$ | | |
| H | $CH_2F$ | A-4 | $X_3 = OCH_3$ | | |
| H | $CF_2H$ | A-2 | $X_1 = CH_3$ | $Y_1 = CH_2$ | |
| H | $CF_2H$ | A-3 | $X_1 = CH_3$ | | |
| H | $CF_2H$ | A-3 | $X_1 = OCH_3$ | | |
| H | $CF_2H$ | A-4 | $X_3 = OCH_3$ | | |
| H | $SO_2NHCH_3$ | A-2 | $X_1 = CH_3$ | $Y_1 = CH_2$ | |
| H | $SO_2NHCH_3$ | A-3 | $X_1 = CH_3$ | | |
| H | $SO_2NHCH_3$ | A-3 | $X_1 = OCH_3$ | | |
| H | $SO_2NHCH_3$ | A-4 | $X_3 = OCH_3$ | | |
| H | $SO_2NHCH_2CH_2OCH_3$ | A-2 | $X_1 = CH_3$ | $Y_1 = CH_2$ | |
| H | $SO_2NHCH_2CH_2OCH_3$ | A-3 | $X_1 = CH_3$ | | |
| H | $SO_2NECH_2CH_2OCH_3$ | A-3 | $X_1 = OCH_3$ | | |
| H | $SO_2NHCH_2CH_2OCH_3$ | A-4 | $X_3 = OCH_3$ | | |
| H | $CO_2CH_2CH_2OH$ | A-2 | $X_1 = CH_3$ | $Y_1 = CH_2$ | |
| H | $CO_2CH_2CH_2OH$ | A-3 | $X_1 = CH_3$ | | |
| H | $CO_2CH_2CH_2OH$ | A-3 | $X_1 = OCH_3$ | | |
| H | $CO_2CH_2CH_2OH$ | A-4 | $X_3 = OCH_3$ | | |
| H | $CO_2CH_2CH_2CN$ | A-2 | $X_1 = CH_3$ | $Y_1 = CH_2$ | |
| H | $CO_2CH_2CH_2CN$ | A-3 | $X_1 = CH_3$ | | |
| H | $CO_2CH_2CH_2CN$ | A-3 | $X_1 = OCH_3$ | | |
| H | $CO_2CH_2CH_2CN$ | A-4 | $X_3 = OCH_3$ | | |
| H | $CO_2CH_2CF_2$ | A-2 | $X_1 = CH_3$ | $Y_1 = CH_2$ | |
| H | $CO_2CH_2CF_2$ | A-3 | $X_1 = CH_3$ | | |
| H | $CO_2CH_2CF_2$ | A-3 | $X_1 = OCH_3$ | | |
| 6-$OCH_3$ | $SO_2N(CH_3)_2$ | A-2 | $X_1 = CH_3$ | $Y_1 = CH_2$ | |
| 6-$OCH_3$ | $SO_2N(CH_3)_2$ | A-3 | $X_1 = CH_3$ | | |
| 6-$OCH_3$ | $SO_2N(CH_3)_2$ | A-Y | $X_1 = OCH_3$ | | |
| 6-$OCH_3$ | $SO_2N(CH_3)_2$ | A-4 | $X_3 = OCH_3$ | | |
| 6-$SCH_3$ | $SO_2N(CH_3)_2$ | A-2 | $X_1 = CH_3$ | $Y_1 = CH_2$ | |
| 6-$SCH_3$ | $SO_2N(CH_3)_2$ | A-3 | $X_1 = CH_3$ | | |
| 6-$SCH_3$ | $SO_2N(CH_3)_2$ | A-3 | $X_1 = OCH_3$ | | |
| 6-$SCH_3$ | $SO_2N(CH_3)_2$ | A-4 | $X_3 = OCH_3$ | | |
| 6-$N(CH_3)_2$ | $SO_2N(CH_3)_2$ | A-2 | $X_1 = CH_3$ | $Y_1 = CH_2$ | |
| 6-$N(CH_3)_2$ | $SO_2N(CH_3)_2$ | A-3 | $X_1 = CH_3$ | | |
| 6-$N(CH_3)_2$ | $SO_2N(CH_3)_2$ | A-3 | $X_1 = OCH_3$ | | |
| 6-$N(CH_3)_2$ | $SO_2N(CH_3)_2$ | A-4 | $X_3 = OCH_3$ | | |
| 6-$NHCH_3$ | $SO_2N(CH_3)_2$ | A-2 | $X_1 = CH_3$ | $Y_1 = CH_2$ | |
| 6-$NHCH_3$ | $SO_2N(CH_3)_2$ | A-3 | $X_1 = CH_3$ | | |
| 6-$NHCH_3$ | $SO_2N(CH_3)_2$ | A-3 | $X_1 = OCH_3$ | | |
| 6-$NHCH_3$ | $SO_2N(CH_3)_2$ | A-4 | $X_3 = OCH_3$ | | |
| 6-$OCH_3$ | $CO_2CH_3$ | A-2 | $X_1 = CH_3$ | $Y_1 = CH_2$ | |
| 6-$OCH_3$ | $CO_2CH_3$ | A-3 | $X_1 = CH_3$ | | |
| 6-$OCH_3$ | $CO_2CH_3$ | A-3 | $X_1 = OCH_3$ | | |
| 6-$OCH_3$ | $CO_2CH_3$ | A-4 | $X_3 = OCH_3$ | | |
| 6-$SCH_3$ | $CO_2CH_3$ | A-2 | $X_1 = CH_3$ | $Y_1 = CH_2$ | |
| 6-$SCH_3$ | $CO_2CH_3$ | A-3 | $X_1 = CH_3$ | | |
| 6-$SCH_3$ | $CO_2CH_3$ | A-3 | $X_1 = OCH_3$ | | |
| 6-$SCH_3$ | $CO_2CH_3$ | A-4 | $X_3 = OCH_3$ | | |
| 6-$N(CH_3)_2$ | $CO_2CH_3$ | A-2 | $X_1 = CH_3$ | $Y_1 = CH_2$ | |
| 6-$N(CH_3)_2$ | $CO_2CH_3$ | A-3 | $X_1 = CH_3$ | | |
| 6-$N(CH_3)_2$ | $CO_2CH_3$ | A-3 | $X_3 = OCH_3$ | | |
| 6-$N(CH_3)_2$ | $CO_2CH_3$ | A-4 | $X_3 = OCH_3$ | | |
| 6-$NHCH_3$ | $SO_2N(CH_3)_2$ | A-2 | $X_1 = CH_3$ | $Y_1 = CH_2$ | |
| 6-$NHCH_3$ | $SO_2N(CH_3)_2$ | A-3 | $X_1 = CH_3$ | | |
| 6-$NHCH_3$ | $SO_2N(CH_3)_2$ | A-3 | $X_1 = OCH_3$ | | |
| 6-$NHCH_3$ | $SO_2N(CH_3)_2$ | A-4 | $X_3 = OCH_3$ | | |
| 6-$OCH_3$ | $SO_2N(CH_3)_2$ | A-2 | $X_1 = CH_3$ | $Y_1 = CH_2$ | |
| 6-$OCH_3$ | $SO_2N(CH_3)_2$ | A-3 | $X_1 = CH_3$ | | |
| 6-$OCH_3$ | $SO_2N(CH_3)_2$ | A-3 | $X_1 = OCH_3$ | | |
| 6-$OCH_3$ | $SO_2N(CH_3)_2$ | A-4 | $X_3 = OCH_3$ | | |
| 6-$SCH_3$ | $SO_2N(CH_3)_2$ | A-2 | $X_1 = CH_3$ | $Y_1 = CH_2$ | |
| 6-$SCH_3$ | $SO_2N(CH_3)_2$ | A-3 | $X_1 = CH_3$ | | |
| 6-$SCH_3$ | $SO_2N(CH_3)_2$ | A-3 | $X_1 = OCH_3$ | | |
| 6-$SCH_3$ | $SO_2N(CH_3)_2$ | A-4 | $X_3 = OCH_3$ | | |
| 6-$N(CH_3)_2$ | $SO_2N(CH_3)_2$ | A-2 | $X_1 = CH_3$ | $Y_1 = CH_2$ | |
| 6-$N(CH_3)_2$ | $SO_2N(CH_3)_2$ | A-3 | $X_1 = CH_3$ | | |
| 6-$N(CH_3)_2$ | $SO_2N(CH_3)_2$ | A-3 | $X_1 = OCH_3$ | | |
| 6-$N(CH_3)_2$ | $SO_2N(CH_3)_2$ | A-4 | $X_3 = OCH_3$ | | |
| 6-$NHCH_3$ | $CO_2CH_3$ | A-2 | $X_1 = CH_3$ | $Y_1 = CH_2$ | |
| 6-$NHCH_3$ | $CO_2CH_3$ | A-3 | $X_1 = CH_3$ | | |
| 6-$NHCH_3$ | $CO_2CH_3$ | A-3 | $X_1 = OCH_3$ | | |
| 6-$NHCH_3$ | $CO_2CH_3$ | A-4 | $X_3 = OCH_3$ | | |
| 6-$OCH_3$ | $SO_2NHOCH_3$ | A-2 | $X_1 = CH_3$ | $Y_1 = CH$ | |
| 6-$OCH_3$ | $SO_2NHOCH_3$ | A-3 | $X_1 = CH_3$ | | |
| 6-$OCH_3$ | $SO_2NHOCH_3$ | A-3 | $X_1 = OCH_3$ | | |
| 6-$OCH_3$ | $SO_2NHOCH_3$ | A-4 | $X_3 = OCH_3$ | | |
| 6-$SCH_3$ | $SO_2NHOCH_3$ | A-2 | $X_1 = CH_3$ | $Y_1 = CH_2$ | |
| 6-$SCH_3$ | $SO_2NHOCH_3$ | A-3 | $X_1 = CH_3$ | | |
| 6-$SCH_3$ | $SO_2NHOCH_3$ | A-3 | $X_1 = OCH_3$ | | |

TABLE VII-continued

General Formula 7

| $R_1$ | $R_7$ | A | X | Y | m.p.(°C.) |
|---|---|---|---|---|---|
| 6-SCH$_3$ | SO$_2$NHOCH$_3$ | A-4 | X$_3$ = OCH$_3$ | | |
| 6-N(CH$_3$)$_2$ | SO$_2$NHOCH$_3$ | A-2 | X$_1$ = CH$_3$ | Y$_1$ = CH$_2$ | |
| 6-N(CH$_3$)$_2$ | SO$_2$NHOCH$_3$ | A-3 | X$_1$ = CH$_3$ | | |
| 6-N(CH$_3$)$_2$ | SO$_2$NHOCH$_3$ | A-3 | X$_1$ = OCH$_3$ | | |
| 6-N(CH$_3$)$_2$ | SO$_2$NHOCH$_3$ | A-4 | X$_3$ = OCH$_3$ | | |
| 6-NHCH$_3$ | SO$_2$NHOCH$_3$ | A-2 | X$_1$ = CH$_3$ | Y$_1$ = CH$_2$ | |
| 6-NHCH$_3$ | SO$_2$NHOCH$_3$ | A-3 | X$_1$ = CH$_3$ | | |
| 6-NHCH$_3$ | SO$_2$NHOCH$_3$ | A-3 | X$_1$ = OCH$_3$ | | |
| 6-NHCH$_3$ | SO$_2$NHOCH$_3$ | A-4 | X$_3$ = OCH$_3$ | | |
| 6-OCH$_3$ | CO$_2$CH$_2$CH$_3$ | A-2 | X$_1$ = CH$_3$ | Y$_1$ = CH$_2$ | |
| 6-OCH$_3$ | CO$_2$CH$_2$CH$_3$ | A-3 | X$_1$ = CH$_3$ | | |
| 6-OCH$_3$ | CO$_2$CH$_2$CH$_3$ | A-3 | X$_1$ = OCH$_3$ | | |
| 6-OCH$_3$ | CO$_2$CH$_2$CH$_3$ | A-4 | X$_4$ = OCH$_3$ | | |
| 6-OCH$_3$ | CO$_2$CH$_2$CH$_3$ | A-2 | X$_1$ = CH$_3$ | Y$_1$ = CH$_2$ | |
| 6-OCH$_3$ | CO$_2$CH$_2$CH$_3$ | A-3 | X$_1$ = CH$_3$ | | |
| 6-OCH$_3$ | CO$_2$CH$_2$CH$_3$ | A-3 | X$_1$ = OCH$_3$ | | |
| 6-OCH$_3$ | CO$_2$CH$_2$CH$_3$ | A-4 | X$_3$ = OCH$_3$ | | |
| 6-OCH$_3$ | CO$_2$CH$_2$CH$_3$ | A-2 | X$_1$ = CH$_3$ | Y$_1$ = CH$_2$ | |
| 6-OCH$_3$ | CO$_2$CH$_2$CH$_3$ | A-3 | X$_1$ = CH$_3$ | | |
| 6-OCH$_3$ | CO$_2$CH$_2$CH$_3$ | A-3 | X$_1$ = OCH$_3$ | | |
| 6-OCH$_3$ | CO$_2$CH$_2$CH$_3$ | A-4 | X$_3$ = OCH$_3$ | | |
| 6-OCH$_3$ | CO$_2$CH$_2$CH$_3$ | A-2 | X$_1$ = CH$_3$ | Y$_1$ = CH$_2$ | |
| 6-OCH$_3$ | CO$_2$CH$_2$CH$_3$ | A-3 | X$_1$ = CH$_3$ | | |
| 6-OCH$_3$ | CO$_2$CH$_2$CH$_3$ | A-3 | X$_1$ = OCH$_3$ | | |
| 6-OCH$_3$ | CO$_2$CH$_2$CH$_3$ | A-4 | X$_3$ = OCH$_3$ | | |

TABLE VIII

General Formula 8

| $R_1$ | $R_3$ | A | X | X | m.p.(°C.) |
|---|---|---|---|---|---|
| H | SOCH$_3$ | A-2 | X$_1$ = CH$_3$ | Y$_1$ = CH$_2$ | |
| H | SOCH$_3$ | A-3 | X$_1$ = CH$_3$ | | |
| H | SOCH$_3$ | A-3 | X$_1$ = OCH$_3$ | | |
| H | SOCH$_3$ | A-4 | X$_3$ = OCH$_3$ | | |
| H | SOCH$_2$CH$_3$ | A-2 | X$_1$ = CH$_3$ | Y$_1$ = CH$_2$ | |
| H | SOCH$_2$CH$_3$ | A-3 | X$_1$ = CH$_3$ | | |
| H | SOCH$_2$CH$_3$ | A-3 | X$_1$ = OCH$_3$ | | |
| H | SOCH$_2$CH$_3$ | A-4 | X$_3$ = OCH$_3$ | | |
| H | SOCH$_2$CH$_2$CH$_3$ | A-2 | X$_1$ = CH$_3$ | Y$_1$ = CH$_2$ | |
| H | SOCH$_2$CH$_2$CH$_3$ | A-3 | X$_1$ = CH$_3$ | | |
| H | SOCH$_2$CH$_2$CH$_3$ | A-3 | X$_1$ = OCH$_3$ | | |
| H | SOCH$_2$CH$_2$CH$_3$ | A-4 | X$_3$ = OCH$_3$ | | |
| H | S-cyclopropyl | A-2 | X$_1$ = CH$_3$ | Y$_1$ = CH$_2$ | |
| H | S-cyclopropyl | A-3 | X$_1$ = CH$_3$ | | |
| H | S-cyclopropyl | A-3 | X$_1$ = OCH$_3$ | | |
| H | S-cyclopropyl | A-4 | X$_3$ = OCH$_3$ | | |
| H | SO$_2$-cyclopropyl | A-2 | X$_1$ = CH$_3$ | Y$_1$ = CH$_2$ | |
| H | SO$_2$-cyclopropyl | A-3 | X$_1$ = CH$_3$ | | |
| H | SO$_2$-cyclopropyl | A-3 | X$_1$ = OCH$_3$ | | |
| H | SO$_2$-cyclopropyl | A-4 | X$_3$ = OCH$_3$ | | |
| H | OSO$_2$CH$_3$ | A-2 | X$_1$ = CH$_3$ | Y$_1$ = CH$_2$ | |
| H | OSO$_2$CH$_3$ | A-3 | X$_1$ = CH$_3$ | | |
| H | OSO$_2$CH$_3$ | A-3 | X$_1$ = OCH$_3$ | | |
| H | OSO$_2$CH$_3$ | A-4 | X$_3$ = OCH$_3$ | | |
| H | OSO$_2$CH$_2$CH$_3$ | A-2 | X$_1$ = CH$_3$ | Y$_1$ = CH$_2$ | |
| H | OSO$_2$CH$_2$CH$_3$ | A-3 | X$_1$ = CH$_3$ | | |
| H | OSO$_2$CH$_2$CH$_3$ | A-3 | X$_1$ = OCH$_3$ | | |
| H | OSO$_2$CH$_2$CH$_3$ | A-4 | X$_3$ = OCH$_3$ | | |
| H | OSO$_2$CF$_3$ | A-2 | X$_1$ = CH$_3$ | Y$_1$ = CH$_2$ | |
| H | OSO$_2$CF$_3$ | A-3 | X$_1$ = CH$_3$ | | |
| H | OSO$_2$CF$_3$ | A-3 | X$_1$ = OCH$_3$ | | |
| H | OSO$_2$CF$_3$ | A-4 | X$_3$ = OCH$_3$ | | |
| H | OCO$_2$CCl$_3$ | A-2 | X$_1$ = CH$_3$ | Y$_1$ = CH$_2$ | |
| H | OSO$_2$CCl$_3$ | A-3 | X$_1$ = CH$_3$ | | |
| H | OSO$_2$CCl$_3$ | A-3 | X$_1$ = OCH$_3$ | | |
| H | OSO$_2$CCl$_3$ | A-4 | X$_3$ = OCH$_3$ | | |
| H | CH$_2$F | A-2 | X$_1$ = CH$_3$ | Y$_1$ = CH$_2$ | |
| H | CH$_2$F | A-3 | X$_1$ = CH$_3$ | | |
| H | CH$_2$F | A-3 | X$_1$ = OCH$_3$ | | |
| H | CH$_2$F | A-4 | X$_3$ = OCH$_3$ | | |
| H | SO$_2$NHCH$_3$ | A-2 | X$_1$ = CH$_3$ | Y$_1$ = CH$_2$ | |
| H | SO$_2$NHCH$_3$ | A-3 | X$_1$ = CH$_3$ | | |
| H | SO$_2$NHCH$_3$ | A-3 | X$_1$ = OCH$_3$ | | |
| H | SO$_2$NHCH$_3$ | A-4 | X$_3$ = OCH$_3$ | | |
| H | CO$_2$CH$_2$CH$_2$OH | A-2 | X$_1$ = CH$_3$ | Y$_1$ = CH$_2$ | |
| H | CO$_2$CH$_2$CH$_2$OH | A-3 | X$_1$ = CH$_3$ | | |
| H | CO$_2$CH$_2$CH$_2$OH | A-3 | X$_1$ = OCH$_3$ | | |
| H | CO$_2$CH$_2$CH$_2$OH | A-4 | X$_3$ = OCH$_3$ | | |

TABLE VIII-continued

General Formula 8

| $R_1$ | $R_3$ | A | X | X | m.p.(°C.) |
|---|---|---|---|---|---|
| H | $CO_2CH_2CN_2CN$ | A-2 | $X_1 = CH_3$ | $Y_1 = CH_2$ | |
| H | $CO_2CH_2CH_2CN$ | A-3 | $X_1 = CH_3$ | | |
| H | $CO_2CH_2CH_2CN$ | A-3 | $X_1 = OCH_3$ | | |
| H | $CO_2CH_2CH_2CN$ | A-4 | $X_3 = OCH_3$ | | |
| H | $CO_2CH_2CF_3$ | A-2 | $X_1 = CH_3$ | $Y_1 = CH_2$ | |
| H | $CO_2CH_2CF_3$ | A-3 | $X_1 = CH_3$ | | |
| H | $CO_2CH_2CF_3$ | A-3 | $X_1 = OCH_3$ | | |
| H | $CO_2CH_2CF_3$ | A-4 | $X_3 = OCH_3$ | | |

TABLE IX

General Formula 9

| $R_f$ | $R_4$ | A | X | Y | m.p.(°C.) |
|---|---|---|---|---|---|
| H | $SOCH_3$ | A-2 | $X_1 = CH_3$ | $Y_1 = CH_2$ | |
| H | $SOCH_3$ | A-3 | $X_1 = CH_3$ | | |
| H | $SOCH_3$ | A-3 | $X_1 = OCH_3$ | | |
| H | $SOCH_3$ | A-4 | $X_3 = OCH_3$ | | |
| H | $SOCH_2CN_3$ | A-2 | $X_1 = CH_3$ | $Y_1 = CH_2$ | |
| H | $SOCH_2CH_3$ | A-3 | $X_1 = CH_3$ | | |
| H | $SOCH_2CH_3$ | A-3 | $X_1 = OCH_3$ | | |
| H | $SOCH_2CH_3$ | A-4 | $X_3 = OCH_3$ | | |
| H | $SOCH_2CH_2CH_3$ | A-2 | $X_1 = CH_3$ | $Y_1 = CH_2$ | |
| H | $SOCH_2CH_2CH_3$ | A-3 | $X_1 = CH_3$ | | |
| H | $SOCH_2CH_2CH_3$ | A-3 | $X_1 = OCH_3$ | | |
| H | $SOCH_2CH_2CH_3$ | A-4 | $X_3 = OCH_3$ | | |
| H | S-cyclopropyl | A-2 | $X_1 = CH_3$ | $Y_1 = CH_2$ | |
| H | S-cyclopropyl | A-3 | $X_1 = CH_3$ | | |
| H | S-cyclopropyl | A-3 | $X_1 = OCH_3$ | | |
| H | S-cyclopropyl | A-4 | $X_3 = OCH_3$ | | |
| H | SO-cyclopropyl | A-2 | $X_1 = CH_3$ | $Y_1 = CH_2$ | |
| H | SO-cyclopropyl | A-3 | $X_1 = CH_3$ | | |
| H | SO-cyclopropyl | A-3 | $X_1 = OCH_3$ | | |
| H | SO-cyclopropyl | A-4 | $X_3 = OCH_3$ | | |
| H | $SO_2$-cyclopropyl | A-2 | $X_1 = CH_3$ | $Y_1 = CH_2$ | |
| H | $SO_2$-cyclopropyl | A-3 | $X_1 = CH_3$ | | |
| H | $SO_2$-cyclopropyl | A-3 | $X_1 = OCH_3$ | | |
| H | $SO_2$-cyclopropyl | A-4 | $X_3 = OCH_3$ | | |
| H | $OSO_2CH_3$ | A-2 | $X_1 = CH_3$ | $Y_1 = CH_2$ | |
| H | $OSO_2CH_3$ | A-3 | $X_1 = CH_3$ | | |
| H | $OSO_2CH_3$ | A-3 | $X_1 = OCH_3$ | | |
| H | $OSO_2CH_3$ | A-4 | $X_3 = OCH_3$ | | |
| H | $OSO_2CH_2CH_3$ | A-2 | $X_1 = CH_3$ | $Y_1 = CH_2$ | |
| H | $OSO_2CH_2CH_3$ | A-3 | $X_1 = CH_3$ | | |
| H | $OSO_2CH_2CH_3$ | A-3 | $X_1 = OCH_3$ | | |
| H | $OSO_2CH_2CH_3$ | A-4 | $X_3 = OCH_3$ | | |
| H | $OSO_2CF_3$ | A-2 | $X_1 = CH_3$ | $Y_1 = CH_2$ | |
| H | $OSO_2CF_3$ | A-3 | $X_1 = CH_3$ | | |
| H | $OSO_2CF_3$ | A-3 | $X_1 = OCH_3$ | | |
| H | $OSO_2CF_3$ | A-4 | $X_3 = OCH_3$ | | |
| H | $CH_2F$ | A-2 | $X_1 = CH_3$ | $Y_1 = CH_2$ | |
| H | $CH_2F$ | A-3 | $X_1 = CH_3$ | | |
| H | $CH_2F$ | A-3 | $X_1 = OCH_3$ | | |
| H | $CH_2F$ | A-4 | $X_3 = OCH_3$ | | |
| H | CN | A-2 | $X_1 = CH_3$ | $Y_1 = CH_2$ | |
| H | CN | A-3 | $X_1 = CH_3$ | | |
| H | CN | A-3 | $X_1 = OCH_3$ | | |
| H | CN | A-4 | $X_3 = OCH_3$ | | |
| H | $SO_2N(OCH_3)CH_3$ | A-2 | $X_1 = CH_3$ | $Y_1 = CH_2$ | |
| H | $SO_2N(OCH_3)CH_3$ | A-3 | $X_1 = CH_3$ | | |
| H | $SO_2N(OCH_3)CH_3$ | A-3 | $X_1 = OCH_3$ | | |
| H | $SO_2N(OCH_3)CH_3$ | A-4 | $X_3 = OCH_3$ | | |
| H | $SO_2NHCH_3$ | A-2 | $X_1 = CH_3$ | $Y_1 = CH_2$ | |
| H | $SO_2NHCH_3$ | A-3 | $X_1 = CH_3$ | | |
| H | $SO_2NHCH_3$ | A-3 | $X_1 = OCH_3$ | | |
| H | $SO_2NHCH_3$ | A-4 | $X_3 = OCH_3$ | | |
| H | $CO_2CH_2CH_2OH$ | A-2 | $X_1 = CH_3$ | $Y_1 = CH_2$ | |
| H | $CO_2CH_2CH_2OH$ | A-3 | $X_1 = CH_3$ | | |
| H | $CO_2CH_2CN_2OH$ | A-3 | $X_1 = OCH_3$ | | |
| H | $CO_2CH_2CH_2OH$ | A-4 | $X_3 = OCH_3$ | | |
| H | $CO_2CH_2CH_2CN$ | A-2 | $X_1 = CH_3$ | $Y_1 = CH_2$ | |
| H | $CO_2CH_2CH_2CN$ | A-3 | $X_1 = CH_3$ | | |
| H | $CO_2CH_2CH_2CN$ | A-3 | $X_1 = OCH_3$ | | |
| H | $CO_2CH_2CH_2CN$ | A-4 | $X_3 = OCH_3$ | | |
| H | $CO_2CH_2CF_3$ | A-2 | $X_1 = CH_3$ | $Y_1 = CH_2$ | |
| H | $CO_2CH_2CF_3$ | A-3 | $X_1 = CH_3$ | | |
| H | $CO_2CH_2CF_3$ | A-3 | $X_1 = OCH_3$ | | |

TABLE IX-continued

General Formula 9

| $R_f$ | $R_4$ | A | X | Y | m.p.(°C.) |
|---|---|---|---|---|---|
| H | $CO_2CH_2CF_3$ | A-4 | $X_3 = OCH_3$ | | |

TABLE X

General Formula 10

| $R_f$ | $R_5$ | A | X | Y | m.p.(°C.) |
|---|---|---|---|---|---|
| H | $SOCH_3$ | A-2 | $X_1 = CH_3$ | $Y_1 = CH_2$ | |
| H | $SOCH_3$ | A-3 | $X_1 = CH_3$ | | |
| H | $SOCH_3$ | A-3 | $X_1 = OCH_3$ | | |
| H | $SOCH_3$ | A-4 | $X_3 = OCH_3$ | | |
| H | $SOCH_2CH_3$ | A-2 | $X_1 = CH_3$ | $Y_1 = CH_2$ | |
| H | $SOCH_2CH_3$ | A-3 | $X_1 = CH_3$ | | |
| H | $SOCH_2CH_3$ | A-3 | $X_1 = OCH_3$ | | |
| H | $SOCH_2CH_3$ | A-4 | $X_3 = OCH_3$ | | |
| H | $SOCH_2CH_2CH_3$ | A-2 | $X_1 = CH_3$ | $Y_1 = CH_2$ | |
| H | $SOCH_2CH_2CH_3$ | A-3 | $X_1 = CH_3$ | | |
| H | $SOCH_2CH_2CH_3$ | A-3 | $X_1 = OCH_3$ | | |
| H | $SOCH_2CH_2CH_3$ | A-4 | $X_3 = OCH_3$ | | |
| H | $SO_2CH_3$ | A-2 | $X_1 = CH_3$ | $Y_1 = CH_2$ | |
| H | $SO_2CH_3$ | A-3 | $X_1 = CH_3$ | | |
| H | $SO_2CH_3$ | A-3 | $X_1 = OCH_3$ | | |
| H | $SO_2CH_3$ | A-4 | $X_3 = OCH_3$ | | |
| H | $SO_2CH_2CH_3$ | A-2 | $X_1 = CH_3$ | $Y_1 = CH_2$ | |
| H | $SO_2CH_2CH_3$ | A-3 | $X_1 = CH_3$ | | |
| H | $SO_2CH_2CH_3$ | A-3 | $X_1 = OCH_3$ | | |
| H | $SO_2CH_2CH_3$ | A-4 | $X_3 = OCH_3$ | | |
| H | $SO_2CH_2CH_2CH_3$ | A-2 | $X_1 = CH_3$ | $Y_1 = CH_2$ | |
| H | $SO_2CH_2CH_2CH_3$ | A-3 | $X_1 = CH_3$ | | |
| H | $SO_2CH_2CH_2CH_3$ | A-3 | $X_1 = OCH_3$ | | |
| H | $SO_2CH_2CH_2CH_3$ | A-4 | $X_3 = OCH_3$ | | |
| H | S-cyclopropyl | A-2 | $X_1 = CH_3$ | $Y_1 = CH_2$ | |
| H | S-cyclopropyl | A-3 | $X_1 = CH_3$ | | |
| H | S-cyclopropyl | A-3 | $X_1 = OCH_3$ | | |
| H | S-cyclopropyl | A-4 | $X_3 = OCH_3$ | | |
| H | SO-cyclopropyl | A-2 | $X_1 = CH_3$ | $Y_1 = CH_2$ | |
| H | SO-cyclopropyl | A-3 | $X_1 = CH_3$ | | |
| H | SO-cyclopropyl | A-3 | $X_1 = OCH_3$ | | |
| H | SO-cyclopropyl | A-4 | $X_3 = OCH_3$ | | |
| H | $SO_2$-cyclopropyl | A-2 | $X_1 = CH_3$ | $Y_1 = CH_2$ | |
| H | $SO_2$-cyclopropyl | A-3 | $X_1 = CH_3$ | | |
| H | $SO_2$-cyclopropyl | A-3 | $X_1 = OCH_3$ | | |
| H | $SO_2$-cyclopropyl | A-4 | $X_3 = OCH_3$ | | |
| H | $OSO_2CH_3$ | A-2 | $X_1 = CH_3$ | $Y_1 = CH_2$ | |
| H | $OSO_2CH_3$ | A-3 | $X_1 = CH_3$ | | |
| H | $OSO_2CH_3$ | A-3 | $X_1 = OCH_3$ | | |
| H | $OSO_2CH_3$ | A-4 | $X_3 = OCH_3$ | | |
| H | $CH_2F$ | A-2 | $X_1 = CH_3$ | $Y_1 = CH_2$ | |
| H | $CH_2F$ | A-3 | $X_1 = CH_3$ | | |
| H | $CH_2F$ | A-3 | $X_1 = OCH_3$ | | |
| H | $CH_2F$ | A-4 | $X_3 = OCH_3$ | | |
| H | CN | A-2 | $X_1 = CH_3$ | $Y_1 = CH_2$ | |
| H | CN | A-3 | $X_1 = CH_3$ | | |
| H | CN | A-3 | $X_1 = OCH_3$ | | |
| H | CN | A-4 | $X_3 = OCH_3$ | | |
| H | $SO_2N(OCH_3)CH_3$ | A-2 | $X_1 = CH_3$ | $Y_1 = CH_2$ | |
| H | $SO_2N(OCH_3)CH_3$ | A-3 | $X_1 = CH_3$ | | |
| H | $SO_2N(OCH_3)CH_3$ | A-3 | $X_1 = OCH_3$ | | |
| H | $SO_2N(OCH_3)CH_3$ | A-4 | $X_3 = OCH_3$ | | |
| H | $SO_2NHCH_3$ | A-2 | $X_1 = CH_3$ | $Y_1 = CH_2$ | |
| H | $SO_2NHCH_3$ | A-3 | $X_1 = CH_3$ | | |
| H | $SO_2NHCH_3$ | A-3 | $X_1 = OCH_3$ | | |
| H | $SO_2NHCH_3$ | A-4 | $X_3 = OCH_3$ | | |
| H | $SO_2NBCH_2CH_3$ | A-2 | $X_1 = CH_3$ | $Y_1 = CH_2$ | |
| H | $SO_2NHCH_2CH_3$ | A-3 | $X_1 = CH_3$ | | |
| H | $SO_2NHCH_2CH_3$ | A-3 | $X_1 = OCH_3$ | | |
| H | $SO_2NHCH_2CH_3$ | A-4 | $X_3 = OCH_3$ | | |
| H | $CO_2CH_2CH_2OH$ | A-2 | $X_1 = CH_3$ | $Y_1 = CH_2$ | |
| H | $CO_2CH_2CH_2OH$ | A-3 | $X_1 = CH_3$ | | |
| H | $CO_2CH_2CH_2OH$ | A-3 | $X_1 = OCH_3$ | | |
| H | $CO_2CH_2CH_2OH$ | A-4 | $X_3 = OCH_3$ | | |
| H | $CO_2CH_2CH_2CN$ | A-2 | $X_1 = CH_3$ | $Y_1 = CH_2$ | |
| H | $CO_2CH_2CH_2CH$ | A-3 | $X_1 = CH_3$ | | |
| H | $CO_2CH_2CH_2CN$ | A-3 | $X_1 = OCH_3$ | | |
| H | $CO_2CH_2CH_2CN$ | A-4 | $X_3 = OCH_3$ | | |
| H | $CO_2CH_2CF_3$ | A-2 | $X_1 = CH_3$ | $Y_1 = CH_2$ | |
| H | $CO_2CH_2CF_3$ | A-3 | $X_1 = CH_3$ | | |
| H | $CO_2CH_2CF_3$ | A-3 | $X_1 = OCH_3$ | | |

TABLE X-continued

General Formula 10

| $R_f$ | $R_5$ | A | X | Y | m.p.(°C.) |
|---|---|---|---|---|---|
| H | $CO_2CH_2CF_3$ | A-4 | $X_3 = OCH_3$ | | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, | 3–50 | 40–95 | 0–15 |
| Emulsions, Solutions, (including Emulsifiable Concentrates) | | | |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed Dotland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1963, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 24

High Strength Concentrate

| | |
|---|---|
| N2-[(4,6-Dimethoxypyrimidin-2-yl)aminocarbonyl]-N3-methyl-2,3-pyridinedisulfonamide | 99% |
| trimethylnonyl polyethylene glycol ether | 1% |

The surfactant is sprayed upon the active ingredient in a blender and the mixture sifted through a U. S. S. no. 40 sieve (0.42 mm openings) prior to packaging. The concentrate may be formulated further for practical use.

EXAMPLE 25

Wettable Powder

| | |
|---|---|
| 2-[[(4,6-Dimethoxypyrimidin-2-yl)aminocarbonyl]-aminosulfonyl]-3-pyridinecarboxylic acid, methyl ester | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE 26

Aqueous Suspension

| | |
|---|---|
| N2-[(4,6-Dimethoxypyrimidin-2-yl)aminocarbonyl]-N3-methyl-2,3-pyridinedisulfonamide | 40.0% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 27

Oil Suspension

| | |
|---|---|
| N-[(4,6-dimethoxypyrimidin-2-yl)aminocarbonyl]-3-(1-propylsulfonyl)-2-pyridinesulfonamide methyl ester | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE 28

Oil Suspension

| | |
|---|---|
| N-[(4,6-dimethoxypyrimidin-2-yl)aminocarbonyl]-3-(1-methylsulfonyloxy)-2-pyridinesulfonamide methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 29

Aqueous Suspension

| | |
|---|---|
| N-[(4,6-dimethoxypyrimidin-2-yl)aminocarbonyl]-3-(1-ethylsulfonyl)-2-pyridinesulfonamide methyl ester | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 29

Wettable Powder

| | |
|---|---|
| N2-[(4,6-Dimethoxypyrimidin-2-yl)aminocarbonyl]-N3-methyl-2,3-pyridinedisulfonamide | 40.0% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 30

Granule

| | |
|---|---|
| wettable powder of Example 29 | 15% |
| gypsum | 69% |
| potassium sulfate | 16% |

The ingredients are blended in a rotating mixer and water sprayed on to accomplish granulation. When most of the material has reached the desired range of 1.0 to 0.42 cm (U.S.S.#18 to 40 sieves), the granules are removed, dried, and screened. Oversized material is crushed to produce additional material in the desired range. These granules contain % active ingredient.

EXAMPLE 31

Wettable Powder

| | |
|---|---|
| N-[(4,6-dimethoxypyrimidin-2-yl)aminocarbonyl-3-(ethylsulfonyl)-2-pyridinesulfonamide methyl ester | 50% |
| sodium alkylnaphthalenesulfonate | 2% |
| low viscosity methyl cellulose | 2% |
| diatomaceous earth | 46% |

The ingredients are blended, coarsely hammermilled and the air milled to produce particles of active essentially all below 10 microns in diameter. The product is reblended before packaging.

EXAMPLE 32

Extruded Pellet

| | |
|---|---|
| N-[(4,6-dimethoxypyrimidin-2-yl)aminocarbonyl-3-(ethylsulfonyl)-2-pyridinesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 33

Wettable Powder

| | |
|---|---|
| N-[(4,6-dimethoxypyrimidin-2-yl)aminocarbonyl]- | 80% |

-continued

| | |
|---|---|
| 3-(1-ethylsulfonyl)-2-pyridinesulfonamide | |
| sodium alkylnaphthalenesulfonate | 2% |
| sodium ligninsulfonate | 2% |
| synthetic amorphous silica | 3% |
| kaolinite | 13% |

The ingredients are blended and then ground in a hammermill to produce particles with an average particle size less than 25 microns in diameter. The material is reblended and sifted through a U.S.S. No. 50 sieve (0.3 mm opening) before being packaged.

EXAMPLE 34

High Strength Concentrate

| | |
|---|---|
| N-[(4,6-dimethoxypyrimidin-2-yl)aminocarbonyl]-3-(1-ethylsulfonyl)-2-pyridinesulfonamide | 98.5% |
| silica aerogel | 0.5% |
| synthetic amorphous fine silica | 1.0% |

The ingredients are blended and ground in a hammer mill to produce a high strength concentrate essentially all passing a U.S.S. No. 50 sieve (0.3 mm openings). This material may then be formulated in a variety of ways.

EXAMPLE 35

Wettable Powder

| | |
|---|---|
| 2-[[(4,6-Dimethoxypyrimidin-2-yl)aminocarbonyl]-aminosulfonyl]-3-pyridinecarboxylic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended and then ground in a hammermill to produce particles with an average particle size less than 25 microns in diameter. The material is reblended and sifted through a U.S.S. No. 50 sieve (0.3 mm opening) before being packaged.

EXAMPLE 36

High Strength Concentrate

| | |
|---|---|
| N2-[(4,6-Dimethoxypyrimidin-2-yl)aminocarbonyl]-N3-methyl-2,3-pyridinedisulfonamide | 98.5% |
| silica aerogel | 0.5% |
| synthetic amorphous fine silica | 1.0% |

The ingredients are blended and ground in a hammer mill to produce a high strength concentrate essentially all passing a U.S.S. No. 50 sieve (0.3 mm openings). This material may then be formulated in a variety of ways.

Utility

Test results indicate that the compounds of the present invention are highly active preemergent and/or postemergent herbicides or plant growth regulants. Many of them have utility for broad-spectrum pre- and/or postemergence weed control in areas where complete control of all vegetation is desired, such as around fuel storage tanks, industrial storage areas, parking lots, drive-in theaters, around billboards, highway and railroad structures. Some of the compounds have utility for selective weed control in plantation crops, Solanaceae family crops such as tomatoes, potatoes and peppers, other crops such as wheat, barley, corn, cotton or soybeans, and their fallow land. In particular, some compounds of this invention control weeds in corn (maize) both pre- and postemergence without significant crop damage. Some compounds of this invention also control weeds in potato (*Solanum tuberosum*) and tomato (*Lycopersicon esculentum*) without significant crop damage. These compounds are particularly useful to control such problem weeds as foxtail (Setaria spp.), fall panicum (*Panicum dichotomiflorum*), barnyardgrass (*Echinochloa crusgalli*), seedling johnsongrass (*Sorghum halepense*) and shattercane (*Sorghum bicolor*). They can be used preemergence or postemergence and are most effective when applied postemergence to young weeds. They are also effective on certain broadleaf weeds such as lambsquarters (*Chenopodium album*), pigweed (Amaranthus spp.) and velvetleaf (*Abutlion theophrasti*).

Alternatively, the subject compounds are useful to modify plant growth and as citrus abscission agents.

Rates of application for compounds of this invention are determined by a number of factors, including their use as plant growth modifiers or as herbicides, crop species involved, types of weeds to be controlled, weather and climate, formulations selected, mode of application, amount of foliage present, etc. In general terms, the subject compounds should be applied at levels of around 0.001 to 20 kg/ha, the lower rates being suggested for use on lighter soils and/or those having a low organic matter content, for plant growth modification or for situations where only short-term persistence is required.

Compounds of this invention may be used in combination with any other commercial herbicide, examples of which are those of the triazine, triazole, imidazolinone, uracil, urea, amide, diphenylether, cineole, carbamate and bipyridylium types. They are particularly useful in combination with the following herbicides.

| Common Name | Chemical Name |
|---|---|
| alachlor | 2-chloro-2',6'-diethyl-N-(methoxymethyl)-acetanilide |
| atrazine | 2-chloro-4-(ethylamino)-6-(isopropylamino)-s-triazine |
| butylate | s-ethyl-diisobutylthiocarbamate |
| cyanazine | 2-[[4-chloro-6-(ethylamino)-s-triazin-2-yl]amino]-2-methylpropionitrile |
| dicamba | 3,6-dichloro-o-anisic acid |
| EPTC | S-ethyl dipropylthiocarbamate |
| linuron | 3-(3,4-dichlorophenyl)-1-methoxy-1-methylurea |
| metolachlor | 2-chloro-N-(2-ethyl-6-methylphenyl)-N-(2-methoxy-1-methylethyl)acetamide |
| metribuzin | 4-amino-6-tert-butyl-3-(methylthio)-as-triazine-5(4H)-one |
| tridiphane | 2-(3,5-dichlorophenyl)-2-(2,2,2-trichloroethyl)oxirane |
| 2,4-D | (2,4-dichlorophenoxy)acetic acid |
| bromoxynil | 3,5-dibromo-4-hydroxyphenylcyanide |
| paraquat | 1,1'-dimethyl-4,4-bipyridinium ion |
| glyphosate | N-(phosphonomethyl)glycine |
| DCPA | dimethyl tetrachloroterephthalate |
| dalapon | 2,2-dichloropropionic acid |
| dinoseb | 2-(1-methylpropyl)-4,6-dinitrophenol |
| diphenamid | N,N-dimethyl-2,2-diphenylacetamide |
| pendimethalin | N-(1-ethylpropyl)-3,4-dimethyl-2,6-dinitrobenamine |
| oryzalin | 3,5-dinitro-N,N-dipropylsulfanilamide |
| trifluralin | α,α,α-trifluoro-2,6-dinitro-N,N-dipropyl-p-toluidine |

| | -continued |
|---|---|
| | Chemical Name |
| chloramben | 3-amino-2,5-dichlorobenzoic acid |
| napropamide | 2-(α-naphthoxy)-N,N-diethylpropionamide |
| pebulate | S-propyl butylethylthiocarbamate |
| chlorpropham | isopropyl m-chlorocarbanilate |
| bensulide | S-(O,O-diisopropyl phosphorodithioate) ester of N-(2-mercaptoethyl)benzenesulfonamide |
| Trade Name | |
| Harmony ® | 3-[[(4-methoxy-6-methyl-1,3,5-triazin-2-yl)aminocarbonyl]aminosulfonyl]-2- |

| | -continued |
|---|---|
| | Chemical Name |
| | thiophenecarboxylic acid, methyl ester |
| Cinch ® | 1-methyl-4-(1-methylethyl)-2-exo-[(2-methylphenyl)-methoxy]-7-oxabicyclo-[2.2.1]heptane |
| — | 2-ethoxy-N-[[4-(2,2,2-trifluoroethoxy)-6-methoxy-1,3,5-triazin-2-yl]aminocarbonyl]benzenesulfonamide |

Herbicidal properties of the subject compounds were discovered in a series of greenhouse tests. Test procedures and results follow.

Compounds

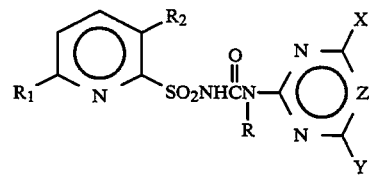

| Compound | R₂ | R | R₁ | X | Y | Z |
|---|---|---|---|---|---|---|
| 1 | SO₂CH₂CH₂CH₃ | H | H | OCH₃ | OCH₃ | CH |
| 2 | SO₂CH₂CH₂CH₃ | H | H | CH₃ | OCH₃ | CH |
| 3 | SO₂CH₂CH₂CH₃ | H | H | Cl | OCH₃ | CH |
| 4 | SO₂CH₂CH₂CH₃ | H | H | CH₃ | CH₃ | CH |
| 5 | SO₂CH₂CH₂CH₃ | H | H | OCH₃ | OCH₃ | N |
| 6 | SO₂CH₂CH₂CH₃ | H | H | CH₃ | OCH₃ | N |
| 7 | SO₂CH₂CH₂CH₃ | H | H | OCH₂CH₃ | NHCH₃ | N |
| 8 | S(O)CH₂CH₂CH₃ | H | H | OCH₃ | OCH₃ | CH |
| 9 | S(O)CH₂CH₂CH₃ | H | H | CH₃ | OCH₃ | CH |
| 10 | S(O)CH₂CH₂CH₃ | H | H | Cl | OCH₃ | CH |
| 11 | S(O)CH₂CH₂CH₃ | H | H | CH₃ | CH₃ | CH |
| 12 | S(O)CH₂CH₂CH₃ | H | H | OCH₃ | OCH₃ | N |
| 13 | S(O)CH₂CH₂CH₃ | H | H | CH₃ | OCH₃ | N |
| 14 | S(O)CH₂CH₂CH₃ | H | H | OCH₂CH₃ | NHCH₃ | N |
| 15 | S(O)CH₂CH₃ | H | H | OCH₃ | OCH₃ | CH |
| 16 | S(O)CH₂CH₃ | H | H | OCH₃ | CH₃ | CH |
| 17 | S(O)CH₂CH₃ | H | H | Cl | OCH₃ | CH |
| 18 | S(O)CH₂CH₃ | H | H | CH₃ | CH₃ | CH |
| 19 | S(O)CH₂CH₃ | H | H | OCH | OCH₃ | N |
| 20 | S(O)CH₂CH₃ | H | H | OCH₃ | CH₃ | N |
| 21 | SO₂CH₂CH₃ | H | H | OCH₃ | OCH₃ | CH |
| 22 | SO₂CH₂CH₃ | H | H | OCH₃ | CH₃ | CH |
| 23 | SO₂CH₂CH₃ | H | H | Cl | OCH₃ | CH |
| 24 | SO₂CH₂CH₃ | H | H | CH₃ | CH₃ | CH |
| 25 | SO₂CH₂CH₃ | H | H | OCH₃ | OCH₃ | N |
| 26 | SO₂CH₂CH₃ | H | H | OCH₃ | CH₃ | N |
| 27 | SO₂CH₂CH₃ | CH₃ | H | OCH₃ | CH₃ | N |
| 28 | S(O)CH₃ | H | H | OCH₃ | OCH₃ | CH |
| 29 | S(O)CH₃ | H | H | OCH₃ | CH₃ | CH |
| 30 | S(O)CH₃ | H | H | Cl | OCH₃ | CH |
| 31 | S(O)CH₃ | H | H | CH₃ | CH₃ | CH |
| 32 | S(O)CH₃ | H | H | OCH₃ | CH₃ | N |
| 33 | S(O)CH₃ | CH₃ | H | OCH₃ | CH₃ | N |
| 34 | SO₂CH₃ | H | H | OCH₃ | OCH₃ | CH |
| 35 | SO₂CH₃ | H | H | OCH₃ | CH₃ | CH |
| 36 | SO₂CH₃ | H | H | Cl | OCH₃ | CH |
| 37 | SO₂CH₃ | H | H | CH₃ | CH₃ | CH |
| 38 | SO₂CH₃ | H | H | OCH₃ | OCH₃ | N |
| 39 | SO₂CH₃ | H | H | OCH₃ | CH₃ | N |
| 40 | S(O)CH(CH₃)₂ | H | H | OCH₃ | OCH₃ | CH |
| 41 | S(O)CH(CH₃)₂ | H | H | OCH₃ | CH₃ | CH |
| 42 | S(O)CH(CH₃)₂ | H | H | Cl | OCH₃ | CH |
| 43 | S(O)CH(CH₃)₂ | H | H | CH₃ | CH₃ | CH |
| 44 | S(O)CH(CH₃)₂ | H | H | OCH₃ | OCH₃ | N |
| 45 | S(O)CH(CH₃)₂ | H | H | OCH₃ | CH₃ | N |
| 46 | SO₂CH(CH₃)₂ | H | H | OCH₃ | OCH₃ | CH |
| 47 | SO₂CH(CH₃)₂ | H | H | OCH₃ | CH₃ | CH |
| 48 | SO₂CH(CH₃)₂ | H | H | Cl | OCH₃ | CH |
| 49 | SO₂CH(CH₃)₂ | H | H | CH₃ | CH₃ | CH |
| 50 | SO₂CH(CH₃)₂ | H | H | OCH₃ | OCH₃ | N |
| 51 | SO₂CH(CH₃)₂ | H | H | OCH₃ | CH₃ | N |
| 52 | SO₂CH(CH₃)₂ | CH₃ | H | OCH₃ | CH₃ | N |
| 53 | SO₂(CH₂)₃CH₃ | H | H | OCH₃ | OCH₃ | CH |

-continued

Compounds

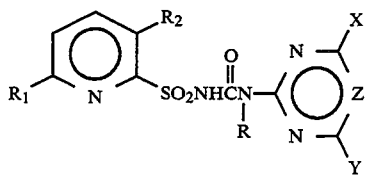

| Compound | R₂ | R | R₁ | X | Y | Z |
|---|---|---|---|---|---|---|
| 54 | SO₂(CH₂)₃CH₃ | H | H | OCH₃ | CH₃ | CH |
| 55 | SO₂(CH₂)₃CH₃ | H | H | Cl | OCH₃ | CH |
| 56 | SO₂(CH₂)₃CH₃ | H | H | CH₃ | CH₃ | CH |
| 57 | SO₂(CH₂)₃CH₃ | H | H | OCH₃ | OCH₃ | N |
| 58 | SO₂(CH₂)₃CH₃ | H | H | OCH₃ | CH₃ | N |
| 59 | SO₂(CH₂)₃CH₃ | CH₃ | H | OCH₃ | CH₃ | N |
| 60 | SO₂CH₂CH₃ | H | CH₃ | OCH₃ | OCH₃ | CH |
| 61 | SO₂CH₂CH₃ | H | CH₃ | OCH₃ | CH₃ | CH |
| 62 | SO₂CH₂CH₃ | H | CH₃ | CH₃ | CH₃ | CH |
| 63 | SO₂CH₂CH₃ | H | CH₃ | OCH₃ | CH₃ | N |
| 64 | SO₂CH₂CH₃ | H | OCH₃ | OCH₃ | OCH₃ | CH |
| 65 | OSO₂CH₃ | H | H | OCH₃ | OCH₃ | CH |
| 66 | OSO₂CH₃ | H | H | OCH₃ | CH₃ | CH |
| 67 | OSO₂CH₃ | H | H | Cl | OCH₃ | CH |
| 68 | OSO₂CH₃ | H | H | CH₃ | CH₃ | CH |
| 69 | OSO₂CH₃ | H | H | OCH₃ | CH₃ | N |
| 70 | OSO₂C₂H₅ | H | H | OCH₃ | OCH₃ | CH |
| 71 | OSO₂C₂H₅ | H | H | CH₃ | OCH₃ | CH |
| 72 | OSO₂C₂H₅ | H | H | Cl | OCH₃ | CH |
| 73 | OSO₂C₂H₅ | H | H | CH₃ | CH₃ | CH |
| 74 | OSO₂C₂H₅ | H | H | OCH₃ | OCH₃ | N |
| 75 | OSO₂C₂H₅ | H | H | CH₃ | OCH₃ | N |
| 76 | SO₂C₂H₅ | H | F | OCH₃ | OCH₃ | CH |
| 77 | SO₂C₂H₅ | H | F | CH₃ | CH₃ | CH |
| 78 | SO₂C₂H₅ | H | Cl | OCH₃ | OCH₃ | CH |
| 79 | SO₂C₂H₅ | H | Cl | Cl | OCH₃ | CH |
| 80 | SO₂C₂H₅ | H | Cl | CH₃ | CH₃ | CH |
| 81 | OSO₂CF₃ | H | H | OCH₃ | OCH₃ | CH |
| 82 | OSO₂CF₃ | H | H | Cl | OCH₃ | CH |
| 83 | OSO₂CF₃ | H | H | CH₃ | CH₃ | CH |
| 84 | OSO₂CF₃ | H | H | OCH₃ | OCH₃ | N |
| 85 | OSO₂CF₃ | H | H | CH₃ | OCH₃ | N |
| 86 | CH₂Cl | H | H | OCH₃ | OCH₃ | CH |
| 87 | CH₂Cl | H | H | Cl | OCH₃ | CH |
| 88 | CH₂Cl | H | H | CH₃ | OCH₃ | N |
| 89 | P(O)(OCH₂CH₃)₂ | H | H | OCH₃ | OCH₃ | CH |
| 90 | P(O)(OCH₂CH₃)₂ | H | H | CH₃ | OCH₃ | CH |
| 91 | P(O)(OCH₂CH₃)₂ | H | H | CH₃ | CH₃ | CH |
| 92 | SO₂NHCH₃ | H | H | OCH₃ | OCH₃ | CH |
| 93 | SO₂NHCH₃ | H | H | Cl | OCH₃ | CH |
| 94 | SO₂NHCH₃ | H | H | CH₃ | CH₃ | CH |
| 95 | SO₂NHCH₃ | H | H | OCH₃ | CH₃ | N |
| 96 | SO₂N(OCH₃)CH₃ | H | H | OCH₃ | OCH₃ | CH |
| 97 | SO₂N(OCH₃)CH₃ | H | H | CH₃ | CH₃ | CH |
| 98 | SO₂N(OCH₃)CH₃ | H | H | OCH₃ | CH₃ | N |
| 99 | SO₂N(OCH₂)CH₃ | CH₃ | H | OCH₃ | CH₃ | N |
| 100 | SO₂NHCH₂CH₃ | H | H | OCH₃ | OCH₃ | CH |
| 101 | SO₂NHCH₂CH₃ | H | H | Cl | OCH₃ | CH |
| 102 | SO₂NHCH₂CH₃ | H | H | CH₃ | CH₃ | CH |
| 103 | SO₂NHCH₂CH₃ | H | H | OCH₃ | OCH₃ | N |
| 104 | SO₂NHCH₂CH₃ | H | H | OCH₃ | CH₃ | N |
| 105 | SO₂NHCH₂CH₃ | CH₃ | H | OCH₃ | CH₃ | N |
| 106 | SO₂NHCH₂CH₂CH₃ | H | H | OCH₃ | OCH₃ | CH |
| 107 | SO₂NHCH₂CH₂CH₃ | H | H | CH₃ | OCH₃ | CH |
| 108 | SO₂NHCH₂CH₂CH₃ | H | H | Cl | OCH₃ | CH |
| 109 | SO₂NHCH₂CH₂CH₃ | H | H | OCH₃ | OCH₃ | N |
| 110 | SO₂N (CH₂)₄ | H | H | OCH₃ | OCH₃ | CH |
| 111 | SO₂N (CH₂)₄ | H | H | CH₃ | CH₃ | CH |

-continued

Compounds

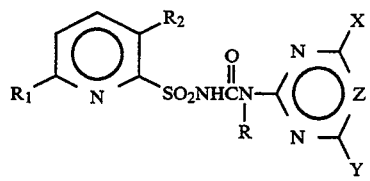

| Compound | R2 | R | R1 | X | Y | Z |
|---|---|---|---|---|---|---|
| 112 | CO2CH2cyclopropyl | H | H | OCH3 | OCH3 | CH |
| 113 | CO2CH2cyclopropyl | H | H | Cl | OCH3 | CH |
| 114 | CO2CH2cyclopropyl | H | H | CH3 | CH3 | CH |
| 115 | CO2CH2cyclopropyl | H | H | OCH3 | OCH3 | N |
| 116 | CO2CH3 | H | OCH3 | OCH3 | OCH3 | CH |
| 117 | CO2CH3 | H | OCH3 | CH3 | OCH3 | CH |
| 118 | CO2CH3 | H | OCH3 | Cl | OCH3 | CH |
| 119 | CO2CH3 | H | OCH3 | CH3 | CH3 | CH |
| 120 | CO2CH3 | H | OCH3 | OCH3 | OCH3 | N |
| 121 | CO2CH3 | H | OCH3 | CH3 | OCH3 | N |

Test A

Seeds of large crabgrass (*Digitaria sanguinalis*), barnyardgrass (*Echinochloa crus-galli*), giant foxtail (*Setaria faberi*), wild oats (*Avena fatua*), cheatgrass (*Bromus secalinus*), velvetleaf (*Abutlion theophrasti*), cultivated morningglory (*Ipomoea coccinea*, variety Scarlet O'-Hara), cocklebur (*Xanthium pensylvanicum*), G522 sorghum (*Sorghum vulgare*, variety Funk G522), G4646 corn (*Zea mays*, variety Funk G4646), Williams soybeans (*Glycine max*, variety Williams), USH11 sugarbeet (*Beta vulgaris*, variety Union Sugarbeet Co. USH11), Coker cotton (*Gossypium hirsutum*, variety Coker 315), dry seeded rice (*Oryza sativa*, variety California Rice Coop. M101), Era wheat (*Triticum aestivum*, variety Era spring), Klages barley (*Hordeum vulgare*, variety Klages spring) and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

"POSOL" and "PRSOL" in Table A denote post- and preemergence treatments, respectively.

TABLE A

| RATE = KG/HA | CMPD 1 | | CMPD 2 | | CMPD 3 | | CMPD 4 | | CMPD 5 | | CMPD 6 | | CMPD 7 | | CMPD 8 | | CMPD 9 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | | | | | | | POSOL | | | | | | | | | | | |
| COKER COTTON | 9C | 4C,9H | 0 | 0 | 2G | 0 | 0 | 0 | 0 | 0 | 0 | 0 | 0 | 0 | 4C,9H | 2C,5G | 3C,9H | 9H |
| CULT MORNINGLRY | 10C | 10C | 1H | 0 | 9C | 4C,8G | 1H | 0 | 0 | 0 | 0 | 0 | 0 | 0 | 10C | 4C,9G | 9C | 5C,9G |
| COCKLEBUR | 10C | 9C | 1H | 0 | 5C,9G | 3C,8G | 2H,5G | 0 | 2G | 0 | 0 | 0 | 0 | 0 | 10C | 10C | 10C | 9C |
| PURPLE NUTSEDGE | 9C | 4C,9G | 0 | 0 | 3C,8G | 2C | 0 | 0 | 2G | 0 | 0 | 0 | 0 | 0 | 6C,9G | 2C,9G | 4C,8G | 2C,5G |
| LARGE CRABGRASS | 2C,8G | 5G | 0 | 0 | 0 | 0 | 0 | 0 | 2G | 0 | 4C,9G | 0 | 0 | 0 | 2G | 0 | 3G | 0 |
| BARNYARRDGRASS | 9C | 9C | 2H | 0 | 3C,8H | 3C,7H | 1H | 0 | 4C,8H | 0 | 10C | 0 | 0 | 0 | 9C | 4C,9H | 3C,9H | 3C,7H |
| WILD OATS | 4C,9G | 4C,9G | 0 | 0 | 3C,8G | 0 | 0 | 0 | 9C | 0 | 3C,9G | 0 | 0 | 0 | 9G | 9G | 3C,9G | 8G |
| ERA WHEAT | 9C | 0 | 2G | 0 | 6G | 0 | 2G | 0 | 9G | 0 | 4C,9G | 0 | 0 | 0 | 2C,9G | 9C | 9C | 7G |
| G4646 CORN | 2H | 0 | 0 | 0 | 0 | 0 | 0 | 0 | 3C,9G | 0 | 8G | 0 | 0 | 0 | 4C,9G | 3C,7H | 3C,8H | 1H |
| WILLMS SOYBEANS | 4C,9H | 2C,4G | 0 | 0 | 1C | 0 | 0 | 0 | 0 | 0 | 2G | 0 | 0 | 0 | 4C,9G | 2C,7H | 4C,8H | 3H |
| RICE DRY SEEDED | 6C,9G | 9C | 0 | 0 | 5G | 0 | 0 | 0 | 8G | 0 | 3C,8G | 10C | 0 | 0 | 9C | 9C | 9C | 5C,9G |
| G522 SORGHUM | 9C | 9C | 3G | 0 | 9C | 0 | 0 | 0 | 3C,8H | 0 | 9C | 0 | 0 | 0 | 9C | 9C | 5C,9G | 4C,9G |
| CHEAT GRASS | 10C | 9C | 2G | 0 | 9C | 0 | 2C,2G | 0 | 3C,8G | 0 | 10C | 0 | 0 | 0 | 9C | 4C,8G | 4C,9G | 3C,7G |
| USH11 SUGARBEET | 9C | 9C | 0 | 0 | 5C,8G | 3C,7H | 0 | 0 | 0 | 0 | 0 | 0 | 0 | 0 | 4C,8G | 0 | 0 | 0 |
| VELVETLEAF | 10C | 5C,9G | 0 | 0 | 9C | 0 | 0 | 0 | 0 | 0 | 0 | 0 | 0 | 0 | 10C | 4C,9H | 9C | 4C,9H |
| GIANT FOXTAIL | 9C | 6C,9G | 2G | 0 | 2C,4G | 2G | 0 | 0 | 2C,5G | 0 | 0 | 0 | 0 | 9C | 4C,9G | 4C,8G | 3C,5G | 2G |
| KLAGES BARLEY | 5C,9G | 2C,8G | 0 | 0 | 2C,6G | 0 | 0 | 0 | 3C,7G | 0 | 0 | 0 | 0 | 0 | 9G | 7G | 2C,8G | 4G |

| RATE = KG/HA | CMPD 10 | | CMPD 11 | | CMPD 12 | | CMPD 13 | | CMPD 14 | | CMPD 15 | | CMPD 16 | | CMPD 17 | | CMPD 18 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | | | | | | | POSOL | | | | | | | | | | | |
| COKER COTTON | 3C,8H | 2C,3G | 3C,8H | 2G | 0 | 0 | 0 | 0 | 0 | 0 | 10C | 3C,9H | 3C,9H | 3C,8H | 4C,8H | 0 | 3C,9H | 2C |
| CULT MORNINGLRY | 4C,9H | 3C,5H | 3C,7H | 2C,2H | 0 | 0 | 1C,3G | 0 | 0 | 0 | 10C | 10C | 6C,9H | 6C,9H | 5C,9G | 2C,7H | 4C,8H | 3G |
| COCKLEBUR | 4C,9H | 3C,7H | 3C,9H | 2C,3H | 2H | 0 | 3C,9G | 3H | 0 | 0 | 10C | 9C | 4C,9H | 1H | 4C,8H | 1H | 3C,8H | 3C,5G |
| PURPLE NUTSEDGE | 2C,4G | 0 | 0 | 0 | 4C,8H | 0 | 0 | 0 | 2C,5G | 0 | 9G | 2C,5G | 6G | 0 | 3C,5G | 0 | 2G | 2G |
| LARGE CRABGRASS | 0 | 0 | 0 | 0 | 0 | 0 | 0 | 0 | 0 | 0 | 10C | 10C | 9G | 0 | 0 | 0 | 0 | 3C,5G |
| BARNYARRDGRASS | 3C,6H | 5H | 3H | 0 | 2H | 0 | 5H | 0 | 0 | 0 | 10C | 3C,9G | 9C | 0 | 5C,9H | 3C,7H | 3C,8H | 3C,6H |
| WILD OATS | 2C,6G | 0 | 2C,8G | 5G | 2G | 0 | 7H | 0 | 0 | 0 | 3C,9G | 3C,9G | 4C,9G | 0 | 9G | 4G | 2C,9G | 9G |
| ERA WHEAT | 4G | 0 | 7G | 0 | 3G | 0 | 7G | 0 | 0 | 0 | 4C,9G | 8G | 9G | 0 | 7G | 3G | 9G | 8G |
| G4646 CORN | 0 | 0 | 0 | 0 | 5H | 0 | 8G | 0 | 0 | 0 | 3C,8H | 2G | 3G | 0 | 9C | 0 | 1H | 3H |
| WILLMS SOYBEANS | 1C,1H | 0 | 3H | 0 | 0 | 0 | 6H | 0 | 0 | 2G | 9C | 3C,8G | 5C,9G | 0 | 3C,6H | 2G | 3C,8G | 3C,3H |
| RICE DRY SEEDED | 9G | 5G | 5G | 2C,5G | 2G | 0 | 2G | 0 | 0 | 0 | 10C | 9C | 9C | 0 | 5C,9G | 2G | 5C,9G | 5C,9G |
| G522 SORGHUM | 4C,9G | 4C,9G | 9C | 3C,7H | 2G | 0 | 8G | 0 | 0 | 0 | 10C | 9C | 3C,9G | 0 | 5C,9G | 4C,9G | 3C,9G | 4C,9G |
| CHEAT GRASS | 8G | 3G | 5G | 3G | 3G | 0 | 7G | 0 | 0 | 0 | 10C | 9C | 4C,9G | 0 | 9G | 9C | 9G | 9G |
| USH11 SUGARBEET | 3C,8H | 6G | 4C,8G | 3C,3H | 2H | 0 | 3H | 0 | 0 | 0 | 10C | 9C | 9C | 9C | 4C,8H | 3C,6G | 3C,7H | 3C,5G |
| VELVETLEAF | 2C,3G | 0 | 3C,7H | 2C,5G | 0 | 0 | 0 | 0 | 0 | 0 | 9C | 5C,9H | 5C,9H | 0 | 4C,8H | 5G | 3C,7G | 3C,6G |
| GIANT FOXTAIL | 1C | 0 | 0 | 0 | 2G | 0 | 2G | 0 | 0 | 0 | 10C | 9C | 3C,9G | 0 | 9C | 3C,7G | 3C,9G | 3C,6G |
| KLAGES BARLEY | 2G | 0 | 3G | 0 | 0 | 0 | 0 | 0 | 0 | 4G | 9C | 3C,8G | 6G | 0 | 4G | 0 | 2C,8G | 6G |

| RATE = KG/HA | CMPD 19 | | CMPD 20 | | CMPD 21 | | CMPD 22 | | CMPD 23 | | CMPD 24 | | CMPD 25 | | CMPD 26 | | CMPD 27 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.06 | 0.01 | 0.05 | 0.01 | 0.05 | 0.01 | 0.05 | 0.01 | 0.05 | 0.01 |
| | | | | | | | POSOL | | | | | | | | | | | |
| COKER COTTON | 0 | 0 | 0 | 0 | 10C | 9C | 2C,5G | 0 | 10C | 2C,6G | 2G | 0 | 0 | 0 | 0 | 0 | 5C,9G | 4C,8G |
| CULT MORNINGLRY | 0 | 0 | 0 | 0 | 10C | 10C | 2C,7G | 0 | 10C | 4C,9G | 2C,5H | 0 | 0 | 0 | 2C | 5C,9G | 2C,7G | 2C,8G |
| COCKLEBUR | 2H | 0 | 2H | 0 | 10C | 10C | 5G | 0 | 10C | 7H | 4G | 0 | 1H | 0 | 0 | 1H | 10C | 0 |
| PURPLE NUTSEDGE | 0 | 0 | 0 | 0 | 10C | 9G | 0 | 7G | 3C,8G | 7G | 0 | 0 | 0 | 0 | 0 | 0 | 0 | 0 |
| LARGE CRABGRASS | 0 | 0 | 2G | 0 | 5C,9G | 3G | 2C,5H | 0 | 2G | 2G | 2C,5G | 0 | 3G | 0 | 0 | 0 | 3C,7G | 4G |
| BARNYARRDGRASS | 0 | 0 | 0 | 0 | 9C | 9C | 0 | 0 | 5C,9H | 5C,9H | 2G | 0 | 8G | 0 | 0 | 0 | 3C,6G | 0 |
| WILD OATS | 2G | 0 | 3G | 0 | 3C,9G | 3C,9G | 0 | 0 | 8G | 6G | 0 | 0 | 0 | 0 | 0 | 0 | 6G | 0 |

TABLE A-continued

| | CMPD 28 | | CMPD 29 | | CMPD 30 | | CMPD 31 POSOL | | CMPD 32 | | CMPD 33 | | CMPD 34 | | CMPD 35 | | CMPD 36 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| ERA WHEAT | 5G | 0 | 3G | 0 | 5C,9G | 10C | 0 | 0 | 8G | 4G | 6G | 0 | 9G | 0 | 3G | 0 | 4C,9G | 0 |
| G4646 CORN | 0 | 0 | 0 | 0 | 1C,4H | 2G | 0 | 0 | 3C,8H | 0 | 3C,5H | 0 | 3G | 4C,9G | 0 | 0 | 2H | 0 |
| WILLMS SOYBEANS | 2C,2H | 0 | 3C | 0 | 9C | 5C,9G | 3C,4H | 1C,1H | 10C | 3C,4G | 3G | 1H | 2C,2H | 4C,9H | 0 | 0 | 4C,9G | 3C,8G |
| RICE DRY SEEDED | 0 | 0 | 0 | 0 | 9C | 9C | 3G | 3G | 9C | 5C,9G | 3C,7G | 2G | 4G | 4C,9H | 0 | 0 | 5G | 2G |
| G522 SORGHUM | 0 | 0 | 3C,3G | 0 | 9C | 9C | 3C,8G | 3G | 5C,9G | 9G | 3G | 0 | 2G | 2C,9G | 0 | 0 | 4C,9G | 3C,8G |
| CHEAT GRASS | 0 | 0 | 0 | 0 | 9C | 9C | 5G | 0 | 9C | 9G | 3C,7G | 3H | 8G | 9G | 0 | 0 | 7G | 3G |
| USH11 SUGARBEET | 1C | 0 | 2H | 0 | 10C | 10C | 2C,5G | 2G | 5C,9G | 5C,9G | 3G | 0 | 2H | 9G | 0 | 0 | 6C,9G | 3C,6G |
| VELVETLEAF | 3G | 0 | 0 | 0 | 10C | 10C | 2G | 0 | 9C | 8G | 3C,7G | 2G | 0 | 2C,9G | 0 | 0 | 6C,9G | 3C,7G |
| GIANT FOXTAIL | 2G | 0 | 0 | 0 | 10C | 10C | 6G | 0 | 10C | 4C,9G | 2C,7G | 3H | 0 | 2C,8G | 0 | 0 | 4C,8G | 5G |
| KLAGES BARLEY | 2G | 0 | 0 | 0 | 5C,9G | 4C,9G | 0 | 0 | 3C,9G | 3G | 0 | 5G | 7G | 2G | 0 | 0 | 2G | 5G |
| RATE = KG/HA | | | | | | | | | | | | | | | | | | |

| | CMPD 37 | | CMPD 38 | | CMPD 39 | | CMPD 40 POSOL | | CMPD 41 | | CMPD 42 | | CMPD 43 | | CMPD 44 | | CMPD 45 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.06 | 0.01 | 0.05 | 0.01 | 0.05 | 0.01 | 0.05 | 0.01 | 0.05 | 0.01 |
| COKER COTTON | 0 | 0 | 4C,8H | 3G | 0 | 0 | 4C,9G | 9H | 3C,9G | 3C,8G | 3C,5H | 0 | 9C | 0 | 0 | 0 | 6G | 2G |
| CULT MORNINGLRY | 0 | 0 | 4C,9G | 3C,7H | 3C,6G | 0 | 10C | 4C,8H | 9C | 3C,8G | 3C,3H | 0 | 6C,9G | 1H | 3G | 0 | 5C,9H | 3C,7H |
| COCKLEBUR | 0 | 0 | 4C,9H | 2C,6H | 2H | 0 | 10C | 4C,9G | 9C | 3C,9G | 3C,6H | 2C,2H | 10C | 1C,1H | 2C,4G | 0 | 4C,9H | 4C,6H |
| PURPLE NUTSEDGE | 0 | 0 | 2C,8G | 5G | 2C,4G | 0 | 9G | 0 | 3G | 0 | 0 | 0 | 2C,9G | 0 | 0 | 0 | 3G | 0 |
| LARGE CRABGRASS | 0 | 0 | 3C,7G | 2C,5G | 0 | 0 | 3G | 3C,9G | 9C | 4C,8G | 0 | 0 | 5C,9G | 9G | 0 | 0 | 2C,8G | 5G |
| BARNYARRDGRASS | 0 | 0 | 9C | 4C,8H | 4C,9H | 3C,6H | 9C | 8G | 4C,9G | 3C,8G | 0 | 0 | 9C | 4C,9G | 2C,8H | 0 | 9C | 2C,8H |
| WILD OATS | 0 | 0 | 4C,9G | 2C,9G | 9G | 3G | 3C,9G | 8G | 3C,9G | 5G | 0 | 0 | 2C,9G | 9G | 8G | 0 | 9G | 3G |
| ERA WHEAT | 0 | 0 | 2C,9G | 2C,5G | 7G | 4G | 9G | 8G | 3C,9G | 2G | 0 | 0 | 4C,9G | 2C,8G | 9G | 0 | 9G | 0 |
| G4646 CORN | 2H | 0 | 2C,9G | 4C,5H | 0 | 0 | 4C,9H | 2G | 7G | 0 | 0 | 0 | 9C | 5C,9G | 0 | 0 | 0 | 0 |
| WILLMS SOYBEANS | 0 | 0 | 5C,9G | 5C,9G | 3C,3H | 1C | 4C,9G | 4G | 4C,7G | 3C,3G | 2C,5H | 0 | 5C,9G | 4C,9G | 1C,5H | 2C | 4C,8G | 2C,4H |
| RICE DRY SEEDED | 0 | 0 | 9C | 9C | 8G | 0 | 5C,9G | 1H | 5C,9G | 3C,7G | 1C | 0 | 9C | 6C,9G | 7G | 0 | 4C,9G | 2C,6G |
| G522 SORGHUM | 0 | 0 | 4C,9G | 3C,7G | 3C,8H | 3C,3H | 4C,9G | 2C,2H | 5C,9G | 4C,9G | 0 | 0 | 9C | 2C,6H | 2G | 0 | 3C,9G | 3C,9G |
| CHEAT GRASS | 0 | 0 | 5C,9G | 4C,9G | 3C,9G | 7G | 9C | 0 | 5C,9G | 4C,8G | 0 | 0 | 9C | 2C,6H | 8G | 4G | 3C,9G | 9G |
| USH11 SUGARBEET | 0 | 0 | 5C,9G | 2C,4G | 3C,4H | 2C | 9C | 7G | 4C,8G | 3C,7G | 2C | 0 | 4C,9H | 4C,9H | 2G | 0 | 4C,8H | 2C,7G |
| VELVETLEAF | 0 | 0 | 4C,9H | 3C,6H | 5G | 0 | 4C,9H | 4C,7H | 3C,9G | 3C,6H | 1C | 0 | 10C | 10C | 5G | 0 | 7G | 0 |
| GIANT FOXTAIL | 0 | 0 | 5C,9G | 3C,7G | 4C,9G | 2C,5G | 4C,9G | 3C,7G | 4C,8H | 3G | 0 | 0 | 9C | 9G | 7G | 0 | 4C,9G | 3C,9G |
| KLAGES BARLEY | 0 | 0 | 4C,9G | 3C,7G | 2C,5G | 3G | 8G | 7G | 3C,7G | 5G | 0 | 0 | 4C,9G | 3C,8G | 4G | 0 | 3C,8G | 2C,7G |

| | CMPD 46 | | CMPD 47 | | CMPD 48 | | CMPD 49 | | CMPD 50 | | CMPD 51 | | CMPD 52 | | CMPD 53 | | CMPD 54 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COKER COTTON | 0 | 0 | 0 | 0 | 0 | 0 | 0 | 0 | 2C,3G | 0 | 3C,5H | 0 | 0 | 0 | 0 | 0 | 0 | 0 |
| CULT MORNINGLRY | 0 | 0 | 0 | 0 | 0 | 0 | 0 | 0 | 3C,6G | 1H | 3C,3H | 0 | 1H | 0 | 0 | 0 | 2C,2H | 0 |
| COCKLEBUR | 0 | 0 | 0 | 0 | 0 | 0 | 0 | 0 | 3C,6G | 1C,1H | 3C,6H | 2C,2H | 1C,1H | 1H | 2C,2H | 0 | 0 | 0 |
| PURPLE NUTSEDGE | 0 | 0 | 0 | 0 | 0 | 0 | 0 | 0 | 0 | 0 | 0 | 0 | 0 | 0 | 0 | 0 | 0 | 0 |
| LARGE CRABGRASS | 0 | 0 | 0 | 0 | 0 | 0 | 0 | 0 | 2G | 0 | 3C,4G | 0 | 0 | 0 | 0 | 0 | 0 | 0 |
| BARNYARRDGRASS | 0 | 0 | 0 | 0 | 0 | 0 | 0 | 0 | 3C,7G | 0 | 5G | 0 | 0 | 0 | 0 | 0 | 0 | 0 |
| WILD OATS | 0 | 0 | 0 | 0 | 0 | 0 | 0 | 0 | 9G | 2G | 2G | 0 | 2G | 0 | 0 | 0 | 0 | 0 |
| ERA WHEAT | 0 | 0 | 0 | 0 | 0 | 0 | 0 | 0 | 9G | 2G | 0 | 0 | 2G | 0 | 0 | 0 | 0 | 0 |
| G4646 CORN | 0 | 0 | 0 | 0 | 0 | 0 | 4C,9H | 0 | 7G | 0 | 0 | 0 | 0 | 0 | 0 | 0 | 0 | 0 |
| WILLMS SOYBEANS | 2H | 0 | 0 | 0 | 0 | 0 | 4C,9H | 2G | 1C | 0 | 3G | 0 | 0 | 0 | 0 | 0 | 0 | 0 |
| RICE DRY SEEDED | 0 | 0 | 0 | 0 | 0 | 0 | 4C,9G | 4C,9G | 4C,8G | 0 | 3G | 0 | 4G | 0 | 0 | 0 | 0 | 0 |
| G522 SORGHUM | 0 | 0 | 0 | 0 | 0 | 0 | 5C,9G | 4C,9G | 4C,8H | 0 | 3C,9G | 0 | 8G | 0 | 0 | 0 | 0 | 0 |
| CHEAT GRASS | 0 | 0 | 0 | 0 | 0 | 0 | 9C | 6G | 3C,9G | 0 | 6G | 0 | 0 | 0 | 0 | 0 | 0 | 0 |
| USH11 SUGARBEET | 0 | 0 | 0 | 0 | 0 | 0 | 9C | 9C | 3C,6G | 0 | 9C | 0 | 0 | 0 | 0 | 0 | 0 | 0 |
| VELVETLEAF | 0 | 0 | 4G | 0 | 0 | 0 | 4C,9H | 4C,7H | 2C,2G | 0 | 0 | 0 | 0 | 0 | 0 | 0 | 0 | 0 |
| GIANT FOXTAIL | 0 | 0 | 0 | 0 | 0 | 0 | 4C,9G | 3C,7G | 3C,7G | 0 | 0 | 0 | 4G | 0 | 0 | 0 | 0 | 0 |
| KLAGES BARLEY | 0 | 0 | 0 | 0 | 0 | 0 | 8G | 7G | 7G | 0 | 0 | 0 | 4G | 0 | 0 | 0 | 0 | 0 |
| RATE = KG/HA | | | | | | | | | | | | | | | | | | |

TABLE A-continued

| RATE = KG/HA | CMPD 55 | | CMPD 56 | | CMPD 57 | | CMPD 58 POSOL | | CMPD 59 | | CMPD 60 | | CMPD 61 | | CMPD 62 | | CMPD 63 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COKER COTTON | 3C,8G | 3C,7H | 0 | 0 | 0 | 0 | 0 | 0 | 2G | 0 | 2C,7H | 0 | 3C,5H | 3G | 5G | 0 | 3C,8H | 3C,6G |
| CULT MORNINGLRY | 10C | 9C | 2G | 0 | 3C,8H | 3C,6H | 2H | 0 | 2C,7H | 0 | 2C,6H | 0 | 2C,6H | 2C,2H | 3C,7G | 3C,5H | 3C,7G | 3C,3H |
| COCKLEBUR | 3C,9H | 2C,8G | 0 | 0 | 3C,8H | 2C | 0 | 0 | 2C,6H | — | 2C,6H | 9C | 1C,4G | 0 | 3C,5G | 3G | 3C,7G | 2C,2H |
| PURPLE NUTSEDGE | 9G | 2C,9G | 0 | 0 | 5G | 3G | 0 | 0 | 0 | 0 | 0 | 8G | 0 | 0 | 3C,8G | 0 | 2G | — |
| LARGE CRABGRASS | 6G | 4G | 2G | 0 | 7H | 4H | 2G | 0 | 3G | 0 | 4G | 2G | 2G | 0 | 0 | 0 | 0 | 0 |
| BARNYARRDGRASS | 9C | 9C | 0 | 0 | 0 | 0 | 2G | 0 | 4G | 0 | 4G | 9C | 4G | 2G | 3C,8H | 4H | 3G | 0 |
| WILD OATS | 8G | 2G | 2G | 0 | 7H | 0 | 2G | 0 | 4G | 0 | 2G | 7G | 2G | 0 | 2C,9G | 0 | 3G | 0 |
| ERA WHEAT | 8G | 8G | 0 | 0 | 0 | 0 | 0 | 0 | 4G | 0 | 4G | 9G | 4G | 0 | 7G | 0 | 0 | 0 |
| G4646 CORN | 3G | 0 | 0 | 0 | 0 | 0 | 0 | 0 | 0 | 0 | 0 | 0 | 0 | 0 | 0 | 0 | 0 | 0 |
| WILLMS SOYBEANS | 4C,9G | 3C,7H | 0 | 0 | 2C,7G | 2G | 0 | 0 | 0 | 0 | 1C | 5C,9G | 0 | 0 | 0 | 0 | 3C,7G | 2C,3H |
| RICE DRY SEEDED | 9C | 4C,9G | 0 | 0 | 3C,9G | 3C,7H | 0 | 0 | 0 | 0 | 3G | 9C | 2C,2G | 0 | 3H | 5G | 6G | 0 |
| G522 SORGHUM | 4C,9G | 4C,9G | 4G | 0 | 5G | 3G | 0 | 0 | 0 | 0 | 3G | 5C,9G | 4H | 0 | 2G | 7G | 7G | 0 |
| CHEAT GRASS | 5C,8G | 5G | 4G | 0 | 2C,4G | 0 | 0 | 0 | 0 | 0 | 2G | 9C | 2G | 0 | 0 | 4H | 0 | 0 |
| USH11 SUGARBEET | 6C,8G | 3C,7G | 3H | 0 | — | 1H | 0 | 0 | 0 | 0 | 2G | 4C,9G | 2C,5G | 5G | 5C,9G | 3C,7G | 3C,8H | 3C,8G |
| VELVETLEAF | 4C,9H | 2C,7H | 0 | 0 | 0 | 0 | 0 | 0 | 2C,7G | 0 | 3G | 10C | 6G | 2G | 3C,7G | 3G | 3C,7G | 3G |
| GIANT FOXTAIL | 4C,9G | 2C,8G | 0 | 0 | 4G | 0 | 0 | 0 | 0 | 0 | 3G | 7G | 5G | 3C,5G | 0 | 0 | 0 | 5G |
| KLAGES BARLEY | 9C | 7G | 2G | 0 | 0 | 0 | 0 | 0 | 3G | 5G | 3G | 6G | 2C,5G | 0 | 7G | 3G | 3C,9H | 2C,7G |

| RATE = KG/HA | CMPD 64 | | CMPD 65 | | CMPD 66 | | CMPD 67 POSOL | | CMPD 68 | | CMPD 69 | | CMPD 70 | | CMPD 71 | | CMPD 72 | |
|---|---|---|---|---|---|---|---|---|---|---|---|---|---|---|---|---|---|---|
| | 0.05 | 0.01 | 0.05 | 0.01 | 0.05 | 0.01 | 0.06 | 0.01 | 0.06 | 0.01 | 0.05 | 0.01 | 0.05 | 0.01 | 0.05 | 0.01 | 0.05 | 0.01 |
| COKER COTTON | 5C,9G | 9C | 9C | 9C | 9C | 4C,8G | 10C | 9C | 9C | 4C,9G | 3C,5G | 3C,4G | 9C | 9C | 9C | 9C | 9C | 9C |
| CULT MORNINGLRY | 10C | 10C | 10C | 10C | 10C | 10C | 10C | 4C,9G | 10C | 4C,9H | 3C,6G | 3G | 10C | 10C | 10C | 10C | 10C | 10C |
| COCKLEBUR | 10C | 10C | 9C | 10C | 10C | 10C | 9C | 9C | 10C | 8G | 3G | 2G | 10C | 10C | 10C | 10C | 10C | 10C |
| PURPLE NUTSEDGE | 5C,9G | 5C,9G | 6C,9G | 5C,9G | 5C,9G | 3C,7G | 5C,9G | 3C,9G | 5C,9G | 4C,3G | 5G | 0 | 10C | 4G | 8G | 5G | 2C,7G | 3C,9G |
| LARGE CRABGRASS | 6G | 4G | 9C | 4C,9G | 9C | 3C,8G | 9C | 8G | 6C,9G | 2G | 6G | 0 | 10C | 9G | 9C | 9C | 9G | — |
| BARNYARRDGRASS | 9C | 3C,9H | 9C | 9C | 9C | 9C | 9C | 9C | 9C | 9C | 9C | 4G | 5C,9G | 9G | 4C,9G | 9C | 9G | 0 |
| WILD OATS | 8G | 2C,3G | 10C | 9C | 9C | 5C,9G | 5C,9G | 9G | 4C,9G | 10C | 6G | 2C,2H | 5C,9G | 9G | 9G | 9C | 9G | 0 |
| ERA WHEAT | 7G | 5G | 6C,9G | 6C,9G | 9G | 9G | 9G | 5G | 5C,9G | 7G | 9C | 1C | 9G | 7G | 9G | 8G | 5G | 0 |
| G4646 CORN | 3C,6G | 3G | 7U,9C | 7U,9C | 6U,9G | 3U,9G | 5U,9G | 9H | 3C,7G | 6G | 9G | 9G | 3C,9G | 9C | 3C,9G | 3C,8H | 2C,7G | 2C,3H |

TABLE A-continued

| | CMPD 73 | | CMPD 74 | | CMPD 75 | | CMPD 76 POSOL | | CMPD 77 | | CMPD 78 | | CMPD 79 | | CMPD 80 | | CMPD 81 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.06 | 0.01 | 0.05 | 0.01 | 0.05 | 0.01 | 0.05 | 0.01 | 0.05 | 0.01 |
| WILLMS SOYBEANS | 5C,9G | 9C | 9C | 9C | 9C | 5C,9G | 5C,9G | 5C,9G | 5C,9H | 9C | 4C,8H | 2C,5G | 9C | 9C | 9C | 9C | 9C | 3C,8H |
| RICE DRY SEEDED | 9C | 5C,9G | 9C | 9C | 9C | 9C | 5C,9G | 9C | 9C | 9C | 9C | 5C,9G | 9C | 9C | 9C | 3C,8G | 9C | 8G |
| G522 SORGHUM | 3C,9G | 4C,9G | 9C | 9C | 6C,9G | 4C,9G | 9C | 9C | 9C | 9C | 3C,7G | 3C,3G | 9C | 9C | 9C | 9G | 9C | 9C |
| CHEAT GRASS | 3C,8G | 4C,9G | 9C | 9C | 9C | 9C | 9C | 9C | 10C | 6C,9G | 5C,9G | 9G | 10C | 5C,9G | 10C | 4C,9G | 9C | 9G |
| USH11 SUGARBEET | 9G | 3C,9G | 9C | 9C | 9C | 10C | 9C | 9C | 10C | 9C | 9C | 10C | 9C | 3C,5G | 5H | 9C | 10C | 9C |
| VELVETLEAF | 9C | 5C,9G | 9C | 9C | 9C | 9C | 9C | 10C | 10C | 4C,9H | 2H | 3G | 10C | 9C | 9C | 9C | 9C | 8G |
| GIANT FOXTAIL | 7G | 3G | 9C | 9C | 10C | 9C | 9C | 8G | 10C | 5C,9G | 3C,9G | 2G | 10C | 9C | 9C | 3C,8G | 4C,9G | 2C,7G |
| KLAGES BARLEY | 7C,7G | 2C,6G | 9C | 6C,9G | 6C,9G | 4C,9G | 3C,8G | 5G | 6C,9G | 5C,9G | 5C,9G | 3C,9G | 3C,9G | 6G | 4C,9G | 7G | 2C,9G | 4G |
| RATE = KG/HA | | | | | | | | | | | | | | | | | | |

| | CMPD 82 | | CMPD 83 | | CMPD 84 | | CMPD 85 POSOL | | CMPD 86 | | CMPD 87 | | CMPD 88 | | CMPD 89 | | CMPD 90 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COKER COTTON | 5C,9G | 3C,8G | 0 | 0 | 0 | 0 | 0 | 0 | 9C | 4G | 0 | 0 | 0 | 0 | 0 | 0 | 4C,9G | 0 |
| CULT MORNINGLRY | 10C | 9C | 3C,7G | 0 | 3C,7G | 0 | 3C,4H | 0 | 4C,8G | 3C,3G | 0 | 0 | 0 | 0 | 0 | 0 | 4C,9G | 3C,6G |
| COCKLEBUR | 10C | 10C | 4C,9H | 3C,8H | 4C,9H | 2H | 4C,9H | 2H | 5C,9G | 1C | 0 | 0 | 0 | 0 | 0 | 0 | 10C | 10C |
| PURPLE NUTSEDGE | 4C,9G | 4C,8G | 0 | 0 | 0 | 0 | — | — | 10C | 10C | — | 0 | 0 | 0 | 0 | 0 | — | 5C,9G |
| LARGE CRABGRASS | 5C,9G | 3C,7G | 3C,7G | 0 | 3C,7G | 0 | 5G | 0 | 9C | 3C,6G | 0 | 0 | 0 | 0 | 0 | 0 | 0 | 0 |
| BARNYARRDGRASS | 10C | 9C | 4C,9G | 3G | 4C,9G | 3C,6G | 9C | 3C,8G | 9C | 3C,8H | 0 | 0 | 0 | 0 | 0 | 0 | 10C | 3C,9H |
| WILD OATS | 5C,9G | 3C,9G | 3G | 0 | 2H | 0 | — | — | 9C | 0 | 0 | 1C,3G | 0 | 0 | 0 | 0 | 2C,5G | 0 |
| ERA WHEAT | 2C,9G | 9G | 0 | 0 | — | 0 | 3C,8G | 0 | 3C,5G | 0 | 0 | 0 | 0 | 0 | 0 | 0 | 2G | 0 |
| G4646 CORN | 3C,9H | 6G | 3C,7H | 0 | 4C,9G | 4C,8G | 5C,9G | 9G | 4C,9G | 3C,7G | 0 | 0 | 0 | 0 | 0 | 0 | 9C | 9G |
| WILLMS SOYBEANS | 9C | 2C,9G | 0 | 0 | 3C,3H | 0 | 3G | 0 | 9C | 4C,9G | 2G | 0 | 0 | 0 | 0 | 0 | 3C,8G | 4G |
| RICE DRY SEEDED | 9C | 5G | 4C,9G | 7G | 5C,9G | 8G | 9C | 3C,8G | 9C | 3C,8G | 0 | 0 | 0 | 0 | 0 | 0 | 9C | 5C,9G |
| G522 SORGHUM | 3C,8G | 9C | 9C | 2C,8G | 5C,9G | 3C,8G | 5C,9G | 3C,9G | 3C,7G | 2C,6G | 0 | 0 | 0 | 3C,9H | 0 | 0 | 9C | 4C,9G |
| CHEAT GRASS | 5C,9H | 2C,8G | 4C,9G | 0 | 0 | 0 | 0 | — | — | 0 | 0 | 0 | 0 | 0 | 0 | 0 | 2C,6G | 2G |
| USH11 SUGARBEET | 2C,5G | 0 | 3C,5H | 0 | 2H | 0 | 2H | 0 | 10C | 10C | — | 0 | 2C,6G | 0 | 0 | 0 | 10C | 9C |
| VELVETLEAF | 9C | 2C,4H | 4G | 4G | — | 0 | — | 0 | 9C | 10C | 3G | 0 | 3G | 3G | 3G | 0 | 10C | 9C |
| GIANT FOXTAIL | 5G | 0 | 3C,5H | 0 | 2C,5G | 0 | 3C,7G | 0 | 2G | 2G | 0 | 0 | 0 | 0 | 0 | 1H | 9C | 9G |
| KLAGES BARLEY | 0 | 0 | 0 | 0 | 2C,5G | 4C,9G | 0 | 0 | 10C | 10C | 0 | 0 | 0 | 0 | 0 | 0 | 9C | 4C,8G |
| DOWNY BROME | 4G | 0 | 0 | 0 | 2C,5G | 0 | — | — | 5C,9G | 0 | 0 | 0 | 0 | 0 | 0 | 0 | 8G | 7G |
| RATE = KG/HA | | | | | | | | | | | | | | | | | | |

| | CMPD 91 | | CMPD 92 | | CMPD 93 | | CMPD 94 | | CMPD 95 | | CMPD 96 | | CMPD 97 | | CMPD 98 | | CMPD 99 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COKER COTTON | | | | | | | | | | | | | | | 1H | 0 | 0 | 0 |
| CULT MORNINGLRY | | | | | | | | | | | | | | | 3C,4G | 0 | 0 | 0 |
| COCKLEBUR | | | | | | | | | | | | | | | 3C,6G | 0 | 0 | 0 |
| PURPLE NUTSEDGE | | | | | | | | | | | | | | | 0 | 0 | 0 | 0 |
| LARGE CRABGRASS | | | | | | | | | | | | | | | — | — | 0 | 0 |
| BARNYARRDGRASS | | | | | | | | | | | | | | | 4C,9H | 2G | 0 | 0 |
| WILD OATS | | | | | | | | | | | | | | | 2C,5G | 0 | 0 | 0 |
| ERA WHEAT | | | | | | | | | | | | | | | 3C,5G | 0 | 0 | 0 |
| G4646 CORN | | | | | | | | | | | | | | | 3C,8H | 0 | 0 | 0 |
| WILLMS SOYBEANS | | | | | | | | | | | | | | | 3C,7G | 1H | 3H | 0 |
| RICE DRY SEEDED | | | | | | | | | | | | | | | 6G | 0 | 0 | 0 |
| G522 SORGHUM | | | | | | | | | | | | | | | 2C,4G | 0 | 0 | 0 |
| CHEAT GRASS | | | | | | | | | | | | | | | — | — | — | — |
| USH11 SUGARBEET | | | | | | | | | | | | | | | 10C | 4G | 3G | 0 |
| VELVETLEAF | | | | | | | | | | | | | | | 3C,6G | 0 | 0 | 0 |
| GIANT FOXTAIL | | | | | | | | | | | | | | | 2C,5G | 0 | 0 | 0 |
| KLAGES BARLEY | | | | | | | | | | | | | | | 3C,8G | 0 | 0 | 0 |
| DOWNY BROME | | | | | | | | | | | | | | | 4C,7G | 0 | 0 | 0 |
| RATE = KG/HA | | | | | | | | | | | | | | | | | | |

TABLE A-continued

POSOL

| | CMPD 100 | | CMPD 101 | | CMPD 102 | | CMPD 103 | | CMPD 104 | | CMPD 105 | | CMPD 106 | | CMPD 107 | | CMPD 108 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COKER COTTON | 5C,9G | 0 | 10C | 10C | 6C,9G | 4C,9G | 2C,5G | 0 | 0 | 0 | 4C,8G | 5G | 0 | 0 | 0 | 4C,9G | 3C,9H |
| CULT MORNINGLRY | 9C | 5C,9G | 10C | 10C | 9C | 4C,9G | 1H | 2C | 0 | 0 | 10C | 10C | 2C,7G | 0 | 2G | 3C,8G | 2C,5H |
| COCKLEBUR | 10C | 9C | 10C | 10C | 10C | 3C,8H | 0 | 0 | 0 | 0 | 10C | 4C,9H | 2C | 0 | 0 | 4C,9H | 3C,8H |
| PURPLE NUTSEDGE | 4C,9G | 2C,9G | 9C | 5C,9G | 2C,9G | 0 | 3G | 0 | 0 | 0 | 9G | 2C,5G | 5G | 0 | 4G | 0 | 0 |
| LARGE CRABGRASS | 3C,7G | 3C,7G | 8G | 5G | 5G | 3C,7H | 4G | 0 | 0 | 0 | 10C | 9G | 0 | 0 | 0 | 0 | 0 |
| BARNYARRDGRASS | 9C | 9C | 9C | 3C,9H | 3C,9H | 3G | 1H | 0 | 0 | 0 | 10C | 9C | 0 | 0 | 0 | 0 | 0 |
| WILD OATS | 5C,9G | 3C,9G | 5C,9G | 3C,8G | 5G | 3G | 0 | 0 | 0 | 0 | 10C | 9C | 2G | 0 | 0 | 0 | 0 |
| ERA WHEAT | 9G | 9G | 6C,9G | 9C | 8G | 0 | 0 | 0 | 0 | 0 | 3C,9H | 9C | 0 | 0 | 0 | 2C,6G | 0 |
| G4646 CORN | 5C,9G | 3C,9G | 6G | 3G | 3G | 0 | 0 | 0 | 0 | 0 | 3C,9H | 5G | 0 | 0 | 0 | 4C,8H | 3C,6H |
| WILLMS SOYBEANS | 9G | 9G | 9C | 9C | 9C | 2C,6H | 2H | 0 | 0 | 0 | 5C,9H | 6C,9G | 2H | 0 | 0 | 2G | 0 |
| RICE DRY SEEDED | 3C,9H | 1C | 9C | 6C,9G | 3C,7G | 5C,9G | 0 | 0 | 0 | 0 | 5C,9G | 3C,9G | 0 | 0 | 0 | 3C,7H | 6G |
| G522 SORGHUM | 5C,9G | 4C,9H | 9C | 5C,9G | 6C,9G | 9C | 2G | 0 | 0 | 0 | 9C | 9G | 4G | 0 | 0 | 5G | 0 |
| CHEAT GRASS | 9C | 9C | 9C | 9C | 9C | 8G | 0 | 0 | 0 | 0 | 9C | 9G | 0 | 0 | 0 | 10C | 6H |
| USH11 SUGARBEET | 9C | — | 9C | 9C | 2C,9G | 9C | 0 | 0 | 0 | 0 | 10C | 3C,7G | 8G | 4G | 7G | 5G | 0 |
| VELVETLEAF | 9C | 9C | 10C | 10C | 4C,9H | 5H | 0 | 0 | 0 | 0 | 9C | 9G | 0 | 0 | 3G | 10C | 6H |
| GIANT FOXTAIL | 9C | 9C | 9C | 9C | 3C,8G | 3C,6G | 2C,7G | 0 | 0 | 0 | 10C | 9G | 0 | 0 | 2C | 9G | 7G |
| KLAGES BARLEY | 5C,9G | 5C,9G | 2C,8G | 2C,8G | 2C,5G | 0 | 2G | 0 | 0 | 0 | 6C,9G | 5C,9G | 0 | 0 | 0 | 0 | 0 |
| DOWNY BROME | — | — | — | — | — | — | — | — | — | — | 8G | | | | | | | |

RATE = KG/HA

| | CMPD 109 | | CMPD 110 | | CMPD 111 | | CMPD 112 | | CMPD 113 | | CMPD 114 | | CMPD 115 | | CMPD 116 | | CMPD 117 | |
|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.06 | 0.01 | 0.05 | 0.01 | 0.05 | 0.01 | 0.05 | 0.01 | 0.05 | 0.01 |

POSOL

| | | | | | | | | | | | | | | | | | | |
|---|---|---|---|---|---|---|---|---|---|---|---|---|---|---|---|---|---|---|
| COKER COTTON | 5C,9G | 0 | 4C,9G | 4C,8H | 0 | 0 | 4C,8H | 3C,8H | 3C,9H | 3C,7G | 6G | 0 | 2C,2G | 0 | 10C | 9C | 5C,9G | 9C |
| CULT MORNINGLRY | 9C | 0 | 6C,9G | 3C,8H | 0 | 0 | 10C | 10C | 10C | 3C,8G | 0 | 2G | 1C | 0 | 9C | 9C | 10C | 10C |
| COCKLEBUR | 10C | 0 | 5C,9G | 3C,9G | 0 | 0 | 10C | 10C | 9C | 4C,9G | 3C,7G | 7G | 3C,8G | 2H | 10C | 10C | 10C | 10C |
| PURPLE NUTSEDGE | 0 | 0 | 4G | 3G | 0 | 0 | 9C | 5C,9G | 9C | 2C,8G | 3G | 0 | 0 | 0 | 10C | 2G | 10C | 10C |
| LARGE CRABGRASS | 0 | 0 | 9C | 2G | 0 | 0 | 0 | — | 0 | 0 | 3C,3G | 0 | 0 | 0 | 3C,5G | 0 | 3C,9G | 3G |
| BARNYARRDGRASS | 2G | 0 | 9C | 3C,8H | 0 | 0 | 9C | 5C,9G | 3C,9G | 3C,7G | 3C,3G | 3C,6G | 3C,9H | 3C,7G | 9C | 2G | 3C,9G | 5C,9G |
| WILD OATS | 0 | 0 | 2C,7G | 4G | 0 | 0 | 4C,9G | 3G | 0 | 0 | 3G | 2C,6G | 3C,7G | 2G | 5C,9G | 2C,7G | 3C,9G | 9G |
| ERA WHEAT | 0 | 0 | 3C,9G | 0 | 0 | 0 | 3G | 3G | 3C,7G | 3C,7H | 3G | 3C,6G | 2G | 5C,9G | 9G | 2C,9G | 9G | 9G |
| G4646 CORN | 0 | 0 | 3C,8H | 2C,4G | 0 | 3C,8G | 5U,9C | 3C,9C | 3C,7H | 3C,7H | 3C,7G | 2C,6G | 5C,9G | 2C,7H | 7U,9C | 5U,9C | 4C,9G | 9G |

TABLE A-continued

| | CMPD 1 | | CMPD 2 | | CMPD 3 | | CMPD 4 | | CMPD 5 | | CMPD 6 | | CMPD 7 | | CMPD 118 | | CMPD 119 | | CMPD 120 | | CMPD 121 | |
|---|---|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| WILLMS SOYBEANS | | | 3C,7H | 0 | 0 | 0 | 9C | 4C,9G | 2H | 2C,5G | 3C,7G | 2G | 2H | 0 | 9C | 4C,9G | 2H | 0 | 9C | 9C | 9C | 6C,9G |
| RICE DRY SEEDED | | | 3C,9G | 0 | 0 | 1H | 5C,9G | 2C,8G | 7G | 3C,9G | 2G | 0 | 5C,9G | 4C,9G | 5C,9G | 3C,8G | 9C | 6C,9G | 5C,9G | 5C,9G |
| G522 SORGHUM | | | 9C | 0 | 0 | 1C | 3C,9G | 3C,9H | 3C,9G | | 3G | 3G | 3C,9G | 9G | 9G | 9G | 4C,9G | 9G | 9G |
| CHEAT GRASS | | | 2C,8G | 0 | 0 | 8G | | 5G | | | | | | | | 5C,9G | 6G | 9G | 9G |
| USH11 SUGARBEET | | | 10C | 0 | 0 | 5G | 10C | 9C | 9C | 3C,7H | 5G | 3C,8G | 4C,9H | 3C,7H | 10C | 9C | 10C | 9C | 10C | 10C |
| VELVETLEAF | | | 5C,9G | 0 | 0 | 2G | 10C | 5C,9G | 9C | 2C,7G | 3C,8G | 2C,7G | 0 | 0 | 10C | 9C | 9C | 10C | 10C |
| GIANT FOXTAIL | | | 4C,9H | 0 | 3G | 0 | 4C,9G | 0 | 3C,9G | | 4G | | 3C,7G | 2G | 4C,9G | 3C,7G | 2G | 9C | 10C | 4C,9G | 2C,9G |
| KLAGES BARLEY | | | 3C,8G | 0 | 2G | 2G | 7G | 3G | 2G | | 3G | | 3G | 3G | 3G | 3G | 5C,9G | 7G | 9G |
| DOWNY BROME | | | — | — | — | — | 9C | 9C | 3C,9G | 3G | 2C,5G | 2G | 9C | 2G | | | | | | |

| | CMPD 118 | | CMPD 119 | | CMPD 120 | | CMPD 121 | |
|---|---|---|---|---|---|---|---|---|
| RATE = KG/HA | 0.05 | 0.01 | 0.05 | 0.01 | 0.05 | 0.01 | 0.05 | 0.01 |

POSOL

| | CMPD 5 | | CMPD 6 | | CMPD 7 | | CMPD 8 | | CMPD 9 | |
|---|---|---|---|---|---|---|---|---|---|---|
| | 0.05 | 0.01 | 0.05 | 0.01 | 0.05 | 0.01 | 0.05 | 0.01 | 0.05 | 0.01 |
| COKER COTTON | 0 | 0 | 9C | 9C | 4C,9G | 6C,9G | 9C | 3C,8H | 5C,9G | 4C,8G |
| CULT MORNINGLRY | 0 | 0 | 10C | 10C | 4C,8H | 2C,6G | 9C | 4C,9H | 10C | 4C,9G |
| COCKLEBUR | 0 | 0 | 10C | 10C | 10C | 10C | 8H | 3C,5H | 10C | 4C,9H |
| PURPLE NUTSEDGE | — | — | 9C | 6G | 9C | 9C | 3C,7H | 3C,9G | 6G | 0 |
| LARGE CRABGRASS | 0 | 0 | 7G | 5C,9H | 4C,9G | 2C,7G | 2C,7G | 5G | 3C,8G | 2G |
| BARNYARRDGRASS | 0 | 2G | 10C | 7G | 10C | 2C,9G | 3C,9G | 2C | 3C,9G | 9C |
| WILD OATS | 0 | 0 | 9G | 8G | 3C,9G | 9C | 9H | 3C,8H | 3C,9G | 4C,9G |
| ERA WHEAT | 0 | 0 | 2C,9G | 7G | 3C,9G | 3C,9G | 7G | 6G | 4C,9G | 9G |
| G4646 CORN | 0 | 0 | 5C,9G | 2C,7H | 6C,9G | 5C,9G | 9C | 6G | 6U,9G | 6U,9G |
| WILLMS SOYBEANS | — | — | 5C,9G | 3C,8H | 5C,9G | 5C,9G | 4C,9G | 2G | 6C,9G | 5C,9G |
| RICE DRY SEEDED | 0 | 2G | 6C,9G | 4C,9G | 9C | 9C | 9C | 3G | 9C | 5C,9G |
| G522 SORGHUM | 0 | 0 | 9G | 9H | 5C,9G | 4C,9G | 9G | 5G | 3C,9G | 9G |
| CHEAT GRASS | — | — | 10C | 7G | 10C | 3C,9G | 5C,9G | 3C,9H | 10C | 9G |
| USH11 SUGARBEET | 0 | 0 | 9C | 9G | 10C | 9C | 10C | 3C,9H | 10C | 4C,8H |
| VELVETLEAF | 0 | 0 | 4C,9G | 3C,8G | 10C | 4C,9H | 9C | 3C,8G | 10C | 5C,9H |
| GIANT FOXTAIL | 0 | 0 | 9G | 5G | 6C,9G | 3C,6G | 4C,9G | 2C,3G | 4C,9G | 4C,9G |
| KLAGES BARLEY | 0 | 2G | | | | | 6G | 3G | 4G | 4G |
| | CMPD 14 | | CMPD 15 | | CMPD 16 | | CMPD 17 | | CMPD 18 | |

PRSOL

| | CMPD 1 | | CMPD 2 | | CMPD 3 | | CMPD 4 | |
|---|---|---|---|---|---|---|---|---|
| | 0.05 | 0.01 | 0.05 | 0.01 | 0.05 | 0.01 | 0.05 | 0.01 |
| COKER COTTON | 8G | 5G | 0 | 0 | 2G | 0 | 2G | 0 |
| CULT MORNINGLRY | 9C | 8H | 0 | 0 | 5H | 1H | 1C | 0 |
| COCKLEBUR | 9H | 9H | 0 | 0 | 3G | 1C | 0 | 0 |
| PURPLE NUTSEDGE | 10E | 3C,7G | 0 | 0 | 9G | 8G | 0 | 0 |
| LARGE CRABGRASS | 9G | — | 9G | 0 | 9G | 5G | 8G | 0 |
| BARNYARRDGRASS | 9H | 9H | 0 | 0 | 3C,7G | 2G | 2G | 2G |
| WILD OATS | 4C,8G | 1C | 0 | 0 | 0 | 4G | 2G | 0 |
| ERA WHEAT | 10E | 8G | 0 | 0 | 0 | 0 | 2G | 0 |
| G4646 CORN | 5G | 0 | 0 | 0 | 2G | 2G | 0 | 0 |
| WILLMS SOYBEANS | 3G | — | 0 | 0 | 3G | 6G | 5G | 0 |
| RICE DRY SEEDED | 10E | 4C,9H | 0 | 0 | 3C,8G | 3C,8G | 2C,5G | 0 |
| G522 SORGHUM | 10E | 10H | 0 | 0 | 2C,9G | 2G | 2C | 0 |
| CHEAT GRASS | 9H | 8G | 6G | 0 | 7G | 4H | 5G | 0 |
| USH11 SUGARBEET | 9G | 6G | 0 | 0 | 7G | 0 | 8G | 0 |
| VELVETLEAF | 8H | 3H | 0 | 0 | 2G | 0 | 0 | 4G |
| GIANT FOXTAIL | 9H | 3C,8G | 0 | 0 | 2C | 0 | 2G | 0 |
| KLAGES BARLEY | 8G | 7G | — | — | 6G | 0 | 6G | 0 |
| | CMPD 10 | | CMPD 11 | | CMPD 12 | | CMPD 13 | |

TABLE A-continued

| RATE = KG/HA | CMPD 19 | | CMPD 20 | | CMPD 21 | | CMPD 22 PRSOL | | CMPD 23 | | CMPD 24 | | CMPD 25 | | CMPD 26 | | CMPD 27 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COKER COTTON | 0 | 0 | 2G | 0 | 5G | 8G | 0 | 0 | 0 | 0 | 3C,9G | 8G | 5G | 0 | 0 | 0 | 0 | 0 |
| CULT MORNINGLRY | 3H | 0 | 1H | 0 | 0 | 8G | 0 | 0 | 0 | 0 | 9G | 2C,9H | 3C,7H | 0 | 2C,3H | 0 | 0 | 0 |
| COCKLEBUR | 0 | 0 | 4H | 0 | 1H | 8G | 0 | 0 | 0 | 0 | 8H | 2H | 1C,2G | 0 | 0 | 0 | 0 | 0 |
| PURPLE NUTSEDGE | 0 | 0 | 0 | 0 | 0 | 5G | 0 | 0 | 0 | 0 | 10E | 9C | 3G | 0 | 8G | 0 | 8G | 0 |
| LARGE CRABGRASS | 0 | 0 | 0 | 0 | 0 | 0 | 0 | 0 | 0 | 0 | 9H | 2G | 2G | 0 | 3G | 0 | 0 | 0 |
| BARNYARRDGRASS | 3G | 0 | 2G | 0 | 0 | 9H | 0 | 0 | 0 | 0 | 9H | 4C,8H | 3G | 0 | 7G | 0 | 2C | 0 |
| WILD OATS | 2C,4G | 0 | 7G | 0 | 0 | 6G | 0 | 0 | 0 | 0 | 3C,7G | 6G | 2C,6G | 6G | 4G | 0 | 7G | 2G |
| ERA WHEAT | 0 | 0 | 0 | 0 | 2G | 8H | 0 | 0 | 0 | 0 | 3C,9H | 6G | 7G | 4G | 2G | 0 | 6G | 2G |
| G4646 CORN | 0 | 0 | 2G | 0 | 0 | 2G | 0 | 0 | 0 | 0 | 4G | 4G | 3G | 0 | 0 | 0 | 0 | 0 |
| WILLMS SOYBEANS | 0 | 0 | 0 | 0 | 0 | 3C,6H | 0 | 0 | 0 | 0 | 8H | 3C,6H | 3C,7H | 2C,4G | 2C,2H | 2G | 0 | 0 |
| RICE DRY SEEDED | 5G | 2G | 2G | 4G | 0 | 10H | 0 | 0 | 0 | 0 | 10H | 10H | 10H | 4C,9H | 9H | 2G | 8H | 2G |
| G522 SORGHUM | 3C,8H | 3C,7H | 3C,5G | 0 | 0 | 9H | 0 | 0 | 0 | 0 | 10H | 4C,9H | 9H | 4C,9H | 9H | 3C,8H | 4C,9H | 2C,7G |
| CHEAT GRASS | 7G | 0 | 4G | 0 | 0 | 9H | 0 | 0 | 0 | 0 | 9H | 3C,9G | 3C,8H | 2C,7H | 7G | 0 | 7G | 2G |
| USH11 SUGARBEET | 3C,3H | 0 | 5H | 0 | 3H | 9H | 0 | 0 | 0 | 0 | 3C,8H | 3C,8H | 2C,3G | 8G | 5H | 5H | 0 | 0 |
| VELVETLEAF | 0 | 0 | 1H | 0 | 0 | 9H | 0 | 0 | — | 0 | 3C,9H | 3C,6H | 2C,5G | 0 | 3G | 0 | 0 | 0 |
| GIANT FOXTAIL | 0 | 0 | 0 | 0 | 0 | 9H | 0 | 0 | 0 | 0 | 5C,9H | 2C,8H | 2C | 0 | 2G | 0 | 0 | 0 |
| KLAGES BARLEY | 0 | 0 | 2G | 0 | 0 | 8G | 0 | 0 | 0 | 0 | 3C,8G | 7G | 2C,7G | 2G | 5G | 0 | 3G | 1C |

| RATE = KG/HA | CMPD 28 | | CMPD 29 | | CMPD 30 | | CMPD 31 PRSOL | | CMPD 32 | | CMPD 33 | | CMPD 34 | | CMPD 35 | | CMPD 36 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.06 | 0.01 | 0.05 | 0.01 | 0.05 | 0.01 | 0.05 | 0.01 | 0.05 | 0.01 |
| COKER COTTON | 8G | 6G | 0 | 3G | 0 | 0 | 2G | 0 | 6G | 3G | 0 | 0 | 0 | 0 | 0 | 0 | 4G | 4G |
| CULT MORNINGLRY | 7H | 7H | 5G | 0 | 3C,7G | 2G | 2G | 0 | 9G | 2G | 1C | 0 | 1C,1H | 8G | 4G | — | 8G | 0 |
| COCKLEBUR | 1H | — | 3G | 0 | 2C,3H | 0 | 7G | 0 | 8G | 0 | 0 | 0 | — | 8G | 0 | 2C | 7G | 0 |
| PURPLE NUTSEDGE | 10E | 3G | 0 | — | 0 | 0 | 0 | 0 | 10E | 7G | 5G | 0 | 0 | — | 0 | 0 | 2G | 0 |
| LARGE CRABGRASS | 2C,8G | 8G | 4G | 0 | — | 0 | — | 0 | 8G | 0 | 0 | 0 | 0 | 9G | 0 | 0 | 9G | 8G |
| BARNYARRDGRASS | 9H | 2C,6G | 2G | 0 | 0 | 9H | 0 | 0 | 9H | 3C,8H | 0 | 0 | 0 | 10E | 0 | 0 | 10E | 2G |
| WILD OATS | 3C,8G | 2C,7G | 3G | 0 | 0 | 6G | 0 | 0 | 4G | 0 | 0 | 0 | 4C,9H | 9H | 0 | 0 | 9H | 8G |
| ERA WHEAT | 3C,9G | 3C,8G | 2G | 0 | 0 | 8H | 0 | 0 | 5G | 0 | 0 | 0 | 9H | 3C,8H | 0 | 0 | 0 | 4G |
| G4646 CORN | 2C,8G | 3C,7G | 0 | — | 2C | 8G | 0 | 0 | 2G | 0 | 0 | 0 | 3C,8H | 6G | 0 | 0 | 2G | 3G |
| WILLMS SOYBEANS | | | | | | | | | 7H | 3G | | | 4C,9H | 8G | | | | |
| RICE DRY SEEDED | | | | | | | | | 4C,9G | 2G | | | 9G | 2C,4G | | | | |

TABLE A-continued

| | CMPD 37 | | CMPD 38 | | CMPD 39 | | CMPD 40 | | CMPD 41 | | CMPD 42 | | CMPD 43 | | CMPD 44 | | CMPD 45 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.06 | 0.01 | 0.05 | 0.01 | 0.05 | 0.01 | 0.05 | 0.01 | 0.05 | 0.01 |
| | | | | | | | | | PRSOL | | | | | | | | | |
| WILLMS SOYBEANS | 3C,7G | 2C,4G | 3C,3H | 2G | 2C,2H | 2H | 4G | 2G | 0 | 0 | 0 | 0 | 3C,6G | 2G | 2C | 0 | 0 | 10E |
| M03E DRY SEEDED | 9H | 1C | 3C,6G | 2C,3G | 2G | 2G | 2G | 2G | 2C,7H | 2C,5H | 0 | 0 | 10H | 0 | 3G | 0 | 0 | 3C,6H |
| G522 SORGHUM | 5C,9H | 5C,9H | 4C,5G | 2G | 2C | 0 | 2G | 0 | 2C,4H | 3G | 0 | 0 | 9G | 0 | 0 | 0 | 10E | 2G |
| CHEAT GRASS | 2C,8G | 8G | 3G | 2G | 0 | 0 | 0 | 0 | 0 | 0 | 0 | 0 | 6G | 0 | 0 | — | 7G | 4G |
| USH11 SUGARBEET | 4C,9G | 1C | 7G | 5H | 7G | 2H | 2H | 0 | 0 | 0 | 5H | 0 | 7G | 0 | 0 | 0 | 7G | 2C |
| VELVETLEAF | 7G | 3G | 2G | 0 | 4G | 0 | 4G | 0 | 0 | — | 3G | 0 | 2C,8G | 0 | 0 | 0 | 1C,3G | 4G |
| GIANT FOXTAIL | 9H | 7G | 4G | 0 | 5G | 5G | 2G | 0 | 0 | 0 | 0 | 0 | 9H | 0 | 0 | 0 | 9H | 2C |
| KLAGES BARLEY | 2C,7G | 8G | 2C,6G | 0 | 2C | 0 | 0 | 0 | 0 | 0 | 0 | 0 | 3C,8G | 0 | 2G | 0 | 0 | 4G |
| RATE = KG/HA | | | | | | | | | | | | | | | | | | |

| | CMPD 46 | | CMPD 47 | | CMPD 48 | | CMPD 49 | | CMPD 50 | | CMPD 51 | | CMPD 52 | | CMPD 53 | | CMPD 54 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.06 | 0.01 | 0.05 | 0.01 | 0.05 | 0.01 | 0.05 | 0.01 | 0.05 | 0.01 |
| | | | | | | | | | PRSOL | | | | | | | | | |
| COKER COTTON | 0 | 0 | 0 | 0 | 0 | 0 | 0 | 0 | 0 | 0 | 0 | — | 0 | 4H | 0 | 0 | 0 | 0 |
| CULT MORNINGLRY | 0 | 0 | 0 | 0 | 1C | 0 | 0 | 0 | 0 | 1H | 0 | 1H | 0 | 0 | 0 | 0 | 4G | 0 |
| COCKLEBUR | 0 | 0 | 0 | 0 | 1H | — | 0 | 0 | — | 0 | 0 | 0 | 0 | 0 | 0 | 0 | 0 | 0 |
| PURPLE NUTSEDGE | 0 | 0 | 4G | 0 | 0 | — | 0 | 0 | 0 | 0 | 0 | 0 | 2H | 0 | 0 | 0 | 0 | 0 |
| LARGE CRABGRASS | 0 | 0 | 0 | 0 | 0 | 0 | 0 | 0 | 0 | 0 | 0 | 0 | 0 | 0 | 0 | 0 | 0 | 0 |
| BARNYARRDGRASS | 0 | 0 | 0 | 0 | 0 | 0 | 0 | 0 | 0 | 0 | 0 | 0 | 0 | 0 | 0 | 0 | 0 | 0 |
| WILD OATS | 0 | 0 | 0 | 0 | 0 | 0 | 0 | 0 | 0 | 0 | 0 | 0 | 0 | 0 | 0 | 0 | 0 | 0 |
| ERA WHEAT | 0 | 0 | 0 | 0 | 0 | 0 | 0 | 0 | 0 | 0 | 0 | 0 | 0 | 0 | 0 | 0 | 0 | 0 |
| G4646 CORN | 0 | 0 | 0 | 0 | 2G | 0 | 0 | 0 | 0 | 0 | 0 | 0 | 0 | 0 | 0 | 0 | 0 | 0 |
| WILLMS SOYBEANS | 0 | 0 | 0 | 0 | 2G | 0 | 0 | 0 | 0 | 0 | 0 | 0 | 0 | 0 | 0 | 0 | 0 | 0 |
| RICE DRY SEEDED | 0 | 0 | 0 | 0 | 3C,9H | 2C,3H | 0 | 0 | 0 | 0 | 0 | 0 | 0 | 0 | 0 | 0 | 0 | 0 |
| G522 SORGHUM | 0 | 0 | 0 | 0 | 2C,8H | 2C,4G | 0 | 0 | 0 | 0 | 0 | 0 | 0 | 0 | 0 | 0 | 0 | 0 |
| CHEAT GRASS | 0 | 0 | 0 | 0 | 2G | 0 | 0 | 0 | 0 | 0 | 0 | 0 | 0 | 0 | 0 | 0 | 0 | 0 |
| USH11 SUGARBEET | 4H | 0 | 0 | 0 | 2C,4H | 2H | 0 | 0 | 0 | 0 | 0 | 0 | 0 | 0 | 0 | 0 | 0 | 0 |
| VELVETLEAF | 0 | 0 | 0 | 0 | 0 | 0 | 0 | 0 | 0 | 0 | 0 | 0 | 0 | 0 | 0 | 0 | 0 | 0 |
| GIANT FOXTAIL | 0 | 0 | 0 | 0 | 3G | 0 | 0 | 0 | 0 | 0 | 0 | 0 | 0 | 0 | 0 | 0 | 0 | 0 |
| KLAGES BARLEY | 0 | 0 | 0 | 0 | 5G | 0 | 0 | 0 | 0 | 0 | 0 | 0 | 0 | 0 | 0 | 0 | 0 | 0 |
| RATE = KG/HA | | | | | | | | | | | | | | | | | | |

| | CMPD 55 | | CMPD 56 | | CMPD 57 | | CMPD 58 | | CMPD 59 | | CMPD 60 | | CMPD 61 | | CMPD 62 | | CMPD 63 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COKER COTTON | 3C,5H | 2C,4G | 0 | 0 | 0 | 0 | 0 | 0 | 0 | 0 | 0 | 0 | 2G | 0 | 0 | 0 | 0 | 0 |
| CULT MORNINGLRY | 9H | 1C | 0 | 0 | 0 | 0 | 0 | 0 | 0 | 1H | 0 | 1H | 1H | 0 | 0 | 0 | 0 | 0 |
| COCKLEBUR | 9H | 0 | 0 | 0 | 0 | 0 | 0 | 0 | — | 0 | 0 | 0 | — | 0 | 0 | 0 | 0 | 0 |
| PURPLE NUTSEDGE | 10E | 10E | 4G | 0 | 1H | 0 | 0 | 0 | 0 | 0 | 0 | 0 | 0 | 0 | 0 | 0 | 0 | 0 |
| LARGE CRABGRASS | 9H | 0 | 0 | 0 | 0 | 0 | 0 | 0 | 0 | 0 | 0 | 0 | 2H | 0 | 0 | 0 | 0 | 0 |
| BARNYARRDGRASS | 2C,9H | 3C,7H | 0 | 0 | 0 | 0 | 0 | 0 | 0 | 0 | 0 | 0 | 0 | 0 | 0 | 0 | 0 | 0 |
| WILD OATS | 2C,4G | 4G | 0 | 0 | 0 | 0 | 0 | 0 | 0 | 0 | 0 | 0 | 2H | 0 | 0 | 0 | 2G | 0 |
| ERA WHEAT | 9H | 7G | 0 | 0 | 0 | 0 | 0 | 0 | 0 | 0 | 0 | 0 | 4G | 0 | 0 | 0 | 0 | 0 |
| G4646 CORN | 5G | 0 | 0 | 0 | 0 | 0 | 0 | 0 | 0 | 0 | 0 | 0 | 6G | 0 | 0 | 0 | 0 | 0 |
| WILLMS SOYBEANS | 3C,9H | 2C,2H | 0 | 0 | 2G | 0 | 0 | 0 | 0 | 0 | 0 | 0 | 5G | 0 | 0 | 0 | 0 | 0 |
| RICE DRY SEEDED | 9H | 4C,8H | 0 | 0 | 3C,9H | 2C,3H | 0 | 0 | 0 | 0 | 0 | 0 | 2G | 0 | 0 | 0 | 0 | 0 |
| G522 SORGHUM | 9H | 3C,9H | 0 | 0 | 2C,8H | 2C,4G | 0 | 0 | 0 | 0 | 0 | 0 | 6G | 0 | 0 | 0 | 0 | 0 |
| CHEAT GRASS | 9H | 7G | 0 | 0 | 2G | 0 | 0 | 0 | 0 | 0 | 0 | 0 | 2C,6G | 0 | 0 | 0 | 0 | 0 |
| USH11 SUGARBEET | 4C,8G | 3H | 4H | 0 | 2C,4H | 2H | 0 | 0 | 0 | 0 | 0 | 0 | 7G | 0 | 0 | 0 | 0 | 0 |
| VELVETLEAF | 3C,8G | 1C,4H | 0 | 0 | 0 | 0 | 0 | 0 | 0 | 0 | 0 | 0 | 6G | 0 | 0 | 0 | 2G | 0 |
| GIANT FOXTAIL | 3C,9H | 8G | 0 | 0 | 3G | 0 | 0 | 0 | 0 | 0 | 0 | 0 | 0 | 0 | 3G | 0 | 0 | 0 |
| KLAGES BARLEY | 2C,9H | 2C,9H | 0 | 0 | 5G | 0 | 0 | 0 | 0 | 0 | 0 | 0 | 8G | 0 | 0 | 0 | 0 | 0 |
| RATE = KG/HA | | | | | | | | | | | | | | | | | | |

TABLE A-continued

| | CMPD 64 | | CMPD 65 | | CMPD 66 | | CMPD 67 | | CMPD 68 | | CMPD 69 | | CMPD 70 | | CMPD 71 | | CMPD 72 | |
|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COKER COTTON | 0 | 0 | 0 | 0 | 0 | 0 | 0 | 0 | 0 | 0 | 0 | 0 | 0 | 0 | 0 | 0 | 0 | 0 |
| CULT MORNINGLRY | 0 | 0 | 0 | 0 | 0 | 0 | 0 | 0 | 0 | 0 | 0 | 0 | 0 | 0 | 0 | 0 | 0 | 0 |
| COCKLEBUR | 0 | 0 | 3G | 0 | 0 | 0 | 0 | 0 | 0 | 0 | 0 | 0 | 0 | 0 | 0 | 0 | — | — |
| PURPLE NUTSEDGE | 0 | 0 | 0 | 0 | 0 | 0 | 0 | 0 | 0 | 0 | 0 | 0 | 0 | 0 | 0 | 0 | 0 | 0 |
| LARGE CRABGRASS | 0 | 0 | 0 | 0 | 0 | 0 | 0 | 0 | 0 | 0 | 0 | 0 | 0 | 0 | 0 | 0 | 4G | 0 |
| BARNYARRDGRASS | 0 | 0 | 0 | 0 | 0 | 0 | 0 | 0 | 0 | 0 | 0 | 0 | 0 | 0 | 0 | 0 | 0 | 0 |
| WILD OATS | 0 | 0 | 0 | 0 | 0 | 0 | 0 | 0 | 0 | 0 | 0 | 0 | 0 | 0 | 0 | 0 | 0 | 0 |
| ERA WHEAT | 0 | 0 | 0 | 0 | 0 | 0 | 0 | 0 | 0 | 0 | 0 | 0 | 0 | 0 | 0 | 0 | 0 | 0 |
| WILLMS SOYBEANS | 0 | 0 | 0 | 0 | 0 | 0 | 0 | 0 | 0 | 0 | 0 | 0 | 0 | 0 | 0 | 0 | 0 | 0 |
| RICE DRY SEEDED | 0 | 0 | 0 | 0 | 0 | 0 | 0 | 0 | 0 | 0 | 0 | 0 | 0 | 0 | 0 | 0 | 2G | 0 |
| G522 SORGHUM | 0 | 0 | 0 | 0 | 0 | 0 | 0 | 0 | 0 | 0 | 0 | 0 | 0 | 0 | 0 | 0 | 0 | 0 |
| CHEAT GRASS | 0 | 0 | 0 | 0 | 0 | 0 | 0 | 0 | 0 | 0 | 0 | 0 | 0 | 0 | 0 | 0 | 0 | 0 |
| USH11 SUGARBEET | 0 | 0 | 0 | 0 | 0 | 0 | 0 | 0 | 0 | 0 | 0 | 0 | 0 | 0 | 0 | 0 | 0 | 0 |
| VELVETLEAF | 0 | 0 | 3G | 0 | 0 | 0 | 0 | 0 | 0 | 0 | 0 | 0 | 4G | 0 | 0 | 0 | 2H | 0 |
| GIANT FOXTAIL | 0 | 0 | 0 | 0 | 0 | 0 | 0 | 0 | 0 | 0 | 0 | 0 | 3H | 0 | 0 | 0 | 4G | 1H |
| KLAGES BARLEY | 0 | 0 | 0 | 0 | 0 | 0 | 0 | 0 | 0 | 0 | 0 | 0 | 0 | 0 | 0 | 0 | 0 | 0 |

PRSOL

| | CMPD 73 | | CMPD 74 | | CMPD 75 | | CMPD 76 | | CMPD 77 | | CMPD 78 | | CMPD 79 | | CMPD 80 | | CMPD 81 | |
|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.06 | 0.05 | 0.01 | 0.05 | 0.01 | 0.05 | 0.01 | 0.05 | 0.01 |
| COKER COTTON | 3C,7H | 2C,2G | 2G | 0 | 0 | 0 | 8G | 0 | 9G | 5G | 7G | 2G | 9G | 8G | 2C,9G | 3G | 8G | 2C,6G |
| CULT MORNINGLRY | 9G | 8H | 0 | 0 | 0 | 0 | 9G | 0 | 9G | 7G | 6G | 4G | 9G | 7G | 9G | 4G | 9G | 9H |
| COCKLEBUR | 3C,8H | 3C,2H | 0 | 0 | 0 | 0 | 8G | 0 | 8H | 4G | 2H | 4G | 9H | 3C,6H | 8H | 3C,6H | 9H | 3H |
| PURPLE NUTSEDGE | 10E | 3C,9G | 0 | 0 | 0 | 0 | 10E | 0 | 9G | 9G | 0 | 0 | 10E | 0 | 10E | 0 | 10E | 10E |
| LARGE CRABGRASS | 4C,9G | 3C,5G | 7G | 0 | 9H | 0 | 5C,9H | 0 | 9C | 3C,8G | 3C,7G | 0 | 4C,8G | 5G | 2C,8G | 4G | 5G | 2G |
| BARNYARRDGRASS | 9H | 9H | 3G | 0 | 3c,5G | 0 | 9H | — | 9H | 5G | 5G | 0 | 9H | 8H | 9H | 9H | 9H | 8H |
| WILD OATS | 3C,8H | 3C,8H | 6G | 0 | 7G | 2G | 4C,8G | — | 4C,9G | 3C,6H | 2C,6G | 6G | 3C,7G | 5G | 4C,8G | 2G | 5G | 0 |
| ERA WHEAT | 3C,9H | 2C,9H | 7G | 0 | 8G | 2G | 9H | — | 9H | 3C,7G | 8G | 6G | 8H | 4G | 9H | 9H | 9H | 3G |
| G4646 CORN | 3C,9H | 3C,7H | 3C,7G | 2C,5G | 9G | 3G | 9H | — | 3C,9G | 3C,8G | 3C,8G | 5G | 5G | 5G | 2C,9H | 0 | 2G | 0 |
| WILLMS SOYBEANS | 3C,9H | 3C,5H | 2G | 0 | 9G | 6G | 9H | — | 9H | 3C,7G | 8G | 7G | 9H | 4G | 9H | 2C,4G | 5C,9H | 7G |
| RICE DRY SEEDED | 10E | 9H | 7G | 0 | 8G | 7G | 3C,9H | — | 10E | 3C,8G | 8G | 4G | 10E | 9G | 9H | 3C,7H | 5G | 2C,2H |

TABLE A-continued

| | CMPD 82 | | CMPD 83 | | CMPD 84 | | CMPD 85 PRSOL | | CMPD 86 | | CMPD 87 | | CMPD 88 | | CMPD 89 | | CMPD 90 | |
|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.06 | 0.01 | 0.05 | 0.01 | 0.05 | 0.01 | 0.05 | 0.01 | 0.05 | 0.01 |
| G522 SORGHUM | 9H | 3C,9G | 3C,8H | 2C,6G | 3C,9G | 3C,8H | 0 | 0 | 0 | 0 | 0 | 0 | 0 | 0 | 5C,9H | 0 | 5G | 0 |
| CHEAT GRASS | 3C,9H | 9H | 7G | 0 | 8G | 3G | 0 | 0 | 2C,6G | 0 | 0 | 0 | 0 | 0 | 0 | 0 | 9G | 8G |
| USH11 SUGARBEET | 4C,9G | 3C,7H | 2H | 0 | 0 | 2H | 0 | 0 | 3G | 0 | 0 | 0 | 0 | 0 | 0 | 0 | 0 | 0 |
| VELVETLEAF | 3C,8H | 5G | 5G | 0 | 4G | 0 | 0 | 0 | 5G | 0 | 0 | 0 | 0 | 0 | 0 | 0 | 5H | 3C,5G |
| GIANT FOXTAIL | 9H | 3C,7H | 7G | 2G | 3C,8H | 3G | 0 | 0 | 3C,7G | 0 | 0 | 0 | 0 | 0 | 0 | 0 | 2C,9G | 3C,8G |
| KLAGES BARLEY | 9G | 3C,8H | 3C,7G | 0 | 9G | 2G | 0 | 0 | 9H | 0 | 0 | 0 | 0 | 0 | 0 | 0 | 2C,9G | 3C,8G |

| | CMPD 91 | | CMPD 92 | | CMPD 93 | | CMPD 94 PRSOL | | CMPD 95 | | CMPD 96 | | CMPD 97 | | CMPD 98 | | CMPD 99 | |
|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.06 | 0.01 | 0.05 | 0.01 | 0.05 | 0.01 | 0.05 | 0.01 | 0.05 | 0.01 |
| COKER COTTON | 2G | 0 | 0 | 0 | 0 | 1C | 0 | 0 | 0 | 0 | 2C,8G | 5G | 0 | 0 | 0 | 0 | 0 | 0 |
| CULT MORNINGLRY | 5G | 0 | 0 | 0 | 0 | 1C | 0 | 0 | 0 | 0 | 9G | 0 | 0 | 0 | 0 | 0 | 0 | 0 |
| COCKLEBUR | 3C,3G | 3C,8H | 3C,8H | 0 | 3C,8H | 2H | 0 | 0 | 0 | 0 | 8H | 2C,6H | 0 | 1H | 1H | 0 | 0 | 0 |
| PURPLE NUTSEDGE | 10E | 0 | 10E | 0 | 10E | 10E | 0 | 0 | 0 | 0 | 9G | 8G | 0 | 0 | 0 | 0 | 0 | 0 |
| LARGE CRABGRASS | 3G | 0 | 3C,8G | 0 | 3C,5G | 0 | 0 | 0 | 0 | 0 | 10E | 3C,6G | 0 | 0 | 0 | 0 | 0 | 0 |
| BARNYARRDGRASS | 7G | 0 | 9H | 3C,8H | 3C,8H | 2C,7G | 0 | 0 | 3C,7G | 0 | 4C,9H | 4G | 0 | 0 | 0 | 0 | 0 | 0 |
| WILD OATS | 0 | 0 | 2C,7G | 5G | 5G | 0 | 0 | 0 | 9H | 0 | 7G | 2G | 0 | 0 | 0 | 0 | 0 | 0 |
| ERA WHEAT | 0 | 0 | 3C,9H | 3C,8H | 5G | 0 | 0 | 0 | 0 | 0 | 9H | 7G | 0 | 0 | 0 | 0 | 0 | 0 |
| G4646 CORN | 6G | 2G | 2C,6G | 3G | 0 | 2H | 0 | 0 | 2G | 0 | 2C,7G | 3G | 0 | 0 | 0 | 0 | 0 | 0 |
| WILLMS SOYBEANS | 2C,3G | 0 | 3C,9H | 3C,7H | 3G | 9H | 0 | 0 | 3C,6G | 0 | 9H | 8G | 0 | 0 | 0 | 0 | 0 | 0 |
| RICE DRY SEEDED | 10H | 4C,9H | 10E | 10E | 10E | 9H | 0 | 0 | 3C,5H | 0 | 4C,9H | 3C,8H | 0 | 0 | 0 | 0 | 2C,3G | 0 |
| G522 SORGHUM | 9H | 4C,9G | 10H | 6C,9H | 7C,9H | 6G | 0 | 0 | 8G | 0 | 9H | 9H | 0 | 0 | 0 | 0 | 0 | 0 |
| CHEAT GRASS | 3G | 0 | 9G | 9G | 9H | 6H | 2G | 0 | 9G | 2C | 9G | 2G | 0 | 0 | 0 | 0 | 8G | 0 |
| USH11 SUGARBEET | 7G | 5G | 5C,9G | 9G | 4C,8H | 0 | 0 | 0 | — | 5G | 5G | 5G | 0 | 0 | 0 | 0 | 8G | 0 |
| VELVETLEAF | 3G | 1H | 3C,8G | 4G | 0 | 0 | 0 | 5G | 9G | 5G | 3C,8G | 2G | 0 | 0 | 0 | 0 | 3G | 0 |
| GIANT FOXTAIL | 3G | 0 | 9H | 2C,8G | 3C,5G | 6H | 0 | 7G | 7G | 5G | 9H | 2C,9G | 0 | 0 | 0 | 0 | 2G | 0 |
| KLAGES BARLEY | 7G | 2G | 2C,7G | 7G | 7G | 0 | 0 | 2G | 0 | 0 | 8G | 2C,2G | — | 0 | 0 | 0 | 0 | 0 |
| DOWNY BROME | | | | | | | | | 7G | | | | | | | | | |

| | CMPD 100 | | CMPD 101 | | CMPD 102 | | CMPD 103 | | CMPD 104 | | CMPD 105 | | CMPD 106 | | CMPD 107 | | CMPD 108 | |
|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |

TABLE A-continued

| | CMPD 109 | | CMPD 110 | | CMPD 111 | | CMPD 112 | | CMPD 113 | | CMPD 114 | | CMPD 115 | | CMPD 116 | | CMPD 117 | |
| --- | --- | --- | --- | --- | --- | --- | --- | --- | --- | --- | --- | --- | --- | --- | --- | --- | --- | --- |
| | | | | | | | PRSOL | | | | | | | | | | | |
| | 0.05 | 0.01 | 0.05 | 0.01 | 0.05 | 0.01 | 0.05 | 0.01 | 0.06 | 0.01 | 0.05 | 0.01 | 0.05 | 0.01 | 0.05 | 0.01 | 0.05 | 0.01 |
| COKER COTTON | 8H | 2C,6G | 5G | 2C,3G | 2G | 0 | 0 | 0 | 0 | 0 | 0 | 0 | 0 | 0 | 9G | 8G | 2C,6G | 2C,6G |
| CULT MORNINGLRY | 9G | 9G | 8G | 7H | 1C | 0 | 0 | 0 | 0 | 0 | 0 | 0 | 0 | 0 | 9G | 9G | 9G | 9G |
| COCKLEBUR | 9H | 3C,7H | — | 2C | 1H | 0 | 0 | 0 | 0 | 0 | 0 | 0 | 0 | 0 | 9H | 9H | 8H | 9H |
| PURPLE NUTSEDGE | 10E | 9G | 10E | 5G | 0 | 0 | 10E | 0 | 8G | 0 | 0 | 0 | 10E | 3G | 9G | 9G | 5C,9G | 3C,7H |
| LARGE CRABGRASS | 6G | 4G | 2C,5G | 2C | 0 | 0 | 3G | 0 | 2C,2H | 4G | 0 | 0 | 0 | 0 | 5G | 2G | 2C,3G | 9G |
| BARNYARRDGRASS | 9H | 5H | 9H | 6G | 0 | 0 | 8H | 0 | 5H | 0 | 0 | 0 | 0 | 0 | 9H | 4H | 9H | 6G |
| WILD OATS | 3C,8H | 6G | 5G | 0 | 0 | 0 | 10E | 0 | 9G | 1C | 0 | 0 | 7H | 0 | 5G | 5G | 2C,3G | 2C,5G |
| ERA WHEAT | 9H | 9H | 7G | 0 | 0 | 0 | 0 | 0 | 0 | 0 | 0 | 0 | 2C,3G | 0 | 9H | 4H | 9H | 2G |
| G4646 CORN | 2G | 2G | 2G | 0 | 0 | 0 | 7H | 0 | 8H | 0 | 0 | 0 | 6G | 0 | 7G | 5G | 2C,7G | 7G |
| WILLMS SOYBEANS | 3C,4H | 3C,6H | 4G | 2H | 2G | 0 | 3G | 0 | 2G | 0 | 0 | 0 | 2C,4G | 0 | 4C,9G | 3C,7G | 3C,7H | 3C,8H |
| RICE DRY SEEDED | 10E | 10E | 9H | 8H | 0 | 0 | 8G | 0 | 2C,7G | 0 | 0 | 0 | 1C | 0 | 3C,9G | 9G | 9G | 3C,6G, |
| G522 SORGHUM | 9H | 9H | 9H | 4C,9H | 0 | 0 | 1C,1H | 0 | 1C | 0 | 0 | 0 | 8H | 0 | 4C,8H | 3C,8G | 4C,9H | 4C,8H |
| CHEAT GRASS | 8H | 7H | 8G | 5G | 0 | 3H | 8H | 0 | 8G | 6G | 0 | 0 | 2C,8H | 0 | 10E | 10E | 10H | 3C,9H |
| USH11 SUGARBEET | 9G | 9G | 9G | 5G | 5G | 0 | 7H | 0 | 8G | 8G | 0 | 0 | 4G | 0 | 9H | 7G | 3C,9H | 8G |
| VELVETLEAF | 3C,8H | 3C,5H | 4G | 0 | 2G | 0 | 9G | 0 | — | 0 | 0 | 0 | 2G | 0 | 4C,8G | 9G | 3C,8H | 3C,9G |
| GIANT FOXTAIL | 9H | 9H | 3C,8H | 5G | 0 | 0 | 7H | 0 | 8G | 4H | 3H | 0 | 6G | 0 | 5C,9G | 9G | 4C,9G | 4C,9G |
| KLAGES BARLEY | 9G | 8G | 3C,7G | 7G | 0 | — | 9H | 0 | 2C,5G | 0 | 0 | 0 | 9H | 0 | 5G | 2H | 3C,7H | 3C,8H |
| DOWNY BROME | — | | — | | — | | 9H | 7G | 10C | 3G | 0 | 0 | 5G | 0 | — | 2C,6G | 8G | 6G |
| RATE = KG/HA | | | | | | | | | | | | | | | | | | |

| | CMPD 118 | | CMPD 119 | | CMPD 120 | | CMPD 121 | |
| --- | --- | --- | --- | --- | --- | --- | --- | --- |
| | | | | | | PRSOL | | |
| | 0.05 | 0.01 | 0.05 | 0.01 | 0.05 | 0.01 | 0.05 | 0.01 |
| COKER COTTON | 9G | 9G | 9G | 8G | 4C,8G | 5G | 9G | 2C,6G |
| CULT MORNINGLRY | 9G | 9G | 8G | 8G | 8G | 2C,5G | 9G | 9G |
| COCKLEBUR | 8H | — | 10C | 9H | 8H | 3C,6H | 9H | 9H |
| PURPLE NUTSEDGE | 10E | 7G | 10E | 10E | 5G | 2G | 7G | 7G |
| LARGE CRABGRASS | 7G | 4G | 10E | 9G | 2C,9G | 2C,4G | 4C,8G | 2C,5G |
| BARNYARRDGRASS | 9H | 2C,7H | 3C,9G | 3C,8H | 4C,9G | 2G | 4C,9H | 3C,7H |
| WILD OATS | 2G | — | 9H | 6G | 5C,9H | 5G | 4C,8G | 2G |
| ERA WHEAT | 2C,8H | 8G | 3C,8G | 8G | 5G | 7G | 4C,9H | 4G |
| G4646 CORN | 9G | 3C,8G | 5C,9H | 3C,9H | 2C,9G | 2C,6G | 3C,9H | 3C,7H |
| RATE = KG/HA | | | | | | | | |

TABLE A-continued

|  |  |  |  |  |  |  |  |  |
|---|---|---|---|---|---|---|---|---|
| WILLMS SOYBEANS | 2C,9H | 3C,7H | 9H | 9H | 9H | 4C,8H | 9H | 4C,8H |
| RICE DRY SEEDED | 10H | 9H | 10E | 10H | 10H | 3C,7H | 10H | 4C,8H |
| G522 SORGHUM | 9H | 9H | 5C,9H | 4C,9H | 4C,8H | 3C,6H | 3C,9H | 5C,8H |
| CHEAT GRASS | 8G | 8G | 9H | 8H | 3C,8G | 0 | 4C,8H | 3C,8H |
| USH11 SUGARBEET | 4C,9G | 4C,9G | 5C,9G | 7G | 5C,9G | 2C,4G | 5C,9G | 4C,9G |
| VELVETLEAF | 4C,9G | 3C,7G | 4C,9G | 3C,9G | 9C | 2G | 4C,8G | 3C,3G |
| GIANT FOXTAIL | 8G | 3C,7H | 9H | 8G | 7G | 0 | 9H | 7G |
| KLAGES BARLEY | 8G | 8G | 9G | 2C,8G | 5G | 9G/7G | | |

It is noted that a few compounds such as compounds 6, 19, 20, 26, 32, 37–39, 44, 49, 54–59, 76–78 and 88 show little or no herbicidal activity at the rate tested. It is thought they would show more herbicidal activity at higher rates.

Test B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), chickweed (*Stellaria media*), lambsquarters (*Chenopodium album*), rice (*Oryza satira*, variety California Rice Coop. M101) and teaweed (*Sida spinosa*). The second pot was planted with green foxtail (*Setaria viridis*), cocklebur (*Xanthium pensylvanicum*), morningglory (*Ipomoea coccinea*, variety Scarlet O'Hara), cotton (*Gossypium hirsutum*, variety Coker 315), johnsongrass (*Sorghum halepense*), barnyardgrass (*Echinochloa crus-galli*), corn (*Zea mays*, variety Funk G4646), soybeans (*Glycine max*, variety Williams) and giant foxtail (*Setaria faberi*). The third pot was planted with wheat (*Triticum aestivum*, variety Era spring), barley (*Hordeum vulgare*, variety Klages spring), wild buckwheat (*Polgonum convolvulus*), cheatgrass (*Bromus secalinus*), sugarbeet (*Beta vulgaris*, variety Union Sugarbeet Co. USH11), wild oats (*Avena fatua*), field violet (*Viola arvensis*), blackgrass (*Alopecurus myosuroides*), and rape (*Brassica napus*, variety Altex). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, chickweed, lambsquarters, rice and teaweed. The second pot was planted with green foxtail, cocklebur, morningglory, cotton, johnsongrass, barnyardgrass, corn, soybean and giant foxtail. The third pot was planted with wheat, barley, wild buckwheat, cheatgrass, sugarbeet, wild oat, field violet, blackgrass and rape. The three pans were sprayed preemergence with the chemicals dissolved in a non-phytotoxic solvent.

Treated plants and controls were maintained in the greenhouse for 24 days, then all treated plants were compared to controls and visually rated for plant response.

Response ratings are based on a scale of 0 to 100 where 0=no effect and 100=complete control. A dash (—) response means no test.

Response ratings are contained in Table B.

TABLE B

| | Cmpd 1 | | | | |
|---|---|---|---|---|---|
| RATE (g/ha) | 1 | 4 | 16 | 62 | 250 |
| PREEMERGENCE | | | | | |
| Barley | 20 | 30 | 80 | 80 | 90 |
| Barnyardgrass | 0 | 20 | 100 | 95 | 95 |
| Blackgrass | 0 | 20 | 80 | 85 | 100 |
| Cheatgrass | 30 | 70 | 90 | 100 | 100 |
| Chickweed | — | — | — | — | — |
| Cocklebur | 0 | 0 | 30 | 85 | 90 |
| Corn | 0 | 0 | 0 | 0 | 10 |
| Cotton | 0 | 10 | 85 | 85 | 90 |

TABLE B-continued

| | | | | | |
|---|---|---|---|---|---|
| Crabgrass | 0 | 0 | 40 | 50 | 75 |
| Field violet | — | — | — | — | — |
| Giant foxtail | 20 | 20 | 80 | 85 | 90 |
| Green foxtail | 20 | 90 | 95 | 100 | 99 |
| Jimsonweed | — | 0 | — | 50 | — |
| Johnsongrass | 60 | 85 | 90 | 100 | 100 |
| Lambsquarters | 0 | 0 | 50 | 70 | 80 |
| Morningglory | 0 | 0 | 20 | 80 | 95 |
| Nutsedge | 20 | 30 | 80 | 90 | 95 |
| Rape | 0 | 50 | 80 | 90 | 95 |
| Rice | 20 | 85 | 90 | 95 | 100 |
| Sicklepod | — | 0 | — | — | — |
| Soybean | 0 | 0 | 0 | 10 | 30 |
| Sugarbeet | 20 | 60 | 70 | 80 | 90 |
| Teaweed | — | — | 30 | 80 | 80 |
| Velvetleaf | 0 | 20 | 30 | 40 | 70 |
| Wheat | 0 | 20 | 30 | 80 | 90 |
| Wild buckwheat | 0 | 50 | 70 | 80 | 90 |
| Wild oat | 10 | 20 | 30 | 60 | 70 |

| | Cmpd 21 | | | |
|---|---|---|---|---|
| RATE (g/ha) | 1 | 4 | 16 | 62 |
| PREEMERGENCE | | | | |
| Barley | 30 | 50 | 80 | 90 |
| Barnyardgrass | 30 | 60 | 90 | 100 |
| Blackgrass | 60 | 70 | 80 | 90 |
| Cheatgrass | 30 | 70 | 100 | 100 |
| Chickweed | — | — | — | — |
| Cocklebur | 0 | 30 | 50 | 70 |
| Corn | 0 | 0 | 0 | 0 |
| Cotton | 0 | 30 | 50 | 80 |
| Crabgrass | 30 | 50 | 70 | 90 |
| Field violet | 30 | 50 | 70 | 90 |
| Giant foxtail | 30 | 70 | 90 | 100 |
| Green foxtail | 30 | 70 | 100 | 100 |
| Jimsonweed | 60 | 70 | 80 | 90 |
| Johnsongrass | 50 | 70 | 80 | 90 |
| Lambsquarters | 50 | 60 | 70 | 90 |
| Morningglory | 0 | 30 | 60 | 90 |
| Nutsedge | 0 | 30 | 80 | 100 |
| Rape | 70 | 90 | 100 | 100 |
| Rice | 60 | 100 | 100 | 100 |
| Sicklepod | — | — | — | — |
| Soybean | 0 | 0 | 30 | 90 |
| Sugarbeet | 30 | 60 | 90 | 100 |
| Teaweed | 30 | 50 | 70 | 90 |
| Velvetleaf | 30 | 50 | 70 | 90 |
| Wheat | 0 | 30 | 60 | 90 |
| Wild buckwheat | 70 | 80 | 90 | 90 |
| Wild oat | 0 | 0 | 30 | 80 |

| | Cmpd 46 | | | |
|---|---|---|---|---|
| RATE (g/ha) | 4 | 16 | 62 | 250 |
| PREEMERGENCE | | | | |
| Barley | 20 | 40 | 60 | 80 |
| Barnyardgrass | 60 | 90 | 100 | 100 |
| Blackgrass | 50 | 70 | 80 | 90 |
| Cheatgrass | 60 | 70 | 80 | 90 |
| Chickweed | 30 | 50 | 70 | 90 |
| Cocklebur | 0 | 30 | 50 | 70 |
| Corn | 0 | 0 | 0 | 30 |
| Cotton | 0 | 30 | 40 | 60 |
| Crabgrass | 0 | 30 | 50 | 70 |
| Field violet | — | — | — | — |
| Giant foxtail | 50 | 80 | 90 | 100 |
| Green foxtail | 30 | 50 | 80 | 100 |
| Jimsonweed | 0 | 30 | 60 | 90 |
| Johnsongrass | 50 | 70 | 80 | 90 |
| Lambsquarters | 30 | 50 | 80 | 90 |
| Morningglory | 30 | 50 | 70 | 90 |
| Nutsedge | 30 | 60 | 90 | 100 |
| Rape | 50 | 70 | 90 | 100 |
| Rice | 80 | 90 | 100 | 100 |
| Sicklepod | 30 | 60 | 90 | 100 |
| Soybean | 0 | 0 | 70 | — |
| Sugarbeet | 70 | 90 | 100 | — |
| Teaweed | 0 | 30 | 50 | 80 |
| Velvetleaf | 30 | 60 | 90 | 100 |
| Wheat | 30 | 50 | 70 | 80 |
| Wild buckwheat | 30 | 50 | 70 | 90 |
| Wild oat | 0 | 30 | 40 | 60 |

TABLE B-continued

| | Cmpd 60 | | | |
|---|---|---|---|---|
| RATE (g/ha) | 4 | 16 | 62 | 250 |
| PREEMERGENCE | | | | |
| Barley | 20 | 30 | 30 | 90 |
| Barnyardgrass | 20 | 100 | 100 | 100 |
| Blackgrass | 70 | 80 | 100 | 100 |
| Cheatgrass | 30 | 70 | 100 | 100 |
| Chickweed | 60 | 100 | 100 | 100 |
| Cocklebur | 0 | 50 | 60 | 90 |
| Corn | 0 | 20 | 30 | 40 |
| Cotton | 0 | 50 | 90 | 90 |
| Crabgrass | 60 | 60 | 70 | 80 |
| Field violet | — | — | — | — |
| Giant foxtail | — | — | — | — |
| Green foxtail | 0 | 70 | 100 | 100 |
| Jimsonweed | 0 | 50 | 70 | 80 |
| Johnsongrass | 70 | 80 | 100 | 100 |
| Lambsquarters | 30 | 50 | 90 | 100 |
| Morningglory | 20 | 80 | 90 | 100 |
| Nutsedge | 0 | 80 | 90 | 100 |
| Rape | 80 | 90 | 90 | 100 |
| Rice | 90 | 90 | 100 | 100 |
| Sicklepod | 50 | 80 | 90 | 90 |
| Soybean | 30 | 60 | 90 | 100 |
| Sugarbeet | 80 | 90 | 90 | 90 |
| Teaweed | 50 | 70 | 90 | 90 |
| Velvetleaf | 30 | 40 | 80 | 100 |
| Wheat | 30 | 40 | 60 | 90 |
| Wild buckwheat | 50 | 70 | 80 | 90 |
| Wild oat | 0 | 30 | 50 | 70 |

| | Cmpd 64 | | | |
|---|---|---|---|---|
| RATE (g/ha) | 4 | 16 | 62 | 250 |
| PREEMERGENCE | | | | |
| Barley | 0 | 30 | 60 | 90 |
| Barnyardgrass | 30 | 50 | 70 | 90 |
| Blackgrass | 30 | 70 | 80 | 90 |
| Cheatgrass | 50 | 70 | 80 | 90 |
| Chickweed | 30 | 50 | 70 | 90 |
| Cocklebur | 50 | 70 | 80 | 90 |
| Corn | 0 | 30 | 60 | 90 |
| Cotton | 30 | 50 | 70 | 90 |
| Crabgrass | 0 | 30 | 50 | 70 |
| Field violet | — | — | — | — |
| Giant foxtail | 0 | 50 | 70 | 90 |
| Green foxtail | 30 | 50 | 70 | 90 |
| Jimsonweed | 30 | 50 | 70 | 90 |
| Johnsongrass | 30 | 50 | 70 | 90 |
| Lambsquarters | 30 | 50 | 70 | 90 |
| Morningglory | 50 | 80 | 90 | 100 |
| Nutsedge | 80 | 90 | 100 | 100 |
| Rape | 80 | 100 | 100 | 100 |
| Rice | 50 | 70 | 100 | 100 |
| Sicklepod | 30 | 50 | 70 | 90 |
| Soybean | 30 | 60 | 80 | 90 |
| Sugarbeet | 80 | 90 | 100 | 100 |
| Teaweed | 30 | 50 | 70 | 90 |
| Velvetleaf | 50 | 70 | 90 | 100 |
| Wheat | 30 | 50 | 70 | 90 |
| Wild buckwheat | 70 | 80 | 90 | 95 |
| Wild oat | 0 | 30 | 50 | 70 |

| | Cmpd 65 | | | |
|---|---|---|---|---|
| RATE (g/ha) | 1 | 4 | 16 | 62 |
| PREEMERGENCE | | | | |
| Barley | 20 | 40 | 80 | 100 |
| Barnyardgrass | 0 | 30 | 40 | 50 |
| Blackgrass | 40 | 50 | 90 | 100 |
| Cheatgrass | 70 | 80 | 100 | 100 |
| Chickweed | 70 | 90 | 100 | 100 |
| Cocklebur | 0 | 20 | 90 | 100 |
| Corn | 0 | 0 | 90 | 90 |
| Cotton | 0 | 20 | 80 | 100 |
| Crabgrass | 20 | 60 | 90 | 90 |
| Field violet | — | — | — | — |
| Giant foxtail | 0 | 20 | 100 | 100 |
| Green foxtail | 0 | 20 | 100 | 100 |
| Jimsonweed | 0 | 30 | 100 | 100 |
| Johnsongrass | 0 | 30 | 90 | 90 |
| Lambsquarters | 20 | 40 | 100 | 100 |
| Morningglory | 0 | 30 | 100 | 100 |
| Nutsedge | 0 | 30 | 90 | 90 |
| Rape | 70 | 100 | 100 | 100 |
| Rice | 0 | 20 | 100 | 100 |
| Sicklepod | 0 | 50 | 90 | 100 |
| Soybean | 0 | 0 | 30 | 50 |
| Sugarbeet | 70 | 90 | 100 | 100 |
| Teaweed | 20 | 50 | 100 | 100 |
| Velvetleaf | 0 | 20 | 80 | 90 |
| Wheat | 0 | 60 | 80 | 100 |
| Wild buckwheat | 80 | 100 | 100 | 100 |
| Wild oat | 20 | 40 | 80 | 100 |

| | Cmpd 66 | | | |
|---|---|---|---|---|
| RATE (g/ha) | 1 | 4 | 16 | 62 |
| PREEMERGENCE | | | | |
| Barley | 0 | 30 | 60 | 90 |
| Barnyardgrass | 0 | 0 | 20 | 30 |
| Blackgrass | 30 | 50 | 90 | 100 |
| Cheatgrass | 60 | 70 | 100 | 100 |
| Chickweed | 70 | 80 | 90 | 100 |
| Cocklebur | 0 | 0 | 20 | 80 |
| Corn | 0 | 0 | 50 | 70 |
| Cotton | 0 | 0 | 0 | 0 |
| Crabgrass | 20 | 70 | 100 | 100 |
| Field violet | — | — | — | — |
| Giant foxtail | 20 | 40 | 70 | 90 |
| Green foxtail | 0 | 20 | 90 | 100 |
| Jimsonweed | 20 | 20 | 40 | 80 |
| Johnsongrass | 0 | 0 | 30 | 70 |
| Lambsquarters | 0 | 0 | 20 | 80 |
| Morningglory | 0 | 20 | 90 | 90 |
| Nutsedge | 0 | 20 | 40 | 80 |
| Rape | 40 | 60 | 90 | 100 |
| Rice | 0 | 20 | 60 | 100 |
| Sicklepod | 20 | 40 | 80 | 100 |
| Soybean | 0 | 0 | 30 | 80 |
| Sugarbeet | 40 | 60 | 100 | 100 |
| Teaweed | 20 | 30 | 90 | 90 |
| Velvetleaf | 0 | 0 | 40 | 60 |
| Wheat | 0 | 30 | 90 | 100 |
| Wild buckwheat | 0 | 40 | 100 | 100 |
| Wild oat | 20 | 30 | 40 | 90 |

| | Cmpd 67 | | | |
|---|---|---|---|---|
| RATE (g/ha) | 1 | 4 | 16 | 62 |
| PREEMERGENCE | | | | |
| Barley | 0 | 20 | 70 | 100 |
| Barnyardgrass | 0 | 20 | 100 | 100 |
| Blackgrass | 30 | 50 | 80 | 90 |
| Cheatgrass | 30 | 70 | 80 | 100 |
| Chickweed | 30 | 70 | 80 | 90 |
| Cocklebur | 0 | 20 | 70 | 80 |
| Corn | 0 | 20 | 80 | 100 |
| Cotton | — | 0 | 20 | 90 |
| Crabgrass | 30 | 70 | 100 | 100 |
| Field violet | — | — | — | — |
| Giant foxtail | 20 | 40 | 100 | 100 |
| Green foxtail | 0 | 20 | 90 | 100 |
| Jimsonweed | 0 | 40 | 100 | 100 |
| Johnsongrass | 0 | 30 | 100 | 100 |
| Lambsquarters | 0 | 30 | 90 | 100 |
| Morningglory | 0 | 20 | 30 | 100 |
| Nutsedge | 20 | 60 | 100 | 100 |
| Rape | 30 | 70 | 100 | 100 |
| Rice | 20 | 50 | 100 | 100 |
| Sicklepod | 0 | 20 | 30 | 40 |
| Soybean | 0 | 0 | 40 | 80 |
| Sugarbeet | 60 | 70 | 100 | 100 |
| Teaweed | 0 | 20 | 70 | 80 |
| Velvetleaf | 0 | 30 | 70 | 100 |
| Wheat | 0 | 20 | 50 | 90 |
| Wild buckwheat | 60 | 90 | 100 | 100 |
| Wild oat | 0 | 20 | 30 | 40 |

| | Cmpd 68 | | | |
|---|---|---|---|---|
| RATE (g/ha) | 1 | 4 | 16 | 62 |
| PREEMERGENCE | | | | |
| Barley | 0 | 40 | 80 | 90 |
| Barnyardgrass | 20 | 30 | 60 | 80 |
| Blackgrass | 30 | 50 | 80 | 90 |

TABLE B-continued

| | | | | |
|---|---|---|---|---|
| Cheatgrass | 30 | 40 | 100 | 100 |
| Chickweed | 40 | 60 | 70 | 80 |
| Cocklebur | 0 | 20 | 30 | 40 |
| Corn | 0 | 0 | 0 | 40 |
| Cotton | 0 | 0 | 20 | 40 |
| Crabgrass | 0 | 40 | 100 | 100 |
| Field violet | — | — | — | — |
| Giant foxtail | 20 | 40 | 90 | 100 |
| Green foxtail | 0 | 30 | 90 | 100 |
| Jimsonweed | 0 | 30 | 70 | 90 |
| Johnsongrass | 20 | 30 | 90 | 90 |
| Lambsquarters | 0 | 30 | 70 | 90 |
| Morningglory | 0 | 30 | 50 | 80 |
| Nutsedge | 0 | 30 | 100 | 100 |
| Rape | 30 | 70 | 100 | 100 |
| Rice | 0 | 30 | 100 | 100 |
| Sicklepod | 0 | 30 | 80 | 90 |
| Soybean | 0 | 0 | 30 | 70 |
| Sugarbeet | 30 | 40 | 100 | 100 |
| Teaweed | 0 | 30 | 80 | 80 |
| Velvetleaf | 0 | 30 | 80 | 90 |
| Wheat | 0 | 30 | 60 | 100 |
| Wild buckwheat | 40 | 70 | 90 | 90 |
| Wild oat | 40 | 50 | 80 | 100 |

| | Cmpd 92 | |
|---|---|---|
| RATE (g/ha) | 16 | 62 |
| PREEMERGENCE | | |
| Barley | 40 | 70 |
| Barnyardgrass | 100 | 100 |
| Blackgrass | 70 | 100 |
| Cheatgrass | 70 | 90 |
| Chickweed | 50 | 80 |
| Cocklebur | 30 | 50 |
| Corn | 0 | 40 |
| Cotton | 50 | 90 |
| Crabgrass | 60 | 70 |
| Field violet | — | — |
| Giant foxtail | — | — |
| Green foxtail | 90 | 100 |
| Jimsonweed | 70 | 90 |
| Johnsongrass | 90 | 100 |
| Lambsquarters | 90 | 100 |
| Morningglory | 70 | 90 |
| Nutsedge | 80 | 90 |
| Rape | 90 | 100 |
| Rice | 100 | 100 |
| Sicklepod | 60 | 80 |
| Soybean | 70 | 100 |
| Sugarbeet | 80 | 90 |
| Teaweed | — | 90 |
| Velvetleaf | 50 | 60 |
| Wheat | 40 | 70 |
| Wild buckwheat | 80 | 80 |
| Wild oat | 30 | 50 |

| | Cmpd 93 | | | |
|---|---|---|---|---|
| RATE (g/ha) | 1 | 4 | 16 | 62 |
| PREEMERGENCE | | | | |
| Barley | 0 | 20 | 40 | 60 |
| Barnyardgrass | 0 | 30 | 50 | 70 |
| Blackgrass | 30 | 50 | 70 | 100 |
| Cheatgrass | 0 | 30 | 50 | 70 |
| Chickweed | — | — | — | — |
| Cocklebur | 0 | 0 | 30 | 40 |
| Corn | 0 | 0 | 0 | 0 |
| Cotton | 0 | 0 | 0 | 20 |
| Crabgrass | 0 | 20 | 30 | 60 |
| Field violet | 20 | 30 | 60 | 80 |
| Giant foxtail | 30 | 50 | 70 | 80 |
| Green foxtail | 0 | 0 | 30 | 60 |
| Jimsonweed | 0 | 30 | 60 | 90 |
| Johnsongrass | 70 | 80 | 90 | 100 |
| Lambsquarters | 0 | 30 | 60 | 90 |
| Morningglory | 0 | 20 | 30 | 50 |
| Nutsedge | 0 | 0 | 30 | 70 |
| Rape | 50 | 70 | 80 | 90 |
| Rice | 30 | 50 | 90 | 100 |
| Sicklepod | 0 | 20 | 30 | 50 |
| Soybean | 0 | 0 | 0 | 0 |
| Sugarbeet | 30 | 50 | 80 | 90 |
| Teaweed | 30 | 50 | 70 | 90 |
| Velvetleaf | 0 | 30 | 50 | 70 |
| Wheat | 0 | 0 | 20 | 40 |
| Wild buckwheat | 0 | 30 | 50 | 70 |
| Wild oat | 0 | 0 | 30 | 50 |

| | Cmpd 96 | | | |
|---|---|---|---|---|
| RATE (g/ha) | 1 | 4 | 16 | 62 |
| PREEMERGENCE | | | | |
| Barley | 0 | 20 | 30 | 80 |
| Barnyardgrass | 0 | 20 | 80 | 80 |
| Blackgrass | 0 | 50 | 50 | 70 |
| Cheatgrass | 0 | 30 | 50 | 80 |
| Chickweed | 0 | 0 | 40 | 40 |
| Cocklebur | 0 | 30 | 50 | 60 |
| Corn | 0 | 0 | 0 | 0 |
| Cotton | 0 | 0 | 40 | 70 |
| Crabgrass | 0 | 0 | 40 | 100 |
| Field violet | — | — | — | — |
| Giant foxtail | 0 | 20 | 90 | 100 |
| Green foxtail | 0 | 70 | 100 | 100 |
| Jimsonweed | 0 | 60 | 80 | 90 |
| Johnsongrass | 0 | 40 | 70 | 90 |
| Lambsquarters | 0 | 20 | 30 | 70 |
| Morningglory | 0 | 0 | 30 | 60 |
| Nutsedge | 0 | 20 | 40 | 60 |
| Rape | 0 | 70 | 70 | 90 |
| Rice | 0 | 50 | 90 | 90 |
| Sicklepod | 0 | 0 | 40 | 80 |
| Soybean | 0 | 20 | 50 | 60 |
| Sugarbeet | 0 | 0 | 60 | 80 |
| Teaweed | 0 | 0 | 30 | 30 |
| Velvetleaf | 0 | 30 | 30 | 40 |
| Wheat | 0 | 0 | 30 | 60 |
| Wild buckwheat | 0 | 0 | 50 | 90 |
| Wild oat | 0 | 30 | 40 | 40 |

| | Cmpd 100 | | | |
|---|---|---|---|---|
| RATE (g/ha) | 1 | 4 | 16 | 62 |
| PREEMERGENCE | | | | |
| Barley | 30 | 50 | 70 | 90 |
| Barnyardgrass | 30 | 50 | 80 | 100 |
| Blackgrass | 50 | 60 | 70 | 90 |
| Cheatgrass | 50 | 70 | 80 | 90 |
| Chickweed | 30 | 50 | 70 | 90 |
| Cocklebur | 0 | 30 | 60 | 90 |
| Corn | 0 | 0 | 0 | 0 |
| Cotton | 0 | 30 | 50 | 60 |
| Crabgrass | 0 | 30 | 50 | 80 |
| Field violet | — | — | — | — |
| Giant foxtail | 70 | 90 | 100 | 100 |
| Green foxtail | 50 | 70 | 90 | 100 |
| Jimsonweed | 0 | 30 | 50 | 80 |
| Johnsongrass | 50 | 70 | 80 | 90 |
| Lambsquarters | 70 | 100 | 100 | 100 |
| Morningglory | 0 | 30 | 50 | 80 |
| Nutsedge | 0 | 30 | 60 | 90 |
| Rape | 70 | 100 | 100 | 100 |
| Rice | 30 | 60 | 80 | 90 |
| Sicklepod | 30 | 50 | 70 | 90 |
| Soybean | 0 | 30 | 40 | 60 |
| Sugarbeet | 70 | 90 | 100 | 100 |
| Teaweed | 0 | 30 | 50 | 70 |
| Velvetleaf | 30 | 60 | 90 | 95 |
| Wheat | 0 | 30 | 60 | 90 |
| Wild buckwheat | 0 | 30 | 60 | 90 |
| Wild oat | 0 | 0 | 30 | 50 |

| | Cmpd 106 | | |
|---|---|---|---|
| RATE (g/ha) | 16 | 62 | 250 |
| PREEMERGENCE | | | |
| Barley | 50 | 80 | 90 |
| Barnyardgrass | 20 | 40 | 100 |
| Blackgrass | 80 | 100 | 100 |
| Cheatgrass | 70 | 100 | 100 |
| Chickweed | 0 | 10 | 20 |
| Cocklebur | 0 | 40 | 80 |
| Corn | 0 | 0 | 10 |
| Cotton | 0 | 10 | 20 |
| Crabgrass | 40 | 80 | 80 |
| Field violet | — | — | — |

Cmpd 96 section also includes (at top):

| | | | | |
|---|---|---|---|---|
| Teaweed | 30 | 50 | 70 | 90 |
| Velvetleaf | 0 | 30 | 50 | 70 |
| Wheat | 0 | 0 | 20 | 40 |
| Wild buckwheat | 0 | 30 | 50 | 70 |
| Wild oat | 0 | 0 | 30 | 50 |

TABLE B-continued

| | | | |
|---|---|---|---|
| Giant foxtail | 40 | 90 | 100 |
| Green foxtail | 40 | 90 | 100 |
| Jimsonweed | 0 | — | 20 |
| Johnsongrass | 70 | 90 | 100 |
| Lambsquarters | 80 | 90 | 100 |
| Morningglory | 20 | 40 | 50 |
| Nutsedge | 40 | 50 | 70 |
| Rape | 80 | 90 | 100 |
| Rice | 80 | 100 | 100 |
| Sicklepod | 0 | 20 | 60 |
| Soybean | 0 | 0 | 20 |
| Sugarbeet | 30 | 80 | 100 |
| Teaweed | 30 | 50 | 70 |
| Velvetleaf | 0 | 20 | 60 |
| Wheat | 20 | 40 | 60 |
| Wild buckwheat | 30 | 60 | 80 |
| Wild oat | 20 | 60 | 80 |

Cmpd 1

| RATE (g/ha) | 0.25 | 1 | 4 | 16 | 62 |
|---|---|---|---|---|---|
| POSTEMERGENCE | | | | | |
| Barley | 0 | 0 | 30 | 80 | 90 |
| Barnyardgrass | 30 | 60 | 100 | 100 | 100 |
| Blackgrass | 50 | 50 | 70 | 85 | 100 |
| Cheatgrass | 20 | 30 | 65 | 85 | 95 |
| Chickweed | — | — | — | — | — |
| Cocklebur | 0 | 20 | 80 | 80 | 100 |
| Corn | 0 | 0 | 0 | 0 | 10 |
| Cotton | 0 | 20 | 30 | 80 | 85 |
| Crabgrass | 30 | 20 | 20 | 50 | 60 |
| Field violet | — | 0 | 0 | 20 | — |
| Giant foxtail | 0 | 20 | 50 | 70 | 85 |
| Green foxtail | 0 | 20 | 30 | 75 | 85 |
| Jimsonweed | 0 | 0 | 10 | 20 | 30 |
| Johnsongrass | 60 | 80 | 100 | 100 | 100 |
| Lambsquarters | 0 | 0 | 20 | 20 | 50 |
| Morningglory | 10 | 30 | 50 | 85 | 90 |
| Nutsedge | 0 | 30 | 70 | 75 | 80 |
| Rape | 20 | 60 | 90 | 100 | 90 |
| Rice | 20 | 40 | 70 | 90 | 100 |
| Sicklepod | 0 | 50 | 80 | 70 | 100 |
| Soybean | 0 | 0 | 10 | 20 | 70 |
| Sugarbeet | 10 | 0 | 30 | 80 | 100 |
| Teaweed | 0 | 20 | 30 | 60 | 70 |
| Velvetleaf | 0 | 20 | 40 | 60 | 100 |
| Wheat | 10 | 10 | 60 | 100 | 100 |
| Wild buckwheat | 0 | 30 | 40 | 70 | — |
| Wild oat | 0 | 0 | 20 | 60 | 100 |

Cmpd 21

| RATE (g/ha) | 0.25 | 1 | 4 | 16 | 62 |
|---|---|---|---|---|---|
| POSTEMERGENCE | | | | | |
| Barley | 20 | 20 | 60 | 70 | 70 |
| Barnyardgrass | 50 | 80 | 95 | 100 | 100 |
| Blackgrass | 0 | 50 | 80 | 90 | 90 |
| Cheatgrass | 20 | 30 | 50 | 90 | 100 |
| Chickweed | — | — | — | — | — |
| Cocklebur | 0 | 0 | 40 | 80 | 100 |
| Corn | 0 | 0 | 0 | 0 | 0 |
| Cotton | 0 | 30 | 60 | 80 | 100 |
| Crabgrass | 0 | 0 | 0 | 70 | 80 |
| Field violet | 0 | 30 | 40 | 80 | 80 |
| Giant foxtail | 40 | 70 | 100 | 100 | 100 |
| Green foxtail | 60 | 90 | 100 | 100 | 100 |
| Jimsonweed | 0 | 0 | 20 | 50 | 80 |
| Johnsongrass | 70 | 80 | 100 | 100 | 100 |
| Lambsquarters | 0 | — | 0 | — | 100 |
| Morningglory | 0 | 20 | 95 | 95 | 100 |
| Nutsedge | 0 | 30 | 40 | 70 | 100 |
| Rape | 50 | 80 | 100 | 100 | 100 |
| Rice | 0 | 40 | 90 | 100 | 100 |
| Sicklepod | 0 | 30 | 90 | 100 | 100 |
| Soybean | 40 | 50 | 80 | 90 | 90 |
| Sugarbeet | 0 | 20 | 40 | 70 | 80 |
| Teaweed | 0 | — | — | — | 80 |
| Velvetleaf | 0 | 0 | 50 | 90 | 100 |
| Wheat | 50 | 60 | 60 | 100 | 100 |
| Wild buckwheat | 20 | 20 | 50 | 60 | 80 |
| Wild oat | 0 | 20 | 70 | 80 | 100 |

Cmpd 46

| RATE (g/ha) | 1 | 4 | 16 | 62 |
|---|---|---|---|---|
| POSTEMERGENCE | | | | |
| Barley | 30 | 50 | 60 | 70 |
| Barnyardgrass | 50 | 70 | 80 | 90 |
| Blackgrass | 30 | 50 | 70 | 100 |
| Cheatgrass | 30 | 50 | 70 | 90 |
| Chickweed | 30 | 50 | 70 | 90 |
| Cocklebur | 30 | 40 | 50 | 60 |
| Corn | 0 | 0 | 0 | 0 |
| Cotton | 0 | 30 | 50 | 60 |
| Crabgrass | 0 | 0 | 30 | 50 |
| Field violet | — | — | — | — |
| Giant foxtail | 30 | 50 | 80 | 90 |
| Green foxtail | 30 | 50 | 70 | 80 |
| Jimsonweed | 0 | 0 | 30 | 60 |
| Johnsongrass | 30 | 60 | 90 | 100 |
| Lambsquarters | 0 | 0 | 30 | 50 |
| Morningglory | 30 | 50 | 70 | 80 |
| Nutsedge | 0 | 30 | 60 | 90 |
| Rape | 60 | 90 | 100 | 100 |
| Rice | 30 | 50 | 70 | 90 |
| Sicklepod | 0 | 30 | 60 | 90 |
| Soybean | 0 | 30 | 60 | 90 |
| Sugarbeet | 30 | 50 | 70 | 90 |
| Teaweed | 0 | 20 | 40 | 60 |
| Velvetleaf | 30 | 60 | 80 | 100 |
| Wheat | 30 | 50 | 80 | 100 |
| Wild buckwheat | 30 | 50 | 70 | 90 |
| Wild oat | 0 | 0 | 30 | 60 |

Cmpd 60

| RATE (g/ha) | 1 | 4 | 16 | 62 |
|---|---|---|---|---|
| POSTEMERGENCE | | | | |
| Barley | 0 | 40 | 60 | 90 |
| Barnyardgrass | 60 | 100 | 100 | 100 |
| Blackgrass | 60 | 100 | 100 | 100 |
| Cheatgrass | 40 | 60 | 80 | 100 |
| Chickweed | 30 | 60 | 90 | 100 |
| Cocklebur | 50 | 100 | 100 | 100 |
| Corn | — | 20 | 50 | 70 |
| Cotton | 20 | 30 | 90 | 100 |
| Crabgrass | 0 | 0 | 30 | 40 |
| Field violet | — | — | — | — |
| Giant foxtail | 20 | 20 | 80 | 90 |
| Green foxtail | 30 | 50 | 80 | 90 |
| Jimsonweed | 20 | 30 | 40 | 60 |
| Johnsongrass | 20 | 90 | 100 | 100 |
| Lambsquarters | 0 | 50 | 50 | 90 |
| Morningglory | — | 60 | 60 | 80 |
| Nutsedge | 20 | 30 | 80 | 90 |
| Rape | 80 | 100 | 100 | 100 |
| Rice | 60 | 60 | 90 | 100 |
| Sicklepod | 30 | 60 | 90 | 100 |
| Soybean | 60 | 80 | 90 | 100 |
| Sugarbeet | — | 60 | 80 | 100 |
| Teaweed | 20 | 30 | 40 | 60 |
| Velvetleaf | 70 | 80 | 100 | 100 |
| Wheat | 0 | 30 | 60 | 100 |
| Wild buckwheat | 70 | 70 | 80 | 90 |
| Wild oat | 0 | 40 | 60 | 80 |

Cmpd 64

| RATE (g/ha) | 1 | 4 | 16 | 62 |
|---|---|---|---|---|
| POSTEMERGENCE | | | | |
| Barley | 0 | 30 | 50 | 70 |
| Barnyardgrass | 30 | 50 | 80 | 100 |
| Blackgrass | 30 | 50 | 70 | 90 |
| Cheatgrass | 0 | 30 | 50 | 70 |
| Chickweed | 30 | 50 | 70 | 90 |
| Cocklebur | 70 | 80 | 90 | 100 |
| Corn | 0 | 0 | 20 | 60 |
| Cotton | 30 | 50 | 70 | 90 |
| Crabgrass | 0 | 0 | 30 | 50 |
| Field violet | — | — | — | — |
| Giant foxtail | 0 | 30 | 50 | 80 |
| Green foxtail | 0 | 30 | 50 | 70 |
| Jimsonweed | 0 | 30 | 60 | 90 |
| Johnsongrass | 30 | 50 | 70 | 90 |
| Lambsquarters | 60 | 70 | 80 | 90 |
| Morningglory | 50 | 70 | 90 | 100 |

TABLE B-continued

|  | | | | |
|---|---|---|---|---|
| Nutsedge | 70 | 100 | 100 | 100 |
| Rape | 100 | 100 | 100 | 100 |
| Rice | 30 | 50 | 70 | 90 |
| Sicklepod | 50 | 70 | 100 | 100 |
| Soybean | 80 | 90 | 100 | 100 |
| Sugarbeet | 50 | 70 | 90 | 100 |
| Teaweed | 50 | 60 | 70 | 80 |
| Velvetleaf | 70 | 80 | 100 | 100 |
| Wheat | 0 | 30 | 50 | 70 |
| Wild buckwheat | 30 | 60 | 80 | 90 |
| Wild oat | 0 | 0 | 30 | 60 |

| | Cmpd 65 | | | |
|---|---|---|---|---|
| RATE (g/ha) | 0.25 | 1 | 4 | 16 |
| POSTEMERGENCE | | | | |
| Barley | 30 | 70 | 100 | 100 |
| Barnyardgrass | 60 | 100 | 100 | 100 |
| Blackgrass | 30 | 60 | 80 | 90 |
| Cheatgrass | 70 | 90 | 90 | 100 |
| Chickweed | 50 | 90 | 100 | 100 |
| Cocklebur | 50 | 80 | 100 | 100 |
| Corn | 90 | 100 | 100 | 100 |
| Cotton | 0 | 20 | 30 | 100 |
| Crabgrass | 30 | 60 | 90 | 100 |
| Field violet | — | — | — | — |
| Giant foxtail | 80 | 100 | 100 | 100 |
| Green foxtail | 70 | 100 | 100 | 100 |
| Jimsonweed | 0 | 20 | 80 | 100 |
| Johnsongrass | 60 | 100 | 100 | 100 |
| Lambsquarters | 80 | 100 | 100 | 100 |
| Morningglory | 40 | 90 | 100 | 100 |
| Nutsedge | 30 | 80 | 100 | 100 |
| Rape | 80 | 100 | 100 | 100 |
| Rice | 30 | 100 | 100 | 100 |
| Sicklepod | 50 | 90 | 100 | 100 |
| Soybean | 80 | 100 | 100 | 100 |
| Sugarbeet | 80 | 100 | 100 | 100 |
| Teaweed | 0 | 60 | 100 | 100 |
| Velvetleaf | 60 | 100 | 100 | 100 |
| Wheat | 80 | 90 | 100 | 100 |
| Wild buckwheat | 40 | 80 | 100 | 100 |
| Wild oat | 40 | 90 | 100 | 100 |

| | Cmpd 66 | | | |
|---|---|---|---|---|
| RATE (g/ha) | 0.25 | 1 | 4 | 16 |
| POSTEMERGENCE | | | | |
| Barley | 20 | 40 | 80 | 100 |
| Barnyardgrass | 30 | 80 | 100 | 100 |
| Blackgrass | 20 | 30 | 40 | 90 |
| Cheatgrass | 30 | 60 | 90 | 90 |
| Chickweed | 20 | 50 | 90 | 100 |
| Cocklebur | 0 | 30 | 90 | 100 |
| Corn | 30 | 50 | 90 | 100 |
| Cotton | 0 | 0 | 30 | 40 |
| Crabgrass | 0 | 40 | 60 | 100 |
| Field violet | — | — | — | — |
| Giant foxtail | 30 | 50 | 100 | 100 |
| Green foxtail | 0 | 50 | 90 | 100 |
| Jimsonweed | 0 | 60 | 90 | 100 |
| Johnsongrass | 40 | 60 | 80 | 100 |
| Lambsquarters | 50 | 60 | 90 | 100 |
| Morningglory | 20 | 40 | 90 | 100 |
| Nutsedge | 0 | 20 | 40 | 100 |
| Rape | 30 | 90 | 100 | 100 |
| Rice | 20 | 40 | 90 | 100 |
| Sicklepod | 0 | 30 | 90 | 100 |
| Soybean | 50 | 80 | 100 | 100 |
| Sugarbeet | 30 | 50 | 100 | 100 |
| Teaweed | 0 | 30 | 70 | 90 |
| Velvetleaf | 20 | 70 | 90 | 100 |
| Wheat | 40 | 80 | 90 | 100 |
| Wild buckwheat | 0 | 30 | 50 | 80 |
| Wild oat | 20 | 80 | 90 | 100 |

| | Cmpd 67 | | | |
|---|---|---|---|---|
| RATE (g/ha) | 1 | 4 | 16 | 62 |
| POSTEMERGENCE | | | | |
| Barley | 20 | 40 | 80 | 90 |
| Barnyardgrass | 90 | 100 | 100 | 100 |
| Blackgrass | 40 | 80 | 90 | 90 |
| Cheatgrass | 40 | 80 | 90 | 100 |
| Chickweed | 40 | 60 | 90 | 100 |
| Cocklebur | 40 | 60 | 100 | 100 |
| Corn | 30 | 80 | 100 | 100 |
| Cotton | 0 | 40 | 80 | 100 |
| Crabgrass | 30 | 40 | 80 | 100 |
| Field violet | — | — | — | — |
| Giant foxtail | 0 | 30 | 100 | 100 |
| Green foxtail | 20 | 40 | 70 | 90 |
| Jimsonweed | 70 | 100 | 100 | 100 |
| Johnsongrass | 80 | 100 | 100 | 100 |
| Lambsquarters | 80 | 100 | 100 | 100 |
| Morningglory | 60 | 90 | 100 | 100 |
| Nutsedge | 30 | 80 | 90 | 100 |
| Rape | 80 | 100 | 100 | 100 |
| Rice | 30 | 80 | 100 | 100 |
| Sicklepod | 30 | 100 | 100 | 100 |
| Soybean | 60 | 90 | 100 | 100 |
| Sugarbeet | 80 | 100 | 100 | 100 |
| Teaweed | 30 | 70 | 90 | 100 |
| Velvetleaf | 50 | 80 | 90 | 100 |
| Wheat | 0 | 30 | 40 | 70 |
| Wild buckwheat | 30 | 60 | 80 | 100 |
| Wild oat | 20 | 30 | 80 | 90 |

| | Cmpd 68 | | | |
|---|---|---|---|---|
| RATE (g/ha) | 1 | 4 | 16 | 62 |
| POSTEMERGENCE | | | | |
| Barley | 40 | 90 | 100 | 100 |
| Barnyardgrass | 60 | 100 | 100 | 100 |
| Blackgrass | 30 | 80 | 100 | 100 |
| Cheatgrass | 80 | 90 | 100 | 100 |
| Chickweed | 40 | 70 | 90 | 100 |
| Cocklebur | 40 | 80 | 100 | 100 |
| Corn | 0 | 20 | 90 | 100 |
| Cotton | 0 | 30 | 80 | 100 |
| Crabgrass | 30 | 70 | 90 | 100 |
| Field violet | — | — | — | — |
| Giant foxtail | 30 | 90 | 100 | 100 |
| Green foxtail | 40 | 80 | 100 | 100 |
| Jimsonweed | 70 | 100 | 100 | 100 |
| Johnsongrass | 70 | 90 | 100 | 100 |
| Lambsquarters | 70 | 90 | 100 | 100 |
| Morningglory | 30 | 80 | 100 | 100 |
| Nutsedge | 20 | 70 | 80 | 100 |
| Rape | 40 | 100 | 100 | 100 |
| Rice | 50 | 90 | 100 | 100 |
| Sicklepod | 30 | 90 | 100 | 100 |
| Soybean | 70 | 100 | 100 | 100 |
| Sugarbeet | 40 | 100 | 100 | 100 |
| Teaweed | 20 | 80 | 90 | 90 |
| Velvetleaf | 40 | 90 | 100 | 100 |
| Wheat | 60 | 90 | 100 | 100 |
| Wild buckwheat | 30 | 70 | 90 | 100 |
| Wild oat | 70 | 90 | 100 | 100 |

| | Cmpd 92 | |
|---|---|---|
| RATE (g/ha) | 4 | 16 |
| POSTEMERGENCE | | |
| Barley | 70 | 80 |
| Barnyardgrass | 60 | 90 |
| Blackgrass | 90 | 90 |
| Cheatgrass | 90 | 100 |
| Chickweed | 70 | 90 |
| Cocklebur | 80 | 100 |
| Corn | 0 | 0 |
| Cotton | 90 | 90 |
| Crabgrass | 0 | 60 |
| Field violet | — | — |
| Giant foxtail | 90 | 90 |
| Green foxtail | 70 | 80 |
| Jimsonweed | 50 | 50 |
| Johnsongrass | 100 | 100 |
| Lambsquarters | 80 | 90 |
| Morningglory | 70 | 100 |
| Nutsedge | 0 | 60 |
| Rape | 100 | 100 |
| Rice | 60 | 100 |
| Sicklepod | 90 | 100 |
| Soybean | 70 | 100 |
| Sugarbeet | 100 | 100 |
| Teaweed | 20 | 60 |

TABLE B-continued

|  | 70 | 70 |  |
|---|---|---|---|
| Velvetleaf | 70 | 70 |  |
| Wheat | 90 | 90 |  |
| Wild buckwheat | 70 | 80 |  |
| Wild oat | 60 | 80 |  |

|  | Cmpd 93 | | | |
|---|---|---|---|---|
| RATE (g/ha) | 1 | 4 | 16 | 62 |
| POSTEMERGENCE | | | | |
| Barley | 0 | 0 | 0 | 10 |
| Barnyardgrass | 30 | 40 | 60 | 70 |
| Blackgrass | 50 | 50 | 70 | 80 |
| Cheatgrass | 0 | 0 | 30 | 70 |
| Chickweed | — | — | — | — |
| Cocklebur | 60 | 60 | 70 | 90 |
| Corn | 0 | 0 | 0 | 10 |
| Cotton | — | 40 | 50 | 70 |
| Crabgrass | 0 | 0 | 0 | 20 |
| Field violet | 0 | 0 | 0 | 30 |
| Giant foxtail | — | 0 | 20 | 60 |
| Green foxtail | — | 40 | 50 | 90 |
| Jimsonweed | 60 | 80 | 90 | 100 |
| Johnsongrass | 90 | 90 | 100 | 100 |
| Lambsquarters | — | 50 | 60 | 70 |
| Morningglory | 70 | 70 | 80 | 80 |
| Nutsedge | 0 | 0 | 30 | 40 |
| Rape | 100 | 100 | 100 | 100 |
| Rice | 0 | 0 | 60 | 80 |
| Sicklepod | 0 | 0 | 40 | 70 |
| Soybean | — | 0 | 10 | 50 |
| Sugarbeet | — | 30 | 80 | 100 |
| Teaweed | 0 | 0 | 0 | 50 |
| Velvetleaf | 0 | 0 | 20 | 70 |
| Wheat | 0 | 0 | 10 | 40 |
| Wild buckwheat | 0 | 0 | 30 | 30 |
| Wild oat | 0 | 0 | 0 | 50 |

|  | Cmpd 96 | | | |
|---|---|---|---|---|
| RATE (g/ha) | 0.25 | 1 | 4 | 16 |
| POSTEMERGENCE | | | | |
| Barley | 0 | 20 | 40 | 90 |
| Barnyardgrass | 30 | 40 | 90 | 100 |
| Blackgrass | 0 | 0 | 70 | 80 |
| Cheatgrass | 0 | 0 | 70 | 70 |
| Chickweed | 0 | 0 | 40 | 60 |
| Cocklebur | 0 | 0 | 30 | 70 |
| Corn | 0 | 0 | 20 | 80 |
| Cotton | 0 | 0 | 0 | 20 |
| Crabgrass | 0 | 0 | 40 | 80 |
| Field violet | — | — | — | — |
| Giant foxtail | 0 | — | 40 | 100 |
| Green foxtail | 0 | 40 | 70 | 90 |
| Jimsonweed | 0 | 30 | 50 | 60 |
| Johnsongrass | 0 | 70 | 90 | 100 |
| Lambsquarters | 0 | 0 | 0 | 40 |
| Morningglory | 0 | 0 | 30 | 60 |
| Nutsedge | 0 | 20 | 30 | 60 |
| Rape | 20 | 30 | 90 | 100 |
| Rice | 0 | 0 | 50 | 90 |
| Sicklepod | 0 | 0 | 40 | 80 |
| Soybean | 30 | 40 | 90 | 90 |
| Sugarbeet | 0 | 20 | 30 | 60 |
| Teaweed | 0 | 0 | 20 | 70 |
| Velvetleaf | 0 | 0 | 20 | 60 |
| Wheat | 20 | 40 | 50 | 60 |
| Wild buckwheat | 0 | 0 | — | 80 |
| Wild oat | 0 | 30 | 50 | 70 |

|  | Cmpd 100 | | | |
|---|---|---|---|---|
| RATE (g/ha) | 1 | 4 | 16 | 62 |
| POSTEMERGENCE | | | | |
| Barley | 50 | 70 | 100 | 100 |
| Barnyardgrass | 30 | 40 | 80 | 100 |
| Blackgrass | 70 | 90 | 100 | 100 |
| Cheatgrass | 70 | 80 | 100 | 100 |
| Chickweed | 50 | 70 | 90 | 100 |
| Cocklebur | 70 | 100 | 100 | 100 |
| Corn | — | 0 | 20 | 40 |
| Cotton | 50 | 80 | 90 | 90 |
| Crabgrass | 0 | 0 | 50 | 60 |
| Field violet | — | — | — | — |
| Giant foxtail | 40 | 50 | 90 | 100 |
| Green foxtail | 30 | 50 | 80 | 90 |
| Jimsonweed | 0 | 0 | 20 | 40 |
| Johnsongrass | 70 | 100 | 100 | 100 |
| Lambsquarters | 50 | 70 | 100 | 100 |
| Morningglory | 60 | 90 | 100 | 100 |
| Nutsedge | 0 | 30 | 60 | 100 |
| Rape | 100 | 100 | 100 | 100 |
| Rice | 50 | 90 | 100 | 100 |
| Sicklepod | 50 | 70 | 100 | 100 |
| Soybean | 80 | 80 | 100 | 100 |
| Sugarbeet | 90 | 100 | 100 | 100 |
| Teaweed | 0 | 30 | 50 | 70 |
| Velvetleaf | 30 | 80 | 90 | 100 |
| Wheat | 50 | 70 | 100 | 100 |
| Wild buckwheat | 30 | 60 | 90 | 100 |
| Wild oat | 40 | 70 | 100 | 100 |

|  | Cmpd 106 | | | |
|---|---|---|---|---|
| RATE (g/ha) | 1 | 4 | 16 | 62 |
| POSTEMERGENCE | | | | |
| Barley | 0 | 30 | 50 | 90 |
| Barnyardgrass | 30 | 60 | 90 | 100 |
| Blackgrass | 50 | 70 | 90 | 90 |
| Cheatgrass | 0 | 30 | 70 | 90 |
| Chickweed | 0 | 0 | 30 | 70 |
| Cocklebur | 0 | 50 | 70 | 100 |
| Corn | 0 | 0 | 0 | 20 |
| Cotton | 0 | 0 | 10 | 20 |
| Crabgrass | 0 | 0 | 0 | 0 |
| Field violet | — | — | — | — |
| Giant foxtail | 0 | 20 | 40 | 90 |
| Green foxtail | 20 | 40 | 80 | 90 |
| Jimsonweed | 0 | 0 | 20 | 40 |
| Johnsongrass | 50 | 50 | 70 | 90 |
| Lambsquarters | 40 | 60 | 80 | 90 |
| Morningglory | 0 | 50 | 90 | 90 |
| Nutsedge | 0 | 0 | 20 | 30 |
| Rape | 70 | 100 | 100 | 100 |
| Rice | 0 | 30 | 70 | 100 |
| Sicklepod | — | 20 | — | 50 |
| Soybean | 0 | 40 | 50 | 90 |
| Sugarbeet | 40 | 70 | 80 | 90 |
| Teaweed | 0 | 0 | 20 | 30 |
| Velvetleaf | 0 | 30 | 70 | 90 |
| Wheat | 0 | 40 | 80 | 100 |
| Wild buckwheat | 0 | 0 | 50 | 70 |
| Wild oat | 0 | 60 | 90 | 100 |

Test C

Postemergence

Six round pots (17 cm diameter by 15 cm deep) were used to grow plants to the treatment stage. Four were planted with seeds or tubers of four species each and another with soybeans using Sassafras sandy loam as the growing media. The sixth pot was planted to corn using a Tama silt loam. During spraying, the soil of this pot was temporarily covered with perlite then later removed so any effects noted would be from foliar uptake only. A separate pot of corn (25.5 cm diameter by 19.5 cm deep) grown in Sassafras sandy loam was also included to determine foliar/soil treatment effects on plant growth. Plants were grown 10 to 20 days and were in the 2 to 5 leaf stage when sprayed postemergence with compounds of the invention. Species included were as follows: G4646 corn [maize] (*Zea mays*, variety Funk G4646), Williams soybeans (*Glycine max*, variety Williams), green foxtail (*Setaria viridis*), giant foxtail (*Setaria faberi*), fall panicum (*Panicum dichotomiflorum*), crabgrass (*Digitaria sanguinalis*), barnyardgrass (*Echinochloa crus-galli*), johnsongrass (*Sorghum halepense*), G522 sorghum (*Sorghum vulgare*, variety Funk G522), nutsedge (*Cyperus rotundus*), velvetleaf (*Abutlion theophrasti*), cocklebur (*Xanthium pensylvanicum*), smartweed (*Polygonum persicaria*, lambsquarter (*Chenopodium album*), pigweed (*Amaranthus retroflexus*), ivyleaf morningglory (*Ipomoea hederacea*), jimsonweed (*Datura stramonium*), ragweed (*Ambrosia artemisiifolia*).

Preemergence

Plantings were made as above except all in Tama silt loam. Compounds were sprayed preemergence the day after planting. All pots were then watered to simulate rainfall.

After treatment, all plantings were maintained in a greenhouse about 20 days and then visually rated for plant response. Ratings are based on a scale of 0 to 100 where 0=no effect and 100=complete control. Response ratings are shown in Table C.

TABLE C

| CMPD 1 | | | | | | |
|---|---|---|---|---|---|---|
| RATE GM/HA | 0004 | 0008 | 0016 | 0032 | 0064 | 0125 |
| POST | | | | | | |
| SOIL TYPE | SAS | SAS | SAS | SAS | SAS | SAS |
| G4646 CORN | 0 | 0 | 0 | 0 | 25 | 40 |
| WILLMS SOYBEANS | 0 | 20 | 35 | 50 | 65 | 85 |
| GREEN FOXTAIL | 50 | 65 | 80 | 90 | 95 | 100 |
| GIANT FOXTAIL | 40 | 65 | 70 | 90 | 95 | 100 |
| FALL PANICUM | 70 | 90 | 95 | 100 | 100 | 100 |
| LARGE CRABGRASS | 0 | 0 | 0 | 30 | 70 | 80 |
| BARNYARD-GRASS | 90 | 100 | 100 | 100 | 100 | 100 |
| JOHNSONGRASS | 100 | 100 | 100 | 100 | 100 | 100 |
| G522 SORGHUM | 100 | 100 | 100 | 100 | 100 | 100 |
| PURPLE NUTSEDGE | 30 | 50 | 75 | 90 | 100 | 100 |
| VELVETLEAF | 20 | 45 | 75 | 85 | 95 | 100 |
| COCKLEBUR | 50 | 85 | 100 | 100 | 100 | 100 |
| LADY SMARTWEED | 0 | 0 | 0 | 25 | 50 | 70 |
| LAMBSQUARTER | 0 | 0 | 0 | 0 | 35 | 50 |
| REDROOT PIGWEED | 70 | 85 | 100 | 100 | 100 | 100 |
| IVY MORNINGLORY | 50 | 85 | 100 | 100 | 100 | 100 |
| JIMSONWEED | 0 | 0 | 0 | 0 | 0 | 35 |
| PERLITE CORN | 0 | 0 | 0 | 0 | 20 | 30 |

| CMPD 21 | | | | | | | |
|---|---|---|---|---|---|---|---|
| RATE GM/HA | 0002 | 0004 | 0008 | 0016 | 0032 | 0064 | 0125 |
| POST | | | | | | | |
| SOIL TYPE | SAS | SAS | SAS | SAS | SAS | SAS | SAS |
| G4646 CORN | 0 | 0 | 0 | 0 | 10 | 20 | 70 |
| WILLMS SOYBEANS | 95 | 98 | 100 | 100 | 100 | 100 | 100 |
| GREEN FOXTAIL | 80 | 90 | 90 | 100 | 100 | 100 | 100 |
| GIANT FOXTAIL | 70 | 90 | 90 | 95 | 100 | 100 | 100 |
| FALL PANICUM | 80 | 95 | 98 | 100 | 100 | 100 | 100 |
| LARGE CRABGRASS | 0 | 0 | 0 | 30 | 40 | 60 | 70 |
| BARNYARD-GRASS | 100 | 100 | 100 | 100 | 100 | 100 | 100 |
| JOHNSONGRASS | 100 | 100 | 100 | 100 | 100 | 100 | 100 |
| G522 SORGHUM | 100 | 100 | 100 | 100 | 100 | 100 | 100 |
| VELVETLEAF | 40 | 60 | 60 | 60 | 90 | 100 | 100 |
| COCKLEBUR | 40 | 40 | 40 | 90 | 100 | 100 | 100 |
| LADY SMARTWEED | 0 | 0 | 0 | 30 | 50 | 80 | 80 |
| LAMBSQUARTER | 30 | 30 | 30 | 60 | 40 | 50 | 70 |
| REDROOT PIGWEED | 90 | 100 | 100 | 100 | 100 | 100 | 100 |
| IVY MORNINGLORY | 0 | 0 | 0 | 20 | 30 | 40 | 70 |
| JIMSONWEED | 0 | 20 | 20 | 30 | 40 | 40 | 50 |
| PERLITE CORN | 0 | 0 | 0 | 10 | 10 | 20 | 60 |

| CMPD 46 | | | | | | | |
|---|---|---|---|---|---|---|---|
| RATE GM/HA | 0002 | 0004 | 0008 | 0016 | 0032 | 0064 | 0125 |

TABLE C-continued

| POST | | | | | | | |
|---|---|---|---|---|---|---|---|
| SOIL TYPE | SAS | SAS | SAS | SAS | SAS | SAS | SAS |
| G4646 CORN | 0 | 0 | 0 | 0 | 0 | 0 | 30 |
| WILLMS SOYBEANS | 25 | 45 | 75 | 90 | 100 | 100 | 100 |
| GREEN FOXTAIL | 0 | 30 | 60 | 75 | 85 | 90 | 100 |
| GIANT FOXTAIL | 0 | 30 | 60 | 75 | 85 | 90 | 100 |
| TALL PANICUM | 0 | 35 | 70 | 90 | 100 | 100 | 100 |
| LARGE CRABGRASS | 0 | 0 | 0 | 0 | 25 | 35 | 45 |
| BARNYARD-GRASS | 45 | 90 | 100 | 100 | 100 | 100 | 100 |
| JOHNSONGRASS | 60 | 80 | 95 | 100 | 100 | 100 | 100 |
| G522 SORGHUM | 75 | 90 | 100 | 100 | 100 | 100 | 100 |
| PURPLE NUTSEDGE | 0 | 35 | 45 | 60 | 80 | 95 | 100 |
| VELVETLEAF | 0 | 0 | 35 | 70 | 70 | 85 | 95 |
| COCKLEBUR | 0 | 30 | 40 | 60 | 75 | 95 | 95 |
| LADY SMARTWEED | 0 | 30 | 75 | 85 | 95 | 100 | 100 |
| LAMBSQUARTER | 0 | 0 | 0 | 30 | 40 | 55 | 65 |
| REDROOT PIGWEED | 35 | 70 | 100 | 100 | 100 | 100 | 100 |
| IVY MORNINGLORY | 0 | 0 | 20 | 40 | 60 | 70 | 80 |
| JIMSONWEED | 0 | 0 | 0 | 0 | 25 | 40 | 60 |
| PERLITE CORN | 0 | 0 | 0 | 0 | 0 | 0 | 25 |

| CMPD 60 | | | | | | | |
|---|---|---|---|---|---|---|---|
| RATE GM/HA | 0002 | 0004 | 0008 | 0016 | 0032 | 0064 | 0125 |
| POST | | | | | | | |
| SOIL TYPE | SAS | SAS | SAS | SAS | SAS | SAS | SAS |
| G4646 CORN | 0 | 0 | 0 | 0 | 30 | 60 | 85 |
| WILLMS SOYBEANS | 100 | 100 | 100 | 100 | 100 | 100 | 100 |
| GREEN FOXTAIL | 20 | 35 | 45 | 65 | 75 | 85 | 95 |
| GIANT FOXTAIL | 0 | 25 | 40 | 60 | 75 | 90 | 100 |
| TALL PANICUM | 60 | 75 | 90 | 95 | 100 | 100 | 100 |
| LARGE CRABGRASS | 0 | 0 | 0 | 30 | 40 | 60 | 80 |
| BARNYARD-GRASS | 80 | 95 | 100 | 100 | 100 | 100 | 100 |
| JOHNSONGRASS | 95 | 100 | 100 | 100 | 100 | 100 | 100 |
| G522 SORGHUM | 100 | 100 | 100 | 100 | 100 | 100 | 100 |
| PURPLE NUTSEDGE | 30 | 50 | 65 | 75 | 100 | 100 | 100 |
| VELVETLEAF | 20 | 35 | 55 | 85 | 100 | 100 | 100 |
| COCKLEBUR | 35 | 40 | 60 | 70 | 85 | 100 | 100 |
| LADY SMARTWEED | 20 | 30 | 40 | 60 | 80 | 100 | 100 |
| LAMBSQUARTER | 0 | 0 | 0 | 35 | 60 | 90 | 95 |
| REDROOT PIGWEED | 60 | 75 | 100 | 100 | 100 | 100 | 100 |
| IVY MORNINGLORY | 0 | 0 | 20 | 40 | 65 | 80 | 95 |
| JIMSONWEED | 0 | 0 | 0 | 20 | 40 | 65 | 85 |
| PERLITE CORN | 0 | 0 | 0 | 0 | 25 | 50 | 70 |

| CMPD 160 | | | | |
|---|---|---|---|---|
| RATE GM/HA | 0016 | 0032 | 0064 | 0125 |
| PRE | | | | |
| SOIL TYPE | TAM | TAM | TAM | TAM |
| G4646 CORN | 0 | 0 | 0 | 0 |
| WILLMS SOYBEANS | 30 | 40 | 60 | 85 |
| GREEN FOXTAIL | 20 | 25 | 35 | 60 |
| GIANT FOXTAIL | 20 | 20 | 30 | 40 |
| FALL PANICUM | 70 | 80 | 95 | 100 |
| LARGE CRABGRASS | 0 | 0 | 20 | — |
| BARNYARD-GRASS | 65 | 70 | 90 | 100 |
| JOHNSONGRASS | 70 | 90 | 100 | 100 |
| G522 SORGHUM | 75 | 100 | 100 | 100 |
| PURPLE NUTSEDGE | 35 | 60 | 80 | — |
| VELVETLEAF | 0 | 0 | 0 | — |
| COCKLEBUR | 0 | 0 | 0 | — |

TABLE C-continued

| | | | | |
|---|---|---|---|---|
| LADY SMARTWEED | 50 | 65 | 95 | — |
| LAMBSQUARTER | 25 | 40 | 60 | — |
| REDROOT PIGWEED | 50 | 60 | 90 | — |
| IVY MORNINGLORY | 0 | 0 | 0 | — |
| JIMSONWEED | 0 | 0 | 0 | — |

CMPD 92

| RATE GM/HA | 0016 | 0032 | 0064 | 0125 |
|---|---|---|---|---|
| PRE | | | | |
| SOIL TYPE | TAM | TAM | TAM | TAM |
| G4646 CORN | 0 | 0 | 0 | 0 |
| WILLMS SOYBEANS | 0 | 25 | 50 | 80 |
| GREEN FOXTAIL | 0 | 35 | 70 | 100 |
| GIANT FOXTAIL | 0 | 30 | 70 | 95 |
| TALL PANICUM | 20 | 45 | 85 | 95 |
| LARGE CRABGRASS | 0 | 20 | 40 | 70 |
| BARNYARD-GRASS | 25 | 45 | 85 | 100 |
| JOHNSONGRASS | 50 | 65 | 100 | 100 |
| G522 SORGHUM | 45 | 55 | 90 | 100 |
| PURPLE NUTSEDGE | 0 | 25 | 65 | 80 |
| VELVETLEAF | 0 | 0 | 0 | 30 |
| COCKLEBUR | 0 | 0 | 0 | 20 |
| LADY SMARTWEED | 30 | 60 | 95 | 100 |
| LAMBSQUARTER | 20 | 40 | 90 | 100 |
| REDROOT PIGWEED | 50 | 70 | 100 | 100 |
| IVY MORNINGLORY | 0 | 0 | 0 | 25 |
| JIMSONWEED | 0 | 0 | 0 | 35 |

CMPD 92

| RATE GM/HA | 0002 | 0004 | 0008 | 0016 | 0032 | 0064 | 0125 |
|---|---|---|---|---|---|---|---|
| POST | | | | | | | |
| SOIL TYPE | SAS | SAS | SAS | SAS | SAS | SAS | SAS |
| G4646 CORN | 0 | 0 | 0 | 0 | 20 | 35 | 60 |
| WILLMS SOYBEANS | 65 | 85 | 100 | 100 | 100 | 100 | 100 |
| GREEN FOXTAIL | 40 | 60 | 80 | 90 | 95 | 100 | 100 |
| GIANT FOXTAIL | 40 | 65 | 80 | 100 | 100 | 100 | 100 |
| TALL PANICUM | 0 | 40 | 80 | 95 | 100 | 100 | 100 |
| LARGE CRABGRASS | 0 | 0 | 0 | 25 | 40 | 50 | 80 |
| BARNYARD-GRASS | 0 | 30 | 50 | 70 | 100 | 100 | 100 |
| JOHNSONGRASS | 80 | 95 | 100 | 100 | 100 | 100 | 100 |
| G522 SORGHUM | 85 | 95 | 100 | 100 | 100 | 100 | 100 |
| PURPLE NUTSEDGE | 0 | 35 | 60 | 90 | 100 | 100 | 100 |
| VELVETLEAF | 0 | 25 | 40 | 65 | 85 | 95 | 100 |
| COCKLEBUR | 35 | 50 | 90 | 100 | 100 | 100 | 100 |
| LADY SMARTWEED | 25 | 40 | 50 | 60 | 70 | 85 | 95 |
| LAMBSQUARTER | 40 | 65 | 85 | 95 | 100 | 100 | 100 |
| REDROOT PIGWEED | 75 | 95 | 100 | 100 | 100 | 100 | 100 |
| IVY MORNINGLORY | 0 | 30 | 55 | 70 | 85 | 95 | 100 |
| JIMSONWEED | 0 | 0 | 20 | 40 | 60 | 70 | 85 |
| PERLITE CORN | 0 | 0 | 0 | 0 | 0 | 20 | 40 |

CMPD 96

| RATE GM/HA | 0016 | 0032 | 0064 | 0125 | 0250 |
|---|---|---|---|---|---|
| PRE | | | | | |
| SOIL TYPE | TAM | TAM | TAM | TAM | TAM |
| G4646 CORN | 0 | 0 | 0 | 0 | 0 |
| WILLMS SOYBEANS | 0 | 0 | 0 | 20 | 45 |
| GREEN FOXTAIL | 0 | 15 | 20 | 35 | 50 |
| GIANT FOXTAIL | 0 | 15 | 20 | 35 | 50 |
| TALL PANICUM | 0 | 0 | 0 | 0 | 15 |
| LARGE CRABGRASS | 0 | 0 | 0 | 0 | 15 |
| BARNYARD-GRASS | 0 | 15 | 30 | 70 | 85 |
| JOHNSONGRASS | 0 | 20 | 45 | 55 | 75 |
| G522 SORGHUM | 20 | 35 | 55 | 75 | 95 |
| PURPLE NUTSEDGE | 0 | 0 | 0 | 0 | 0 |
| VELVETLEAF | 0 | 0 | 20 | 30 | 40 |
| COCKLEBUR | 0 | 10 | 20 | 35 | 50 |
| LADY SMARTWEED | 15 | 35 | 50 | 60 | 75 |
| LAMBSQUARTER | 0 | 0 | 0 | 15 | 25 |
| REDROOT PIGWEED | 0 | 25 | 45 | 65 | 85 |
| IVY MORNINGLORY | 0 | 0 | 0 | 0 | 0 |
| JIMSONWEED | 0 | 0 | 0 | 15 | 20 |

CMPD 96

| RATE GM/HA | 0002 | 0004 | 0008 | 0016 | 0032 | 0064 |
|---|---|---|---|---|---|---|
| POST | | | | | | |
| SOIL TYPE | SAS | SAS | SAS | SAS | SAS | SAS |
| G4646 CORN | 0 | 20 | 50 | 60 | 80 | 90 |
| WILLMS SOYBEANS | 90 | 90 | 98 | 98 | 100 | 100 |
| GREEN FOXTAIL | 50 | 60 | 70 | 70 | 90 | 98 |
| GIANT FOXTAIL | 40 | 50 | 60 | 70 | 98 | 100 |
| LARGE CRABGRASS | 0 | 0 | 0 | 20 | 40 | 50 |
| BARNYARD-GRASS | 70 | 98 | 100 | 100 | 100 | 100 |
| JOHNSONGRASS | 60 | 98 | 100 | 100 | 100 | 100 |
| G522 SORGHUM | 80 | 90 | 98 | 100 | 100 | 100 |
| PURPLE NUTSEDGE | 0 | 0 | 0 | 0 | 30 | 70 |
| VELVETLEAF | 0 | 0 | 30 | 50 | 60 | 90 |
| COCKLEBUR | 30 | 70 | 80 | 90 | 100 | 100 |
| LADY SMARTWEED | 20 | 30 | 30 | 50 | 70 | 98 |
| LAMBSQUARTER | 0 | 0 | 30 | 30 | 30 | 30 |
| REDROOT PIGWEED | 0 | 0 | 40 | 40 | 80 | 90 |
| IVY MORNINGLORY | 0 | 30 | 30 | 30 | 40 | 50 |
| JIMSONWEED | 40 | 60 | 60 | 60 | 100 | 100 |
| PERLITE CORN | 20 | 20 | 30 | 60 | 60 | 90 |

CMPD 100

| RATE GM/HA | 0016 | 0032 | 0064 | 0125 | 0250 |
|---|---|---|---|---|---|
| PRE | | | | | |
| SOIL TYPE | TAM | TAM | TAM | TAM | TAM |
| G4646 CORN | 0 | 0 | 0 | 0 | 20 |
| WILLMS SOYBEANS | 0 | 25 | 40 | 70 | 80 |
| GREEN FOXTAIL | 25 | 45 | 85 | 95 | 100 |
| GIANT FOXTAIL | 0 | 35 | 70 | 95 | 100 |
| TALL PANICUM | 40 | 85 | 100 | 100 | 100 |
| LARGE CRABGRASS | 0 | 20 | 35 | 50 | 65 |
| BARNYARD-GRASS | 35 | 60 | 100 | 100 | 100 |
| JOHNSONGRASS | 70 | 90 | 100 | 100 | 100 |
| G522 SORGHUM | 75 | 95 | 100 | 100 | 100 |
| PURPLE NUTSEDGE | 30 | 50 | 70 | 90 | 100 |
| VELVETLEAF | 0 | 0 | 0 | 0 | 25 |
| COCKLEBUR | 0 | 0 | 20 | 35 | 50 |
| LADY SMARTWEED | 40 | 70 | 95 | 100 | 100 |
| LAMBSQUARTER | 25 | 40 | 65 | 95 | 100 |
| REDROOT PIGWEED | 30 | 65 | 90 | 100 | 100 |
| IVY MORNINGLORY | 0 | 0 | 0 | 0 | 35 |
| JIMSONWEED | 0 | 0 | 30 | 45 | 70 |

CMPD 100

| RATE GM/HA | 0002 | 0004 | 0008 | 0016 | 0032 | 0064 | 0125 |
|---|---|---|---|---|---|---|---|

TABLE C-continued

| POST SOIL TYPE | SAS | SAS | SAS | SAS | SAS | SAS | SAS |
|---|---|---|---|---|---|---|---|
| G4646 CORN | 0 | 0 | 0 | 0 | 0 | 0 | 30 |
| WILLMS SOYBEANS | 65 | 75 | 90 | 100 | 100 | 100 | 100 |
| GREEN FOXTAIL | 50 | 65 | 80 | 95 | 100 | 100 | 100 |
| GIANT FOXTAIL | 45 | 60 | 80 | 90 | 95 | 100 | 100 |
| FALL PANICUM | 50 | 65 | 80 | 95 | 95 | 100 | 100 |
| LARGE CRABGRASS | 0 | 0 | 0 | 30 | 40 | 50 | 80 |
| BARNYARD-GRASS | 50 | 60 | 70 | 80 | 100 | 100 | 100 |
| JOHNSONGRASS | 95 | 100 | 100 | 100 | 100 | 100 | 100 |
| G522 SORGHUM | 100 | 100 | 100 | 100 | 100 | 100 | 100 |
| PURPLE NUTSEDGE | 0 | 20 | 40 | 65 | 85 | 90 | 95 |
| VELVETLEAF | 0 | 40 | 70 | 80 | 90 | 100 | 100 |
| COCKLEBUR | 45 | 95 | 100 | 100 | 100 | 100 | 100 |
| LADY SMARTWEED | 0 | 20 | 45 | 60 | 70 | 95 | 100 |
| LAMBSQUARTER | 30 | 40 | 60 | 80 | 90 | 100 | 100 |
| REDROOT PIGWEED | 65 | 90 | 100 | 100 | 100 | 100 | 100 |
| IVY MORNINGLORY | 30 | 70 | 85 | 100 | 100 | 100 | 100 |
| JIMSONWEED | 0 | 0 | 0 | 0 | 25 | 45 | 70 |
| PERLITE CORN | 0 | 0 | 0 | 0 | 0 | 0 | 20 |

Test D

Potatoes (*Solanum tuberosum*, cult. 'Green Mountain') were grown in Metro 350 medium in 20 cm plastic pots. Potatoes were 17 days old at time of spraying. Barnyardgrass (*Echinochloa crus-galli*), johnsongrass (*Sorghum halepense*), giant foxtail (*Setaria faberii*), crabgrass (*Digitaria sanguinalis*), purple nutsedge (*Cyperus rotundus*), jimsonweed (*Datura stramonium*), velvetleaf (*Abutilon theophrasti*), cocklebur (*Xanthium pensylvanicum*), and morningglory (*Ipomoea hederacea*) were grown in Sassafras sandy loam (pH 6.5, 1% organic matter) in plastic-lined 25 cm pots. These plants were 9 days old at the time of spraying.

Compound 21 was sprayed at 62, 16, 4, and 1 g/ha. The compound was sprayed at each rate on one pot containing potato plants and at the same time on one pot containing the remaining species. Compound 21 was dissolved in a non-phytotoxic solvent. The solvent was sprayed at 374 1/ha. Plants were maintained in a greenhouse and were evaluated 11 days after spraying.

All sprayed plants were evaluated for injury as compared to control plants. Injury was measured visually using a 0 to 100% scale where 0=no effect and 100=complete control. Results are shown in Table D.

TABLE D

| | Compound 21 | | | |
|---|---|---|---|---|
| | Rate (g/ha) | | | |
| Species | 62 | 16 | 4 | 1 |
| Potato | 0 | 0 | 0 | 0 |
| Barnyardgrass | 100 | 100 | 70 | 30 |
| Johnsongrass | 100 | 100 | 100 | 60 |
| Giant foxtail | 100 | 100 | 90 | 60 |
| Crabgrass | 90 | 85 | 60 | 50 |
| Purple nutsedge | 90 | 90 | 80 | 30 |
| Jimsonweed | 80 | 60 | 40 | 20 |
| Velvetleaf | 100 | 95 | 50 | 20 |
| Cocklebur | 90 | 50 | 30 | 0 |
| Morningglory | 90 | 70 | 40 | 20 |

Test E

Tomatoes (*Lycopersicon esculentum* cult. 'Rutgers') and peppers (*Capsicum frutescens* cult. 'Yolo') were grown in Metro 350 medium in 10 cm plastic pots. Tomatoes and peppers were 19 days old at time of spraying. Purple nutsedge (*Cyperus rotundus*), crabgrass (*Digitaria sanguinalis*), sicklepod (*Cassia tora*), prickley sida (*Sida spinosa*), jimsonweed (*Datura stramonium*), velvetleaf (*Abutilon theophrasti*), lambsquarter (*Chenopodium album*), green foxtail (*Setaria viridis*), cocklebur (*Xanthium pensylvanicum*), morningglory (*Ipomoea hederacea*), johnsongrass (*Sorghum halepense*), barnyardgrass (*Echinochloa crus-galli*), giant foxtail (*Setaria faberii*), wild buckwheat (*Polygonum convolvulus*), downy brome (*Bromus tectorum*), wild oat (*Avena fatua*), chickweed (Stellaria spp.), and blackgrass (*Alopecurus myosuroides*), were grown in Sassafras sandy loam (pH 6.5, 1% organic matter) in plastic-lined 25 cm pots. These plants were 7 to 11 days old at the time of spraying.

Compound 21 was sprayed at 62, 16, 4, and 1 g/ha. The compound was sprayed at each rate on one pot containing tomatoes, one pot containing peppers, and on three pots containing the remaining species. The compound was dissolved in a non-phytotoxic solvent, and the solvent was sprayed at 374 1/ha. Plants were maintained in a greenhouse and were evaluated 16 days after spraying.

All sprayed plants were evaluated for injury as compared to control plants. Injury was measured visually using a 0 to 100% scale where 0=no effect and 100=complete control. Results are shown in Table E.

TABLE E

| | Compound 20 | | | |
|---|---|---|---|---|
| | Rage (g/ha) | | | |
| Species | 62 | 16 | 4 | 1 |
| Tomatoes | 10 | 0 | 0 | 0 |
| Peppers | 80 | 70 | 50 | 30 |
| Nutsedge | 100 | 100 | 30 | 0 |
| Crabgrass | 90 | 80 | 50 | 30 |
| Sicklepod | 100 | 100 | 90 | 40 |
| Prickley sida | 100 | 100 | 50 | 20 |
| Jimsonweed | 100 | 50 | 10 | 0 |
| Velvetleaf | 100 | 100 | 70 | 50 |
| Lambsquarter | 60 | 50 | 40 | 0 |
| Green foxtail | 100 | 100 | 100 | 50 |
| Cocklebur | 100 | 80 | 50 | 20 |
| Morningglory | 90 | 85 | 50 | 20 |
| Johnsongrass | 100 | 100 | 100 | 50 |
| Barnyardgrass | 100 | 100 | 100 | 40 |
| Giant foxtail | 100 | 100 | 90 | 40 |
| Wild buckwheat | 100 | 90 | 90 | 40 |
| Downy brome | 100 | 100 | 80 | 20 |
| Wild oats | 100 | 70 | 30 | 20 |
| Chickweed | 100 | 100 | 90 | 90 |
| Blackgrass | 100 | 100 | 100 | 70 |

What is claimed is:

1. A compound selected from

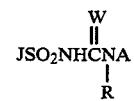

wherein
J is

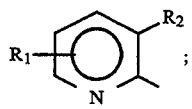 J-1

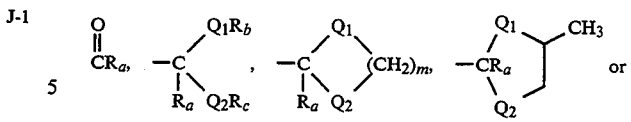

R is H or CH$_3$;
W is O or S;
R$_1$ is R$_f$ or R$_g$;
R$_f$ is H, C$_1$-C$_3$ alkyl, C$_1$-C$_3$ haloalkyl, halogen, NO$_2$, C$_1$-C$_3$ alkoxy, C$_1$-C$_3$ alkylthio or CN;
R$_g$ is C$_1$-C$_3$ haloalkyl, cyclopropyl, C$_1$-C$_3$ alkyl substituted by C$_1$-C$_3$ alkoxy, OH, C$_1$-C$_2$ alkylthio or CN, CN, W$_2$R$_{11}$, amino, C$_1$-C$_3$ alkylamino or C$_1$-C$_3$ dialkylamino;
R$_2$ is C$_1$-C$_4$ alkylsulfinyl, C$_1$-C$_4$ alkylsulfonyl, C$_3$-C$_5$ cycloalkylthio, C$_3$-C$_5$ cycloalkylsulfinyl, C$_3$-C$_5$ cycloalkylsulfonyl, SO$_2$NH$_2$, SO$_2$NR$_d$R$_e$, SO$_2$NR'$_7$R$_8$, SO$_2$NR$_7$R$_8$, OSO$_2$R$_8$, SO$_2$OR$_8$, N$_3$, P(W$_1$)(OC$_1$-C$_2$ alkyl)$_2$, CN, CO$_2$R$_9$, CO$_2$R'$_9$, CH$_2$F, CF$_2$H, CH$_2$Cl, CCl$_2$H or C$_2$-C$_4$ haloalkyl;
R$_7$ is H, C$_2$-C$_3$ cyanoalkyl, C$_3$-C$_4$ alkenyl or C$_3$-C$_4$ alkynyl;
R'$_7$ is C$_1$-C$_4$ alkyl;
R$_8$ is C$_1$-C$_4$ alkyl, C$_1$-C$_4$ haloalkyl, C$_3$-C$_4$ alkenyl, C$_3$-C$_4$ alkynyl, C$_2$-C$_4$ alkoxyalkyl or cyclopropyl; or
R$_7$ and R$_8$ may be taken together as —(CH$_2$)$_3$—, —(CH$_2$)$_4$—, —(CH$_2$)$_5$— or —CH$_2$CH$_2$OCH$_2$CH$_2$—;
R$_9$ is CH$_2$CH$_2$R$_{10}$, CH$_2$CF$_3$, C$_3$-C$_4$ haloalkyl, C$_3$-C$_4$ alknyl, C$_2$-C$_4$ alkylthioalkyl, C$_3$-C$_5$ cycloalkyl or C$_4$-C$_7$ cycloalkylalkyl;
R'$_9$ is C$_1$-C$_4$ alkyl, C$_3$-C$_4$ alkenyl, CH$_2$CH$_2$Cl, CH$_2$CH$_2$Br, CH$_2$CH$_2$OCH$_3$ or CH$_2$CH$_2$OC$_2$H$_5$;
R$_{10}$ is OH, F, CN, OSO$_2$(C$_1$-C$_3$ alkyl) or OSO$_2$(C$_1$-C$_3$ haloalkyl);
R$_{11}$ is C$_1$-C$_3$ alkyl, C$_1$-C$_3$ haloalkyl, C$_3$-C$_4$ alkenyl or C$_3$-C$_4$ alkynyl;
W$_1$ is O or S;
W$_2$ is O or S;
A is

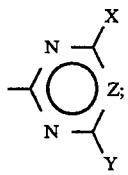 A-1

X is H, C$_1$-C$_4$ alkyl, C$_1$-C$_4$ alkoxy, C$_2$-C$_4$ haloalkoxy, C$_1$-C$_4$ haloalkyl, C$_2$-C$_4$ haloalkylthio, C$_1$-C$_4$ alkylthio, halogen, C$_2$-C$_5$ alkoxyalkyl, C$_2$-C$_5$ alkoxyalkoxy, amino, C$_1$-C$_3$ alkylamino or di(C$_1$-C$_3$ alkyl)amino;
Y is H, C$_1$-C$_4$ alkyl, C$_1$-C$_4$ alkoxy, C$_2$-C$_4$ haloalkoxy, C$_2$-C$_4$ haloalkylthio, C$_1$-C$_4$ alkylthio, C$_2$-C$_5$ alkoxyalkyl, C$_2$-C$_5$ alkoxyalkoxy, amino, C$_1$-C$_3$ alkylamino, di(C$_1$-C$_3$ alkyl)amino, C$_3$-C$_4$ alkenyloxy, C$_3$-C$_4$ alkynyloxy, C$_2$-C$_5$ alkylthioalkyl, C$_2$-C$_5$ alkylsulfinylalkyl, C$_2$-C$_5$ alkylsulfonylalkyl, C$_1$-C$_4$ haloalkyl, C$_2$-C$_4$ alkynyl, C$_3$-C$_5$ cycloalkyl, azido, N(OCH$_3$)CH$_3$;
m is 2 or 3;
Q$_1$ and Q$_2$ are independently O or S;
R$_a$ is H or C$_1$-C$_3$ alkyl;
R$_b$ and R$_c$ are independently C$_1$-C$_3$ alkyl;
R$_d$ is H or C$_1$-C$_2$ alkyl;
R$_e$ is C$_1$-C$_2$ alkoxy;
Z is CH;
and their agriculturally suitable salts; provided that
1) when X is halogen, then Y is OCH$_3$, OC$_2$H$_5$, NH$_2$, NHCH$_3$, N(CH$_3$)$_2$ or N(OCH$_3$)CH$_3$;
2) when W is S, then R is H and Y is CH$_3$, OCH$_3$, OC$_2$H$_5$, CH$_2$OCH$_3$, C$_2$H$_5$, CF$_3$, SCH$_3$, OCH$_2$CH=CH$_2$, OCH$_2$C≡CH, OCH$_2$CH$_2$OCH$_3$,

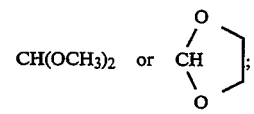

3) when the total number of carbon atoms of X and Y is greater than four, then the combined number of carbons of R$_1$ or R$_2$ is less than or equal to six;
4) when R$_2$ is C$_1$-C$_4$ alkylsulfinyl, C$_1$-C$_4$ alkylsulfonyl, SO$_2$NR$_d$R$_e$, SO$_2$NR'$_7$R$_8$ or CO$_2$R'$_9$, then Y is other than C$_2$-C$_5$ alkoxyalkyl, C$_2$-C$_5$ alkoxyalkoxy, C$_2$-C$_5$ alkylthioalkyl, C$_2$-C$_5$ alkylsulfinylalkyl, C$_2$-C$_5$ alkylsulfonylalkyl,

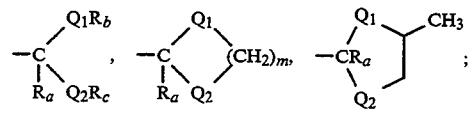

5) when R$_2$ is CO$_2$R'$_9$ or SO$_2$NR'$_7$R, then R$_1$ is R$_g$ and when R$_2$ is other than CO$_2$R'$_9$ or SO$_2$NR'$_7$R$_8$, then R$_1$ is R$_f$;
6) when J is J-1;
R is H or CH$_3$;
X is C$_1$-C$_2$ alkyl, C$_1$-C$_2$ alkoxy, Cl, F, Br, I, CH$_2$F, CF$_3$, OCH$_2$CH$_2$F, OCH$_2$CHF$_2$, OCH$_2$CF$_3$, CH$_2$Cl or CH$_2$Br;
Y is H, C$_1$-C$_2$ alkyl, C$_1$-C$_2$ alkoxy, CH$_2$OCH$_3$, CH$_2$OCH$_2$CH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, OCH$_2$CH$_2$OCH$_3$, C(O)R$_a$, cyclopropyl, C≡CH or C≡CCH$_3$;
R$_a$ is H or CH$_3$;
Z is CH;
W is O;
R$_1$ is R$_f$; and
R$_f$ is H, C$_1$-C$_2$ alkyl, C$_1$ haloalkyl, C$_1$-C$_2$ alkoxy or C$_1$-C$_2$ thioalkyl; then
R$_2$ is other than C$_1$-C$_4$ alkylsulfinyl or C$_1$-C$_4$ alkylsulfonyl and
7) when J is J-1;
W is O;
R is H or CH$_3$;

$R_1$ is $R_f$ or $R_g$;

$R_f$ is $C_1$ haloalkyl, halogen or $OCH_3$;

$R_g$ is $C_1-C_2$ haloalkyl or $W_2R_{11}$;

$W_2$ is O or S;

$R_9$ is $CH_2CH_2R_{10}$, $CH_2CF_3$, $C_3-C_4$ haloalkyl, $C_3-C_4$ alkynyl, $C_2-C_4$ alkylthioalkyl, $C_3-C_5$ cycloalkyl or $C_4-C_7$ cycloalkylalkyl;

$R'_9$ is $C_1-C_4$ alkyl, $C_3-C_4$ alkenyl, $CH_2CH_2Cl$, $CH_2CH_2Br$, $CH_2CH_2OCH_3$ or $CH_2CH_2OC_2H_5$;

$R_{10}$ is OH, F, CN, $OSO_2(C_1-C_3$ alkyl) or $OSO_2(C_1-C_3$ haloalkyl);

$R_{11}$ is $C_1-C_3$ alkyl or $C_1-C_3$ haloalkyl;

A is A-1;

X is $C_1-C_2$ alkyl, $C_1-C_2$ alkoxy, Cl, F, Br, I, $CH_2F$, $CF_3$, $OCH_2CH_2F$, $OCH_2CHF_2$, $OCH_2CF_3$, $CH_2Cl$ or $CH_2Br$;

Y is H, $C_1-C_2$ alkyl, $C_1-C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $C(O)R_a$, cyclopropyl, $C\equiv CH$ or $C\equiv CCH_3$;

$R_a$ is H or $CH_3$; and

Z is CH; then $R_2$ is other than CN, $CO_2R_9$, $CO_2R'_9$.

2. A compound of claim 1 where

X is $C_1-C_2$ alkyl, $C_1-C_2$ alkoxy, Cl, F, Br, I, $CH_2F$, $CF_3$, $OCH_2CH_2F$, $OCH_2CHF_2$, $OCH_2CF_3$, $CH_2Cl$ or $CH_2Br$; and Y is H, $C_1-C_2$ alkyl, $C_1-C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$,

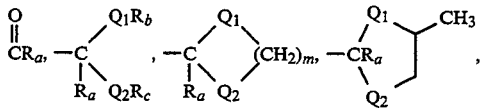

$CH_2SCH_3$, cyclopropyl, $C\equiv CH$ or $C\equiv CCH_3$; and $R_a$ is H or $CH_3$.

3. A compound claim 2 where

W is O;

$R_f$ is H, $CH_3$, $C_1$ haloalkyl, halogen or $OCH_3$;

$R_g$ is $C_1-C_2$ haloalkyl, ethyl, $W_2R_{11}$, $CH_2OCH_3$, $CH_2SCH_3$, $CH_2CN$, $C_1-C_2$ alkylamino or $N(CH_3)_2$;

$R_2$ is $C_1-C_4$ alkylsulfinyl, $C_1-C_4$ alkylsulfonyl, $SO_2NH_2$, $SO_2NR_dR_e$, $SO_2NR_7R_8$, $SO_2NR'_7R_8$, $OSO_2R_8$, $SO_2OR_8$, $N_3$, $P(W_1)(OC_1-C_2$ alkyl$)_2$, CN, $CO_2R_9$, $CO_2R'_9$, $CHF_2$, $CF_2H$, $CH_2Cl$, $CCl_2H$ or $C_2-C_4$ haloalkyl;

$R_7$ is H, $C_2-C_3$ cyanoalkyl, $C_3-C_4$ alkenyl or $C_3-C_4$ alkynyl;

$R_8$ is $C_1-C_4$ alkyl, $C_1-C_4$ haloalkyl, $C_3-C_4$ alkenyl, $C_3-C_4$ alkynyl, $C_2-C_4$ alkoxyalkyl or cyclopropyl; and $R_{11}$ is $C_1-C_3$ alkyl, $C_1-C_2$ haloalkyl, allyl or propargyl.

4. A compound of claim 3 where $R_7$ is H, $C_2-C_3$ cyanoalkyl, allyl or propargyl;

$R'_7$ is $C_1-C_3$ alkyl;

$R_8$ is $C_1-C_3$ alkyl, allyl, propargyl or cyclopropyl;

$R_9$ is $CH_2CH_2R_{10}$, $CH_2CH_2SCH_3$, propargyl or cyclopropylmethyl;

$R'_9$ is $C_1-C_3$ alkyl, allyl, $CH_2CH_2OCH_3$ or $CH_2CH_2Cl$; and $R_{10}$ is OH, CN or $OSO_2CH_3$.

5. A compound of claim 4 where

X is $CH_3$, $OCH_3$, $OCH_2CH_3$, Cl or $OCH_2CF_3$; and

Y is $CH_3$, $OCH_3$, $CH_2CH_3$, $CH_2OCH_3$, $NHCH_3$ or $CH(OCH_3)_2$.

6. The compound of claim 1 which is N2-[(4,6-dimethoxypyrimidin-2-yl)aminocarbonyl]-N3-ethyl-2,3-pyridinedisulfonamide.

7. The compound of claim 1 which is N-[(4,6-dimethoxypyrimidin-2-yl)aminocarbonyl]-3-(methylsulfonyloxy)-2-pyridinesulfonamide.

8. The compound of claim 1 which is N2-[(4,6-dimethoxypyrimidin-2-yl)aminocarbonyl]-N3-methyl-2,3-pyridinedisulfonamide.

9. A composition suitable for controlling the growth of undesired vegetation which comprises an effective amount of a compound of claim 1 and at least one of the following: surfactant, solid inert diluent or liquid inert diluent and mixtures of the foregoing.

10. A method for controlling the growth of undesired vegetation which comprises applying to the locus to be protected an effective amount of a compound of claim 1.

* * * * *